(12) United States Patent
Cui et al.

(10) Patent No.: US 12,404,281 B2
(45) Date of Patent: Sep. 2, 2025

(54) DIARYL MACROCYCLES AS MODULATORS OF PROTEIN KINASES

(71) Applicant: Turning Point Therapeutics, Inc., Princeton, NJ (US)

(72) Inventors: Jingrong Jean Cui, Princeton, NJ (US); Yishan Li, Princeton, NJ (US); Evan W. Rogers, Princeton, NJ (US); Dayong Zhai, Princeton, NJ (US)

(73) Assignee: TURNING POINT THERAPEUTICS, INC., Princeton, NJ (US)

( * ) Notice: Subject to any disclaimer, the term of this patent is extended or adjusted under 35 U.S.C. 154(b) by 0 days.

(21) Appl. No.: 18/227,561

(22) Filed: Jul. 28, 2023

(65) Prior Publication Data

US 2024/0140964 A1    May 2, 2024

Related U.S. Application Data

(63) Continuation of application No. 17/485,942, filed on Sep. 27, 2021, now abandoned, which is a continuation of application No. 16/797,866, filed on Feb. 21, 2020, now abandoned, which is a continuation of application No. 16/204,566, filed on Nov. 29, 2018, now Pat. No. 10,618,912, which is a continuation of application No. 15/609,962, filed on May 31, 2017, now Pat. No. 10,246,466, which is a continuation of application No. 15/113,583, filed as application No. PCT/US2015/012597 on Jan. 23, 2015, now Pat. No. 9,714,258.

(60) Provisional application No. 62/106,301, filed on Jan. 22, 2015, provisional application No. 62/049,326, filed on Sep. 11, 2014, provisional application No. 61/931,506, filed on Jan. 24, 2014.

(51) Int. Cl.
*C07D 487/04* (2006.01)
*C07D 487/08* (2006.01)
*C07D 498/18* (2006.01)

(52) U.S. Cl.
CPC ........ *C07D 498/18* (2013.01); *C07B 2200/13* (2013.01)

(58) Field of Classification Search
CPC ............................ C07D 487/04; C07D 487/08
See application file for complete search history.

(56) References Cited

U.S. PATENT DOCUMENTS

| | | |
|---|---|---|
| 4,838,925 A | 6/1989 | Tseng |
| 4,847,382 A | 7/1989 | Hallenbach |
| 5,639,778 A | 6/1997 | Andersson |
| 5,698,578 A | 12/1997 | Heath et al. |
| 8,497,270 B2 | 7/2013 | Thuring et al. |
| 8,680,111 B2 | 3/2014 | Bailey |
| 8,815,872 B2 | 8/2014 | Yu |
| 8,933,084 B2 | 1/2015 | Andrews |
| 9,090,630 B2 | 7/2015 | Blom et al. |
| 9,714,258 B2 | 7/2017 | Cui |
| 10,246,466 B2 | 4/2019 | Cui et al. |
| 10,294,242 B2 | 5/2019 | Cui et al. |
| 10,316,044 B2 | 6/2019 | Cui et al. |
| 10,618,912 B2 | 4/2020 | Cui et al. |
| 2011/0029480 A1 | 2/2011 | Delucia |
| 2011/0294801 A1 | 12/2011 | Yu |
| 2012/0136859 A1 | 5/2012 | Shamsi et al. |
| 2013/0143895 A1 | 6/2013 | McAllister et al. |
| 2013/0203776 A1 | 8/2013 | Andrews |
| 2013/0245021 A1 | 9/2013 | Bi |
| 2013/0252961 A1 | 9/2013 | Bailey |
| 2014/0107099 A1 | 4/2014 | Blaney |
| 2014/0206605 A1 | 7/2014 | Beutner |
| 2016/0159808 A1 | 6/2016 | Kawasaki |
| 2016/0339027 A1 | 11/2016 | Carter |
| 2017/0002023 A1 | 1/2017 | Cui et al. |
| 2017/0334929 A1 | 11/2017 | Cui |
| 2018/0186813 A1 | 7/2018 | Cui |
| 2018/0194777 A1 | 7/2018 | Cui |
| 2018/0325901 A1 | 11/2018 | Cui |
| 2019/0169207 A1 | 6/2019 | Cui et al. |
| 2020/0216465 A1 | 7/2020 | Cui et al. |

FOREIGN PATENT DOCUMENTS

| | | |
|---|---|---|
| CL | 2012003227 | 2/2013 |
| CN | 102143750 | 8/2011 |
| CN | 102971322 | 3/2013 |
| JP | 2012502043 | 1/2012 |
| JP | 2017503867 A | 2/2017 |
| WO | 1997035550 | 10/1997 |
| WO | 2000071118 | 11/2000 |
| WO | 2002010169 | 2/2002 |

(Continued)

OTHER PUBLICATIONS

Miller et al., "Solvent Systems for Crystallization and Polymorph Selection" Chapter 3 in Solvent Systems and Their Selection in Pharmaceutics and Biopharmaceutics Series Biotechnology: Pharmaceutical Aspects vol. VI Augustijns, Patrick; Brewster, Marcus (Eds.) 2007.

(Continued)

*Primary Examiner* — Bruck Kifle
(74) *Attorney, Agent, or Firm* — Mintz, Levin, Cohn, Ferris, Glovsky and Popeo, P.C.

(57) ABSTRACT

The present invention relates to certain diaryl macrocyclic compounds, pharmaceutical compositions containing them, and methods of using them, including methods for treating cancer, pain, neurological diseases, autoimmune diseases, and inflammation.

7 Claims, 2 Drawing Sheets

(Continued)

(56) References Cited

FOREIGN PATENT DOCUMENTS

| WO | 0246197 A1 | 6/2002 |
|---|---|---|
| WO | 2002076925 | 10/2002 |
| WO | 2004052315 | 6/2004 |
| WO | 2010028116 | 3/2010 |
| WO | 2010033941 | 3/2010 |
| WO | 2010048314 | 4/2010 |
| WO | 2010051549 | 5/2010 |
| WO | 2010063487 | 6/2010 |
| WO | 2010086040 | 8/2010 |
| WO | 2011006074 | 1/2011 |
| WO | 2011071716 | 6/2011 |
| WO | 2011071725 | 6/2011 |
| WO | 2011146336 | 11/2011 |
| WO | 2012034091 | 3/2012 |
| WO | 2012034095 | 3/2012 |
| WO | 2012075393 | 6/2012 |
| WO | 2012136859 | 10/2012 |
| WO | 2013001310 | 1/2013 |
| WO | 2013028465 | 2/2013 |
| WO | 2013045653 | 4/2013 |
| WO | 2013045656 A1 | 4/2013 |
| WO | 2013045701 | 4/2013 |
| WO | 2013045702 | 4/2013 |
| WO | 2013059587 | 4/2013 |
| WO | 20130143895 | 6/2013 |
| WO | 2013132376 | 9/2013 |
| WO | 2013134219 | 9/2013 |
| WO | 2013134228 | 9/2013 |
| WO | 2013147711 | 10/2013 |
| WO | 2014118186 | 8/2014 |
| WO | 2014173928 | 10/2014 |
| WO | 2015073267 | 5/2015 |
| WO | 2015112806 | 7/2015 |
| WO | 2016070241 | 5/2016 |
| WO | 2016097869 | 6/2016 |
| WO | 2016133838 | 8/2016 |
| WO | 2016144844 | 9/2016 |
| WO | 2016144846 | 9/2016 |
| WO | 2016177658 | 11/2016 |
| WO | 2017004342 | 1/2017 |
| WO | 2017007759 | 1/2017 |
| WO | 2017015367 | 1/2017 |
| WO | 20170002023 | 1/2017 |
| WO | 2017075107 | 5/2017 |
| WO | 2017152076 | 9/2017 |
| WO | 2018022911 | 2/2018 |
| WO | 2018112027 | 6/2018 |
| WO | 2018140554 | 8/2018 |
| WO | 2019023417 | 1/2019 |

OTHER PUBLICATIONS

International Search Report and Written Opinion prepared for PCT/US2015/012597, mailed Aug. 28, 2015, 11 pages.
International Search Report and Written Opinion prepared for PCT/US2016/040329, mailed Sep. 7, 2016, 13 pages.
International Search Report and Written Opinion prepared for PCT/US2016/040972, mailed Sep. 13, 2016, 8 pages.
European Search Report issued in EP 16828471, completed Mar. 15, 2019.
European Search Report issued in EP 16818768, completed Jan. 22, 2019.
Wang et al., "Discovery of novel pyrazolo[1,5-a]pyrimidines as potent pan-Pim inhibitors by structure- and property-based drug design," Bioorganic & Medicinal Chemistry Letters (2013), 23(11), 3149-3153.
Gavrin et al., "Synthesis of Pyrazolo[1,5-alpha]pyrimidinone Regioisomers," Journal of Organic Chemistry (2007), 72(3), 1043-1046.
Roever et al., "Identification of 4-methyl-1,2,3,4,10,10a-hexahydropyrazino[1,2-a]indoles as 5-HT2C receptor agonists," Bioorganic & Medicinal Chemistry Letters (2005), 15(15), 3604-3608.
Golubovskaya VM, Front Biosci (Landmark Ed). 2014; 19: 687-706.
Jordan, "Tamoxifen: A Most Unlikely Pioneering Medicine", Nature Reviews, vol. 2, Mar. 2003, pp. 205-213.
Hackam et al., "Translation of Research evidence From Animals to Humans", JAMA, 2006; 296(14): 1731-1732.
Sequist, L.V., et al. Analysis of tumor specimens at the time of acquired resistance to EGFR-TK1 therapy in 155 patients with EGFR-mutant lung cancers. Clin. Cancer Res. 2013, 19, 2240-2247.
Zhang, Z. et al., Nat. Genet. 2012, 44, 852-860.
Cui, J. J. et al., J. Med. Chem. 2011, 54, 6342-6363.
Katayama, R. et al., Sci. Transl. Med. 2012, 4, 120ra17.
Quintas-Cardama, A. et al., Nat. Rev. Drug Discov. 2011, 10(2), 127-40.
Pesu, M. et al., Immunol. Rev. 2008, 223, 132-142.
Murray, P.J., J. Immunol. 2007, 178(5), 2623-2329.
Muller, M. et al., Nature 1993, 366(6451), 129-135.
Neubauer, H. et al., Cell 1998 93(3), 397-409.
Nosaka, T. et al., Science 1995, 270(5237), 800-802.
Vainchenker, W. et al., Semin. Cell. Dev. Biol. 2008, 19(4), 385-393.
Levine, R.L. etal., Cancer Cell 2005, 7(4), 387-397.
Kralovics, R. et al., N. Engl. J. Med. 2005, 253(17), 1779-1790.
James, C. et al., Nature 2005, 434(7037), 1144-1148.
Baxter, E.J. et al. Lancet 2005, 365(9464), 1054-1061.
LaFave, L.M. et al., Trends Pharmacol. Sci. 2012, 33(11), 574-582.
Verstovsek, S. et al., N. Engl. J. Med. 2012, 366(9), 799-807.
Quintas-Cardama, A. et al., Blood 2010, 115(15), 3109-3117.
Nefedova, Y. et al., Cancer Res 2005; 65(20): 9525-35.
Davies, K. D. et al., Clin Cancer Res 2013, 19 (15): 4040-4045.
Awad, M. M. et al., N Engl J Med. 2013, 368(25):2396-2401.
Charest A, et al Genes Chromosomes Cancer 2003, 37, 58.
Takeuchi K, et al Nat. Med. 2012, 18, 378.
Gu TL, et al PLOS One. 2011, 6, el5640.
Lacronique V, et al. Science 1997, 278, 5341, 1309-12.
Zhang S, et al Trends Pharmacol Sci. 2012, 33, 122.
Bromann PA, Oncogene 2004, 23, 7957-7968.
Summy JM, et al. Cancer Metastasis Rev. 2003, 22, 337-358.
Scancier F. et al. PLOS One. 2011, 6(2): el 7237.
Ongusaha PP, et al. EMBO J. 2003, 22, 1289-1301.
Hammerman PS, et al. Cancer Discov. 2011, 1, 78-89.
Tomasson MH, et al. Blood 2008, 111:4797-4808.
Yu J. et al., Cancer Cell, 2010, 17, 5, 443-54.
Advani, A.S. et al. Leukemia Research, 2002, 26, 8, 713-720.
Gottesman, M.M., Annu. Rev. Med., 2002, 53, 615-627.
Anastassiadis T, et al Nat Biotechnol. 2011, 29, 1039.
Vetrie D. et al. Nature 1993, 361, 226-233.
Mohamed AJ et al, immunological Reviews, 2009, 228, 58-73.
Grande, E. et al., Mol. Cancer Ther. 2011, 10, 569-579.
Monti, E. 2007. Molecular Determinants of Intrinsic Multidrug Resistance in Cancer Cells and Tumors in B. Teicher (Ed.), Cancer Drug Resistance (pp. 241-260).
McCarthy et al. "Tropomyosin receptor kinase inhibitors: a patent update 2009-2013," Expert Opinions 2014, pp. 731-744.
Di Paolo JA, et al. Nature Chemical Biology 2011, 7, 41-50.
Park, M. et al., Cell 1986, 45, 895-904.
Trusolino, L. et al., Nature Rev. Mol. Cell Biol. 2010, 11, 834-848.
Sonbol, M.B. et al., Ther. Adv. Hematol. 2013, 4(1), 15-35.
Reiter A, et al. Cancer Res. 2005, 65, 7, 2662-7.
Sen, B., et al. Distinct interactions between SRC and MET in mediating resistance to SRC inhibition in head and neck cancer. Clin Cancer Res. 2010, 17, 1-11.
Xie, Q., et al. Hepatocyte growth factor (HGF) autocrine activation predicts sensitivity to MET inhibition in alioblastoma. Proc. Natl. Acad. Sci. U.S. A. 2012, 109, 570-575.
International Search Report and Written Opinion prepared for PCT/US2016/043132, mailed Sep. 28, 2016, 8 pages.
Liu L, et al. Nature, 2012, 483, 608-612.
Peterson et al., "Expanding the Scope of Crystal Form Evaluation in Parmaceutical Science" Journal of Pharmacy & Pharmaceutical Science 2006 9(3):317-326.

(56) References Cited

OTHER PUBLICATIONS

Gargallonis et al., "The molecular rationale of Src inhibition in colorectal carcinomas", Int. J. Cancer: 134, 2019-2029 (2014). Published online Jun. 21, 2013.
Okamoto et al., "Identification of c-Src as a Potential Activation as a Cause of Resistance to c-Sro Published online Apr. 20, 2010 Inhibition", Therapeutic Target for Gastric Cancer and of MET Mol Cancer Ther., May 2010; 9(5): 1188-97.
Vergani et al., "Identification of MET and SRC Activation in Melanoma Cell Lines Showing Primary Resistance to PLX4032", Neoplasia. Dec. 2011; 13(12): 1132-42.
Pachter et al., "The Chemistry of Hortiamine and 6-Methoxyrhetsinine," J. Am. Chem. Soc., 1961, 83, 635-642.
Kiselyov, Alexander S., "Solid support synthesis of 15-membered macrocycles containing a serotonin unit," Tetrahedron Letters 46 (2005) 3007-3010.
Halland et al. "Small Macrocycles as Highly Active Integrin 0131 Antagonists," ACS Medicinal Chemistry Letters, 2014, Jan. 10, 5, 193-198.
International Search Report and Written Opinion prepared for PCT/US2017/044214, mailed Dec. 1, 2017, 11 pages.
Couronne L, et al. Blood 2013, 122, 811.
Takahashi, M. et al. Cell. 1985, 42:581-588.
Schiller J H et al., N Engl J Med, 346: 92-98, 2002.
Pachnis, V., et al. Development 1993, 119, 1005-1017.
Schuchardt, A. et al. Nature 1994, 367:380-383.
Grieco, M. et al. Cell. 1990, 23; 60 (4):557-63.
Gainor JF, Shaw AT. Oncologist. 2013, 18(7):865-75.
Kentsis, A., et al. Autocrine activation of the MET receptor tyrosine kinase in acute myeloid leukemia. Nat. Medd. 2012, 18, 1118-1122.
Yano, S., et al. Hepatocyte growth factor induces gefitinib resistance of lung adenocarcinoma with epidermal growth factor receptor-activating mutations. Cancer Res. 2008, 68, 9479-9487.
Bardelli, A., et al. Amplification of the MIi'T Receptor Drives Resistance to Anti-EGFR Therapies in Colorectal Cancer. Cancer Discov. 2013, 3, 658-673.
Straussman, R., et al. Tumour micro-environment elicits innate resistance to RAF inhibitors through HGF secretion. Nature 2012, 487, 500-504.
Harbinski, F., et al. Rescue screens with secreted proteins reveal compensatory potential of receptor tyrosine kinases in driving cancer growth. Cancer Discov. 2012, 2, 948-959.
Parsons, S. J., et al. Src family kinases, key regulators of signal transduction. Oncogene, 2004, 23, 7906-7909.
Wojcik, E. J., et al. A novel activating function of SRC and STAT3 on HGF transcription in mammary carcinoma cells. Oncogene. 2006, 25, 2773-84.

Dulak AM et al. HGF-independent potentiation of EGFR action by MIi'I'. Oncogene. 2011, 30, 3625-3635.
Stabile, L. P., et al. c-SRC activation mediates erlotinib resistance in head and neck cancer by stimulating MET. Clin Cancer Res. 2012, 19, 1-13.
Bertotti, A., et al. Inhibition of SRC impairs the growth of MET-addicted gastric tumors. Clin Cancer Res. 2010, 16,3933-3943.
Wrobel CN, et al. Autocrine CSFIR activation promotes SRC-dependent disruption of mammary epithelial architecture. J Cell Biol. 2004, 165, 263-273.
Ravi V, et al. Treatment of tenosynovial giant cell tumor and pigmented villonodular synovitis. Curr Opin Oncol. 2011, 23, 361-366.
Bottaro, D. P. etal., Science 1991, 251, 802-804.
Gherardi, E. et al., Nature Rev. Cancer 2012, 12, 89-103.
Gridelli, C. et al., Cancer Treat Rev. 2014, 40, 300-306.
Liu Z, et al. J. Clin. Endocrinol. Metab. 2004, 89, 3503-3509.
Boccaccio, C.; Comoglio, P. M. Invasive growth: a MET-driven generic programme for cancer and stem cells. Nat. Rev. Cancer 2006, 6, 637-645.
Ma, PC et al. Expression and mutational analysis of MET in human solid cancers. Genes Chromosomes Cancer 2008, 47, 1025-1037.
Maulik, G., et al. Role of the hepatocyte growth factor receptor, MET, in oncogenesis and potential for therapeutic inhibition. Cytokine Growth Factor Rev. 2002, 13, 41-59.
Smolen, G. A., et al. Amplification of MET may identify a subset of cancers with extreme sensitivity to the selective tyrosine kinase inhibitor PHA-665752. Proc. Natl. Acad. Sci. U.S. A. 2006, 103, 2316-2321.
Ghiso, E.; Giordano, S. Targeting MET: why, where and how? Curr. Opin. Pharmacol. 2013, 13, 511-518.
Cooper, C. S., et al Molecular cloning of a new transforming gene from a chemically transformed human cell line. Nature 1984, 311, 29-33.
Otsuka, T., et al. MET autocrine activation induces development of malignant melanoma and acquisition of the metastatic phenotype. Cancer Res. 1998, 58, 5157-5167.
Sawyers, C., Nature 2004, 432, 294-297.
Engelman, J. A. et al., Science 2007, 316, 1039-1043.
Wilson, T.R. et al., Nature 2012, 487, 505-509.
Pulford, K. et al., Cell Mol. Life Sci. 2004, 61, 2939.
Manning, G. et al., Science 2002, 298, 1912-1934.
Morris, S.W. et al., Science 1994, 263, 1281.
Bischof, D. et al., Mol. Cell Biol., 1997, 17, 2312-2325.
Soda, M. et al., Nature 2007, 448, 561-566.
Mosse, Y. P. et al., Nature 2008, 455, 930-935.
Thiele, C. J. et al., Clin. Cancer Res. 2009, 15, 5962-5967.
Pierotti, M.A. et al., Cancer Lett. 2006, 232, 90-98.
Vaishnavi, A. et al., Nat. Med. 2013, 19, 1469-1472.
Verma, A. etal., Mol. Cancer Ther. 2011, 10, 1763-1773.

DIARYL MACROCYCLES AS MODULATORS OF PROTEIN KINASES

CROSS REFERENCE TO RELATED APPLICATIONS

This application claims priority under 35 U.S.C. § 119(e) to U.S. Provisional Applications Ser. No. 61/931,506 filed Jan. 24, 2014. Ser. No. 62/049,326 filed Sep. 11, 2014 and Ser. No. 62/106,301 filed on Jan. 22, 2015, the entire contents of which are hereby incorporated by reference in their entirety.

TECHNICAL FIELD

The present invention relates to certain diaryl macrocyclic derivatives, pharmaceutical compositions containing them, and methods of using them to treat cancer, pain, neurological diseases, autoimmune diseases, and inflammation.

BACKGROUND

Protein kinases are key regulators for cell growth, proliferation and survival. Genetic and epigenetic alterations accumulate in cancer cells leading to abnormal activation of signal transduction pathways which drive malignant processes. Manning, G. et al., *Science* 2002, 298, 1912-1934. Pharmacological inhibition of these signaling pathways presents promising intervention opportunities for targeted cancer therapies. Sawyers, C., *Nature* 2004, 432, 294-297.

MET, along with RON, belongs to a unique subfamily of receptor tyrosine kinases, and is mainly produced in cells of epithelial or endothelial origin. Park, M. et al., *Cell* 1986, 45, 895-904. Hepatocyte growth factor (HGF), also known as scatter factor (SF), is the only known natural high-affinity ligand of MET, and is mainly expressed in cells of mesenchymal origin. Bottaro, D. P. et al., *Science* 1991, 251, 802-804. HGF/MET signaling controls MET-dependent cell proliferation, survival, and migration processes that are critical for invasive growth during embryonic development and postnatal organ regeneration, and are fully active in adults only for wound healing and tissue regeneration processes. Trusolino. L. et al., *Nature Rev. Mol. Cell Biol.* 2010, 11, 834-848. The HGF/MET axis is frequently upregulated in many cancers through activating mutation, gene amplification, aberrant paracrine, or autocrine ligand production, and is strongly linked with tumorigenesis, invasive growth, and metastasis. Gherardi, E. et al., *Nature Rev. Cancer* 2012, 12, 89-103. In addition, the activation of HGF/MET signaling is emerging as an important mechanism in resistance to EGFR and BRAF inhibitor treatments via MET amplification and/or upregulation of stromal HGF. Engelman, J. A. et al., *Science* 2007, 316, 1039-1043; Wilson, T. R. et al., *Nature* 2012, 487, 505-509. Due to the role of aberrant HGF/MET signaling in human oncogenesis, invasion/metastasis, and resistance, inhibition of the HGF/MET signaling pathway has great potential in cancer therapy.

ALK, along with leukocyte tyrosine kinase (LTK), is grouped within the insulin receptor (IR) superfamily of receptor tyrosine kinases. ALK is mainly expressed in the central and peripheral nervous systems suggesting a potential role in normal development and function of the nervous system. Pulford, K. et al., *Cell Mol. Life Sci.* 2004, 61, 2939. ALK was first discovered as a fusion protein, NPM (nucleophosmin)-ALK, encoded by a fusion gene arising from the t(2;5)(p23;q35) chromosomal translocation in anaplastic large cell lymphoma (ALCL) cell lines. Morris, S. W. et al., *Science* 1994, 263, 1281. More than twenty distinct ALK translocation partners have been discovered in many cancers, including ALCL (60-90% incidence), inflammatory myofibroblastic tumors (IMT, 50-60%), non-small cell lung carcinomas (NSCLC, 3-7%), colorectal cancers (CRC, 0-2.4%), breast cancers (0-2.4%), and other carcinomas. Grande, E. et al., *Mol. Cancer Ther.* 2011, 10, 569-579. The ALK-fusion proteins are located in the cytoplasm, and the fusion partners with ALK play a role in dimerization or oligomerization of the fusion proteins through a coil-coil interaction to generate constitutive activation of ALK kinase function. Bischof, D. et al., *Mol. Cell Biol.,* 1997, 17, 2312-2325. EML4-ALK, which comprises portions of the echinoderm microtubule associated protein-like 4 (EML4) gene and the ALK gene, was first discovered in NSCLC, is highly oncogenic, and was shown to cause lung adenocarcinoma in transgenic mice. Soda, M. et al., *Nature* 2007, 448, 561-566. Oncogenic point mutations of ALK in both familial and sporadic cases of neuroblastoma. Mossé, Y. P. et al., *Nature* 2008, 455, 930-935. ALK is an attractive molecular target for cancer therapeutic intervention because of the important roles in haematopoietic, solid, and mesenchymal tumors. Grande, supra.

The tropomyosin-related receptor tyrosine kinases (Trks) are the high-affinity receptor for neurotrophins (NTs), a nerve growth factor (NGF) family of proteins. Members of the Trk family are highly expressed in cells of neural origin. Activation of Trks (TrkA, TrkB, and TrkC) by their preferred neurotrophins (NGF to TrkA, brain-derived neurotrophic factor [BDNF] and NT4/5 to TrkB, and NT3 to TrkC) mediates the survival and differentiation of neurons during development. The NT/Trk signaling pathway functions as an endogenous system that protects neurons after biochemical insults, transient ischemia, or physical injury. Thiele, C. J. et al., *Clin. Cancer Res.* 2009, 15, 5962-5967. However, Trk was originally cloned as an oncogene fused with the tropomyosin gene in the extracellular domain. The activating mutations caused by chromosomal rearrangements or mutations in NTRK1 (TrkA) has been identified in papillary and medullary thyroid carcinoma, and recently in non-small cell lung cancer. Pierotti, M. A. et al., *Cancer Lett.* 2006, 232, 90-98; Vaishnavi, A. et al., *Nat. Med.* 2013, 19, 1469-1472. Because Trks play important roles in pain sensation as well as tumor cell growth and survival signaling, inhibitors of Trk receptor kinases may provide benefits as treatments for pain and cancer.

Receptor tyrosine kinase AXL belongs to the TAM family of proteins and was originally detected in patients with chronic myelogenous leukemia (CML) as an unidentified transforming gene. Verma, A. et al., *Mol. Cancer Ther.* 2011, 10, 1763-1773. The primary ligand for TAM receptors is growth arrest-specific 6 protein (Gas6). AXL is ubiquitously expressed and has been detected in a wide variety of organs and cells, including the hippocampus and cerebellum, monocytes, macrophages, platelets, endothelial cells (EC), heart, skeletal muscle, liver, kidney, and testis. Upregulation of Gas6/AXL has been reported in many human cancers including colon, esophageal, thyroid, breast, lung, liver, and astrocytoma-glioblastoma. Id. Increased activation of AXL has been observed in EGFR-mutant lung cancer models in vitro and in vivo with acquired resistance to erlotinib in the absence of the EGFR T790M alteration or MET activation. Zhang, Z. et al., *Nat. Genet.* 2012, 44, 852-860. Genetic or pharmacological inhibition of AXL restored sensitivity to erlotinib in these tumor models. Increased expression of AXL and, in some cases, of its ligand Gas6 was found in EGFR-mutant lung cancers obtained from individuals with acquired resistance to tyrosine kinase inhibitors. Id. Therefore, AXL is a promising therapeutic target for patients with EGFR-mutant lung cancer who acquired resistance to FGFR inhibitors.

Crizotinib (PF-02341066) is a tyrosine kinase drug targeting MET/ALK/ROS1/RON with moderate activity against TRKs and AXL. Cui, J. J. et al., *J. Med. Chem.* 2011, 54, 6342-6363. It was approved to treat certain patients with late-stage (locally advanced or metastatic) NSCLC that expresses the abnormal ALK fusion gene identified by a companion diagnostic test (Vysis ALK Break Apart FISH Probe Kit). Similar to imatinib and other kinase inhibitor drugs, resistance invariably develops after a certain time of treatment with crizotinib. The resistance mechanisms include ALK gene amplification, secondary ALK mutations, and aberrant activation of other kinases including KIT and EGFR. Katayama, R. et al., *Sci. Transl. Med.* 2012, 4, 120ra17. Based on the clinical success of second generation ABL inhibitors for the treatment of imatinib resistance in CML patients, a second generation of ALK inhibitors is emerging. These drugs target the treatment of crizotinib-refractory or resistant NSCLC patient with more potent inhibition against both wild and mutant ALK proteins. Gridelli, C. et al., *Cancer Treat Rev.* 2014, 40, 300-306.

By modulating multiple targets among the group of structurally related tyrosine kinases MET, ALK, AXL, and TRK, the compounds described herein address crizotinib resistance, EGFR inhibitor drug resistance, and other primary indications with abnormal cell signaling due to MET, ALK, AXL, and/or TRK mutations and gene amplification. Compounds describe herein are inhibitors of MET, wild and mutant ALKs, AXL, and TRKs and will be useful in treating cancer patients with abnormal signaling from any one or more of MET, ALK, AXL, or TRKs.

The Janus family of kinases (JAKs) include JAK1, JAK2, JAK3 and TYK2, and are cytoplastic tyrosine kinases required for the physiologic signaling of cytokines and growth factors. Quintas-Cardama, A. et al., *Nat. Rev. Drug Discov.* 2011, 10(2), 127-40; Pesu, M. et al., *Immunol. Rev.* 2008, 223, 132-142; Murray, P. J., *J. Immunol.* 2007, 178(5), 2623-2329. JAKs activate by ligand-induced oligomerization, resulting in the activation of downstream transcriptional signaling pathway called STAT (signal transducers and activators of transcription). The phosphorylated STATs dimerize and translocate into nucleus to drive the expression of specific genes involved in proliferation, apoptosis, differentiation, which are essential for hematopoiesis, inflammation and immune response. Murray, supra.

Mouse knockout studies have implicated the primary roles of JAK-STAT signaling with some overlap between them. JAK1 plays a critical role in the signaling of various proinflammatory cytokines such as IL-1, IL-4, IL-6, and tumor necrosis factor alpha (TNFα). Muller, M. et al., *Nature* 1993, 366(6451), 129-135. JAK2 functions for hematopoietic growth factors signaling such as Epo, IL-3, IL-5, GM-CSF, thrombopoietin growth hormone, and prolactin-mediated signaling. Neubauer. H. et al., *Cell* 1998 93(3), 397-409. JAK3 plays a role in mediating immune responses, and TYK2 associates with JAK2 or JAK3 to transduce signaling of cytokines, such as IL-12. Nosaka, T. et al., *Science* 1995, 270(5237), 800-802; Vainchenker, W. et al., *Semin. Cell. Dev. Biol.* 2008, 19(4), 385-393.

Aberrant regulation of JAK/STAT pathways has been implicated in multiple human pathological diseases, including cancer (JAK2) and rheumatoid arthritis (JAK1, JAK3). A gain-of-function mutation of JAK2 (JAK2V617F) has been discovered with high frequency in MPN patients. Levine, R. L. et al., *Cancer Cell* 2005, 7(4), 387-397; Kralovics, R. et al., *N. Engl. J. Med.* 2005, 253(17), 1779-1790; James, C. et al., *Nature* 2005, 434(7037), 1144-1148; Baxter. E. J. et al. *Lancet* 2005, 365(9464), 1054-1061. The mutation in the JH2 pseudokinase domain of JAK2 leads to constitutively kinase activity. Cells containing JAK2V617F mutation acquire cytokine-independent growth ability and often become tumor, providing strong rational for the development of JAK inhibitors as target therapy.

Multiple JAK inhibitors in clinical trial showed significant benefit in splenomegaly and disease related constitutional symptoms for the myelofibrosis patients, including the first FDA-approved JAK2 inhibitor ruxolitinib in 2011. Quintas-Cardama, supra; Sonbol, M. B. et al., *Ther. Adv. Hematol.* 2013, 4(1), 15-35; LaFave, L. M. et al., *Trends Pharmacol. Sci.* 2012, 33(11), 574-582. The recently collected clinical data related to ruxolitinib treatment indicated that JAK inhibitors work on both JAK2 wild-type and JAK2 mutated cases. Verstovsek, S. et al., *N. Engl. J. Med.* 2012, 366(9), 799-807; Quintas-Cardama, A. et al., *Blood* 2010, 115(15), 3109-3117. The discovery of selective inhibitors of JAK2 vs JAK1/3 remains an unsolved challenge. In addition, hyperactivation of the JAK2/signal transducers and activators of transcription 3 (JAK2/STAT3) is responsible for abnormal dendritic cell differentiation leading to abnormal dendritic cell differentiation and accumulation of immunosuppressive myeloid cells in cancer (Nefedova, Y. et al., *Cancer Res* 2005; 65(20): 9525-35). In Pten-null senescent tumors, activation of the Jak2/Stat3 pathway establishes an immunosuppressive tumor microenvironment that contributes to tumor growth and chemoresistance (Toso, A. et al., *Cell Reports* 2014, 9, 75-89). Therefore, pharmacologic inhibition of the JAK2/STAT3 pathway can be an important new therapeutic strategy to enhance antitumor activity via the regulation of antitumor immunity.

ROS1 kinase is a receptor tyrosine kinase with an unknown ligand. The normal functions of human ROS1 kinase have not been fully understood. However, it has been reported that ROS1 kinase undergoes genetic rearrangements to create constitutively active fusion proteins in a variety of human cancers including glioblastoma, non-small cell lung cancer (NSCLC), cholangiocarcinoma, ovarian cancer, gastric adenocarcinoma, colorectal cancer, inflammatory myofibroblastic tumor, angiosarcoma, and epithelioid hemangioendothelioma (Davies, K. D. et al., *Clin Cancer Res* 2013, 19 (15): 4040-4045). Targeting ROS1 fusion proteins with crizotinib has demonstrated promising clinical efficacy in NSCLC patients whose tumors are positive for ROS1 genetic abnormalities (Shaw, A. T. et al., *N Engl J Med.* 2014, 371(21):1963-1971). Acquired resistant mutations have been observed in crizotinib treatment patients (Awad, M. M. et al., *N Engl J Med.* 2013, 368(25): 2396-2401). It is urgent to develop the second generation of ROS1 inhibitors for overcoming crizotinib ROS1 resistance.

There remains a need for small molecule inhibitors of these multiple protein or tyrosine kinase targets with desirable pharmaceutical properties. Certain diaryl macrocyclic compounds have been found in the context of this invention to have this advantageous activity profile.

SUMMARY

In one aspect, the invention relates to a compound of the following Formula (I-A):

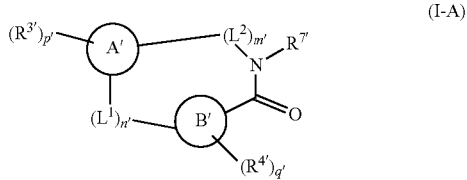

(I-A)

wherein
Ring A' and Ring B' are each independently a monocyclic or bicyclic aryl or heteroaryl; wherein one of Ring A' and Ring B' is a monocyclic aryl or heteroaryl and the other is a bicyclic heteroaryl; and at least one of Ring A' and Ring B' comprises at least one nitrogen ring member;

each $L^1$ and $L^2$ is independently —C($R^{1'}$)($R^{2'}$)—, —O—, —N($R^{k'}$)—, —S—, —S(O)— or —S(O)$_2$—;

each $R^{1'}$ and $R^{2'}$ are independently H, deuterium, halogen, $C_{1-6}$alkyl, $C_{2-6}$alkenyl, $C_{2-6}$alkynyl, $C_{3-6}$cycloalkyl, 3- to 7-membered heterocycloalkyl, $C_{6-10}$ aryl, or mono- or bicyclic heteroaryl, —OR$^{a'}$, —OC(O)R$^{a'}$, —OC(O)NR$^{a'}$R$^{b'}$, —OS(O)R$^{a'}$—, —OS(O)$_2$R$^{a'}$, —SR$^{a'}$, —S(O)R$^{a'}$, —S(O)$_2$R$^{a'}$, —S(O)NR$^{a'}$R$^{b'}$, —S(O)$_2$NR$^{a'}$R$^{b'}$, —OS(O)NR$^{a'}$R$^{b'}$, —OS(O)$_2$NR$^{a'}$R$^{b'}$, —NR$^{a'}$R$^{b'}$, —NR$^{a'}$C(O)R$^{b'}$, —NR$^{a'}$C(O)OR$^{b'}$, —NR$^{a'}$C(O)NR$^{a'}$R$^{b'}$, —NR$^{a'}$S(O)R$^{b'}$, —NR$^{a'}$S(O)$_2$R$^{b'}$, —NR$^{a'}$S(O)NR$^{a'}$R$^{b'}$, —NR$^{a'}$S(O)$_2$NR$^{a'}$R$^{b'}$, —C(O)R$^{a'}$, —C(O)OR$^{a'}$, —C(O)NR$^{a'}$R$^{b'}$, —PR$^{a'}$R$^{b'}$, —P(O)R$^{a'}$R$^{b'}$, —P(O)$_2$R$^{a'}$R$^{b'}$, —P(O)NR$^{a'}$R$^{b'}$, —P(O)$_2$NR$^{a'}$R$^{b'}$, —P(O)OR$^{a'}$, —P(O)$_2$OR$^{a'}$, —CN, or —NO$_2$, or $R^{1'}$ and $R^{2'}$ taken together with the carbon or carbons to which they are attached form a $C_{3-6}$ cycloalkyl or a 4- to 6-membered heterocycloalkyl, wherein each hydrogen atom in $C_{1-6}$alkyl, $C_{2-6}$alkenyl, $C_{2-6}$alkynyl, $C_{3-6}$cycloalkyl, 3- to 7-membered heterocycloalkyl, $C_{6-10}$ aryl, mono- or bicyclic heteroaryl, 4- to 6-membered heterocycloalkyl is independently optionally substituted by deuterium, halogen, $C_{1-6}$alkyl, $C_{1-6}$haloalkyl, —OR$^{e'}$, —OC(O)R$^{e'}$, —OC(O)NR$^{e'}$R$^{f'}$, —OS(O)R$^{e'}$, —OS(O)$_2$R$^{e'}$, —OS(O)NR$^{e'}$R$^{f'}$, —OS(O)$_2$NR$^{e'}$R$^{f'}$, —SR$^{e'}$, —S(O)R$^{e'}$, —S(O$_2$)R$^{e'}$, —S(O)NR$^{e'}$R$^{f'}$, —S(O)$_2$NR$^{e'}$R$^{f'}$, —NR$^{e'}$R$^{f'}$, —NR$^{e'}$C(O)R$^{f'}$, —NR$^{e'}$C(O)OR$^{f'}$, —NR$^{e'}$C(O)NR$^{e'}$R$^{f'}$, —NR$^{e'}$S(O)R$^{f'}$, —NR$^{e'}$S(O)$_2$R$^{f'}$, —NR$^{e'}$S(O)NR$^{e'}$R$^{f'}$, —NR$^{e'}$S(O)$_2$NR$^{e'}$R$^{f'}$, —C(O)R$^{e'}$, —C(O)OR$^{e'}$, —C(O)NR$^{e'}$R$^{f'}$, —PR$^{e'}$R$^{f'}$, —P(O)R$^{e'}$R$^{f'}$, —P(O)$_2$R$^{e'}$R$^{f'}$, —P(O)NR$^{e'}$R$^{f'}$, —P(O)$_2$NR$^{e'}$R$^{f'}$, —P(O)OR$^{e'}$, —P(O)$_2$OR$^{e'}$, —CN, or —NO$_2$;

each $R^{k'}$ is independently H, deuterium, $C_{1-6}$alkyl, $C_{2-6}$alkenyl, $C_{2-6}$alkynyl, $C_{3-6}$cycloalkyl, 3- to 7-membered heterocycloalkyl, $C_{6-10}$ aryl, or mono- or bicyclic heteroaryl, wherein each hydrogen atom in $C_{1-6}$alkyl, $C_{2-6}$alkenyl, $C_{2-6}$alkynyl, $C_{3-6}$cycloalkyl, 3- to 7-membered heterocycloalkyl, $C_{6-10}$ aryl, or mono- or bicyclic heteroaryl is independently optionally substituted by deuterium, halogen, $C_{1-6}$alkyl, $C_{1-6}$haloalkyl, —OR$^{e'}$, —OC(O)R$^{e'}$, —OC(O)NR$^{e'}$R$^{f'}$, —OS(O)R$^{e'}$, —OS(O)$_2$R$^{e'}$, —OS(O)NR$^{e'}$R$^{f'}$, —OS(O)$_2$NR$^{e'}$R$^{f'}$, —SR$^{e'}$, —S(O)R$^{e'}$, —S(O)$_2$R$^{e'}$, —S(O)NR$^{e'}$R$^{f'}$, —S(O)$_2$NR$^{e'}$R$^{f'}$, —NR$^{e'}$R$^{f'}$, —NR$^{e'}$C(O)R$^{f'}$, —NR$^{e'}$C(O)OR$^{f'}$, —NR$^{e'}$C(O)NR$^{e'}$R$^{f'}$, —NR$^{e'}$S(O)R$^{f'}$, —NR$^{e'}$S(O)$_2$R$^{f'}$, —NR$^{e'}$S(O)NR$^{e'}$R$^{f'}$, —NR$^{e'}$S(O)$_2$NR$^{e'}$R$^{f'}$, —C(O)R$^{e'}$, —C(O)OR$^{e'}$, —C(O)NR$^{e'}$R$^{f'}$, —PR$^{e'}$R$^{f'}$, —P(O)R$^{e'}$R$^{f'}$, —P(O)$_2$R$^{e'}$R$^{f'}$, —P(O)NR$^{e'}$R$^{f'}$, —P(O)$_2$NR$^{e'}$R$^{f'}$, —P(O)OR$^{e'}$, —P(O)$_2$OR$^{e'}$, —CN, or —NO$_2$;

each $R^{3'}$ and $R^{4'}$ is independently deuterium, halogen, —OR$^{c'}$, —OC(O)R$^{c'}$, —OC(O)NR$^{c'}$R$^{d'}$, —OC(=N)NR$^{c'}$R$^{d'}$, —OS(O)R$^{c'}$, —OS(O)$_2$R$^{c'}$, —OS(O)NR$^{c'}$R$^{d'}$, —OS(O)$_2$NR$^{c'}$R$^{d'}$, —SR$^{c'}$, —S(O)R$^{c'}$, —S(O)$_2$R$^{c'}$, —S(O)NR$^{c'}$R$^{d'}$, —S(O)$_2$NR$^{c'}$R$^{d'}$, —NR$^{c'}$R$^{d'}$, —NR$^{c'}$C(O)R$^{d'}$, —NR$^{c'}$C(O)OR$^{d'}$, —NR$^{c'}$C(O)NR$^{c'}$R$^{d'}$, —NR$^{c'}$C(=N)NR$^{c'}$R$^{d'}$, —NR$^{c'}$S(O)R$^{d'}$, —NR$^{c'}$S(O)$_2$R$^{d'}$, —NR$^{c'}$S(O)NR$^{c'}$R$^{d'}$, —NR$^{c'}$S(O)$_2$NR$^{c'}$R$^{d'}$, —C(O)R$^{c'}$, —C(O)OR$^{c'}$, —C(O)NR$^{c'}$R$^{d'}$, —C(=N)NR$^{c'}$R$^{d'}$, —PR$^{c'}$R$^{d'}$, —P(O)R$^{c'}$R$^{d'}$, —P(O)$_2$R$^{c'}$R$^{d'}$, —P(O)NR$^{c'}$R$^{d'}$, —P(O)$_2$NR$^{c'}$R$^{d'}$, —P(O)OR$^{c'}$, —P(O)$_2$OR$^{c'}$, —CN, —NO$_2$, $C_{1-6}$alkyl, $C_{2-6}$alkenyl, $C_{2-6}$alkynyl, $C_{3-6}$cycloalkyl, 3- to 7-membered heterocycloalkyl, $C_{6-10}$ aryl, or mono- or bicyclic heteroaryl, or any two $R^{3'}$ groups or any two $R^{4'}$ groups taken together with the ring to which they are attached form a $C_{5-8}$cycloalkyl or a 5- to 8-membered heterocycloalkyl, wherein each hydrogen atom in $C_{1-6}$alkyl, $C_{2-6}$alkenyl, $C_{2-6}$alkynyl, $C_{3-8}$cycloalkyl, 3- to 7-membered heterocycloalkyl, $C_{6-10}$ aryl, mono- or bicyclic heteroaryl $C_{5-8}$cycloalkyl or a 5- to 8-membered heterocycloalkyl is independently optionally substituted by deuterium, halogen, $C_{1-6}$alkyl, $C_{1-6}$haloalkyl, —OR$^{e'}$, —OC(O)R$^{e'}$, —OC(O)NR$^{e'}$R$^{f'}$, —OS(O)R$^{e'}$, —OS(O)$_2$R$^{e'}$, —OS(O)NR$^{e'}$R$^{f'}$, —OS(O)$_2$NR$^{e'}$R$^{f'}$, —SR$^{e'}$, —S(O)R$^{e'}$, —S(O)$_2$R$^{e'}$, —S(O)NR$^{e'}$R$^{f'}$, —S(O)$_2$NR$^{e'}$R$^{f'}$, —NR$^{e'}$R$^{f'}$, —NR$^{e'}$C(O)R$^{f'}$, —NR$^{e'}$C(O)OR$^{f'}$, —NR$^{e'}$C(O)NR$^{e'}$R$^{f'}$, —NR$^{e'}$S(O)R$^{f'}$, —NR$^{e'}$S(O)$_2$R$^{f'}$, —NR$^{e'}$S(O)NR$^{e'}$R$^{f'}$, —NR$^{e'}$S(O)$_2$NR$^{e'}$R$^{f'}$, —C(O)R$^{e'}$, —C(O)OR$^{e'}$, —C(O)NR$^{e'}$R$^{f'}$, —PR$^{e'}$R$^{f'}$, —P(O)R$^{e'}$R$^{f'}$, —P(O)$_2$R$^{e'}$R$^{f'}$, —P(O)NR$^{e'}$R$^{f'}$, —P(O)$_2$NR$^{e'}$R$^{f'}$, —P(O)OR$^{e'}$, —P(O)$_2$OR$^{e'}$, —CN, or —NO$_2$;

$R^{7'}$ is H, deuterium, $C_{1-6}$alkyl, $C_{2-6}$alkenyl, $C_{2-6}$alkynyl, $C_{3-6}$cycloalkyl, 3- to 7-membered heterocycloalkyl, $C_{6-10}$ aryl, or mono- or bicyclic heteroaryl, wherein each hydrogen atom in $C_{1-6}$alkyl, $C_{2-6}$alkenyl, $C_{2-6}$alkynyl, $C_{3-6}$cycloalkyl, 3- to 7-membered heterocycloalkyl, $C_{6-10}$ aryl, or mono- or bicyclic heteroaryl is independently optionally substituted by deuterium, halogen, —OR$^{i'}$, —OC(O)R$^{i'}$, —OC(O)NR$^{i'}$R$^{j'}$, —OS(O)R$^{i'}$, —OS(O)$_2$R$^{i'}$, —OS(O)NR$^{i'}$R$^{j'}$, —OS(O)$_2$NR$^{i'}$R$^{j'}$, —SR$^{i'}$, —S(O)R$^{i'}$, —S(O)$_2$R$^{i'}$, —S(O)NR$^{i'}$R$^{j'}$, —S(O)$_2$NR$^{i'}$R$^{j'}$, —NR$^{i'}$R$^{j'}$, —NR$^{i'}$C(O)R$^{j'}$, —NR$^{i'}$C(O)OR$^{j'}$, —NR$^{i'}$C(O)NR$^{i'}$R$^{j'}$, —NR$^{i'}$S(O)R$^{j'}$, —NR$^{i'}$S(O)$_2$R$^{j'}$, —NR$^{i'}$S(O)NR$^{i'}$R$^{j'}$, —NR$^{i'}$S(O)$_2$NR$^{i'}$R$^{j'}$, —C(O)R$^{i'}$, —C(O)OR$^{i'}$, —C(O)NR$^{i'}$R$^{j'}$, —PR$^{i'}$R$^{j'}$, —P(O)R$^{i'}$R$^{j'}$, —P(O)$_2$R$^{i'}$R$^{j'}$, —P(O)NR$^{i'}$R$^{j'}$, —P(O)$_2$NR$^{i'}$R$^{j'}$, —P(O)OR$^{i'}$, —P(O)$_2$OR$^{i'}$, —CN, or —NO$_2$;

each R$^{a'}$, R$^{b'}$, R$^{c'}$, R$^{d'}$, R$^{e'}$, R$^{f'}$, R$^{i'}$ and R$^{j'}$ is independently selected from the group consisting of H, deuterium, $C_{1-6}$alkyl, $C_{2-6}$alkenyl, $C_{2-6}$alkynyl, $C_{3-6}$cycloalkyl, 3- to 7-membered heterocycloalkyl, $C_{6-10}$ aryl, and heteroaryl;

m' is 2, 3, 4, or 5:

n' is 2, 3, or 4;

p' is 0, 1, 2, 3, or 4; and q' is 0, 1, 2, 3, or 4:

or a pharmaceutically acceptable salt thereof.

In one aspect, the invention relates to a chemical entity of the following Formula (I-A):

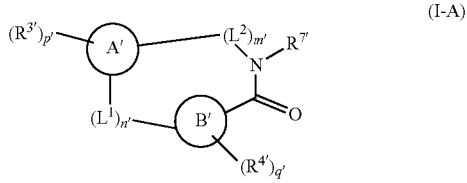

(I-A)

wherein
Ring A' and Ring B' are each independently a monocyclic or bicyclic aryl or heteroaryl;
wherein one of Ring A' and Ring B' is a monocyclic aryl or heteroaryl and the other is a bicyclic heteroaryl; and at least one of Ring A' and Ring B' comprises at least one nitrogen ring member;
each $R^{3'}$ and $R^{4'}$ is independently deuterium, halogen, —$OR^{c'}$, —$OC(O)R^{c'}$, —$OC(O)NR^{c'}R^{d'}$, —$OC(=N)NR^{c'}R^{d'}$, —$OS(O)_{0-2}R^{c'}$, —$OS(O)_{0-2}NR^{c'}R^{d'}$, —$S(O)_{0-2}R^{c'}$, —$S(O)_{0-2}NR^{c'}R^{d'}$, —$NR^{c'}R^{d'}$, —$NR^{c'}C(O)R^{d'}$, —$NR^{c'}C(O)NR^{c'}R^{d'}$, —$NR^{c'}C(=N)NR^{c'}R^{d'}$, —$NR^{c'}S(O)_{0-2}R^{d'}$, —$NR^{c'}S(O)_{0-2}NR^{c'}R^{d'}$, —$C(O)R^{c'}$, —$C(O)OR^{c'}$, —$C(O)NR^{c'}R^{d'}$, —$C(=N)NR^{c'}R^{d'}$, —$P(O)_{0-2}R^{c'}R^{d'}$, —$P(O)_{0-2}NR^{c'}R^{d'}$, —$P(O)_{0-2}OR^{c'}$, —CN, —$NO_2$, $C_{1-6}$alkyl, $C_{2-6}$alkenyl, $C_{2-6}$alkynyl, $C_{3-6}$cycloalkyl, 3- to 7-membered heterocycloalkyl, phenyl, naphthyl, or mono- or bicyclic heteroaryl; or any two $R^{3'}$ groups or any two $R^{4'}$ groups taken together with the ring to which they are attached form a $C_{5-8}$cycloalkyl or a 5- to 8-membered heterocycloalkyl;
wherein each alkyl, alkenyl, alkynyl, cycloalkyl, heterocycloalkyl, phenyl, naphthyl, and mono- or bicyclic heteroaryl is unsubstituted or substituted with one or more substituents selected from the group consisting of deuterium, halogen, $C_{1-6}$alkyl, $C_{1-6}$haloalkyl, —$OR^{e'}$, —$OC(O)R^{e'}$, —$OC(O)NR^{e'}R^{f'}$, —$OS(O)_{0-2}R^{e'}$, —$OS(O)_{0-2}NR^{e'}R^{f'}$, —$S(O)_{0-2}R^{e'}$, —$S(O)_{0-2}NR^{e'}R^{f'}$, —$NR^{e'}R^{f'}$, —$NR^{e'}C(O)R^{f'}$, —$NR^{e'}C(O)NR^{e'}R^{f'}$, —$NR^{e'}S(O)_{0-2}R^{f'}$, —$NR^{e'}S(O)_{0-2}NR^{e'}R^{f'}$, —$C(O)R^{e'}$, —$C(O)OR^{e'}$, —$C(O)NR^{e'}R^{f'}$, —$P(O)_{0-2}R^{e'}R^{f'}$, —$P(O)_{0-2}NR^{e'}R^{f'}$, —$P(O)_{0-2}OR^{e'}$, —CN, and —$NO_2$; and
each $R^{c'}$, $R^{d'}$, $R^{e'}$, and $R^{f'}$ is independently selected from the group consisting of H, deuterium, $C_{1-6}$alkyl, $C_{2-6}$alkenyl, $C_{2-6}$alkynyl, $C_{3-6}$cycloalkyl, 3- to 7-membered heterocycloalkyl, phenyl, naphthyl, and heteroaryl;
$R^{7'}$ is H, deuterium, $C_{1-6}$alkyl, $C_{2-6}$alkenyl, $C_{2-6}$alkynyl, $C_{3-6}$cycloalkyl, 3- to 7-membered heterocycloalkyl, phenyl, naphthyl, or mono- or bicyclic heteroaryl;
wherein each alkyl, alkenyl, alkynyl, cycloalkyl, heterocycloalkyl, phenyl, naphthyl, or heteroaryl is substituted or unsubstituted with one or more substituents selected from the group consisting of deuterium, halogen, —$OR^{i'}$, —$OC(O)R^{i'}$, —$OC(O)NR^{i'}R^{j'}$, —$OS(O)_{0-2}R^{i'}$, —$OS(O)_{0-2}NR^{i'}R^{j'}$, —$S(O)_{0-2}R^{i'}$, —$S(O)_{0-2}NR^{i'}R^{j'}$, —$NR^{i'}R^{j'}$, —$NR^{i'}C(O)R^{j'}$, —$NR^{i'}C(O)NR^{i'}R^{j'}$, —$NR^{i'}S(O)_{0-2}R^{j'}$, —$NR^{i'}S(O)_{0-2}NR^{i'}R^{j'}$, —$C(O)R^{i'}$, —$C(O)OR^{i'}$, —$C(O)NR^{i'}R^{j'}$, —$P(O)_{0-2}R^{i'}R^{j'}$, —$P(O)_{0-2}NR^{i'}R^{j'}$, —$P(O)_{0-2}OR^{i'}$, —CN, and —$NO_2$;
wherein each $R^{i'}$ and $R^{j'}$ is independently H, deuterium, $C_{1-6}$alkyl, $C_{2-6}$alkenyl, $C_{2-6}$alkynyl, $C_{3-6}$cycloalkyl, 3- to 7-membered heterocycloalkyl, phenyl, naphthyl, or mono- or bicyclic heteroaryl;
each $L^1$ and $L^2$ is independently —$C(R^{1'})(R^{2'})$—, —O—, —$N(R^{k'})$—, or —$S(O)_{0-2}$;

wherein each $R^{1'}$ and $R^{2'}$ are independently H, deuterium, halogen, $C_{1-6}$alkyl, $C_{2-6}$alkenyl, $C_{2-6}$alkynyl, $C_{3-6}$cycloalkyl, 3- to 7-membered heterocycloalkyl, phenyl, naphthyl, or mono- or bicyclic heteroaryl; or $R^{1'}$ and $R^{2'}$ taken together with the carbon or carbons to which they are attached form a $C_{3-6}$cycloalkyl or a 4- to 6-membered heterocycloalkyl;
each $R^{k'}$ is independently H, deuterium, $C_{1-6}$alkyl, $C_{2-6}$alkenyl, $C_{2-6}$alkynyl, $C_{3-6}$cycloalkyl, 3- to 7-membered heterocycloalkyl, phenyl, naphthyl, or mono- or bicyclic heteroaryl;
wherein each alkyl, alkenyl, alkynyl, cycloalkyl, heterocycloalkyl, phenyl, naphthyl, or heteroaryl in $R^{1'}$, $R^{2'}$, or $R^{k'}$ is independently unsubstituted or substituted with one or more substituents selected from the group consisting of deuterium, halogen, $C_{1-6}$alkyl, $C_{1-6}$haloalkyl, —$OR^{a'}$, —$OC(O)R^{a'}$, —$OC(O)NR^{a'}R^{b'}$, —$OS(O)_{0-2}R^{a'}$, —$OS(O)_{0-2}NR^{a'}R^{b'}$, —$S(O)_{0-2}R^{a'}$, —$S(O)_{0-2}NR^{a'}R^{b'}$, —$NR^{a'}R^{b'}$, —$NR^{a'}C(O)R^{b'}$, —$NR^{a'}C(O)NR^{a'}R^{b'}$, —$NR^{a'}S(O)_{0-2}R^{b'}$, —$NR^{a'}S(O)_{0-2}NR^{a'}R^{b'}$, —$C(O)R^{a'}$, —$C(O)OR^{a'}$, —$C(O)NR^{a'}R^{b'}$, —$P(O)_{0-2}R^{a'}R^{b'}$, —$P(O)_{0-2}NR^{a'}R^{b'}$, —$P(O)_{0-2}OR^{a'}$, —CN, and —$NO_2$;
wherein each $R^{a'}$ and $R^{b'}$ is independently H, deuterium, $C_{1-6}$alkyl, $C_{2-6}$alkenyl, $C_{2-6}$alkynyl, $C_{3-6}$cycloalkyl, 3- to 7-membered heterocycloalkyl, phenyl, naphthyl, or heteroaryl;
m' is 3, 4, or 5;
n' is 2, 3, or 4;
p' is 0, 1, 2, 3, or 4; and
q' is 0, 1, 2, 3, or 4;
or a pharmaceutically acceptable salt thereof.
In another aspect, the invention relates to a chemical entity of the following Formula (I):

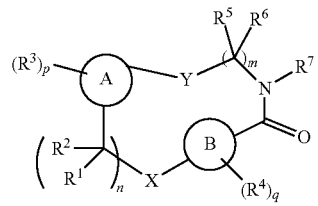

I wherein
Ring A and Ring B are each independently a monocyclic or bicyclic aryl or heteroaryl; wherein one of Ring A and Ring B is monocyclic and the other is bicyclic; and Ring comprises at least one nitrogen ring member;
$R^1$ and $R^2$ are each independently H, deuterium, $C_{1-6}$alkyl, $C_{2-6}$alkenyl, $C_{2-6}$alkynyl, $C_{3-6}$cycloalkyl, 3- to 7-membered heterocycloalkyl, phenyl, naphthyl, or mono- or bicyclic heteroaryl; or $R^1$ and $R^2$ taken together with the carbon to which they are attached form a $C_{3-6}$cycloalkyl or a 4- to 6-membered heterocycloalkyl;
wherein each alkyl, alkenyl, alkynyl, cycloalkyl, heterocycloalkyl, phenyl, naphthyl, or heteroaryl is unsubstituted or substituted with one or more substituents selected from the group consisting of deuterium, halogen, $C_{1-6}$alkyl, $C_{1-6}$haloalkyl, —$OR^a$, —$OC(O)R^a$, —$OC(O)NR^aR^b$, —$OS(O)_{0-2}R^a$, —$OS(O)_{0-2}NR^aR^b$, —$NR^aR^b$, —$NR^aC(O)R^b$, —$NR^aC(O)NR^aR^b$, —$NR^aS(O)_{0-2}R^b$, —$NR^aS(O)_{0-2}NR^aR^b$, —$C(O)R^a$, —C(O)OR$^a$, —C(O)NR$^a$R$^b$, —P(O)$_{0-2}$R$^a$R$^b$, —P(O)$_{0-2}$NR$^a$R$^b$, —P(O)$_{0-2}$OR$^a$, —CN, and —NO$_2$;

wherein each R$^a$ and R$^b$ is independently H, deuterium, C$_{1-6}$alkyl, C$_{2-6}$alkenyl, C$_{2-6}$alkynyl, C$_{3-6}$cycloalkyl, 3- to 7-membered heterocycloalkyl, phenyl, naphthyl, or heteroaryl;

each R$^3$ and R$^4$ is independently deuterium, halogen, —OR$^c$, —OC(O)R$^c$, —OC(O)NR$^c$R$^d$, —OC(=N)NR$^c$R$^d$, —OS(O)$_{0-2}$R$^c$, —OS(O)$_{0-2}$NR$^c$R$^d$, —NR$^c$R$^d$, —NR$^c$C(O)R$^d$, —NR$^c$C(O)NR$^c$R$^d$, —NR$^c$C(=N)NR$^c$R$^d$, —NR$^c$S(O)$_{0-2}$R$^d$, —NR$^c$S(O)$_{0-2}$NR$^c$R$^d$, —C(O)R$^c$, —C(O)OR$^c$, —C(O)NR$^c$R$^d$, —C(=N)NR$^c$R$^d$, —P(O)$_{0-2}$R$^c$R$^d$, —P(O)$_{0-2}$NR$^c$R$^d$, —P(O)$_{0-2}$OR$^c$, —CN, —NO$_2$, C$_{1-6}$alkyl, C$_{2-6}$alkenyl, C$_{2-6}$alkynyl, C$_{3-6}$-cycloalkyl, 3- to 7-membered heterocycloalkyl, phenyl, naphthyl, or mono- or bicyclic heteroaryl;

wherein each alkyl, alkenyl, alkynyl, cycloalkyl, heterocycloalkyl, phenyl, naphthyl, and mono- or bicyclic heteroaryl is unsubstituted or substituted with one or more substituents selected from the group consisting of deuterium, halogen, C$_{1-6}$alkyl, C$_{1-6}$haloalkyl, —OR$^e$, —OC(O)R$^e$, —OC(O)NR$^e$R$^f$, —OS(O)$_{0-2}$R$^e$, —OS(O)$_{0-2}$NR$^e$R$^f$, —NR$^e$R$^f$, —NR$^e$C(O)R$^f$, —NR$^e$C(O)NR$^e$R$^f$, —NR$^e$S(O)$_{0-2}$R$^f$, —NR$^e$S(O)$_{0-2}$NR$^e$R$^f$, —C(O)R$^e$, —C(O)OR$^e$, —C(O)NR$^e$R$^f$, —P(O)$_{0-2}$R$^e$R$^f$, —P(O)$_{0-2}$NR$^e$R$^f$, —P(O)$_{0-2}$OR$^e$, —CN, and —NO$_2$; and each R$^c$, R$^d$, R$^e$, and R$^f$ is independently selected from the group consisting of H, deuterium, C$_{1-6}$alkyl, C$_{2-6}$alkenyl, C$_{2-6}$alkynyl, C$_{3-6}$cycloalkyl, 3- to 7-membered heterocycloalkyl, phenyl, naphthyl, and heteroaryl;

R$^5$ and R$^6$ are each independently H, deuterium, C$_{1-6}$alkyl, C$_{2-6}$alkenyl, C$_{2-6}$alkynyl, C$_{3-6}$cycloalkyl, 3- to 7-membered heterocycloalkyl, phenyl, naphthyl, or mono- or bicyclic heteroaryl; or R$^5$ and R$^6$ taken together with the carbon to which they are attached form a C$_{3-6}$ cycloalkyl or a 4- to 6-membered heterocycloalkyl;

wherein each alkyl, alkenyl, alkynyl, cycloalkyl, heterocycloalkyl, phenyl, naphthyl, or heteroaryl is substituted or unsubstituted with one or more substituents selected from the group consisting of deuterium, halogen, C$_{1-6}$alkyl, C$_{1-6}$haloalkyl, —OR$^g$, —OC(O)R$^g$, —OC(O)NR$^g$R$^h$, —OS(O)$_{0-2}$R$^g$, —OS(O)$_{0-2}$NR$^g$R$^h$, —NR$^g$R$^h$, —NR$^g$C(O)R$^h$, —NR$^g$C(O)NR$^g$R$^h$, —NR$^g$S(O)$_{0-2}$R$^h$, —NR$^g$S(O)$_{0-2}$NR$^g$R$^h$, —C(O)R$^g$, —C(O)OR$^g$, —C(O)NR$^g$R$^h$, —P(O)$_{0-2}$R$^g$R$^h$, —P(O)$_{0-2}$NR$^g$R$^h$, —P(O)$_{0-2}$OR$^g$, —CN, and —NO$_2$;

wherein each R$^g$ and R$^h$ is independently H, deuterium, C$_{1-6}$alkyl, C$_{2-6}$alkenyl, C$_{2-6}$alkynyl, C$_{3-6}$cycloalkyl, 3- to 7-membered heterocycloalkyl, phenyl, naphthyl, or mono- or bicyclic heteroaryl;

R$^7$ is H, deuterium, C$_{1-6}$alkyl, C$_{2-6}$alkenyl, C$_{2-6}$alkynyl, C$_{3-6}$cycloalkyl, 3- to 7-membered heterocycloalkyl, phenyl, naphthyl, or mono- or bicyclic heteroaryl;

wherein each alkyl, alkenyl, alkynyl, cycloalkyl, heterocycloalkyl, phenyl, naphthyl, or heteroaryl is substituted or unsubstituted with one or more substituents selected from the group consisting of deuterium, halogen, —OR$^i$, —OC(O)R$^i$, —OC(O)NR$^i$R$^j$, —OS(O)$_{0-2}$R$^i$, —OS(O)$_{0-2}$NR$^i$R$^j$, —NR$^i$R$^j$, —NR$^i$C(O)R$^j$, —NR$^i$C(O)NR$^i$R$^j$, —NR$^i$S(O)$_{0-2}$R$^j$, —NR$^i$S(O)$_{0-2}$NR$^i$R$^j$, —C(O)R$^i$, —C(O)OR$^i$, —C(O)NR$^i$R$^j$, —P(O)$_{0-2}$R$^i$R$^j$, —P(O)$_{0-2}$NR$^i$R$^j$, —P(O)$_{0-2}$OR$^i$, —CN, and —NO$_2$;

wherein each R$^i$ and R$^j$ is independently H, deuterium, C$_{1-6}$alkyl, C$_{2-6}$alkenyl, C$_{2-6}$alkynyl, C$_{3-6}$cycloalkyl, 3- to 7-membered heterocycloalkyl, phenyl, naphthyl, or mono- or bicyclic heteroaryl;

X and Y are each independently —C(R$^k$)(R$^k$)—, —O—, or —N(R$^k$)—;

wherein each R$^k$ is independently H, deuterium, C$_{1-6}$alkyl, C$_{2-6}$alkenyl, C$_{2-6}$alkynyl, C$_{3-6}$cycloalkyl, 3- to 7-membered heterocycloalkyl, phenyl, naphthyl, or mono- or bicyclic heteroaryl;

m is 2, 3, or 4;
n is 1, 2, or 3;
p is 0, 1, 2, 3, or 4; and
q is 0, 1, 2, 3, or 4;

or a pharmaceutically acceptable salt thereof.

In certain embodiments, the compound of Formula (I) or (I-A) is a compound selected from those species described or exemplified in the detailed description below.

In certain embodiments, the compound of Formula (I) or (I-A) is a compound having the formula

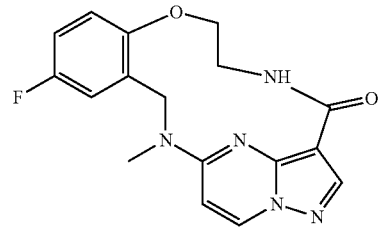 [SMILES: CN1Cc2cc(F)ccc2OCCNC(=O)c2cnn3ccc1nc23]

or a pharmaceutically acceptable salt thereof.

In certain embodiments, the compound of Formula (I) or (I-A) is a compound having the formula

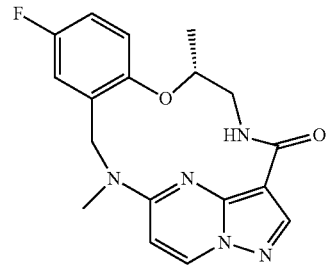 [SMILES: C[C@@H]1CNC(=O)c2cnn3ccc(nc23)N(C)Cc2cc(F)ccc2O1]

or a pharmaceutically acceptable salt thereof.

In certain embodiments, the compound of Formula (I) or (I-A) is a compound the formula

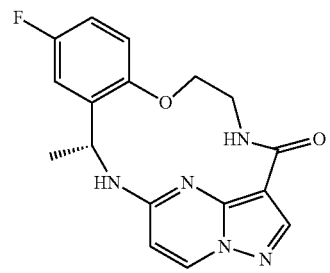 [SMILES: C[C@H]1Nc2ccn3ncc(c3n2)C(=O)NCCOc2ccc(F)cc21]

or a pharmaceutically acceptable salt thereof.

In certain embodiments, the compound of Formula (I) or (I-A) is a compound having the formula

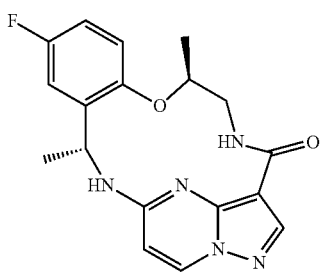 [SMILES: C[C@H]1CNC(=O)c2cnn3ccc(nc23)N[C@H](C)c2cc(F)ccc2O1]

or a pharmaceutically acceptable salt thereof.

In certain embodiments, the compound of Formula (I) or (I-A) is a compound having the formula

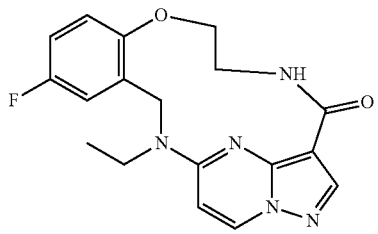 [SMILES: CCN1Cc2cc(F)ccc2OCCNC(=O)c2cnn3ccc1nc23]

or a pharmaceutically acceptable salt thereof.

In certain embodiments, the compound of Formula (I) or (I-A) is a compound having the formula

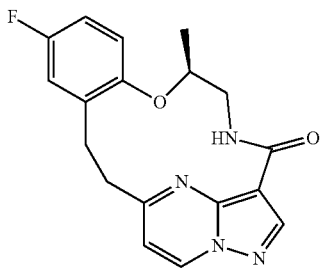 [SMILES: C[C@H]1CNC(=O)c2cnn3ccc(nc23)CCc2cc(F)ccc2O1]

or a pharmaceutically acceptable salt thereof.

In a further aspect, the invention relates to a crystalline form of the free base of the compound of the formula

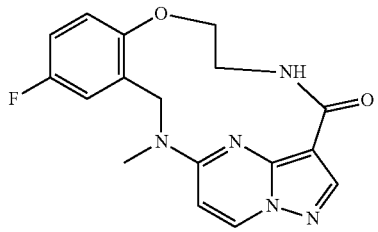 [SMILES: CN1Cc2cc(F)ccc2OCCNC(=O)c2cnn3ccc1nc23]

having a powder X-ray diffraction pattern substantially the same as Fig. XX. In some embodiments, the crystalline polymorph form 1 of the free base of the compound of the formula

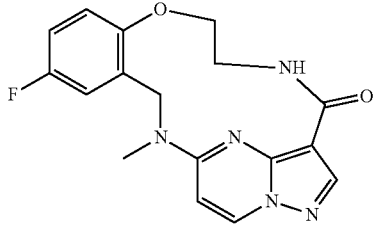

wherein the powder X-ray diffraction pattern has a peak at diffraction angle (2θ) of 21.94. In some embodiments, the polymorph form 1 of the free base of the compound of the formula

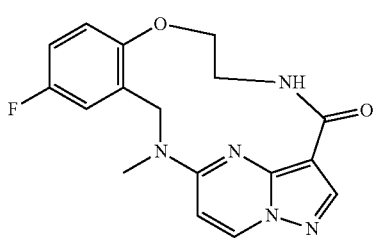 [SMILES: CN1Cc2cc(F)ccc2OCCNC(=O)c2cnn3ccc1nc23]

wherein the powder X-ray diffraction pattern has peaks at diffraction angles (2θ) of 21.94 and 23.96. In some embodiments, the polymorph form 1 of the free base of the compound of the formula

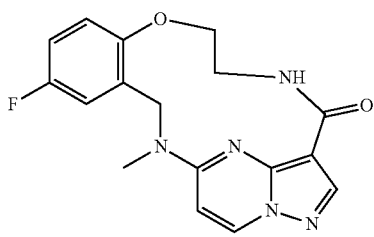

wherein the powder X-ray diffraction pattern has peaks at diffraction angles (2θ) of 21.94, 23.96 and 19.64.

In a further aspect, the invention relates to a pharmaceutical composition comprising at least one compound of Formula (I) or (I-A) or a pharmaceutically acceptable salt thereof.

Pharmaceutical compositions according to the invention may further comprise a pharmaceutically acceptable excipient. The invention is also a compound of Formula (I) or (I-A) or a pharmaceutically acceptable salt thereof for use as a medicament.

In another aspect, the invention is directed to a method of treating cancer, pain, neurological diseases, autoimmune diseases, or inflammation comprising administering to a subject in need of such treatment an effective amount of at least one compound of Formula (I) or (I-A) or a pharmaceutically acceptable salt thereof.

In another aspect, the invention is directed to use of a compound of Formula (I) or (I-A) in the preparation of a medicament for the treatment of such diseases and medical conditions, and the use of such compounds and salts for treatment of such diseases and medical conditions.

In yet another aspect, the invention relates to a method of inhibiting protein or tyrosine kinases, including one or more of MET, ALK. ROS1, AXL. TRKs, and JAKs, comprising contacting a cell comprising one or more of such kinases with an effective amount of at least one compound of Formula (I) or (I-A) or a salt thereof, and/or with at least one pharmaceutical composition of the invention, wherein the contacting is in vitro, ex vivo, or in vivo.

Additional embodiments, features, and advantages of the invention will be apparent from the following detailed description and through practice of the invention.

For the sake of brevity, the disclosures of the publications cited in this specification, including patents, are herein incorporated by reference.

DETAILED DESCRIPTION

Figure 1:
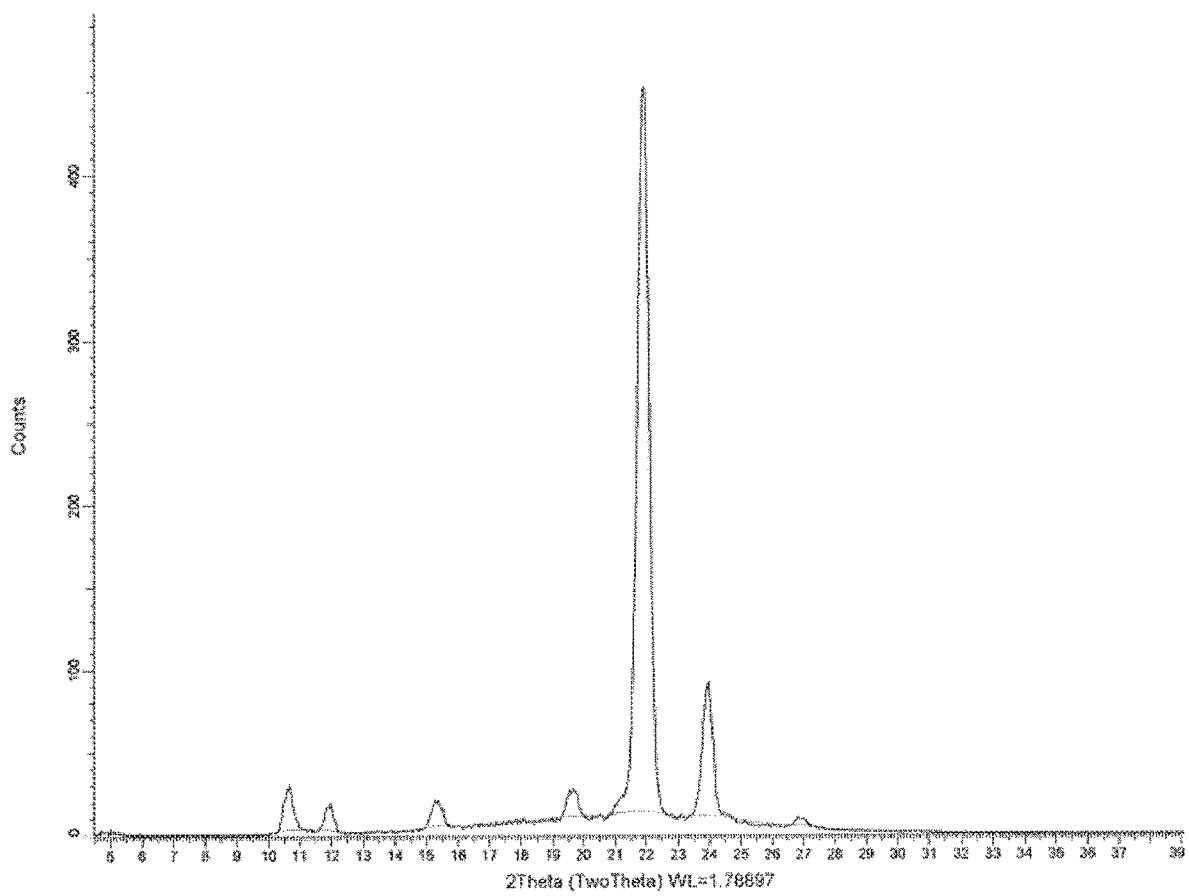
FIG. 1 shows a powder X-ray diffraction pattern of the crystalline polymorph form 1 of the free base of 11-fluoro-14-methyl-6,7,13,14-tetrahydro-1,15-ethenopyrazolo[4,3-f][1,4,8,10]benzoxatriazacyclo-tridecin-4(5H)-one (Example 20).

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as is commonly understood by one of ordinary skill in the art to which this invention belongs. All patents, applications, published applications and other publications referred to herein are incorporated by reference in their entireties. If a definition set forth in this section is contrary to or otherwise inconsistent with a definition set forth in a patent, application, or other publication that is herein incorporated by reference, the definition set forth in this section prevails over the definition incorporated herein by reference.

As used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As used herein, the terms "including," "containing," and "comprising" are used in their open, non-limiting sense.

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

Except as otherwise noted, the methods and techniques of the present embodiments are generally performed according to conventional methods well known in the art and as described in various general and more specific references that are cited and discussed throughout the present specification. See, e.g., Loudon, Organic Chemistry, Fourth Edition, New York: Oxford University Press, 2002, pp. 360-361, 1084-1085; Smith and March, March's Advanced Organic Chemistry: Reactions. Mechanisms, and Structure, Fifth Edition, Wiley-Interscience, 2001.

Chemical nomenclature for compounds described herein has generally been derived using the commercially-available ACD/Name 2014 (ACD/Labs) or ChemBioDraw Ultra 13.0 (Perkin Elmer).

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination. All combinations of the embodiments pertaining to the chemical groups represented by the variables are specifically embraced by the present invention and are disclosed herein just as if each and every combination was individually and explicitly disclosed, to the extent that such combinations embrace compounds that are stable compounds (i.e., compounds that can be isolated, characterized, and tested for biological activity). In addition, all subcombinations of the chemical groups listed in the embodiments describing such variables are also specifically embraced by the present invention and are disclosed herein just as if each and every such sub-combination of chemical groups was individually and explicitly disclosed herein.

Chemical Definitions

The term "alkyl" refers to a straight- or branched-chain alkyl group having from 1 to 12 carbon atoms in the chain. Examples of alkyl groups include methyl (Me), ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples.

The term "alkenyl" refers to a straight- or branched-chain hydrocarbon group having from 2 to 12 carbon atoms in the chain, and having one or more double bonds. Examples of alkenyl groups include ethenyl (or vinyl), allyl, and but-3-en-1-yl. Included within this term are cis and trans isomers and mixtures thereof.

The term "alkynyl" refers to a straight- or branched-chain hydrocarbon group having from 2 to 12 carbon atoms in the chain, and having one or more triple bonds. Examples of alkynyl groups include acetylenyl (—C≡CH) and propargyl (—CH$_2$C≡CH).

The term "cycloalkyl" refers to a saturated or partially saturated, monocyclic or polycyclic carbocycle having 3 to 12 ring atoms. Polycyclic carbocycles include fused, bridged, and spiro polycyclic systems. Illustrative examples of cycloalkyl groups include the following entities, in the form of properly bonded moieties:

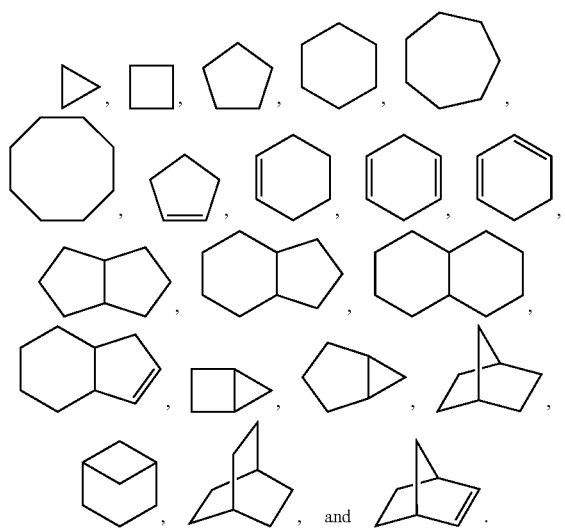

The term "halogen" represents chlorine, fluorine, bromine, or iodine. The term "halo" represents chloro, fluoro, bromo, or iodo.

The term "haloalkyl" refers to an alkyl group with one or more halo substituents, or one, two, or three halo substituents. Examples of haloalkyl groups include —CF$_3$, —(CH$_2$)F, —CHF$_2$, —CH$_2$Br, —CH$_2$CF$_3$, and —CH$_2$CH$_2$F.

The term "aryl" refers to an all-carbon monocyclic or fused-ring polycyclic groups of 6 to 14 carbon atoms (C$_6$-C$_{14}$) having a completely conjugated pi-electron system. Aryl includes all-carbon monocyclic or fused-ring polycyclic groups of 6 to 10 carbon atoms (e.g. "C$_{6-10}$ aryl"). Examples, without limitation, of aryl groups are phenyl, naphthalenyl and anthracenyl. The aryl group may be substituted as described above for alkyl or unsubstituted. Substituent groups also include those described elsewhere in this disclosure in connection with aryl The term "heterocycloalkyl" refers to a monocyclic or polycyclic ring structure that is saturated or partially saturated and has from 3 to 12 ring atoms, with 1 to 5 of the ring atoms selected from nitrogen, oxygen, and sulfur. Polycyclic ring systems include fused, bridged, and spiro systems. The ring structure may optionally contain up to two oxo groups on carbon or sulfur ring members. Illustrative examples of heterocycloalkyl groups include the following entities, in the form of properly bonded moieties:

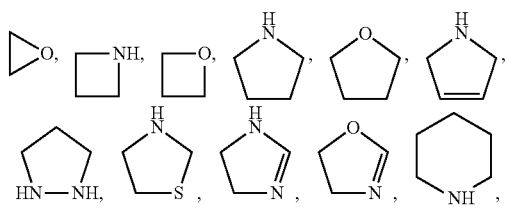

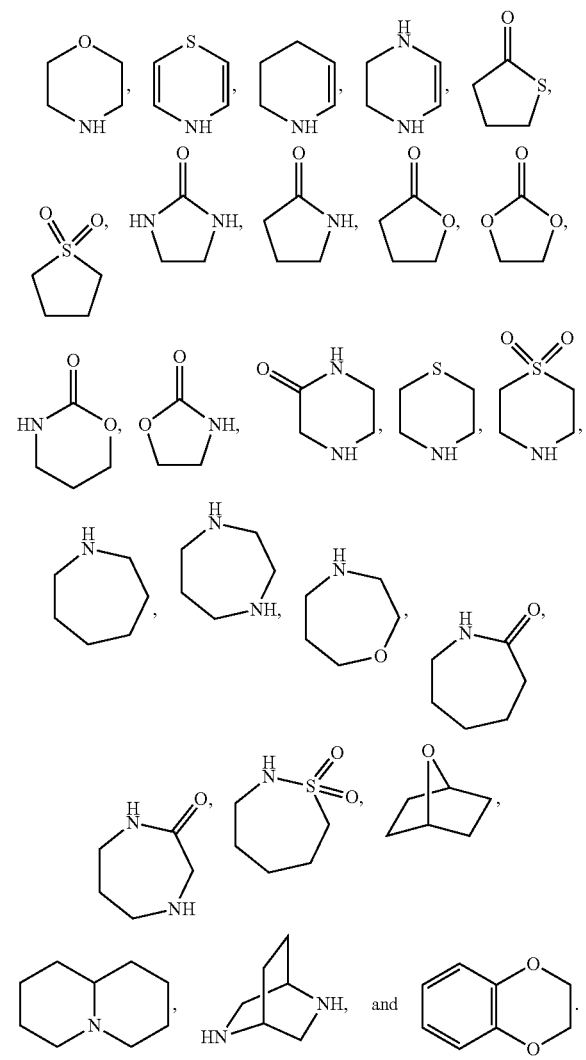

The term "heteroaryl" refers to a monocyclic, fused bicyclic, or fused polycyclic aromatic heterocycle (ring structure having ring atoms or members selected from carbon atoms and up to four heteroatoms selected from nitrogen, oxygen, and sulfur) having from 3 to 12 ring atoms per heterocycle. Illustrative examples of heteroaryl groups include the following entities, in the form of properly bonded moieties:

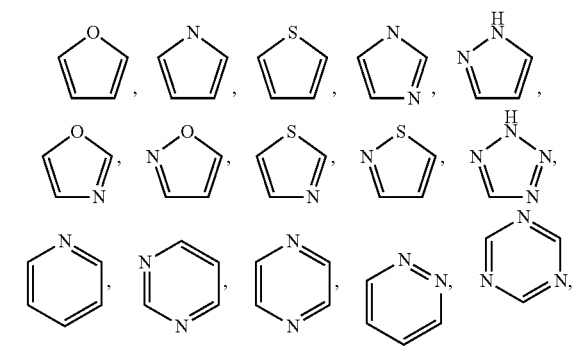

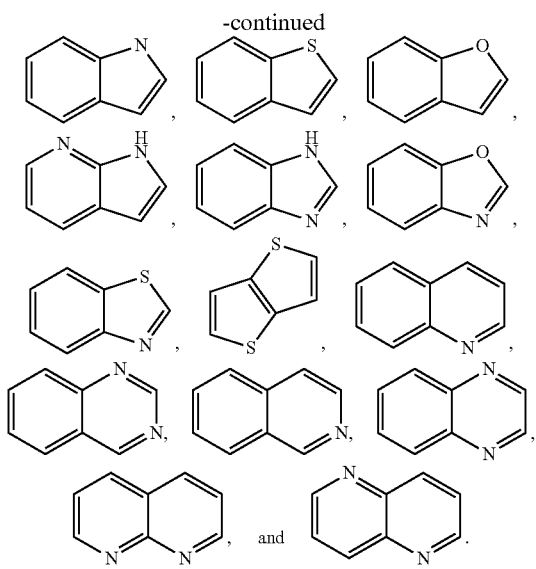

A "monocyclic" heteroaryl is an aromatic five- or six-membered heterocycle. A five-membered heteroaryl contains up to four heteroatom ring atoms, where (a) one ring atom is oxygen and sulfur and zero, one, or two ring atom is nitrogen, or (b) zero ring atoms are oxygen or sulfur and up to four ring atoms are nitrogen. In some embodiments, a five-membered heteroaryl is furan, thiophene, pyrrole, oxazole, isoxazole, thiazole, isothiazole, pyrazole, imidazole, oxadiazole, thiadiazole, triazole, or tetrazole. A six-membered heteroaryl contains one or two nitrogen ring atoms. In some embodiments, a six-membered heteroaryl is pyridine, pyrazine, pyrimidine, pyridazine, or triazine. A "bicyclic heteroaryl" is a fused bicyclic system comprising one heteroaryl ring fused to a phenyl or another heteroaryl ring.

The term "oxo" represents a carbonyl oxygen. For example, a cyclopentyl substituted with oxo is cyclopentanone.

The term "substituted" means that the specified group or moiety bears one or more substituents. The term "unsubstituted" means that the specified group bears no substituents. Where the term "substituted" is used to describe a structural system, the substitution is meant to occur at any valency-allowed position on the system. In some embodiments, "substituted" means that the specified group or moiety bears one, two, or three substituents. In other embodiments. "substituted" means that the specified group or moiety bears one or two substituents. In still other embodiments, "substituted" means the specified group or moiety bears one substituent.

Any formula depicted herein is intended to represent a compound of that structural formula as well as certain variations or forms. For example, a formula given herein is intended to include a racemic form, or one or more enantiomeric, diastereomeric, or geometric isomers, or a mixture thereof. Additionally, any formula given herein is intended to refer also to a hydrate, solvate, or polymorph of such a compound, or a mixture thereof.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, chlorine, and iodine, such as $^{2}H$, $^{3}H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$, and $^{125}I$, respectively. Such isotopically labelled compounds are useful in metabolic studies (preferably with $^{14}C$), reaction kinetic studies (with, for example $^{2}H$ or $^{3}H$), detection or imaging techniques [such as positron emission tomography (PET) or single-photon emission computed tomography (SPECT)] including drug or substrate tissue distribution assays, or in radioactive treatment of patients. Further, substitution with heavier isotopes such as deuterium (i.e., $^{2}H$) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

The nomenclature "(ATOM)$_{i-j}$" with j>i, when applied herein to a class of substituents, is meant to refer to embodiments of this invention for which each and every one of the number of atom members, from i to j including i and j, is independently realized. By way of example, the term $C_{1-3}$ refers independently to embodiments that have one carbon member ($C_1$), embodiments that have two carbon members ($C_2$), and embodiments that have three carbon members ($C_3$).

Any disubstituent referred to herein is meant to encompass the various attachment possibilities when more than one of such possibilities are allowed. For example, reference to disubstituent -A-B-, where A≠B, refers herein to such disubstituent with A attached to a first substituted member and B attached to a second substituted member, and it also refers to such disubstituent with A attached to the second substituted member and B attached to the first substituted member.

The invention also includes pharmaceutically acceptable salts of the compounds represented by Formula (I) or (I-A), preferably of those described above and of the specific compounds exemplified herein, and pharmaceutical compositions comprising such salts, and methods of using such salts.

A "pharmaceutically acceptable salt" is intended to mean a salt of a free acid or base of a compound represented herein that is non-toxic, biologically tolerable, or otherwise biologically suitable for administration to the subject. See, generally, S. M. Berge, et al., "Pharmaceutical Salts," J. Pharm. Sci., 1977, 66, 1-19. Preferred pharmaceutically acceptable salts are those that are pharmacologically effective and suitable for contact with the tissues of subjects without undue toxicity, irritation, or allergic response. A compound described herein may possess a sufficiently acidic group, a sufficiently basic group, both types of functional groups, or more than one of each type, and accordingly react with a number of inorganic or organic bases, and inorganic and organic acids, to form a pharmaceutically acceptable salt.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, γ-hydroxybutyrates, glycolates, tartrates, and mandelates. Lists of other suitable pharmaceutically acceptable salts are found in Remington's Pharmaceutical Sciences, 17th Edition, Mack Publishing Company, Easton, Pa., 1985.

For a compound of Formula (I) or (I-A) that contains a basic nitrogen, a pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, or ethanesulfonic acid, or any compatible mixture of acids such as those given as examples herein, and any other acid and mixture thereof that are regarded as equivalents or acceptable substitutes in light of the ordinary level of skill in this technology.

The invention also relates to pharmaceutically acceptable prodrugs of the compounds of Formula (I) or (I-A), and treatment methods employing such pharmaceutically acceptable prodrugs. The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formula (I) or (I-A)). A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in "Design of Prodrugs", ed. H. Bundgaard, Elsevier, 1985.

The present invention also relates to pharmaceutically active metabolites of compounds of Formula (I) or (I-A), and uses of such metabolites in the methods of the invention. A "pharmaceutically active metabolite" means a pharmacologically active product of metabolism in the body of a compound of Formula (I) or (I-A) or salt thereof. Prodrugs and active metabolites of a compound may be determined using routine techniques known or available in the art. See, e.g., Bertolini et al., *J. Med. Chem.* 1997, 40, 2011-2016; Shan et al., *J. Pharm. Sci.* 1997, 86 (7), 765-767; Bagshawe, *Drug Dev. Res.* 1995, 34, 220-230; Bodor, *Adv. Drug Res.* 1984, 13, 255-331; Bundgaard, Design of Prodrugs (Elsevier Press, 1985); and Larsen. Design and Application of Prodrugs, Drug Design and Development (Krogsgaard-Larsen et al., eds., Harwood Academic Publishers, 1991).

Representative Embodiments

In some embodiments of Formula (I-A), Ring A' is monocyclic aryl or heteroaryl and Ring B' is bicyclic heteroaryl. In other embodiments, Ring A' is bicyclic heteroaryl and Ring B' is monocyclic aryl or heteroaryl. In some embodiments, Ring A' is phenyl or a 6-membered heteroaryl. In other embodiments, Ring B' is bicyclic heteroaryl containing 1, 2, or 3 nitrogen ring atoms. In other embodiments, Ring A' is phenyl or pyridyl.

In still other embodiments. Ring A' is phenyl. In still other embodiments, Ring A' substituted with —(R$^{3'}$)$_{p'}$ is

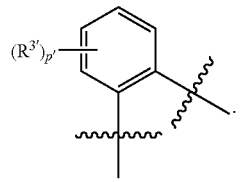

In still other embodiments. Ring A' substituted with —(R$^{3'}$)$_{p'}$ is

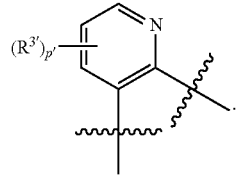

In some embodiments, Ring B' is:

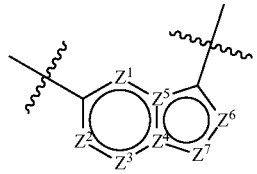

wherein Z$^1$-Z$^7$ are defined as described herein. In still other embodiments, Ring B' is:

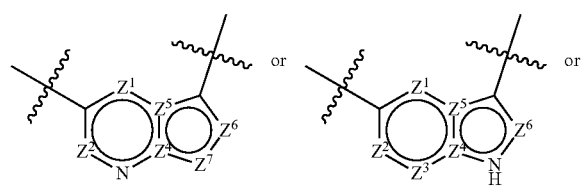

wherein Z$^{1-7}$ are otherwise defined as described herein. In still other embodiments. Ring B' is:

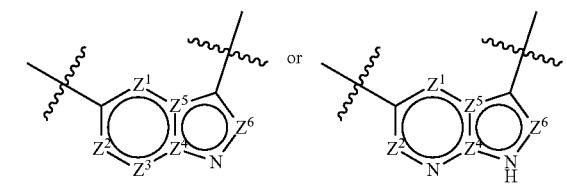

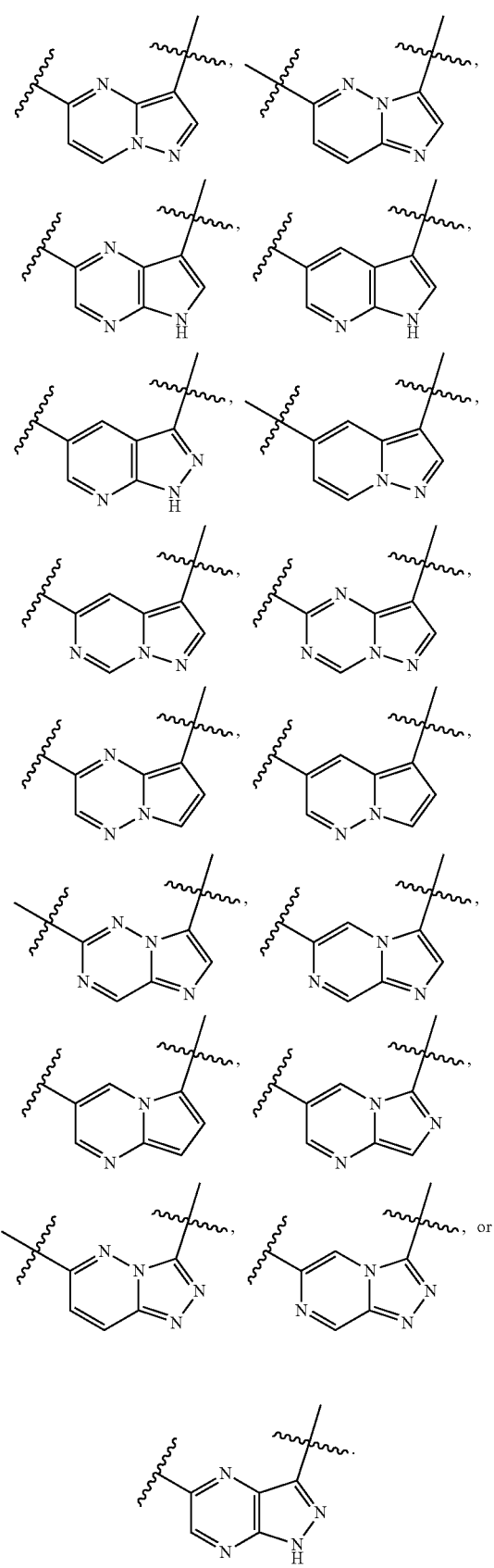
In still other embodiments. Ring B' is
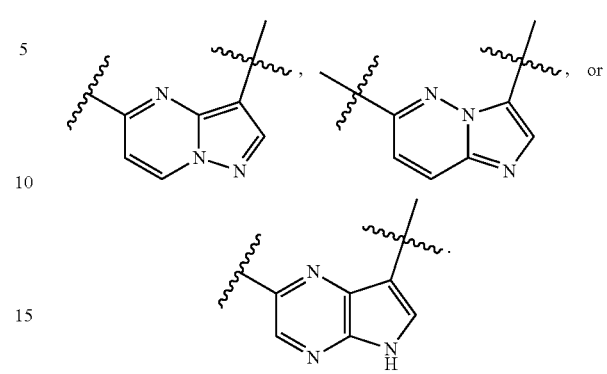
In still other embodiments, Ring B' is
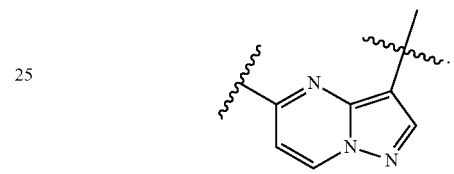
In other embodiments of Formula (I-A), Ring A' is a bicyclic heteroaryl group, and is:
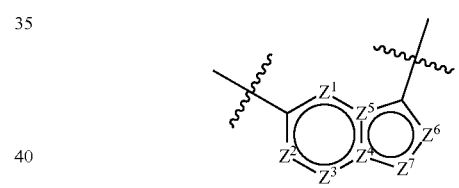
wherein $Z^1$-$Z^7$ are defined as described herein. In still other embodiments, Ring A' is:
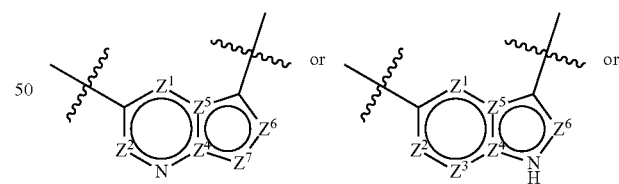
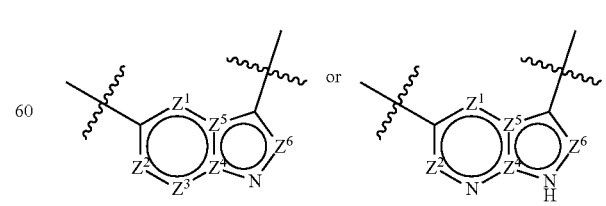
wherein $Z^{1-7}$ are otherwise defined as described herein. In still other embodiments, Ring A' is:

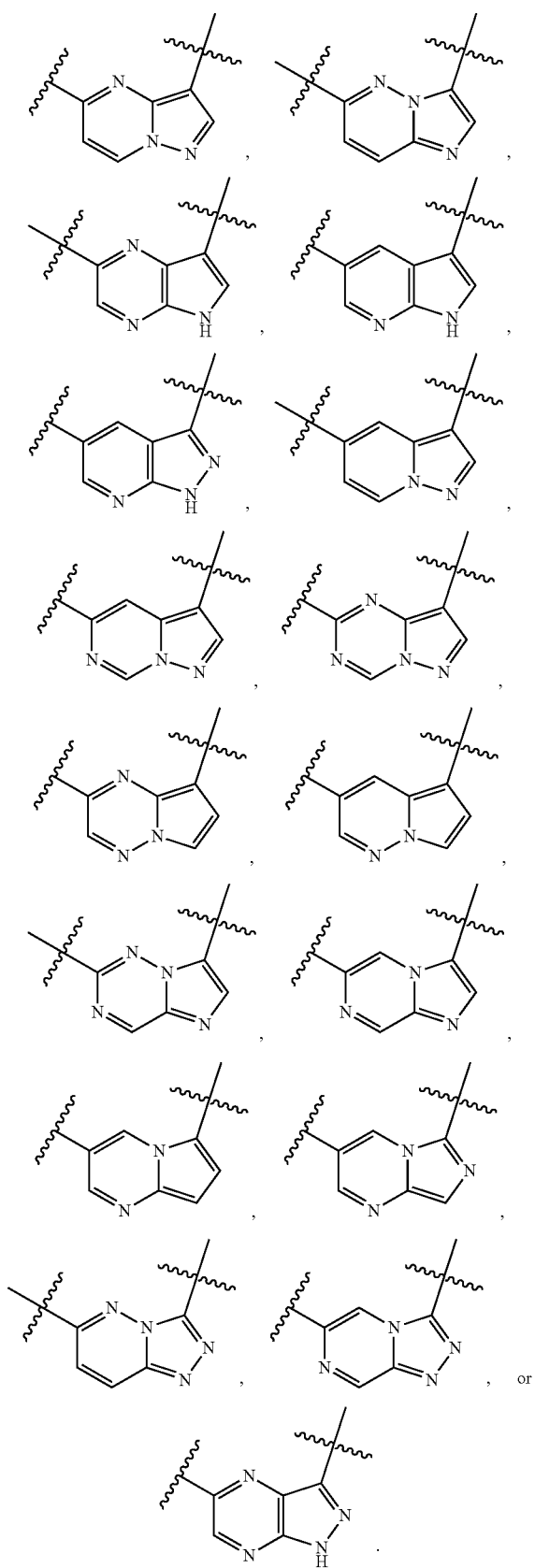

In still other embodiments, Ring A' is

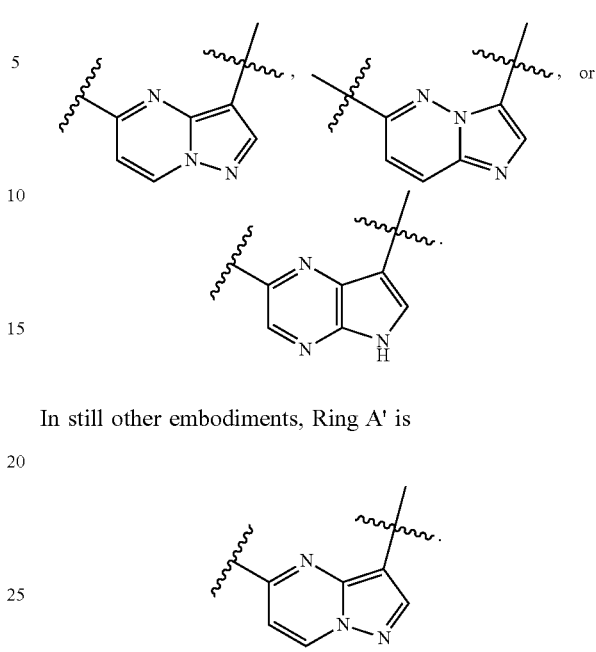

In still other embodiments, Ring A' is

In some embodiments, Ring B' is the monocyclic aryl or heteroaryl. In other embodiments, Ring B' is phenyl. In other embodiments, Ring B' is pyridyl.

In some embodiments, each $R^3$ is independently deuterium, fluoro, chloro, bromo, methyl, ethyl, propyl, isopropyl, methoxy, ethoxy, isopropoxy, —CN, —CF$_3$, —NH$_2$, —NH(C$_{1-4}$alkyl), —N(C$_{1-4}$alkyl)$_2$, —CO$_2$C$_{1-4}$alkyl, —CO$_2$H, —NHC(O)C$_{1-4}$alkyl, —SO$_2$C$_{1-4}$alkyl, —C(O)NH$_2$, —C(O)NH(C$_{1-4}$alkyl), —C(O)N(C$_{1-4}$alkyl)$_2$, cyclopropyl, cyclobutyl, cyclopentyl, cyclohexyl, pyrrolidinyl, piperidinyl, piperazinyl, morpholinyl, or thiomorpholinyl. In still other embodiments, each $R^{3'}$ is independently fluoro, chloro, bromo, methyl, ethyl, propyl, isopropyl, methoxy, ethoxy, isopropoxy, —CN, or —CF$_3$. In still other embodiments, each $R^{3'}$ is fluoro or chloro.

In some embodiments, $R^{7'}$ is H, deuterium, methyl, ethyl, propyl, isopropyl, cyclopropyl, cyclobutyl, cyclopentyl, pyrrolidinyl, furanyl, thiofuranyl, piperidinyl, piperazinyl, morpholinyl, phenyl, or monocyclic heteroaryl, each substituted or unsubstituted as in Formula (I-A). In other embodiments, $R^{7'}$ is H, or is methyl, ethyl, propyl, isopropyl, or cyclopropyl, each unsubstituted or substituted as in Formula (I-A). In still other embodiments, $R^{7'}$ is H or is methyl or ethyl, each unsubstituted or substituted with halogen, —OH, —OC$_{1-4}$alkyl, —NH$_2$, —NH(C$_{1-4}$alkyl), —N(C$_{1-4}$alkyl)$_2$, —CO$_2$H, —CO$_2$C$_{1-4}$alkyl, —CONH$_2$, cycloalkyl, or monocyclic heterocycloalkyl. In still other embodiments, $R^{7'}$ is H, methyl, hydroxyethyl, —CH$_2$CONH$_2$, or 3-pyrrolidinylmethyl. In still other embodiments. $R^{7'}$ is H or methyl.

In some embodiments, $R^{1'}$ and $R^{2'}$ are each independently H, deuterium, methyl, ethyl, propyl, isopropyl, cyclopropyl, cyclobutyl, cyclopentyl, pyrrolidinyl, furanyl, thiofuranyl, piperidinyl, piperazinyl, morpholinyl, phenyl, or monocyclic heteroaryl, each substituted or unsubstituted as in Formula (I-A). In other embodiments, $R^{1'}$ is H. In still other embodiments, $R^{2'}$ is deuterium, methyl, ethyl, propyl, isopropyl, cyclopropyl, cyclobutyl, cyclopentyl, pyrrolidinyl, furanyl, thiofuranyl, piperidinyl, piperazinyl, morpholinyl, phenyl, or monocyclic heteroaryl, each substituted or unsubstituted as in Formula (I-A). In still other embodiments, $R^{2'}$ is H or is methyl or ethyl, each unsubstituted or substituted with halogen, —OH, —OC$_{1-4}$alkyl, —NH$_2$, —NH(C$_{1-4}$alkyl), —N(C$_{1-4}$alkyl)$_2$, —CO$_2$H, —CO$_2$C$_{1-4}$alkyl, —CONH$_2$, cycloalkyl, or monocyclic heterocycloalkyl. In still other embodiments, R$^{2'}$ is H, methyl, fluoromethyl, hydroxymethyl or cyclopropyl. In still other embodiments, R$^{2'}$ is H. In still other embodiments, R$^{2'}$ is methyl.

In some embodiments, each R$^{k'}$ is independently H, methyl, ethyl, propyl, isopropyl, or cyclopropyl. In other embodiments, each R$^{k'}$ is independently H or methyl.

In some embodiments, each L$^1$ and L$^2$ is independently —CH$_2$— or —CH(methyl)-, —CH(substituted methyl)-, —CH(C$_{3-6}$cyclopropyl)-, —CH(OH)—, —O—, —NH—, —N(C$_{1-4}$alkyl)-, —N(C$_{3-6}$cyclopropyl)-, —S—, —S(O)—, or —SO$_2$—. In some embodiments, -(L$^1$)$_{n'}$- is —CH$_2$—O—, —CH(C$_{1-4}$alkyl)-O—, or —CH(C$_{3-6}$cycloalkyl)-O—. In other embodiments, -(L$^1$)$_{n'}$- is —CH(H or optionally substituted C$_{1-4}$alkyl)-N(H or optionally substituted C$_{1-4}$alkyl)-, —CH(CO$_2$C$_{1-4}$alkyl or C(O)N(H or C$_{1-4}$alkyl)$_2$)—N(H or optionally substituted C$_{1-4}$alkyl). In still other embodiments, -(L$^1$)$_{n'}$- is —CH$_2$S(O)$_{0-2}$—. In other embodiments, -(L$^1$)$_{n'}$- is —SO$_2$—N(H or C$_{1-4}$alkyl). In some embodiments, -(L$^1$)$_{n'}$- is —(CH$_2$)$_3$—. In some embodiments, -(L$^1$)$_{n'}$- is —(CH$_2$)$_2$—. In some embodiments, -(L')$_{n'}$- is —CH(CH$_3$)CH$_2$—.

In some embodiments, -(L$^2$)$_{m'}$ is —O—(C(R$^{1'}$)(R$^{2'}$))$_{2-3}$—. In other embodiments, -(L$^2$)$_{m'}$ is —O—(CH$_2$)$_{2-3}$—. In other embodiments, -(L$^2$)$_{m'}$ is —N(R$^{k'}$)—(C(R$^{1'}$)(R$^{2'}$))$_{2-3}$—. In other embodiments, -(L$^2$)$_{m'}$ is —N(H or C$_{1-4}$alkyl)-(CH$_2$)$_{2-3}$—. In other embodiments, -(L$^2$)$_{m'}$ is —S—(C(R$^{1'}$)(R$^{2'}$))$_{2-3}$—. In other embodiments, -(L$^2$)$_{m'}$ is —SO$_2$—(C(R$^{1'}$)(R$^{2'}$))$_{2-3}$—. In still other embodiments. -(L$^2$)$_{m'}$ is —SO$_2$N(R$^{k'}$)—(C(R$^{1'}$)(R$^{2'}$))$_2$—. In still other embodiments, -(L$^2$)$_{m'}$ is —(C(R$^{1'}$)(R$^{2'}$))$_3$—.

In some embodiments, m' is 3. In other embodiments, m' is 4. In still other embodiments, m' is 5. In some embodiments, n' is 2. In other embodiments, n' is 3. In still other embodiments, n' is 4. In some embodiments, p' is 0, 1, or 2. In other embodiments, p' is 1 or 2. In some embodiments, q' is 0. In other embodiments, q' is 1. In still other embodiments, q' is 2.

In some embodiments of Formula (I-A) are compounds of Formula (I), or pharmaceutically acceptable salts thereof. In other embodiments, compounds of Formula (I-A) are compounds of Formula (I), wherein each variable is independently defined as indicated below for Formula (I). In some embodiments, the variables of Formula (I-A) map onto Formula (I) as follows: A' is A; B' is B; R$^{1'}$ is R$^1$; R$^{2'}$ is R$^2$; R$^{3'}$ is R$^3$; R$^{4'}$ is R$^4$; R$^{7'}$ is R$^7$; R$^{a'}$—R$^{f'}$ and R$^{i'}$—R$^{k'}$ map onto R$^a$—R$^f$ and R$^i$—R$^k$, respectively; and L$^1$ and L$^2$ are —Y—(C(R$^5$)(R$^6$))$_m$— and —C((R$^1$)(R$^2$))$_n$—X—, respectively.

In some embodiments of Formula (I). Ring A is phenyl or a 6-membered heteroaryl. In other embodiments, Ring A is phenyl or pyridyl. In still other embodiments, Ring A is phenyl. In still other embodiments, Ring A substituted with —(R$^3$)$_p$ is

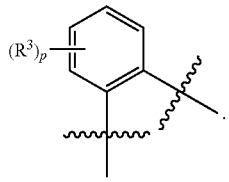

In still other embodiments, Ring A substituted with —(R$^3$)$_p$ is

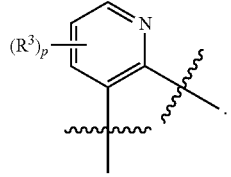

In some embodiments, each R$^3$ is independently deuterium, fluoro, chloro, bromo, methyl, ethyl, propyl, isopropyl, methoxy, ethoxy, isopropoxy, —CN, —CF$_3$. —NH$_2$, —NH(C$_{1-4}$alkyl), —N(C$_{1-4}$alkyl)$_2$, —CO$_2$C$_{1-4}$alkyl, —CO$_2$H, —NHC(O)C$_{1-4}$alkyl, —SO$_2$C$_{1-4}$alkyl, —C(O)NH$_2$, —C(O)NH(C$_{1-4}$alkyl), —C(O)N(C$_{1-4}$alkyl)$_2$, cyclopropyl, cyclobutyl, cyclopentyl, cyclohexyl, pyrrolidinyl, piperidinyl, piperazinyl, morpholinyl, or thiomorpholinyl. In still other embodiments, each R$^3$ is independently fluoro, chloro, bromo, methyl, ethyl, propyl, isopropyl, methoxy, ethoxy, isopropoxy, —CN, or —CF$_3$. In still other embodiments, each R$^3$ is fluoro or chloro.

In still other embodiments, Ring A substituted with —(R$^3$)$_p$ is

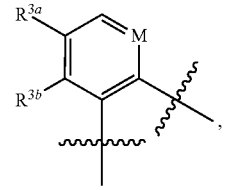

where R$^{3a}$ and R$^{3b}$ are each independently H, fluoro, or chloro and M is CH or N. In some embodiments, R$^{3a}$ is fluoro.

In some embodiments, p is 1 or 2. In other embodiments, p is zero. In still other embodiments, p is 1. In still other embodiments, p is 2.

In some embodiments, Ring B is a bicyclic heteroaryl. In other embodiments, Ring B is a 9-membered bicyclic heteroaryl.

In some embodiments, each R$^4$ is independently deuterium, fluoro, chloro, bromo, methyl, ethyl, propyl, isopropyl, methoxy, ethoxy, isopropoxy, —CN, —CF$_3$, —NH$_2$, —NH(C$_{1-4}$alkyl), —N(C$_{1-4}$alkyl)$_2$. —CO$_2$C$_{1-4}$alkyl, —CO$_2$H, —NHC(O)C$_{1-4}$alkyl, —SO$_2$C$_{1-4}$alkyl, —C(O)NH$_2$, —C(O)NH(C$_{1-4}$alkyl), —C(O)N(C$_{1-4}$alkyl)$_2$, cyclopropyl, cyclobutyl, cyclopentyl, cyclohexyl, pyrrolidinyl, piperidinyl, piperazinyl, morpholinyl, or thiomorpholinyl. In still other embodiments, each R$^4$ is independently fluoro, chloro, bromo, methyl, ethyl, propyl, isopropyl, methoxy, ethoxy, isopropoxy, —CN, or —CF$_3$.

In other embodiments, Ring B substituted with —(R⁴)_q is:

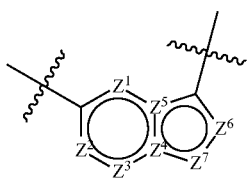

wherein Z¹, Z², Z³, and Z⁶ are each independently —C(Rˣ)— or N;
wherein each Rˣ is independently H, deuterium, halogen. C_{1-4}alkyl, —O—C_{1-4}alkyl, —OH, —NH₂, —NHC_{1-4}alkyl, —NH-phenyl, —NH-heteroaryl, CN, or —CF₃;
Z⁴ and Z⁵ are each independently —C— or —N—; and
Z⁷ is —CH—, —N—, or —NH—;
In other embodiments:
(a) Z¹, Z⁴, and Z⁷ are each —N—;
(b) Z¹, Z⁵, and Z⁷ are each —N—;
(c) Z¹ and Z³ are each —N— and Z⁷ is —NH—;
(d) Z³ is —N— and Z⁷ is —NH—;
(e) Z³ and Z⁶ are each —N— and Z⁷ is —NH—;
(f) Z², Z⁴, and Z⁷ are each —N—;
(g) Z¹, Z², Z⁴, and Z⁷ are each —N—;
(h) Z¹, Z³, and Z⁴ are each —N—;
(i) Z³ and Z⁴ are each —N—;
(j) Z¹, Z², Z⁵, and Z⁷ are each —N—,
(k) Z², Z⁵, and Z⁷ are each —N—;
(l) Z³ and Z⁵ are each —N—;
(m) Z³, Z⁵, and Z⁶ are each —N—;
(n) Z¹, Z⁵, Z⁶, and Z⁷ are each —N—;
(o) Z², Z⁵, Z⁶, and Z⁷ are each —N—; or
(p) Z¹, Z³, and Z⁶ are each —N— and Z⁷ is —NH—.

In still other embodiments of (a)-(p), each Z ring atom that is not defined expressly is independently —C— or —C(Rˣ)— (consistently with the definition of such ring atom). In still other embodiments, Z³ is —N—. In other embodiment, Z⁷ is —N— or —NH—. In still other embodiments, Z³ is —N— and Z⁷ is —N— or —NH—. In still other embodiments, Ring B substituted with —(R⁴)_q is:

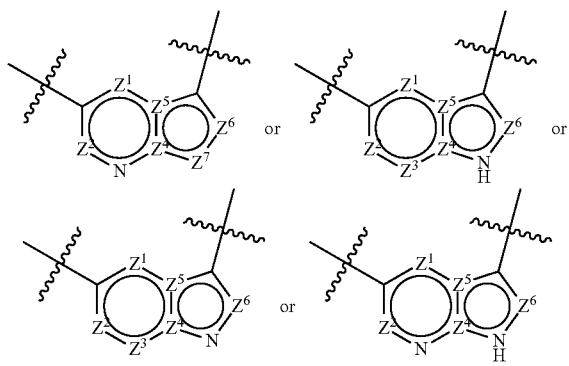

wherein Z^{1-7} are otherwise defined as above.
In still other embodiments, Ring B substituted with —(R⁴)_q is:

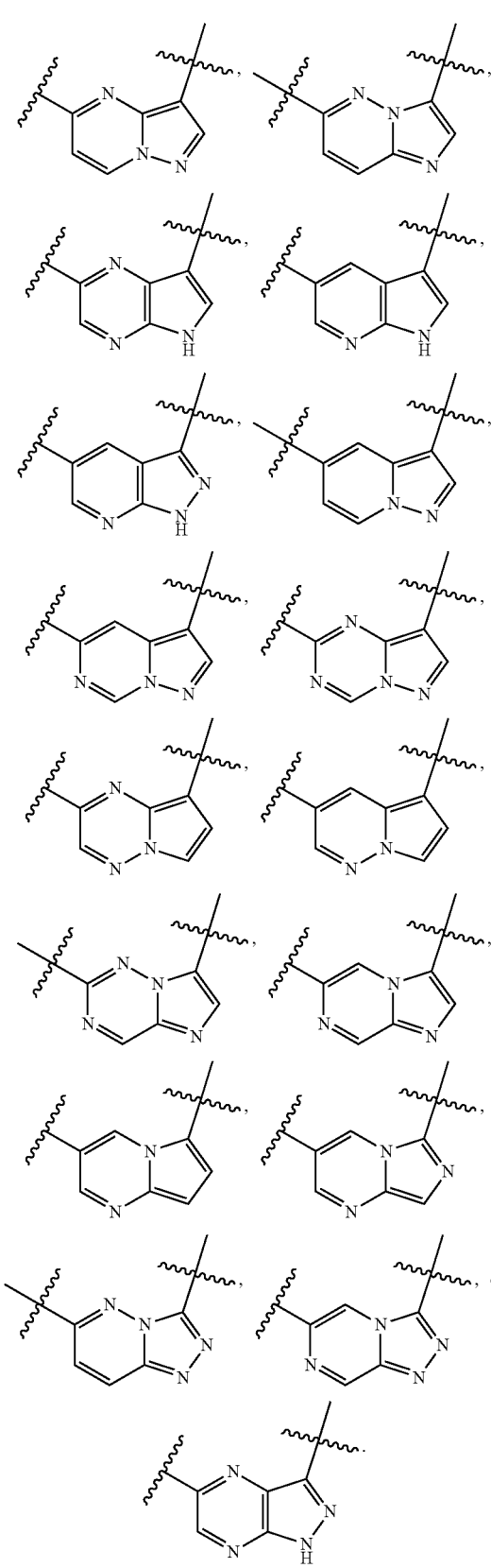

In still other embodiments, Ring B substituted with —(R⁴)_q is

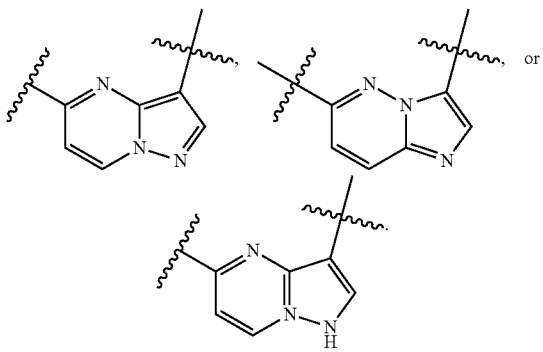

In still other embodiments, Ring B substituted with —(R$^4$)$_q$ is

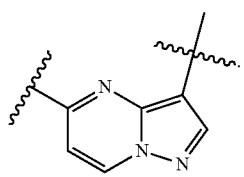 [SMILES: *c1ccn2ncc(*)c2n1]

In some embodiments, q is 0. In other embodiments, q is 1.

In some embodiments, R$^1$ and R$^2$ are each independently H, deuterium, methyl, ethyl, propyl, isopropyl, cyclopropyl, cyclobutyl, cyclopentyl, pyrrolidinyl, furanyl, thiofuranyl, piperidinyl, piperazinyl, morpholinyl, phenyl, or monocyclic heteroaryl, each substituted or unsubstituted as in Formula (I). In still other embodiments, R$^1$ is H. In still other embodiments, R$^2$ is deuterium, methyl, ethyl, propyl, isopropyl, cyclopropyl, cyclobutyl, cyclopentyl, pyrrolidinyl, furanyl, thiofuranyl, piperidinyl, piperazinyl, morpholinyl, phenyl, or monocyclic heteroaryl, each substituted or unsubstituted as in Formula (I). In still other embodiments. R$^2$ is H or is methyl or ethyl, each unsubstituted or substituted with halogen, —OH, —OC$_{1-4}$alkyl, —NH$_2$, —NH(C$_{1-4}$alkyl), —N(C$_{1-4}$alkyl)$_2$, —CO$_2$H, —CO$_2$C$_{1-4}$alkyl, —CONH$_2$, cycloalkyl, or monocyclic heterocycloalkyl. In still other embodiments, R$^2$ is H, methyl, fluoromethyl, hydroxymethyl or cyclopropyl. In still other embodiments, R$^2$ is H. In still other embodiments, R$^2$ is methyl. In still other embodiments, R$^1$ is H, and R$^2$ is not H and is in the stereochemical configuration shown below:

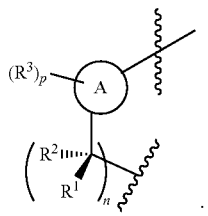

In still other embodiments, R$^1$ and R$^2$ are taken together to form a C$_{3-6}$cycloalkyl. In other embodiments, R$^1$ and R$^2$ are taken together to form a 5- or 6-membered heterocycloalkyl, optionally substituted with C$_{1-4}$alkyl.

In some embodiments, n is 1 or 2. In still other embodiments, n is 1.

In some embodiments, R$^5$ and R$^6$ are each independently H, deuterium, methyl, ethyl, propyl, isopropyl, cyclopropyl, cyclobutyl, cyclopentyl, pyrrolidinyl, furanyl, thiofuranyl, piperidinyl, piperazinyl, morpholinyl, phenyl, or monocyclic heteroaryl, each substituted or unsubstituted as in Formula (I). In other embodiments, each R$^5$ is H. In still other embodiments, each R$^6$ is independently H, or is methyl, ethyl, or cyclopropyl, each substituted or unsubstituted as in Formula (I). In still other embodiments, each R$^6$ is independently H or methyl, unsubstituted or substituted with —OH. In still other embodiments, each R$^6$ is H or methyl. In still other embodiments, R$^5$ and R$^6$ are taken together to form a C$_{3-6}$cycloalkyl. In other embodiments, R$^5$ and R$^6$ are taken together to form a 5- or 6-membered heterocycloalkyl, optionally substituted with C$_{1-4}$alkyl.

In some embodiments, m is 2 or 3. In other embodiments, m is 2.

In some embodiments, R$^7$ is H, deuterium, methyl, ethyl, propyl, isopropyl, cyclopropyl, cyclobutyl, cyclopentyl, pyrrolidinyl, furanyl, thiofuranyl, piperidinyl, piperazinyl, morpholinyl, phenyl, or monocyclic heteroaryl, each substituted or unsubstituted as in Formula (I). In other embodiments. R$^7$ is H, or is methyl, ethyl, propyl, isopropyl, or cyclopropyl, each unsubstituted or substituted as in Formula (I). In still other embodiments, R$^7$ is H or is methyl or ethyl, each unsubstituted or substituted with halogen, —OH, —OC$_{1-4}$alkyl, —NH$_2$, —NH(C$_{1-4}$alkyl), —N(C$_{1-4}$alkyl)$_2$, —CO$_2$H, —CO$_2$C$_{1-4}$alkyl, —CONH$_2$, cycloalkyl, or monocyclic heterocycloalkyl. In still other embodiments, R$^7$ is H, methyl, hydroxyethyl, —CH$_2$CONH$_2$, or 3-pyrrolidinylmethyl. In still other embodiments, R$^7$ is H or methyl.

In some embodiments, each of X and Y is independently —O— or —N(R$^k$)—. In some embodiments, X is —O— or —N(R$^k$)—. In some embodiments, Y is —O—. In some embodiments, each R$^k$ is independently H, methyl, ethyl, propyl, isopropyl, or cyclopropyl. In other embodiments, each R$^k$ is independently H or methyl.

In some embodiments, compounds of Formula (I) or (I-A) are compounds of Formula (II):

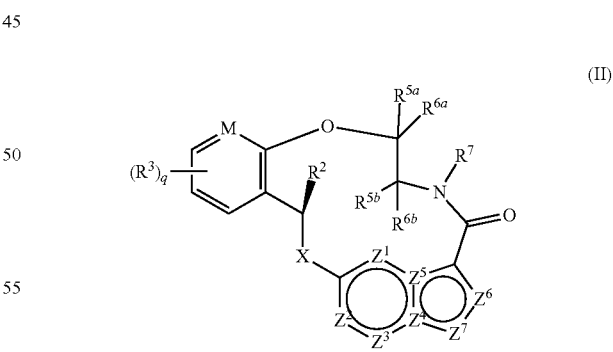

wherein M, R$^3$, q, R$^2$, X, R$^7$, and Z$^{1-7}$ are each as defined in any of the several ways recited above;

R$^{5a}$, R$^{5b}$, R$^{6a}$, and R$^{6b}$ are each R$^5$ and R$^6$ as defined in any of the several ways recited above;

or a pharmaceutically acceptable salt thereof.

In some embodiments, compounds of Formula (I) or (I-A) are compounds of Formula (III):

(III)

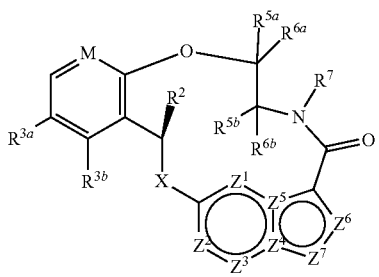

wherein
M is CH or N;
$R^{3a}$ and $R^{3b}$ are each independently H, fluoro, chloro, bromo, methyl, ethyl, propyl, isopropyl, methoxy, ethoxy, isopropoxy, —CN, or —CF$_3$;
$R^{2a}$ is H or is methyl or ethyl, each unsubstituted or substituted with halogen, —OH, —OC$_{1-4}$alkyl, —NH$_2$, —NH(C$_{1-4}$alkyl), —N(C$_{1-4}$alkyl)$_2$, —CO$_2$H, —CO$_2$C$_{1-4}$alkyl, —CONH$_2$, cycloalkyl, or monocyclic heterocycloalkyl;
$X^1$ is O or —N(CH$_3$)—;
$R^{5a}$, $R^{6a}$, $R^{5b}$, and $R^{6b}$ are each independently H, or methyl or ethyl, each unsubstituted or substituted with halogen, —OH, —OC$_{1-4}$alkyl, —NH$_2$, —NH(C$_{1-4}$alkyl), —N(C$_{1-4}$alkyl)$_2$, —CO$_2$H, —CO$_2$C$_{1-4}$alkyl, —CONH$_2$, —CONH(C$_{1-4}$alkyl), —CON(C$_{1-4}$alkyl)$_2$, cycloalkyl, or monocyclic heterocycloalkyl;
$R^{7a}$ is H or is methyl or ethyl, each unsubstituted or substituted with halogen, —OH, —OC$_{1-4}$alkyl, —NH$_2$, —NH(C$_{1-4}$alkyl), —N(C$_{1-4}$alkyl)$_2$, —CO$_2$H, —CO$_2$C$_{1-4}$alkyl, —CONH$_2$, —CONH(C$_{1-4}$alkyl), —CON(C$_{1-4}$alkyl)$_2$, cycloalkyl, or monocyclic heterocycloalkyl;
$Z^{1-7}$ are each as defined in any of the several ways recited above;
or a pharmaceutically acceptable salt thereof.

In some embodiments of Formula (III), M is CH.

In other embodiments, $R^{3a}$ and $R^{3b}$ are each independently H, fluoro, or chloro. In still other embodiments, $R^{3a}$ is H or fluoro. In still other embodiments, $R^{3a}$ is fluoro. In still other embodiments. $R^{3b}$ is H or chloro.

In some embodiments of Formula (III), $R^{2a}$ is H, methyl, fluoromethyl, or cyclopropyl.

In some embodiments or Formula (III), $X^1$ is O. In other embodiments, X is —N(CH$_3$)—.

In some embodiments, $R^{7a}$ is H, methyl, hydroxyethyl, —CH$_2$CONH$_2$, or 3-pyrrolidinylmethyl. In other embodiments, $R^{7a}$ is H or methyl.

In some embodiments, compounds of Formula (I) or (I-A) are compounds of Formula (IV):

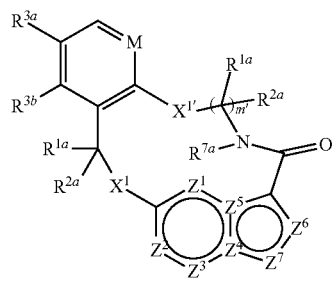
(IV)

wherein
M is CH or N;
$X^1$ and $X^{1'}$ are independently —C(R$^{1a}$)(R$^{2a}$)—, —S—, —S(O)—, —S(O)$_2$—, —O— or —N(R$^{k'}$)—;
each $R^{1a}$ and $R^{2a}$ is independently H, deuterium, C$_{1-6}$alkyl, C$_{3-6}$cycloalkyl, C$_{6-10}$ aryl, —C(O)OR$^{a'}$, —C(O)NR$^{a'}$R$^{b'}$, —NR$^{a'}$R$^{b'}$, —SR$^{a'}$, —S(O)R$^{c'}$, —S(O)NR$^{a'}$, —S(O)$_2$R$^{a'}$, —S(O)$_2$NR$^{a'}$ or —OR$^{a'}$ wherein each hydrogen atom in C$_{1-4}$alkyl is independently optionally substituted by deuterium, halogen, —OH, —OC$_{1-4}$alkyl, —NH$_2$, —NH(C$_{1-4}$alkyl), —N(C$_{1-4}$alkyl)$_2$, NHC(O)C$_{1-4}$alkyl, —N(C$_{1-4}$alkyl)C(O)C$_{1-4}$alkyl, —NHC(O)NHC$_{1-4}$alkyl, —N(C$_{1-4}$alkyl)C(O)NHC$_{1-4}$alkyl, NHC(O)N(C$_{1-4}$alkyl)$_2$, —N(C$_{1-4}$alkyl)C(O)N(C$_{1-4}$alkyl)$_2$, —NHC(O)OC$_{1-4}$alkyl, —N(C$_{1-4}$alkyl)C(O)OC$_{1-4}$alkyl, —CO$_2$H, —CO$_2$C$_{1-4}$alkyl, —CONH$_2$, —CONH(C$_{1-4}$alkyl), —CON(C$_{1-4}$alkyl)$_2$, —SC$_{1-4}$alkyl, —S(O)C$_{1-4}$alkyl, —S(O)$_2$C$_{1-4}$alkyl, —S(O)NH(C$_{1-4}$alkyl), —S(O)$_2$NH(C$_{1-4}$alkyl), —S(O)N(C$_{1-4}$alkyl)$_2$, —S(O)$_2$N(C$_{1-4}$alkyl)$_2$, C$_{3-5}$cycloalkyl, or 3- to 7-membered heterocycloalkyl;
$R^{3a}$ and $R^{3b}$ are each independently H, deuterium, fluoro, chloro, bromo, methyl, ethyl, propyl, isopropyl, methoxy, ethoxy, isopropoxy, —CN, or —CF$_3$;
$R^{7a}$ is H, C$_{1-6}$alkyl or 3- to 7-membered heterocycloalkyl, wherein each hydrogen atom in C$_{1-6}$alkyl or 3- to 7-membered heterocycloalkyl is independently optionally substituted by deuterium, halogen, —CN, —OH, —OC$_{1-4}$alkyl, —NH$_2$, —NH(C$_{1-4}$alkyl), —N(C$_{1-4}$alkyl)$_2$, —CO$_2$H, —CO$_2$C$_{1-4}$alkyl, —CONH$_2$, —CONH(C$_{1-4}$alkyl), —CON(C$_{1-4}$alkyl)$_2$, cycloalkyl, or monocyclic heterocycloalkyl;
each $R^{k'}$ is independently H, deuterium, C$_{1-6}$alkyl, C$_{2-6}$alkenyl, C$_{2-6}$alkynyl, C$_{3-6}$cycloalkyl, 3- to 7-membered heterocycloalkyl, C$_{6-10}$ aryl, or mono- or bicyclic heteroaryl; wherein each hydrogen atom in C$_{1-6}$alkyl, C$_{2-6}$alkenyl, C$_{2-6}$alkynyl, C$_{3-6}$cycloalkyl, 3- to 7-membered heterocycloalkyl, C$_{6-10}$ aryl, or mono- or bicyclic heteroaryl in R$^{k'}$ is independently optionally substituted by deuterium, halogen, C$_{1-6}$alkyl, C$_{1-6}$haloalkyl or —OR$^{a'}$;
wherein each $R^{a'}$ and $R^{b'}$ is independently H, deuterium, C$_{1-6}$alkyl, C$_{2-6}$alkenyl, C$_{2-6}$alkynyl, C$_{3-6}$cycloalkyl, 3- to 7-membered heterocycloalkyl, C$_{6-10}$aryl, or heteroaryl;
each $Z^1$, $Z^2$, $Z^3$, $Z^4$, $Z^5$, $Z^6$ or $Z^7$ is independently N, NH, or C(R$^x$), wherein each R$^x$ when present is independently H, deuterium, halogen, C$_{1-4}$alkyl, —O—C$_{1-4}$alkyl, —OH, —NH$_2$, —NH(C$_{1-4}$alkyl), —NH(phenyl), —NH(heteroaryl), CN, or —CF$_3$, provided that at least one of $Z^1$, $Z^2$, $Z^3$, $Z^4$, $Z^5$, $Z^6$ or $Z^7$ is N or NH; and
m' is 2 or 3;
or a pharmaceutically acceptable salt thereof.

In some embodiments, $Z^1$, $Z^4$ and $Z^7$ are N, and $Z^2$, $Z^3$, $Z^5$ and $Z^7$ are C(R$^x$), wherein each R$^x$ when present is H. In some embodiments, $Z^1$ and $Z^3$ are N, $Z^7$ is NH and $Z^2$, $Z^4$, $Z^5$, and $Z^6$ are C(R$^x$), wherein each R when present is H. In some embodiments, $Z^1$, $Z^3$ and $Z^6$ are N, $Z^7$ is NH and $Z^2$, $Z^4$ and $Z^5$ are C(R$^x$), wherein each R$^x$ when present is H. In some embodiments, $Z^3$ is N, $Z^7$ is NH and $Z^1$, $Z^2$, $Z^4$, $Z^5$, and $Z^6$ are C(R$^x$), wherein each R$^x$ when present is H. In some embodiments. $Z^3$ and $Z^6$ are N, $Z^7$ is NH and $Z^1$, $Z^2$, $Z^4$ and $Z^5$ are C(R$^x$), wherein each R$^x$ when present is H. In some embodiments, $Z^2$, $Z^4$ and $Z^7$ are N and $Z^1$, $Z^3$, $Z^5$ and $Z^6$ are C(R$^x$), wherein each R$^x$ when present is H. In some embodiments, $Z^1$, $Z^5$ and $Z^7$ are N and $Z^2$, $Z^3$, $Z^4$ and $Z^6$ are C(R$^x$), wherein each R$^x$ when present is H. In some embodiments, $Z^1$, $Z^2$, $Z^4$ and $Z^7$ are N and $Z^3$, $Z^5$ and $Z^6$ are C($R^x$), wherein each $R^x$ when present is H. In some embodiments, $Z^1$, $Z^2$, $Z^5$ and $Z^7$ are N and $Z^3$, $Z^4$ and $Z^6$ are C($R^x$), wherein each $R^x$ when present is H. In some embodiments, $Z^3$, $Z^5$ and $Z^6$ are N and $Z^1$, $Z^2$, $Z^4$ and $Z^7$ are C($R^x$), wherein each $R^x$ when present is H. In some embodiments, $Z^1$, $Z^5$, $Z^6$ and $Z^7$ are N and $Z^2$, $Z^3$ and $Z^4$ are C($R^x$), wherein each $R^x$ when present is H. In some embodiments, $Z^1$, $Z^2$ and $Z^4$ are N and $Z^3$, $Z^5$, $Z^6$ and $Z^7$ are C($R^x$), wherein each $R^x$ when present is H. In some embodiments, $Z^1$, $Z^3$ and $Z^4$ are N and $Z^2$, $Z^5$, $Z^6$ and $Z^7$ are C($R^x$), wherein each $R^x$ when present is H. In some embodiments, $Z^3$ and $Z^4$ are N and $Z^1$, $Z^2$, $Z^5$, $Z^6$ and $Z^7$ are C($R^x$), wherein each $R^x$ when present is H. In some embodiments, $Z^2$, $Z^5$ and $Z^7$ are N and $Z^1$, $Z^3$, $Z^4$ and $Z^6$ are C($R^x$), wherein each $R^x$ when present is H. In some embodiments, $Z^3$ and $Z^5$ are N and $Z^1$, $Z^2$, $Z^4$, $Z^6$ and $Z^7$ are C($R^x$), wherein each $R^x$ when present is H. In some embodiments, $Z^2$, $Z^5$, $Z^6$ and $Z^7$ are N and $Z^1$, $Z^3$ and $Z^4$ are C($R^x$), wherein each $R^x$ when present is H.

In some embodiments, $R^{k'}$ is selected from the group consisting of H, methyl, ethyl, propyl, iso-propyl, cyclopropyl, 2-hydroxyethyl, 2-hydroxy-2-methyl-propyl, and N-methyl-pyrrol-3-yl. In some embodiments, M is CH. In some embodiments, M is CH, $Z^1$, $Z^4$ and $Z^7$ are N, and $Z^2$, $Z^3$, $Z^5$ and $Z^6$ are C($R^x$), wherein each $R^x$ when present is H. In some embodiments, M is CH, $Z^1$, $Z^4$ and $Z^7$ are N, $Z^2$, $Z^3$, $Z^5$ and $Z^6$ are C($R^x$), wherein each $R^x$ when present is H, and $X^1$ is —N($R^{k'}$)—. In some embodiments, M is CH, $Z^1$, $Z^4$ and $Z^7$ are N, $Z^2$, $Z^3$, $Z^5$ and $Z^6$ are C($R^x$), wherein each $R^x$ when present is H, $X^1$ is —N($R^{k'}$)—, and $X^{1'}$ is —O—. In some embodiments, M is CH, $Z^1$, $Z^4$ and $Z^7$ are N, $Z^2$, $Z^3$, $Z^5$ and $Z^6$ are C($R^x$), wherein each $R^x$ when present is H, $X^1$ is —C($R^{1a}$)($R^{2a}$)—, and $X^{1'}$ is —O—.

In some embodiments, compounds of Formula (I) or (I-A) are compounds of Formula (V):

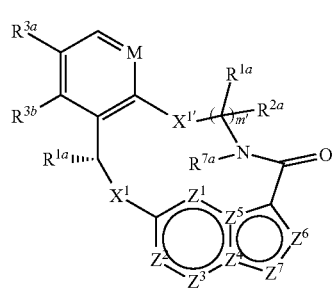

(IV)

wherein

M is CH or N;

$X^1$ and $X^{1'}$ are independently —C($R^{1a}$)($R^{2a}$)—, —S—, —S(O)—, —S(O)$_2$—, —O— or —N($R^{k'}$)—;

each $R^{1a}$ and $R^{2a}$ is independently H, deuterium, $C_{1-6}$alkyl, $C_{3-6}$cycloalkyl, $C_{6-10}$aryl, —C(O)O$R^{a'}$, —C(O)N$R^{a'}R^{b'}$, —N$R^{a'}R^{b'}$, —S$R^{a'}$, —S(O)$R^{a'}$, —S(O)N$R^{a'}$, —S(O)$_2R^{a'}$, —S(O)$_2$N$R^{a'}$ or —O$R^{a'}$ wherein each hydrogen atom in $C_{1-6}$alkyl is independently optionally substituted by deuterium, halogen, —OH, —O$C_{1-4}$alkyl, —NH$_2$, —NH($C_{1-4}$alkyl), —N($C_{1-4}$alkyl)$_2$, NHC(O)$C_{1-4}$alkyl, —N($C_{1-4}$alkyl)C(O)$C_{1-4}$alkyl, —NHC(O)NH$C_{1-4}$alkyl, —N($C_{1-4}$alkyl)C(O)NH$C_{1-4}$alkyl, NHC(O)N($C_{1-4}$alkyl)$_2$, —N($C_{1-4}$alkyl)C(O)N($C_{1-4}$alkyl)$_2$, —NHC(O)O$C_{1-4}$alkyl, —N($C_{1-4}$alkyl)C(O)OC$_{1-4}$alkyl, —CO$_2$H, —CO$_2C_{1-4}$alkyl, —CONH$_2$, —CONH($C_{1-4}$alkyl), —CON($C_{1-4}$alkyl)$_2$, —S$C_{1-4}$alkyl, —S(O)$C_{1-4}$alkyl, —S(O)$_2C_{1-4}$alkyl, —S(O)NH($C_{1-4}$alkyl), —S(O)$_2$NH($C_{1-4}$alkyl), —S(O)N($C_{1-4}$alkyl)$_2$, —S(O)$_2$N($C_{1-4}$alkyl)$_2$, $C_{3-6}$cycloalkyl, or 3- to 7-membered heterocycloalkyl;

$R^{3a}$ and $R^{3b}$ are each independently H, fluoro, chloro, bromo, methyl, ethyl, propyl, isopropyl, methoxy, ethoxy, isopropoxy, —CN, or —CF$_3$;

$R^{7a}$ is H, $C_{1-6}$alkyl or 3- to 7-membered heterocycloalkyl, wherein each hydrogen atom in $C_{1-6}$alkyl or 3- to 7-membered heterocycloalkyl is independently optionally substituted by halogen, —OH, —O$C_{1-4}$alkyl, —NH$_2$, —NH($C_{1-4}$alkyl), —N($C_{1-4}$alkyl)$_2$, —CO$_2$H, —CO$_2C_{1-4}$alkyl, —CONH$_2$, —CONH($C_{1-4}$alkyl), —CON($C_{1-4}$alkyl)$_2$, cycloalkyl, or monocyclic heterocycloalkyl;

each $R^{k'}$ is independently H, deuterium, $C_{1-6}$alkyl, $C_{2-6}$alkenyl, $C_{2-6}$alkynyl, $C_{3-6}$cycloalkyl, 3- to 7-membered heterocycloalkyl, $C_{6-10}$aryl, or mono- or bicyclic heteroaryl; wherein each hydrogen atom in $C_{1-6}$alkyl, $C_{2-6}$alkenyl, $C_{2-6}$alkynyl, $C_{3-6}$cycloalkyl, 3- to 7-membered heterocycloalkyl, $C_{6-10}$aryl, or mono- or bicyclic heteroaryl in $R^{k'}$ is independently optionally substituted by deuterium, halogen, $C_{1-6}$alkyl, $C_{1-6}$haloalkyl or —O$R^{a'}$;

wherein each $R^{a'}$ and $R^{b'}$ is independently H, deuterium, $C_{1-6}$alkyl, $C_{2-6}$alkenyl, $C_{2-6}$alkynyl, $C_{3-6}$cycloalkyl, 3- to 7-membered heterocycloalkyl, $C_{6-10}$aryl, or heteroaryl;

each $Z^1$, $Z^2$, $Z^3$, $Z^4$, $Z^5$, $Z^6$ or $Z^7$ is independently N, NH, or C($R^x$), wherein each $R^x$ when present is independently H, deuterium, halogen, $C_{1-4}$alkyl, —O—$C_{1-4}$alkyl, —OH, —NH$_2$, —NH($C_{1-4}$alkyl), —NH(phenyl), —NH(heteroaryl), CN, or —CF$_3$, provided that at least one of $Z^1$, $Z^2$, $Z^3$, $Z^4$, $Z^5$, $Z^6$ or $Z^7$ is N or NH; and m' is 2 or 3;

or a pharmaceutically acceptable salt thereof.

In some embodiments, $Z^1$, $Z^4$ and $Z^7$ are N, and $Z^2$, $Z^3$, $Z^5$ and $Z^7$ are C($R^x$), wherein each $R^x$ when present is H. In some embodiments, $Z^1$ and $Z^3$ are N, $Z^7$ is NH and $Z^2$, $Z^4$, $Z^5$, and $Z^6$ are C($R^x$), wherein each $R^x$ when present is H. In some embodiments, $Z^1$, $Z^3$ and $Z^6$ are N, $Z^7$ is NH and $Z^2$, $Z^4$ and $Z^5$ are C($R^x$), wherein each $R^x$ when present is H. In some embodiments, $Z^3$ is N, $Z^7$ is NH and $Z^1$, $Z^2$, $Z^4$, $Z^5$, and $Z^6$ are C($R^x$), wherein each $R^x$ when present is H. In some embodiments. $Z^3$ and $Z^6$ are N, $Z^7$ is NH and $Z^1$, $Z^2$, $Z^4$ and $Z^5$ are C($R^x$), wherein each $R^x$ when present is H. In some embodiments, $Z^2$, $Z^4$ and $Z^7$ are N and $Z^1$, $Z^3$, $Z^5$ and $Z^6$ are C($R^x$), wherein each $R^x$ when present is H. In some embodiments, $Z^1$, $Z^5$ and $Z^7$ are N and $Z^2$, $Z^3$, $Z^4$ and $Z^6$ are C($R^x$), wherein each $R^x$ when present is H. In some embodiments, $Z^1$, $Z^2$, $Z^4$ and $Z^7$ are N and $Z^3$, $Z^5$ and $Z^6$ are C($R^x$), wherein each $R^x$ when present is H. In some embodiments, $Z^1$, $Z^2$, $Z^5$ and $Z^7$ are N and $Z^3$, $Z^4$ and $Z^6$ are C($R^x$), wherein each $R^x$ when present is H. In some embodiments, $Z^3$, $Z^5$ and $Z^6$ are N and $Z^1$, $Z^2$, $Z^4$ and $Z^7$ are C($R^x$), wherein each $R^x$ when present is H. In some embodiments, $Z^1$, $Z^5$, $Z^6$ and $Z^7$ are N and $Z^2$, $Z^3$ and $Z^4$ are C($R^x$), wherein each $R^x$ when present is H. In some embodiments, $Z^1$, $Z^2$ and $Z^4$ are N and $Z^3$, $Z^5$, $Z^6$ and $Z^7$ are C($R^x$), wherein each $R^x$ when present is H. In some embodiments, $Z^1$, $Z^3$ and $Z^4$ are N and $Z^2$, $Z^5$, $Z^6$ and $Z^7$ are C($R^x$), wherein each $R^x$ when present is H. In some embodiments, $Z^3$ and $Z^4$ are N and $Z^1$, $Z^2$, $Z^5$, $Z^6$ and $Z^7$ are C($R^x$), wherein each $R^x$ when present is H. In some embodiments, $Z^2$, $Z^5$ and $Z^7$ are N and $Z^1$, $Z^3$, $Z^4$ and $Z^6$ are C($R^x$), wherein each $R^x$ when present is H. In some embodiments, $Z^3$ and $Z^5$ are N and $Z^1$, $Z^2$, $Z^4$, $Z^6$ and $Z^7$ are C($R^x$), wherein each $R^x$ when present is H. In some embodiments, $Z^2$, $Z^5$, $Z^6$ and $Z^7$ are N and $Z^1$, $Z^3$ and $Z^4$ are $C(R^x)$, wherein each $R^x$ when present is H.

In some embodiments, $R^{k'}$ is selected from the group consisting of H, methyl, ethyl, propyl, iso-propyl, cyclopropyl, 2-hydroxyethyl, 2-hydroxy-2-methyl-propyl, and N-methyl-pyrrol-3-yl. In some embodiments, M is CH. In some embodiments, M is CH, $Z^1$, $Z^4$ and $Z^7$ are N, and $Z^7$, $Z^3$, $Z^5$ and $Z^6$ are $C(R^x)$, wherein each $R^x$ when present is H. In some embodiments, M is CH, $Z^1$, $Z^4$ and $Z^7$ are N, $Z^2$, $Z^3$, $Z^5$ and $Z^6$ are $C(R^x)$, wherein each $R^x$ when present is H, and $X^1$ is $—N(R^{k'})—$. In some embodiments, M is CH, $Z^1$, $Z^4$ and $Z^7$ are N, $Z^2$, $Z^3$, $Z^5$ and $Z^6$ are $C(R^x)$, wherein each $R^x$ when present is H, $X^1$ is $—N(R^{k'})—$, and $X^{1'}$ is $—O—$. In some embodiments, M is CH, $Z^1$, $Z^4$ and $Z^7$ are N, Z, $Z^3$, $Z^5$ and $Z^6$ are $C(R^x)$, wherein each $R^x$ when present is H, $X^1$ is $—C(R^{1a})(R^{2a})—$, and $X^{1'}$ is $—O—$.

In some embodiments, compounds of Formula (I) or (I-A) are compounds selected from the group consisting of

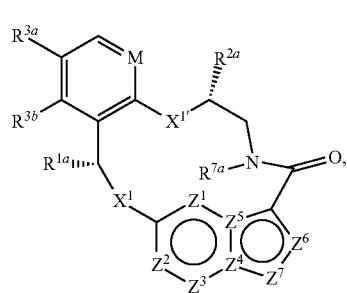

VI

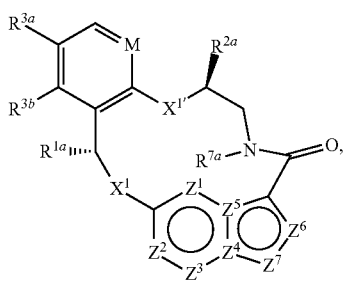

VII

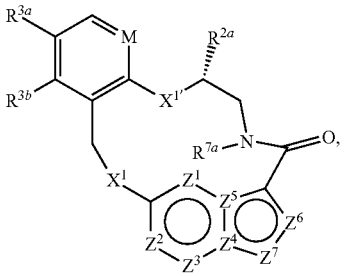

VIII

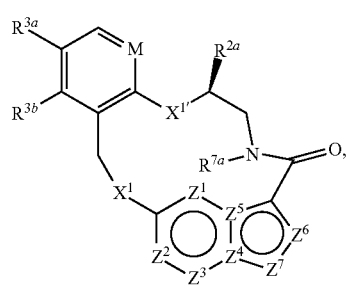

IX

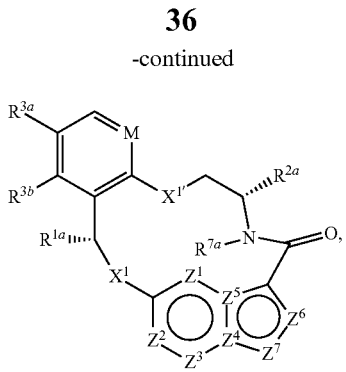

X

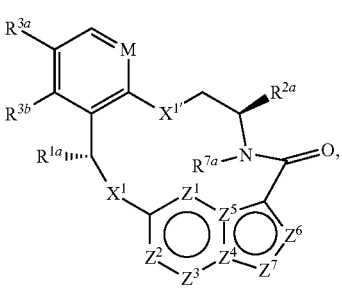

XI

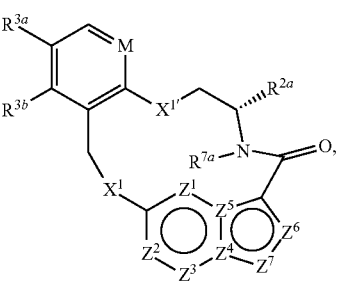

XII

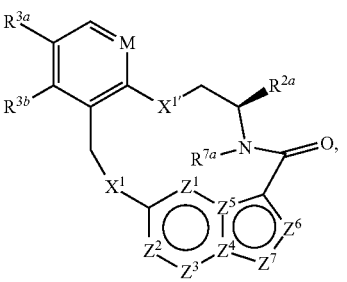

XIII

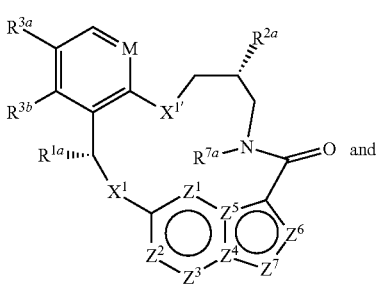

XIV

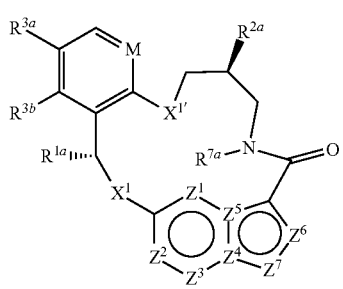

wherein
M is CH or N;
X$^1$ and X$^{1\prime}$ are independently —C(R$^{1a}$)(R$^{2a}$)—, —S—, —S(O)—, —S(O)$_2$—, —O— or —N(R$^{k\prime}$)—;
each R$^{1a}$ and R$^{2a}$ is independently H, deuterium, C$_{1-6}$alkyl, C$_{3-6}$cycloalkyl, C$_{6-10}$ aryl, —C(O)OR$^{a\prime}$, —C(O)NR$^{a\prime}$R$^{b\prime}$, —NR$^{a\prime}$R$^{b\prime}$, —SR$^{a\prime}$, —S(O)R$^{a\prime}$—, —S(O)NR$^{a\prime}$, —S(O)$_2$R$^{a\prime}$, —S(O)$_2$NR$^{a\prime}$ or —OR$^{a\prime}$ wherein each hydrogen atom in C$_{1-6}$alkyl is independently optionally substituted by deuterium, halogen, —OH, —OC$_{1-4}$alkyl, —NH$_2$, —NH(C$_{1-4}$alkyl), —N(C$_{1-4}$alkyl)$_2$, NHC(O)C$_{1-4}$alkyl, —N(C$_{1-4}$alkyl)C(O)C$_{1-4}$alkyl, —NHC(O)NHC$_{1-4}$alkyl, —N(C$_{1-4}$alkyl)C(O)NHC$_{1-4}$alkyl, NHC(O)N(C$_{1-4}$alkyl)$_2$, —N(C$_{1-4}$alkyl)C(O)N(C$_{1-4}$alkyl)$_2$, —NHC(O)OC$_{1-4}$alkyl, —N(C$_{1-4}$alkyl)C(O)OC$_{1-4}$alkyl, —CO$_2$H, —CO$_2$C$_{1-4}$alkyl, —CONH$_2$, —CONH(C$_{1-4}$alkyl), —CON(C$_{1-4}$alkyl)$_2$, —SC$_{1-4}$alkyl, —S(O)C$_{1-4}$alkyl, —S(O)$_2$C$_{1-4}$alkyl, —S(O)NH(C$_{1-4}$alkyl), —S(O)$_2$NH(C$_{1-4}$alkyl), —S(O)N(C$_{1-4}$alkyl)$_2$, —S(O)$_2$N(C$_{1-4}$alkyl)$_2$, C$_{3-6}$cycloalkyl, or 3- to 7-membered heterocycloalkyl;

R$^{3a}$ and R$^{3b}$ are each independently H, fluoro, chloro, bromo, methyl, ethyl, propyl, isopropyl, methoxy, ethoxy, isopropoxy, —CN, or —CF$_3$;

R$^{7a}$ is H. C$_{1-6}$alkyl or 3- to 7-membered heterocycloalkyl, wherein each hydrogen atom in C$_{1-6}$alkyl or 3- to 7-membered heterocycloalkyl is independently optionally substituted by halogen, —OH, —OC$_{1-4}$alkyl. —NH$_2$, —NH(C$_{1-4}$alkyl), —N(C$_{1-4}$alkyl)$_2$, —CO$_2$H, —CO$_2$C$_{1-4}$alkyl, —CONH$_2$, —CONH(C$_{1-4}$alkyl), —CON(C$_{1-4}$alkyl)$_2$, cycloalkyl, or monocyclic heterocycloalkyl;

each R$^{k\prime}$ is independently H, deuterium, C$_{1-6}$alkyl, C$_{2-6}$alkenyl, C$_{2-6}$alkynyl, C$_{3-6}$ cycloalkyl, 3- to 7-membered hetercycloalkyl, C$_{6-10}$ aryl, or mono- or bicyclic heteroaryl; wherein each hydrogen atom in C$_{1-6}$alkyl, C$_{2-6}$alkenyl, C$_{2-6}$alkynyl, C$_{3-6}$cycloalkyl, 3- to 7-membered heterocycloalkyl, C$_{6-10}$ aryl, or mono- or bicyclic heteroaryl in R$^{kn}$ is independently optionally substituted by deuterium, halogen, C$_{1-6}$alkyl, C$_{1-6}$haloalkyl or —OR$^{a\prime}$;

wherein each R$^{a\prime}$ and R$^{b\prime}$ is independently H, deuterium, C$_{1-6}$alkyl, C$_{2-6}$alkenyl, C$_{2-6}$alkynyl, C$_{3-6}$cycloalkyl, 3- to 7-membered heterocycloalkyl, C$_{6-10}$ aryl, or heteroaryl;

each Z$^1$, Z$^2$, Z$^3$, Z$^4$, Z$^5$, Z$^6$ or Z$^7$ is independently N, NH, or C(R$^x$), wherein each R$^x$ when present is independently H, deuterium, halogen, C$_{1-4}$alkyl, —O—C$_{1-4}$alkyl, —OH, —NH$_2$, —NH(C$_{1-4}$alkyl), —NH(phenyl), —NH(heteroaryl), CN, or —CF$_3$, provided that at least one of Z$^1$, Z$^2$, Z$^3$, Z$^4$, Z$^5$, Z$^6$ or Z$^7$ is N or NH; and
m' is 2 or 3;
or a pharmaceutically acceptable salt thereof.

In some embodiments, Z$^1$, Z$^4$ and Z$^7$ are N, and Z$^2$, Z$^3$, Z$^5$ and Z$^6$ are C(R$^x$), wherein each R$^x$ when present is H. In some embodiments, Z$^1$ and Z$^3$ are N, Z$^7$ is NH and Z$^2$, Z$^4$, Z$^5$, and Z$^6$ are C(R$^x$), wherein each R$^x$ when present is H. In some embodiments, Z$^1$, Z$^3$ and Z$^6$ are N, Z$^7$ is NH and Z$^2$, Z$^4$ and Z$^5$ are C(R$^x$), wherein each R$^x$ when present is H. In some embodiments, Z$^3$ is N, Z$^7$ is NH and Z$^1$, Z$^2$, Z$^4$, Z$^5$, and Z$^6$ are C(R$^x$), wherein each R$^x$ when present is H. In some embodiments. Z$^3$ and Z$^6$ are N, Z$^7$ is NH and Z$^1$, Z$^2$, Z$^4$ and Z$^5$ are C(R$^x$), wherein each R$^x$ when present is H. In some embodiments, Z$^2$, Z$^4$ and Z$^7$ are N and Z$^1$, Z$^3$, Z$^5$ and Z$^6$ are C(R$^x$), wherein each R$^x$ when present is H. In some embodiments, Z$^1$, Z$^5$ and Z$^7$ are N and Z$^2$, Z$^3$, Z$^4$ and Z$^6$ are C(R$^x$), wherein each R$^x$ when present is H. In some embodiments, Z$^1$, Z$^2$, Z$^4$ and Z$^7$ are N and Z$^3$, Z$^5$ and Z$^6$ are C(R$^x$), wherein each R$^x$ when present is H. In some embodiments, Z$^1$, Z$^2$, Z$^5$ and Z$^7$ are N and Z$^3$, Z$^4$ and Z$^6$ are C(R$^x$), wherein each R$^x$ when present is H. In some embodiments, Z$^3$, Z$^5$ and Z$^6$ are N and Z$^1$, Z$^2$, Z$^4$ and Z$^7$ are C(R$^x$), wherein each R$^x$ when present is H. In some embodiments, Z$^1$, Z$^5$, Z$^6$ and Z$^7$ are N and Z$^2$, Z$^3$ and Z$^4$ are C(R$^x$), wherein each R$^x$ when present is H. In some embodiments, Z$^1$, Z$^2$ and Z$^4$ are N and Z$^3$, Z$^5$, Z$^6$ and Z$^7$ are C(R$^x$), wherein each R$^x$ when present is H. In some embodiments, Z$^1$, Z$^3$ and Z$^4$ are N and Z$^2$, Z$^5$, Z$^6$ and Z$^7$ are C(R$^x$), wherein each R$^x$ when present is H. In some embodiments, Z$^3$ and Z$^4$ are N and Z$^1$, Z$^2$, Z$^5$, Z$^6$ and Z$^7$ are C(R$^x$), wherein each R$^x$ when present is H. In some embodiments, Z$^2$, Z$^5$ and Z$^7$ are N and Z$^1$, Z$^3$, Z$^4$ and Z$^6$ are C(R$^x$), wherein each R$^x$ when present is H. In some embodiments, Z$^3$ and Z$^5$ are N and Z$^1$, Z$^2$, Z$^4$, Z$^6$ and Z$^7$ are C(R$^x$), wherein each R$^x$ when present is H. In some embodiments, Z$^2$, Z$^5$, Z$^6$ and Z$^7$ are N and Z$^1$, Z$^3$ and Z$^4$ are C(R$^x$), wherein each R$^x$ when present is H.

In some embodiments, R$^{k\prime}$ is selected from the group consisting of H, methyl, ethyl, propyl, iso-propyl, cyclopropyl, 2-hydroxyethyl, 2-hydroxy-2-methyl-propyl, and N-methyl-pyrrol-3-yl. In some embodiments, M is CH. In some embodiments, M is CH, Z$^1$, Z$^4$ and Z$^7$ are N. and Z$^2$, Z$^3$, Z$^5$ and Z$^6$ are C(R$^x$), wherein each R$^x$ when present is H. In some embodiments, M is CH, Z$^1$, Z$^4$ and Z$^7$ are N, Z$^2$, Z$^3$, Z$^5$ and Z$^6$ are C(R$^x$), wherein each R$^x$ when present is H, and X$^1$ is —N(R$^{k\prime}$)—. In some embodiments, M is CH, Z$^1$, Z$^4$ and Z$^7$ are N, Z$^2$, Z$^3$, Z$^5$ and Z$^6$ are C(R$^x$), wherein each R$^x$ when present is H, X$^1$ is —N(R$^{k\prime}$)—, and X$^{1\prime}$ is —O—. In some embodiments. M is CH, Z$^1$, Z$^4$ and Z$^7$ are N, Z$^2$, Z$^3$, Z$^5$ and Z$^6$ are C(R$^x$), wherein each R$^x$ when present is H. X$^1$ is —C(R$^{1a}$)(R$^{2a}$)—, and X$^{1\prime}$ is —O—.

In other embodiments, the compound of Formula (I) or (I-A) is selected from the group consisting of (13R)-5,13-dimethyl-6,7-dihydro-13H-1,15-ethenopyrazolo[4,3-f][1,10,4,8]benzodioxadiazacyclotridecin-4(5H)-one; 5,13-dimethyl-6,7-dihydro-13H-1,15-ethenopyrazolo[4,3-f][1,10,4,8]benzodioxadiazacyclotridecin-4(5H)-one; (13R)-11-fluoro-5,13-dimethyl-6,7-dihydro-13H-1,15-ethenopyrazolo[4,3-f][1,10,4,8]benzodioxadiazacyclotridecin-4(5H)-one; 11-fluoro-5,13-dimethyl-6,7-dihydro-13H-1,15-ethenopyrazolo[4,3-f][1,10,4,8]benzodioxadiazacyclotridecin-4(5H)-one; (13R)-12-chloro-11-fluoro-5,13-dimethyl-6,7-dihydro-13H-1,15-ethenopyrazolo[4,3-f][1,10,4,8]benzodioxadiazacyclotridecin-4(5H)-one; 12-chloro-11-fluoro-5,13-dimethyl-6,7-dihydro-13H-1,15-ethenopyrazolo[4,3-f][1,10,4,8]benzodioxadiazacyclotridecin-4(5H)-one; (13R)-12-chloro-11-fluoro-5-(2-hydroxyethyl)-13-methyl-6,7-dihydro-13H-1,15-ethenopyrazolo[4,3-f][1,10,4,8]benzodioxadiazacyclotridecin-4(5H)-one; 12-chloro-11- fluoro-5-(2-hydroxyethyl)-13-methyl-6,7-dihydro-13H-1,15-ethenopyrazolo[4,3-f][1,10,4,8]benzodioxadiazacyclotridecin-4(5H)-one; 2-[(13R)-12-chloro-11-fluoro-13-methyl-4-oxo-6,7-dihydro-13H-1,15-ethenopyrazolo[4,3-f][1,10,4,8]benzodioxadiazacyclotridecin-5(4H)-yl]acetamide; 2-[12-chloro-11-fluoro-13-methyl-4-oxo-6,7-dihydro-13H-1,15-ethenopyrazolo[4,3-f][1,10,4,8]benzodioxadiazacyclotridecin-5(4H)-yl]acetamide; (13R)-12-chloro-11-fluoro-13-methyl-5-(pyrrolidin-2-ylmethyl)-6,7-dihydro-13H-1,15-ethenopyrazolo[4,3-f][1,10,4,8]benzodioxadiazacyclotridecin-4(5H)-one; 12-chloro-11-fluoro-13-methyl-5-(pyrolidin-2-ylmethyl)-6,7-dihydro-13H-1,15-ethenopyrazolo[4,3-f][1,10,4,8]benzodioxadiazacyclotridecin-4(5H)-one; (13R)-12-chloro-11-fluoro-7-(hydroxymethyl)-5,13-dimethyl-6,7-dihydro-13H-1,15-ethenopyrazolo[4,3-f][1,10,4,8]benzodioxadiazacyclotridecin-4(5H)-one; 12-chloro-11-fluoro-7-(hydroxymethyl)-5,13-dimethyl-6,7-dihydro-13H-1,15-ethenopyrazolo[4,3-f][1,10,4,8]benzodioxadiazacyclotridecin-4(5H)-one; (13S)-11-fluoro-13-(fluoromethyl)-5-methyl-6,7-dihydro-13H-1,15-ethenopyrazolo[4,3-f][1,10,4,8]benzodioxadiazacyclotridecin-4(5H)-one; 11-fluoro-13-(fluoromethyl)-5-methyl-6,7-dihydro-13H-1,15-ethenopyrazolo[4,3-f][1,10,4,8]benzodioxadiazacyclotridecin-4(5H)-one; (13R)-13-cyclopropyl-11-fluoro-5-methyl-6,7-dihydro-13H-1,15-ethenopyrazolo[4,3-f][1,10,4,8]benzodioxadiazacyclotridecin-4(5H)-one; 13-cyclopropyl-11-fluoro-5-methyl-6,7-dihydro-13H-1,15-ethenopyrazolo[4,3-f][1,10,4,8]benzodioxadiazacyclotridecin-4(5H)-one; (13R)-11-fluoro-13-methyl-6,7-dihydro-13H-1,15-ethenopyrazolo[4,3-f][1,10,4,8]benzodioxadiazacyclotridecin-4(5H)-one; 11-fluoro-13-methyl-6,7-dihydro-13H-1,15-ethenopyrazolo[4,3-f][1,10,4,8]benzodioxadiazacyclotridecin-4(5H)-one; (13R)-12-chloro-11-fluoro-13-methyl-6,7-dihydro-13H-1,15-ethenopyrazolo[4,3-f][1,10,4,8]benzodioxadiazacyclotridecin-4(5H)-one; 12-chloro-11-fluoro-13-methyl-6,7-dihydro-13H-1,15-ethenopyrazolo[4,3-f][1,10,4,8]benzodioxadiazacyclotridecin-4(5H)-one; 12-chloro-11-fluoro-6-methyl-6,7-dihydro-131H-1,15-ethenopyrazolo[4,3-f][1,10,4,8]benzodioxadiazacyclotridecin-4(5H)-one; 12-chloro-11-fluoro-7-methyl-6,7-dihydro-13H-1,15-ethenopyrazolo[4,3-f][1,10,4,8]benzodioxadiazacyclotridecin-4(5H)-one; (8R)-9-chloro-10-fluoro-8-methyl-15,16-dihydro-8H-3,6-ethenoimidazo[5,1-f][1,10,4,7,8]benzodioxatriazacyclotridecin-17(14H)-one; 9-chloro-10-fluoro-8-methyl-15,16-dihydro-8H-3,6-ethenoimidazo[5,1-f][1,10,4,7,8]benzodioxatriazacyclotridecin-17(14H)-one; (7R)-8-chloro-9-fluoro-7-methyl-14,15-dihydro-2H,7H-3,5-(azenometheno)pyrrolo[3,4-f][1,10,4,8]benzodioxadiazacyclotridecin-16(13H)-one; 8-chloro-9-fluoro-7-methyl-14,15-dihydro-2H,7H-3,5-(azenometheno)pyrrolo[3,4-f][1,10,4,8]benzodioxadiazacyclotridecin-16(13H)-one; (5R)-3-fluoro-5-methyl-14,15-dihydro-5H,10H-9,7-(azenometheno)pyrido[2,3-k]pyrrolo[3,4-d][1,10,3,7]dioxadiazacyclotridecin-12(13H)-one; 3-fluoro-5-methyl-14,15-dihydro-5H,10H-9,7-(azenometheno)pyrido[2,3-k]pyrrolo[3,4-d][1,10,3,7]dioxadiazacyclotridecin-12(13H)-one; (5R)-3-fluoro-5,16-dimethyl-13,14,15,16-tetrahydro-5H-9,7-(azenometheno)pyrido[2,3-k]pyrrolo[3,4-d][1,3,7,10]oxatriazacyclotridecin-12(10H)-one; 3-fluoro-5,16-dimethyl-13,14,15,16-tetrahydro-5H-9,7-(azenometheno)pyrido[2,3-k]pyrrolo[3,4-d][1,3,7,10]oxatriazacyclotridecin-12(10H)-one; (13R)-12-chloro-11-fluoro-5,13-dimethyl-6,7-dihydro-2H,3H-1,15-(azenometheno)pyrrolo[3,4-f][1,10,4]benzodioxazacyclotridecin-4(5H)-one; 12-chloro-11-fluoro-5,13-dimethyl-6,7-dihydro-2H,13H-1,15-(azenometheno)pyrrolo[3,4-f][1,10,4]benzodioxazacyclotridecin-4(5H)-one; (7R)-8-chloro-9-fluoro-7,15-dimethyl-14,15-dihydro-2H,7H-3,5-(azenometheno)pyrazolo[3,4-f][1,10,4]benzodioxazacyclotridecin-16(13H)-one; 8-chloro-9-fluoro-7,15-dimethyl-14,15-dihydro-2H,7H-3,5-(azenometheno)pyrazolo[3,4-f][1,10,4]benzodioxazacyclotridecin-16(13H)-one; 11-fluoro-14-methyl-6,7,13,14-tetrahydro-1,15-ethenopyrazolo[4,3-f][1,4,8,10]benzoxatriazacyclotridecin-4(5H)-one; (13R)-12-chloro-11-fluoro-13,14-dimethyl-6,7,13,14-tetrahydro-1,15-ethenopyrazolo[4,3-f][1,4,8,10]benzoxatriazacyclotridecin-4(5H)-one; 12-chloro-11-fluoro-13,14-dimethyl-6,7,13,14-tetrahydro-1,15-ethenopyrazolo[4,3-f][1,4,8,10]benzoxatriazacyclotridecin-4(5H)-one; 12-chloro-11-fluoro-5,14-dimethyl-6,7,13,14-tetrahydro-15,1-(azenometheno)pyrazolo[4,3-f][1,4,10]benzoxadiazacyclotridecin-4(5H)-one; 12-chloro-11-fluoro-14-methyl-6,7,13,14-tetrahydro-15,1-(azenometheno)pyrazolo[4,3-f][1,4,8,10]benzoxatriazacyclotridecin-4(5H)-one; 12-chloro-11-fluoro-14-methyl-6,7,13,14-tetrahydro-1,15-(azenometheno)pyrrolo[3,2-f][1,4,8,10]benzoxatriazacyclotridecin-4(5H')-one; 12-chloro-11-fluoro-14-methyl-6,7,13,14-tetrahydro-1,15-(azenometheno)pyrrolo[3,2-f][1,4,10]benzoxadiazacyclotridecin-4(5H)-one; 9-chloro-10-fluoro-7-methyl-7,8,15,16-tetrahydro-3,6-ethenoimidazo[5,1-f][1,4,7,8,10]benzoxatetraazacyclotridecin-17(14H)-one; 9-chloro-10-fluoro-7-methyl-7,8,15,16-tetrahydro-6,3-(azenometheno)imidazo[5,1-f][1,4,7,8,10]benzoxatetraazacyclotridecin-17(14H)-one; 9-chloro-10-fluoro-7-methyl-7,8,15,16-tetrahydro-6,3-(azenometheno)imidazo[5,1-f][1,4,7,10]benzoxatriazacyclotridecin-17(14H)-one; 9-chloro-10-fluoro-7-methyl-7,8,15,16-tetrahydro-3,6-(azenometheno)pyrrolo[2,1-f][1,4,7,10]benzoxatriazacyclotridecin-17(14H)-one; 9-chloro-10-fluoro-7-methyl-7,8,15,16-tetrahydro-3,6-(azenometheno)imidazo[2,1-f][1,4,7,10]benzoxatriazacyclotridecin-17(14H)-one; 9-chloro-10-fluoro-7-methyl-7,8,15,16-tetrahydro-3,6-etheno[1,2,4]triazolo[3,4-f][1,4,7,8,10]benzoxatetraazacyclotridecin-17(14H)-one; 9-chloro-10-fluoro-7-methyl-7,8,15,16-tetrahydro-6,3-(azenometheno)[1,2,4]triazolo[3,4-f][1,4,7,10]benzoxatriazacyclotridecin-17(14H)-one; 8-chloro-9-fluoro-6-methyl-6,7,14,15-tetrahydro-2H-3,5-(azenometheno)pyrrolo[3,4-f][1,4,8,10]benzoxatriazacyclotridecin-16(13H)-one; 8-chloro-9-fluoro-6-methyl-6,7,14,15-tetrahydro-2H-3,5-(azenometheno)pyrazolo[3,4-f][1,4,8,10]benzoxatriazacyclotridecin-16(13H)-one; 8-chloro-9-fluoro-6-methyl-6,7,14,15-tetrahydro-2H-3,5-(azenometheno)pyrazolo[3,4-f][1,4,10]benzoxadiazacyclotridecin-16(13H)-one; 12-chloro-11-fluoro-5,14-dimethyl-6,7,13,14-tetrahydro-2H-1,15-(azenometheno)pyrrolo[3,4-f][1,4,10]benzoxadiazacyclotridecin-4(5H)-one; (8R)-10-fluoro-8,16-dimethyl-15,16-dihydro-8H-3,6-ethenoimidazo[5,1-f][1,10,4,7,8]benzodioxatriazacyclotridecin-17(14H)-one; 10-fluoro-8,16-dimethyl-15,16-dihydro-8H-3,6-ethenoimidazo[5,1-f][1,10,4,7,8]benzodioxatriazacyclotridecin-17(14H)-one; (7R)-9-fluoro-7,15-dimethyl-14,15-dihydro-2H,7H-3,5-(azenometheno)pyrrolo[3,4-f][1,10,4,8]benzodioxadiazacyclotridecin-16(13H)-one; and 9-fluoro-7,15-dimethyl-14,15-dihydro-2H,7H-3,5-(azenometheno)

pyrrolo[3,4-f][1,10,4,8]benzodioxadiazacyclotridecin-16 (13H)-one; or a pharmaceutically acceptable salt thereof.

In other embodiments, the compound of Formula (I) or (I-A) is selected from the group consisting of 12-chloro-11-fluoro-14-methyl-6,7,13,14-tetrahydro-1,15-ethenopyrazolo [4,3-f][1,4,8,10]benzoxatriazacyclotridecin-4(5H)-one; 11-fluoro-3,14-dimethyl-6,7,13,14-tetrahydro-1,15-ethenopyrazolo[4,3-f][1,4,8,10]benzoxatriazacyclotridecin-4(5H)-one; 10-fluoro-8-methyl-15,16-dihydro-8H-3,6-ethenoimidazo[5,1-f][1,10,4,7,8]benzodioxatriazacyclotridecin-17 (14H)-one; 10-fluoro-7-methyl-7,8,15,16-tetrahydro-3,6-ethenoimidazo[5,1-f][1,4,7,8,10]benzoxatetraazacyclotridecin-17(14H)-one; 14-ethyl-11-fluoro-6,7,13,14-tetrahydro-1,15-ethenopyrazolo[4,3-f][1,4,8,10]benzoxatriazacyclotridecin-4(5H1)-one; 11-fluoro-14-propyl-6,7,13,14-tetrahydro-1,15-ethenopyrazolo[4,3-f][1,4,8,10]benzoxatriazacyclotridecin-4(5H)-one; 11-fluoro-14-(propan-2-yl)-6,7,13,14-tetrahydro-1,15-ethenopyrazolo[4,3-f][1,4,8,10]benzoxatriazacyclotridecin-4(5H)-one; 14-cyclopropyl-11-fluoro-6,7,13,14-tetrahydro-1,15-ethenopyrazolo[4,3-f][1,4,8,10]benzoxatriazacyclotridecin-4 (51H)-one; 11-fluoro-14-(2-hydroxyethyl)-6,7,13,14-tetrahydro-1,15-ethenopyrazolo[4,3-f][1,4,8,10]benzoxatriazacyclotridecin-4(5H)-one; 11-fluoro-6,14-dimethyl-6,7,13,14-tetrahydro-1,15-ethenopyrazolo[4,3-f][1,4,8,10]benzoxatriazacyclotridecin-4(5H)-one; 14-methyl-6,7,13,14-tetrahydro-1,15-ethenopyrazolo[4,3-f][1,4,8,10]benzoxatriazacyclotridecin-4(5H)-one; 11-fluoro-6,7,13,14-tetrahydro-1,15-ethenopyrazolo[4,3-f][1,4,8,10]benzoxatriazacyclotridecin-4(5H)-one; 11-fluoro-13-methyl-6,7,13,14-tetrahydro-1,15-ethenopyrazolo[4,3-f][1,4,8,10]benzoxatriazacyclotridecin-4(5H)-one; (13R)-11-fluoro-13-methyl-6,7,13,14-tetrahydro-1,15-ethenopyrazolo[4,3-l][1,4,8,10]benzoxatriazacyclotridecin-4(5H)-one; 12-chloro-11-fluoro-13-methyl-6,7,13,14-tetrahydro-1,15-ethenopyrazolo[4,3-f][1,4,8,10]benzoxatriazacyclotridecin-4(5H)-one; 11-fluoro-14-methyl-4-oxo-4,5,6,7,13,14-hexahydro-1,15-ethenopyrazolo[4,3-f][1,4,8,10]benzoxatriazacyclotridecine-7-carboxamide; 11-fluoro-7-(hydroxymethyl)-14-methyl-6,7,13,14-tetrahydro-1,15-ethenopyrazolo[4,3-f][1,4,8,10]benzoxatriazacyclotridecin-4(5H)-one; 11-fluoro-13-methyl-4-oxo-4,5,6,7,13,14-hexahydro-1,15-ethenopyrazolo[4,3-f][1,4,8,10]benzoxatriazacyclotridecine-7-carboxamide; 11-fluoro-7-(hydroxymethyl)-13-methyl-6,7,13,14-tetrahydro-1,15-ethenopyrazolo[4,3-f][1,4,8,10]benzoxatriazacyclotridecin-4(5H)-one; 11-fluoro-4-oxo-4,5,6,7,13,14-hexahydro-1,15-ethenopyrazolo[4,3-f][1,4,8,10]benzoxatriazacyclotridecine-7-carboxamide; 11-fluoro-7-(hydroxymethyl)-6,7,13,14-tetrahydro-1,15-ethenopyrazolo[4,3-f][1,4,8,10]benzoxatriazacyclotridecin-4(5H)-one; methyl 11-fluoro-4-oxo-4,5,6,7,13,14-hexahydro-1,15-ethenopyrazolo[4,3-f][1,4,8,10]benzoxatriazacyclotridecine-13-carboxylate; 11-fluoro-4-oxo-4,5,6,7,13,14-hexahydro-1,15-ethenopyrazolo[4,3-f][1,4,8,10]benzoxatriazacyclotridecine-13-carboxamide; 11-fluoro-14-methyl-6,7,13,14-tetrahydro-1,15-ethenopyrazolo[4,3-f]pyrido[3,2-l][1,4,8,10]oxatriazacyclotridecin-4(5H)-one; 11-fluoro-13-methyl-6,7,13,14-tetrahydro-1,15-ethenopyrazolo[4,3-f]pyrido[3,2-l][1,4,8,10]oxatriazacyclotridecin-4(5H)-one; 11-fluoro-13-(propan-2-yl)-6,7,13,14-tetrahydro-1,15-ethenopyrazolo[4,3-f]pyrido[3,2-l][1,4,8,10]oxatriazacyclotridecin-4(5H)-one; 13-cyclopropyl-11-fluoro-6,7,13,14-tetrahydro-1,15-ethenopyrazolo[4,3-f]pyrido[3,2-l][1,4,8,10]oxatriazacyclotridecin-4(5H)-one; 13-cyclopropyl-11-fluoro-6,7,13,14-tetrahydro-1,15-ethenopyrazolo[4,3-f][1,4,8,10]benzoxatriazacyclotridecin-4 (5H)-one; 11-fluoro-13-(propan-2-yl)-6,7,13,14-tetrahydro-1,15-ethenopyrazolo[4,3-f][1,4,8,10] benzoxatriazacyclotridecin-4(5H)-one; 11-fluoro-6,7-dihydro-13H-1,15-ethenopyrazolo[4,3-f][1,10,4,8] benzoxathiadiazacyclotridecin-4(5H)-one; 11-fluoro-6,7-dihydro-13H-1,15-ethenopyrazolo[4,3-f][1,10,4,8] benzoxathiadiazacyclotridecin-4(5H)-one 14,14-dioxide; 6,7-dihydro-13H-1,15-ethenopyrazolo[4,3-f][10,1,4,8]benzoxathiadiazacyclotridecin-4(5H)-one; 14-methyl-6,7,13, 14-tetrahydro-1,15-ethenopyrazolo[4,3-f][1,4,8,10]benzothiatriazacyclotridecin-4(5H)-one; 13-methyl-6,7,13,14-tetrahydro-1,15-ethenopyrazolo[4,3-f][1,4,8,10]benzothiatriazacyclotridecin-4(5H)-one; 11-fluoro-6,7-dihydro-5H-1,15-ethenopyrazolo[3,4-e][11,1,2,4,8] benzoxathiatriazacyclotridecin-4(14H)-one 13,13-dioxide; 11-fluoro-14-methyl-6,7-dihydro-5H-1,15-ethenopyrazolo [3,4-e][11,1,2,4,8]benzoxathiatriazacyclotridecin-4(14H)-one 13,13-dioxide; 12-fluoro-15-methyl-5,6,7,8,14,15-hexahydro-4H-1,16-ethenopyrazolo[4,3-g][1,5,9,11] benzoxatriazacyclotetradecin-4-one; 12-fluoro-14-methyl-5,6,7,8,14,15-hexahydro-4H-1,16-ethenopyrazolo[4,3-g][1, 5,9,11]benzoxatriazacyclotetradecin-4-one; (14R)-12-fluoro-14-methyl-5,6,7,8,14,15-hexahydro-4H-1,16-ethenopyrazolo[4,3-g][1,5,9,11] benzoxatriazacyclotetradecin-4-one; 11-fluoro-7,14-dimethyl-4,5,6,7,13,14-hexahydro-8H-1,15-ethenopyrazolo [3,4-e][2,4,10]benzotriazacyclotridecin-8-one; 11-fluoro-7,14-dimethyl-6,7,13,14-tetrahydro-1,15-ethenopyrazolo[3,4-e][7,2,4,10]benzoxatriazacyclotridecin-8(5H)-one; 11-fluoro-7,14-dimethyl-4,5,6,7,13,14-hexahydro-8H-1,15-ethenopyrazolo[3,4-e][2,4,7,10]benzotetraazacyclotridecin-8-one; 11-fluoro-4,7,14-trimethyl-4,5,6,7,13,14-hexahydro-8H-1,15-ethenopyrazolo[3,4-e][2,4,7,10] benzotetraazacyclotridecin-8-one; 11-fluoro-7,14-dimethyl-6,7,13,14-tetrahydro-1,15-ethenopyrazolo[3,4-e][7,2,4,10] benzothiatriazacyclotridecin-8(5H)-one; 11-fluoro-7,14-dimethyl-6,7,13,14-tetrahydro-1,15-ethenopyrazolo[3,4-e] [7,2,4,10]benzothiatriazacyclotridecin-8(5H)-one 4,4-dioxide; and 12-fluoro-8,15-dimethyl-5,6,7,8,14,15-hexahydro-9H-1,16-ethenopyrazolo[3,4-e][7,2,4,8,11] benzothiatetraazacyclotetradecin-9-one 4,4-dioxide; or a pharmaceutically acceptable salt thereof.

In other embodiments, the compound of Formula (I) or (I-A) is selected from the group consisting of 11-chloro-13-methyl-6,7,13,14-tetrahydro-1,15-ethenopyrazolo[4,3-f][1, 4,8,10]benzoxatriazacyclotridecin-4(5H)-one; 13-ethyl-li-fluoro-6,7,13,14-tetrahydro-1,15-ethenopyrazolo[4,3-f][1,4, 8,10]benzoxatriazacyclotridecin-4(5H)-one; 13-cyclobutyl-11-fluoro-6,7,13,14-tetrahydro-1,15-ethenopyrazolo[4,3-f] [1,4,8,10]benzoxatriazacyclotridecin-4(5H)-one; 11-fluoro-14-methyl(6,6,7,7-$^2$H$_4$)-6,7,13,14-tetrahydro-1,15-ethenopyrazolo[4,3-f][1,4,8,10]benzoxatriazacyclotridecin-4(5H)-one; 11-fluoro-13-phenyl-6,7,13,14-tetrahydro-1,15-ethenopyrazolo[4,3-f][1,4,8,10]benzoxatriazacyclotridecin-4(5H)-one; 13-(cyclopropylmethyl)-11-fluoro-6,7,13,14-tetrahydro-1,15-ethenopyrazolo[4,3-f][1,4,8,10] benzoxatriazacyclotridecin-4(5H)-one; (7R,14R)-12-fluoro-7-hydroxy-14-methyl-5,6,7,8,14,15-hexahydro-4H-1,16-ethenopyrazolo[4,3-g][1,5,9,11] benzoxatriazacyclotetradecin-4-one; (7S,14R)-12-fluoro-7-hydroxy-14-methyl-5,6,7,8,14,15-hexahydro-4H-1,16-ethenopyrazolo[4,3-g][1,5,9,11] benzoxatriazacyclotetradecin-4-one; (7R,13R)-11-fluoro-7,13-dimethyl-6,7,13,14-tetrahydro-1,15-ethenopyrazolo[4,3-f][1,4,8,10]benzoxatriazacyclotridecin-4(5H)-one; (7S,13R)-11-fluoro-7,13-dimethyl-6,7,13,14-tetrahydro-1,15-ethenopyrazolo[4,3-l][1,4,8,10]benzoxatriazacyclotridecin- 4(5H)-one; (7R)-11-fluoro-7,14-dimethyl-6,7,13,14-tetrahydro-1,15-ethenopyrazolo[4,3-f][1,4,8,10]benzoxatriazacyclotridecin-4(5H)-one; (6R)-11-fluoro-6,14-dimethyl-6,7,13,14-tetrahydro-1,15-ethenopyrazolo[4,3-f][1,4,8,10]benzoxatriazacyclotridecin-4(5H)-one; 12-fluoro-7-hydroxy-15-methyl-5,6,7,8,14,15-hexahydro-4H-1,16-ethenopyrazolo[4,3-g][1,5,9,11]benzoxatriazacyclotetradecin-4-one; (7S)-11-fluoro-7,14-dimethyl-6,7,13,14-tetrahydro-1,15-ethenopyrazolo[4,3-f][1,4,8,10]benzoxatriazacyclotridecin-4(5H)-one; 11-fluoro-13-(hydroxymethyl)-6,7,13,14-tetrahydro-1,15-ethenopyrazolo[4,3-f][1,4,8,10]benzoxatriazacyclotridecin-4(5H)-one; 12-fluoro-14-(hydroxymethyl)-5,6,7,8,14,15-hexahydro-4H-1,16-ethenopyrazolo[4,3-g][1,5,9,11]benzoxatriazacyclotetradecin-4-one; 11-fluoro-13,14-dimethyl-6,7,13,14-tetrahydro-1,15-ethenopyrazolo[4,3-f][1,4,8,10]benzoxatriazacyclotridecin-4(5H)-one; 11-fluoro-14-(2-hydroxy-2-methylpropyl)-6,7,13,14-tetrahydro-1,15-ethenopyrazolo[4,3-f][1,4,8,10]benzoxatriazacyclotridecin-4(5H)-one; 12-fluoro-5,6,7,8,14,15-hexahydro-4H-1,16-ethenopyrazolo[4,3-g][1,5,9]benzoxadiazacyclotetradecin-4-one; 11-fluoro-14-methyl-6,7,13,14-tetrahydro-1,15-ethenopyrazolo[4,3-J][1,4,8,10]benzothiatriazacyclotridecin-4(5H)-one; 11-fluoro-14-(1-methylpyrrolidin-3-yl)-6,7,13,14-tetrahydro-1,15-ethenopyrazolo[4,3-f][1,4,8,10]benzoxatriazacyclotridecin-4(5H)-one; 11-fluoro-14-methyl-6,7,13,14-tetrahydro-1,15-ethenopyrazolo[4,3-f][1,4,8,10]benzothiatriazacyclotridecin-4(5H)-one 8-oxide; 11-fluoro-14-methyl-6,7,13,14-tetrahydro-1,15-ethenopyrazolo[4,3-fj][1,4,8,10]benzothiatriazacyclotridecin-4(5H)-one 8,8-dioxide; (7S)-11-fluoro-7-methyl-6,7,13,14-tetrahydro-1,15-ethenopyrazolo[4,3-f][1,4,8]benzoxadiazacyclotridecin-4(5H)-one; (6S,13R)-11-fluoro-6,13-dimethyl-6,7,13,14-tetrahydro-1,15-ethenopyrazolo[4,3-f][1,4,8,10]benzoxatriazacyclotridecin-4(5H)-one; (6R,13R)-11-fluoro-6,13-dimethyl-6,7,13,14-tetrahydro-1,15-ethenopyrazolo[4,3-f][1,4,8,10]benzoxatriazacyclotridecin-4(5H)-one; (7S,13S)-11-fluoro-13-(hydroxymethyl)-7-methyl-6,7,13,14-tetrahydro-1,15-ethenopyrazolo[4,3-f][1,4,8,10]benzoxatriazacyclotridecin-4(5H)-one; and 11-fluoro-6,7-dihydro-13H-1,15-ethenopyrazolo[4,3-f][1,10,4,8]benzoxathiadiazacyclotridecin-4(5H)-one; or a pharmaceutically acceptable salt thereof.

In other embodiments, the compound of Formula (I) or (I-A) is selected from the group consisting of (13R)-5,13-dimethyl-6,7-dihydro-13H-1,15-ethenopyrazolo[4,3-f][1,10,4,8]benzodioxadiazacyclotridecin-4(5H)-one; (13R)-11-fluoro-5,13-dimethyl-6,7-dihydro-13H-1,15-ethenopyrazolo[4,3-f][1,10,4,8]benzodioxadiazacyclotridecin-4(5H)-one; (13R)-12-chloro-11-fluoro-5,13-dimethyl-6,7-dihydro-13H-1,15-ethenopyrazolo[4,3-f][1,10,4,8]benzodioxadiazacyclotridecin-4(5H)-one; (13R)-12-chloro-11-fluoro-5-(2-hydroxyethyl)-13-methyl-6,7-dihydro-13H-1,15-ethenopyrazolo[4,3-f][1,10,4,8]benzodioxadiazacyclotridecin-4(5H)-one; 2-[(13R)-12-chloro-11-fluoro-13-methyl-4-oxo-6,7-dihydro-13H-1,15-ethenopyrazolo[4,3-f][1,10,4,8]benzodioxadiazacyclotridecin-5(4H)-yl]acetamide; (13R)-12-chloro-11-fluoro-13-methyl-5-(pyrrolidin-2-ylmethyl)-6,7-dihydro-13H-1,15-ethenopyrazolo[4,3-f][1,10,4,8]benzodioxadiazacyclotridecin-4(5H)-one; (13R)-12-chloro-11-fluoro-7-(hydroxymethyl)-5,13-dimethyl-6,7-dihydro-13H-1,15-ethenopyrazolo[4,3-f][1.10.4.8]benzodioxadiazacyclotridecin-4(5H)-one; (13S)-11-fluoro-13-(fluoromethyl)-5-methyl-6,7-dihydro-13H-1,15-ethenopyrazolo[4,3-f][1,10,4,8]benzodioxadiazacyclotridecin-4(5H)-one; (13R)-13-cyclopropyl-11-fluoro-5-methyl-6,7-dihydro-13H-1,15-ethenopyrazolo[4,3-f][1,10,4,8]benzodioxadiazacyclotridecin-4(5H)-one; (13R)-11-fluoro-13-methyl-6,7-dihydro-13H-1,15-ethenopyrazolo[4,3-f][1,10,4,8]benzodioxadiazacyclotridecin-4(5H)-one; (13R)-12-chloro-11-fluoro-13-methyl-6,7-dihydro-313H-1,15-ethenopyrazolo[4,3-f][1,10,4,8]benzodioxadiazacyclotridecin-4(5H)-one; (8R)-9-chloro-10-fluoro-8-methyl-15,16-dihydro-8H-3,6-ethenoimidazo[5,1-f][1,10,4,7,8]benzodioxatriazacyclotridecin-17(14H)-one; (7R)-8-chloro-9-fluoro-7-methyl-14,15-dihydro-2H,7H-3,5-(azenometheno)pyrrolo[3,4-f][1,10,4,8]benzodioxadiazacyclotridecin-16(13H)-one; (5R)-3-fluoro-5-methyl-14,15-dihydro-5H,10H-9,7-(azenometheno)pyrido[2,3-k]pyrrolo[3,4-d][1,10,3,7]dioxadiazacyclotridecin-12(13H)-one; (5R)-3-fluoro-5,16-dimethyl-13,14,15,16-tetrahydro-5H-9,7-(azenometheno)pyrido[2,3-k]pyrrolo[3,4-d][1,3,7,10]oxatriazacyclotridecin-12(10H)-one; (13R)-12-chloro-11-fluoro-5,13-dimethyl-6,7-dihydro-2H,13H-1,15-(azenometheno)pyrrolo[3,4-f][1,10,4]benzodioxazacyclotridecin-4(5H)-one; (7R)-8-chloro-9-fluoro-7,15-dimethyl-14,15-dihydro-2H,7H-3,5-(azenometheno)pyrazolo[3,4-f][1,10,4]benzodioxazacyclotridecin-16(13H)-one; (13R)-12-chloro-11-fluoro-13,14-dimethyl-6,7,13,14-tetrahydro-1,15-ethenopyrazolo[4,3-f][1,4,8,10]benzoxatriazacyclotridecin-4(5H)-one; (8R)-10-fluoro-8,16-dimethyl-15,16-dihydro-8H-3,6-ethenoimidazo[5,1-f][1,10,4,7,8]benzodioxatriazacyclotridecin-17(14H)-one; (7R)-9-fluoro-7,15-dimethyl-14,15-dihydro-2H,7H-3,5-(azenometheno)pyrazolo[3,4-f][1,10,4,8]benzodioxadiazacyclotridecin-16(13H)-one; (13R)-11-fluoro-13-methyl-6,7,13,14-tetrahydro-1,15-ethenopyrazolo[4,3-f][1,4,8,10]benzoxatriazacyclotridecin-4(5H)-one; (14R)-12-fluoro-14-methyl-5,6,7,8,14,15-hexahydro-4H-1,16-ethenopyrazolo[4,3-g][1,5,9,11]benzoxatriazacyclotetradecin-4-one; (7R,14R)-12-fluoro-7-hydroxy-14-methyl-5,6,7,8,14,15-hexahydro-4H-1,16-ethenopyrazolo[4,3-g][1,5,9,11]benzoxatriazacyclotetradecin-4-one; (7S,14R)-12-fluoro-7-hydroxy-14-methyl-5,6,7,8,14,15-hexahydro-4H-1,16-ethenopyrazolo[4,3-f][1,5,9,11]benzoxatriazacyclotetradecin-4-one; (7R,13R)-11-fluoro-7,13-dimethyl-6,7,13,14-tetrahydro-1,15-ethenopyrazolo[4,3-f][1,4,8,10]benzoxatriazacyclotridecin-4(5H)-one; (7S,13R)-11-fluoro-7,13-dimethyl-6,7,13,14-tetrahydro-1,15-ethenopyrazolo[4,3-f][1,4,8,10]benzoxatriazacyclotridecin-4(5H)-one; (7R)-11-fluoro-7,14-dimethyl-6,7,13,14-tetrahydro-1,15-ethenopyrazolo[4,3-f][1,4,8,10]benzoxatriazacyclotridecin-4(5H)-one; (6R)-11-fluoro-6,14-dimethyl-6,7,13,14-tetrahydro-1,15-ethenopyrazolo[4,3-f][1,4,8,10]benzoxatriazacyclotridecin-4(5H)-one; (7S)-11-fluoro-7,14-dimethyl-6,7,13,14-tetrahydro-1,15-ethenopyrazolo[4,3-f][1,4,8,10]benzoxatriazacyclotridecin-4(5H)-one; (7S)-11-fluoro-7-methyl-6,7,13,14-tetrahydro-1,15-ethenopyrazolo[4,3-f][1,4,8]benzoxadiazacyclotridecin-4(5H)-one; (6S,13R)-11-fluoro-6,13-dimethyl-6,7,13,14-tetrahydro-1,15-ethenopyrazolo[4,3-f][1,4,8,10]benzoxatriazacyclotridecin-4(5H)-one; (6R,13R)-11-fluoro-6,13-dimethyl-6,7,13,14-tetrahydro-1,15-ethenopyrazolo[4,3-f][1,4,8,10]benzoxatriazacyclotridecin-4(5H)-one; and (7S,13S)-11-fluoro-13-(hydroxymethyl)-7-methyl-6,7,13,14-tetrahydro-1,15-ethenopyrazolo[4,3-][1,4,8,10]benzoxatriazacyclotridecin-4(5H)-one; or a pharmaceutically acceptable salt thereof.

The following represent illustrative embodiments of compounds of Formula (I) or (I-A):

| Ex. | Structure | Chemical Name |
|---|---|---|
| 1 | 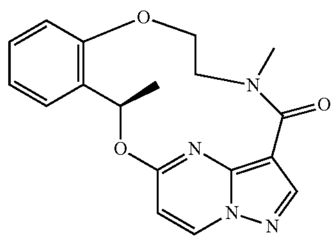 [SMILES: C[C@H]1Oc2ccn3ncc(c3n2)C(=O)N(C)CCOc2ccccc21] | (13R)-5,13-dimethyl-6,7-dihydro-13H-1,15-ethenopyrazolo[4,3-f][1,10,4,8]benzodioxadiazacyclotridecin-4(5H)-one |
| 1-1 | 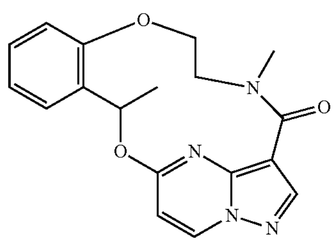 [SMILES: CC1Oc2ccn3ncc(c3n2)C(=O)N(C)CCOc2ccccc21] | 5,13-dimethyl-6,7-dihydro-13H-1,15-ethenopyrazolo[4,3-f][1,10,4,8]benzodioxadiazacyclotridecin-4(5H)-one |
| 2 | 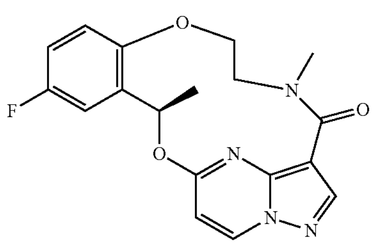 [SMILES: C[C@H]1Oc2ccn3ncc(c3n2)C(=O)N(C)CCOc2ccc(F)cc21] | (1,3R)-11-fluoro-5,13-dimethyl-6,7-dihydro-13H-1,15-ethenopyrazolo[4,3-f][1,10,4,8]benzodioxadiazacyclotridecin-4(5H)-one |
| 2-1 | 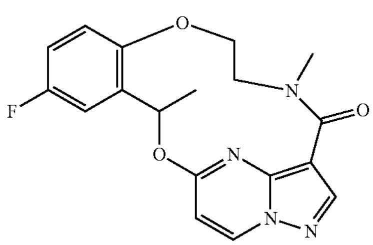 [SMILES: CC1Oc2ccn3ncc(c3n2)C(=O)N(C)CCOc2ccc(F)cc21] | 11-fluoro-5,13-dimethyl-6,7-dihydro-13H-1,15-ethenopyrazolo[4,3-f][1,10,4,8]benzodioxadiazacyclotridecin-4(5H)-one |
| 3 | 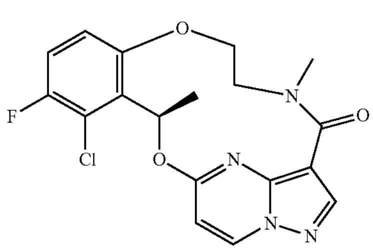 [SMILES: C[C@H]1Oc2ccn3ncc(c3n2)C(=O)N(C)CCOc2ccc(F)c(Cl)c21] | (13R)-12-chloro-11-fluoro-5,13-dimethyl-6,7-dihydro-13H-1,15-ethenopyrazolo[4,3-f][1,10,4,8]benzodioxadiazacyclotridecin-4(5H)-one |
| 3-1 | 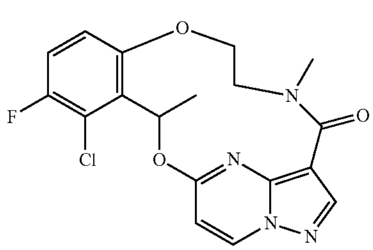 [SMILES: CC1Oc2ccn3ncc(c3n2)C(=O)N(C)CCOc2ccc(F)c(Cl)c21] | 12-chloro-11-fluoro-5,13-dimethyl-6,7-dihydro-13H-1,15-ethenopyrazolo[4,3-f][1,10,4,8]benzodioxadiazacyclotridecin-4(5H)-one |

-continued

| Ex. | Structure | Chemical Name |
|---|---|---|
| 4 | 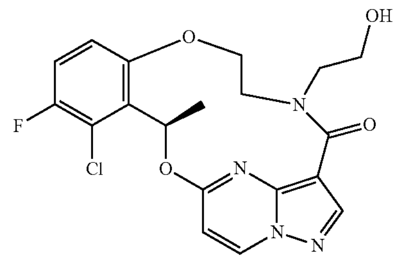 [SMILES: C[C@H]1Oc2ccn3ncc(c3n2)C(=O)N(CCO)CCOc2ccc(F)c(Cl)c21] | (13R)-12-chloro-11-fluoro-5-(2-hydroxyethyl)-13-methyl-6,7-dihydro-13H-1,15-ethenopyrazolo[4,3-f][1,10,4,8]benzodioxadiazacyclotridecin-4(5H)-one |
| 4-1 | 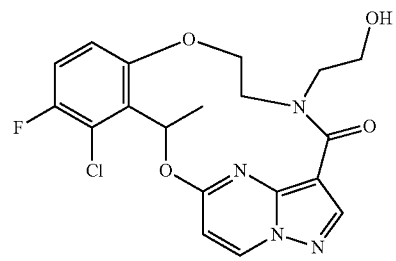 [SMILES: CC1Oc2ccn3ncc(c3n2)C(=O)N(CCO)CCOc2ccc(F)c(Cl)c21] | 12-chloro-11-fluoro-5-(2-hydroxyethyl)-13-methyl-6,7-dihydro-13H-1,15-ethenopyrazolo[4,3-f][1,10,4,8]benzodioxadiazacyclotridecin-4(5H)-one |
| 5 | 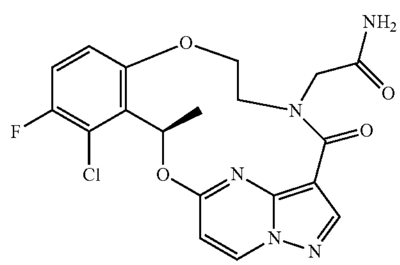 [SMILES: C[C@H]1Oc2ccn3ncc(c3n2)C(=O)N(CC(N)=O)CCOc2ccc(F)c(Cl)c21] | 2-[(13R)-12-chloro-11-fluoro-13-methyl-4-oxo-6,7-dihydro-13H-1,15-ethenopyrazolo[4,3-f][1,10,4,8]benzodioxadiazacyclotridecin-5(4H)-yl]acetamide |
| 5-1 | 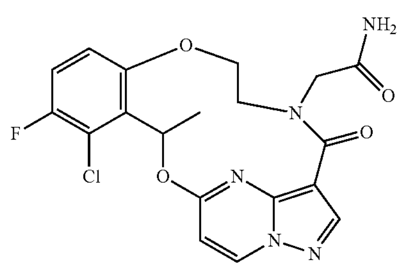 [SMILES: CC1Oc2ccn3ncc(c3n2)C(=O)N(CC(N)=O)CCOc2ccc(F)c(Cl)c21] | 2-[12-chloro-11-fluoro-13-methyl-4-oxo-6,7-dihydro-13H-1,15-ethenopyrazolo[4,3-f][1,10,4,8]benzodioxadiazacyclotridecin-5(4H)-yl]acetamide |
| 6 | 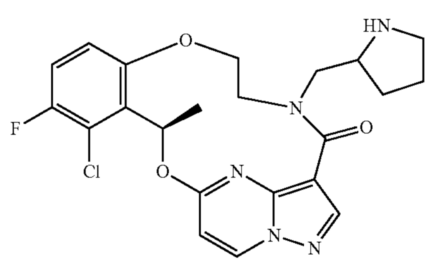 [SMILES: C[C@H]1Oc2ccn3ncc(c3n2)C(=O)N(CC2CCCN2)CCOc2ccc(F)c(Cl)c21] | (13R)-12-chloro-11-fluoro-13-methyl-5-(pyrrolidin-2-ylmethyl)-6,7-dihydro-13H-1,5-ethenopyrazolo[4,3-f][1,10,4,8]benzodioxadiazacyclotridecin-4(5H)-one |
| 6-1 | 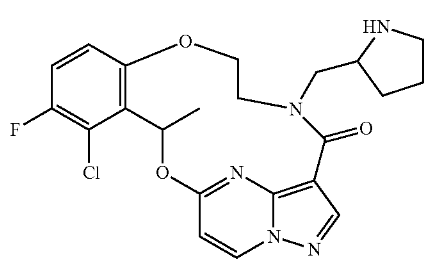 [SMILES: CC1Oc2ccn3ncc(c3n2)C(=O)N(CC2CCCN2)CCOc2ccc(F)c(Cl)c21] | 12-chloro-11-fluoro-13-methyl-5-(pyrrolidin-2-ylmethyl)-6,7-dihydro-13H-1,15-ethenopyrazolo[4,3-f][1,10,4,8]benzodioxadiazacyclotridecin-4(5H)-one |

-continued

| Ex. | Structure | Chemical Name |
|---|---|---|
| 7 | 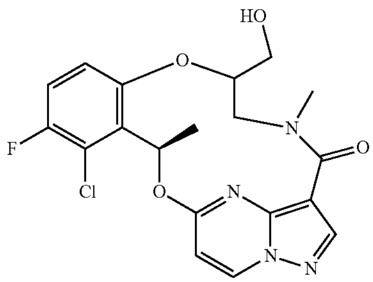 [SMILES: C[C@H]1Oc2ccn3ncc(c3n2)C(=O)N(C)CC(CO)Oc2ccc(F)c(Cl)c21] | (13R)-12-chloro-11-fluoro-7-(hydroxymethyl)-5,13-dimethyl-6,7-dihydro-13H-1,15-ethenopyrazolo[4,3-f][1,10,4,8]benzodioxadiazacyclotridecin-4(5H)-one |
| 7-1 | 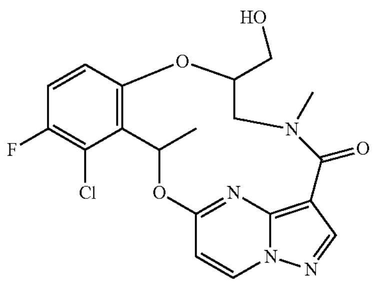 [SMILES: CC1Oc2ccn3ncc(c3n2)C(=O)N(C)CC(CO)Oc2ccc(F)c(Cl)c21] | 12-chloro-11-fluoro-7-(hydroxymethyl)-5,13-dimethyl-6,7-dihydro-13H-1,15-ethenopyrazolo[4,3-f][1,10,4,8]benzodioxadiazacyclotridecin-4(5H)-one |
| 8 | 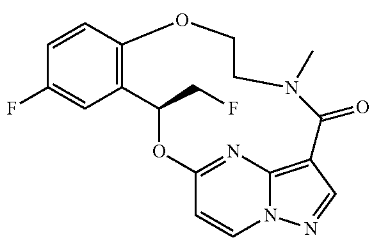 [SMILES: CN1CCOc2ccc(F)cc2[C@@H](CF)Oc2ccn3ncc(c3n2)C1=O] | (13S)-11-fluoro-13-(fluoromethyl)-5-methyl-6,7-dihydro-13H-1,15-ethenopyrazolo[4,3-f][1,10,4,8]benzodioxadiazacyclotridecin-4(5H)-one |
| 8-1 | 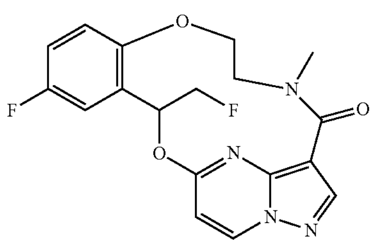 [SMILES: CN1CCOc2ccc(F)cc2C(CF)Oc2ccn3ncc(c3n2)C1=O] | 11-fluoro-13-(fluoromethyl)-5-methyl-6,7-dihydro-13H-1,15-ethenopyrazolo[4,3-f][1,10,4,8]benzodioxadiazacyclotridecin-4(5H)-one |
| 9 | 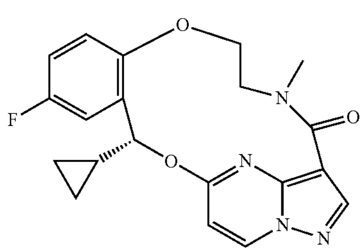 [SMILES: CN1CCOc2ccc(F)cc2[C@@H](C2CC2)Oc2ccn3ncc(c3n2)C1=O] | (13R)-13-cyclopropyl-11-fluoro-5-methyl-6,7-dihydro-13H-1,15-ethenopyrazolo[4,3-f][1,10,4,8]benzodioxadiazacyclotridecin-4(5H)-one |
| 9-1 | 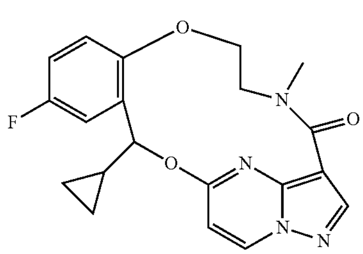 [SMILES: CN1CCOc2ccc(F)cc2C(C2CC2)Oc2ccn3ncc(c3n2)C1=O] | 13-cyclopropyl-11-fluoro-5-methyl-6,7-dihydro-13H-1,15-ethenopyrazolo[4,3-f][1,10,4,8]benzodioxadiazacyclotridecin-4(5H)-one |

-continued

| Ex. | Structure | Chemical Name |
|---|---|---|
| 10 | 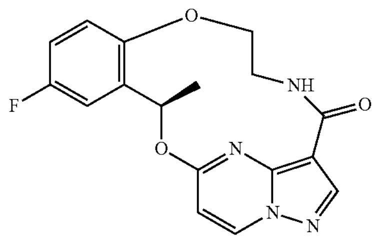 [SMILES: C[C@H]1Oc2ccn3ncc(c3n2)C(=O)NCCOc2ccc(F)cc21] | (13R)-11-fluoro-13-methyl-6,7-dihydro-13H-1,15-ethenopyrazolo[4,3-f][1,10,4,8]benzodioxadiazacyclotridecin-4(5H)-one |
| 10-1 | 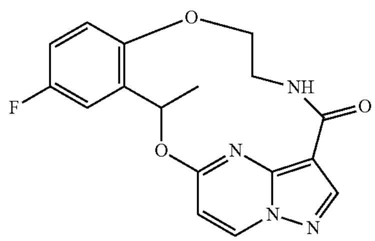 [SMILES: CC1Oc2ccn3ncc(c3n2)C(=O)NCCOc2ccc(F)cc21] | 11-fluoro-13-methyl-6,7-dihydro-13H-1,15-ethenopyrazolo[4,3-f][1,10,4,8]benzodioxadiazacyclotridecin-4(5H)-one |
| 11 | 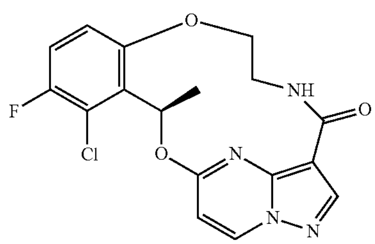 [SMILES: C[C@H]1Oc2ccn3ncc(c3n2)C(=O)NCCOc2ccc(F)c(Cl)c21] | (13R)-12-chloro-11-fluoro-13-methyl-6,7-dihydro-13H-1,15-ethenopyrazolo[4,3-f][1,10,4,8]benzodioxadiazacyclotridecin-4(5H)-one |
| 11-1 | 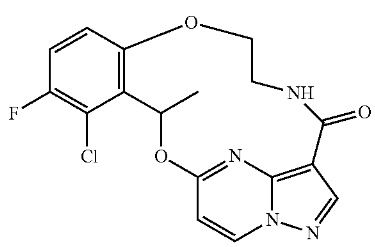 [SMILES: CC1Oc2ccn3ncc(c3n2)C(=O)NCCOc2ccc(F)c(Cl)c21] | 12-chloro-11-fluoro-13-methyl-6,7-dihydro-13H-1,15-ethenopyrazolo[4,3-f][1,10,4,8]benzodioxadiazacyclotridecin-4(5H)-one |
| 12 | 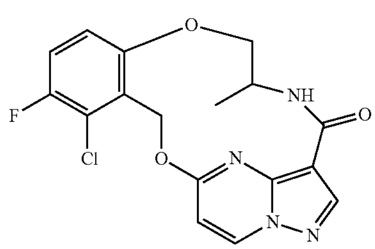 [SMILES: CC1COc2ccc(F)c(Cl)c2COc2ccn3ncc(c3n2)C(=O)N1] | 12-chloro-11-fluoro-6-methyl-6,7-dihydro-13H-1,15-ethenopyrazolo[4,3-f][1,10,4,8]benzodioxadiazacyclotridecin-4(5H)-one |
| 13 | 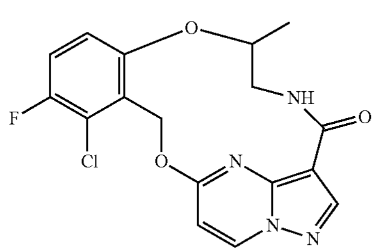 [SMILES: CC1CNC(=O)c2cnn3ccc(nc23)OCc2c(ccc(F)c2Cl)O1] | 12-chloro-11-fluoro-7-methyl-6,7-dihydro-13H-1,15-ethenopyrazolo[4,3-f][1,10,4,8]benzodioxadiazacyclotridecin-4(5H)-one |

| Ex. | Structure | Chemical Name |
|---|---|---|
| 14 | 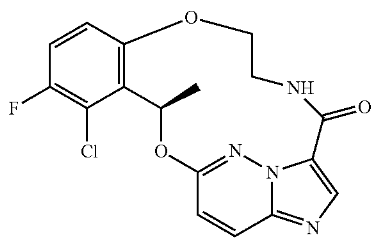 [SMILES: C[C@H]1Oc2ccc3ncc(n3n2)C(=O)NCCOc2ccc(F)c(Cl)c21] | (8R)-9-chloro-10-fluoro-8-methyl-15,16-dihydro-8H-3,6-ethenoimidazo[5,1-f][1,10,4,7,8]benzodioxatriazacyclotridecin-17(14H)-one |
| 14-1 | 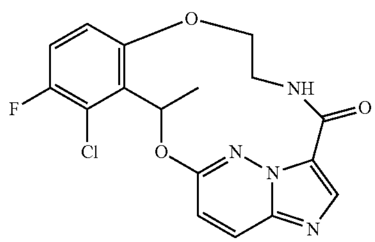 [SMILES: CC1Oc2ccc3ncc(n3n2)C(=O)NCCOc2ccc(F)c(Cl)c21] | 9-chloro-10-fluoro-8-methyl-15,16-dihydro-8H-3,6-ethenoimidazo[5,1-f][1,10,4,7,8]benzodioxatriazacyclotridecin-17(14H)-one |
| 15 | 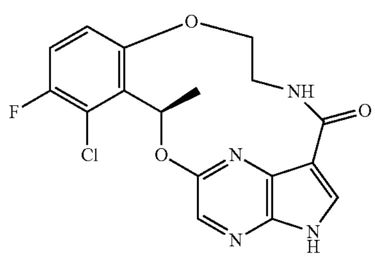 [SMILES: C[C@H]1Oc2cnc3[nH]cc(c3n2)C(=O)NCCOc2ccc(F)c(Cl)c21] | (7R)-8-chloro-9-fluoro-7-methyl-14,15-dihydro-2H,7H-3,5-(azenometheno)pyrrolo[3,4-f][1,10,4,8]benzodioxadiazacyclotridecin-16(13H)-one |
| 15-1 | 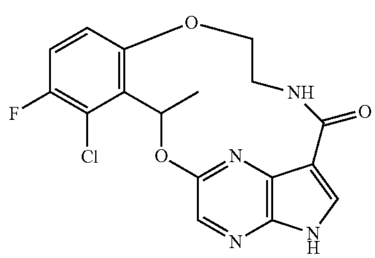 [SMILES: CC1Oc2cnc3[nH]cc(c3n2)C(=O)NCCOc2ccc(F)c(Cl)c21] | 8-chloro-9-fluoro-7-methyl-14,15-dihydro-2H,7H-3,5-(azenometheno)pyrrolo[3,4-f][1,10,4,8]benzodioxadiazacyclotridecin-16(13)-one |
| 16 | 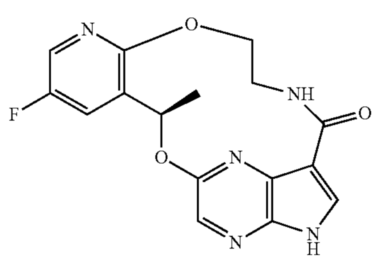 [SMILES: C[C@H]1Oc2cnc3[nH]cc(c3n2)C(=O)NCCOc2ncc(F)cc21] | (5R)-3-fluoro-5-methyl-14,15-dihydro-5H,10H-9,7-(azenometheno)pyrido[2,3-k]pyrrolo[3,4-d][1,10,3,7]dioxadiazacyclotridecin-12(13H)-one |
| 16-1 | 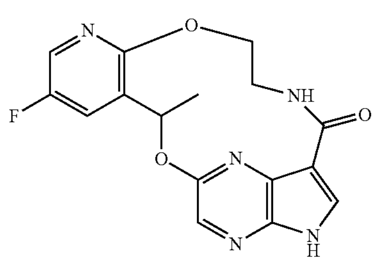 [SMILES: CC1Oc2cnc3[nH]cc(c3n2)C(=O)NCCOc2ncc(F)cc21] | 3-fluoro-5-methyl-14,15-dihydro-5H,10H-9,7-(azenometheno)pyrido[2,3-k]pyrrolo[3,4-d][1,10,3,7]dioxadiazacyclotridecin-12(13H)-one |

| Ex. | Structure | Chemical Name |
|---|---|---|
| 17 | 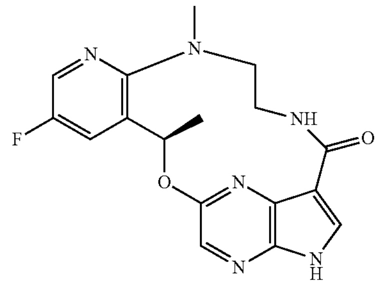 [SMILES: C[C@H]1Oc2cnc3[nH]cc(c3n2)C(=O)NCCN(C)c2ncc(F)cc21] | (5R)-3-fluoro-5,16-dimethyl-13,14,15,16-tetrahydro-5H-9,7-(azenometheno)pyrido[2,3-k]pyrrolo[3,4-d][1,3,7,10]oxatriazacyclotridecin-12(10H)-one |
| 17-1 | 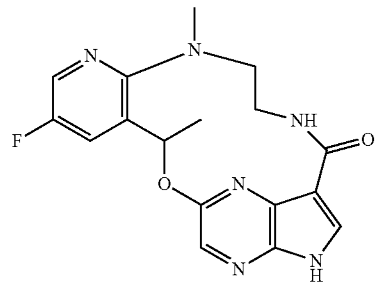 [SMILES: CC1Oc2cnc3[nH]cc(c3n2)C(=O)NCCN(C)c2ncc(F)cc21] | 3-fluoro-5,16-dimethyl-13,14,15,16-tetrahydro-5H-9,7-(azenometheno)pyrido[2,3-k]pyrrolo[3,4-d][1,3,7,10]oxatriazacyclotridecin-12(10H)-one |
| 18 | 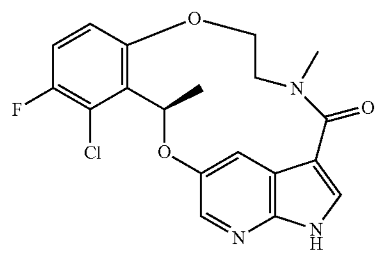 [SMILES: C[C@H]1Oc2cnc3[nH]cc(c3c2)C(=O)N(C)CCOc2ccc(F)c(Cl)c21] | (13R)-12-chloro-11-fluoro-5,13-dimethyl-6,7-dihydro-2H,13H-1,15-(azenometheno)pyrrolo[3,4-f][1,10,4]benzodioxazacyclotridecin-4(5H)-one |
| 18-1 | 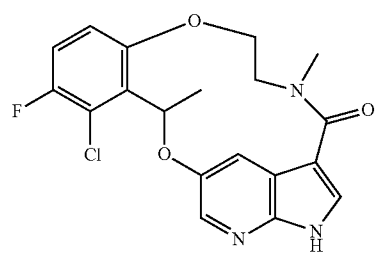 [SMILES: CC1Oc2cnc3[nH]cc(c3c2)C(=O)N(C)CCOc2ccc(F)c(Cl)c21] | 12-chloro-11-fluoro-5,13-dimethyl-6,7-dihydro-2H,13H-1,15-(azenometheno)pyrrolo[3,4-f][1,10,4]benzodioxazacyclotridecin-4(5H)-one |
| 19 | 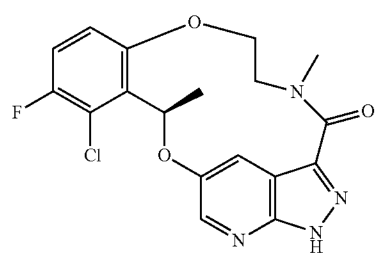 [SMILES: C[C@H]1Oc2cnc3[nH]nc(c3c2)C(=O)N(C)CCOc2ccc(F)c(Cl)c21] | (7R)-8-chloro-9-fluoro-7,15-dimethyl-14,15-dihydro-2H,7H-3,5-(azenometheno)pyrazolo[3,4-f][1,10,4]benzodioxazacyclotridecin-16(13H)-one |
| 19-1 | 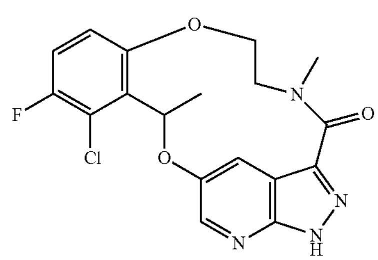 [SMILES: CC1Oc2cnc3[nH]nc(c3c2)C(=O)N(C)CCOc2ccc(F)c(Cl)c21] | 8-chloro-9-fluoro-7,15-dimethyl-14,15-dihydro-2H,7H-3,5-(azenometheno)pyrazolo[3,4-f][1,10,4]benzodioxazacyclotridecin-16(13H)-one |

-continued

| Ex. | Structure | Chemical Name |
|---|---|---|
| 20 | 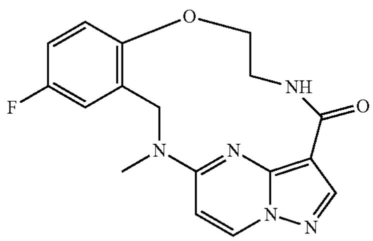 [SMILES: CN1Cc2cc(F)ccc2OCCNC(=O)c2cnn3ccc1nc23] | 11-fluoro-14-methyl-6,7,13,14-tetrahydro-1,15-ethenopyrazolo[4,3-f][1,4,8,10]benzoxatriazacyclotridecin-4(5H)-one |
| 21 | 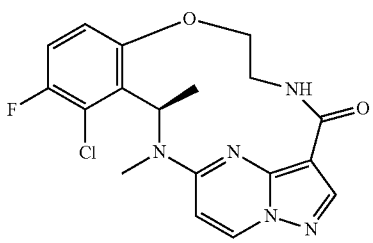 [SMILES: C[C@@H]1c2c(ccc(F)c2Cl)OCCNC(=O)c2cnn3ccc(nc23)N1C] | (13R)-12-chloro-11-fluoro-13,14-dimethyl-6,7,13,14-tetrahydro-1,15-ethenopyrazolo[4,3-f][1,4,8,10]benzoxatriazacyclotridecin-4(5H)-one |
| 21-1 | 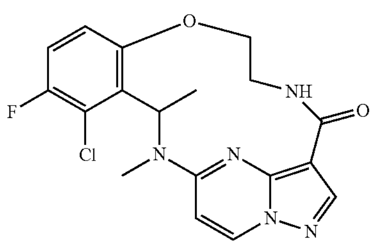 [SMILES: CC1c2c(ccc(F)c2Cl)OCCNC(=O)c2cnn3ccc(nc23)N1C] | 12-chloro-11-fluoro-13,14-dimethyl-6,7,13,14-tetrahydro-1,15-ethenopyrazolo[4,3-f][1,4,8,10]benzoxatriazacyclotridecin-4(5H)-one |
| 22 | 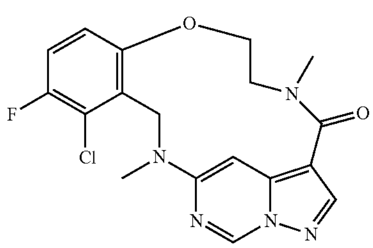 [SMILES: CN1CCOc2ccc(F)c(Cl)c2CN(C)c2cc3c(cnn3cn2)C1=O] | 12-chloro-11-fluoro-5,14-dimethyl-6,7,13,14-tetrahydro-15,1-(azenometheno)pyrazolo[4,3-f][1,4,10]benzoxadiazacyclotridecin-4(5H)-one |
| 23 | 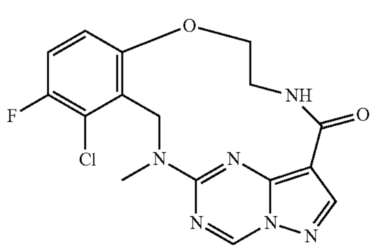 [SMILES: CN1Cc2c(ccc(F)c2Cl)OCCNC(=O)c2cnn3cnc1nc23] | 12-chloro-11-fluoro-14-methyl-6,7,13,14-tetrahydro-15,1-(azenometheno)pyrazolo[4,3-f][1,4,8,10]benzoxatriazacyclotridecin-4(5H)-one |
| 24 | 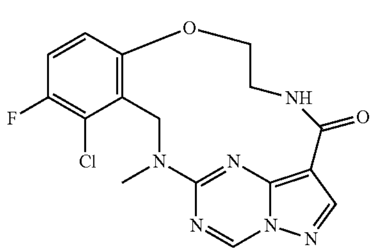 [SMILES: CN1Cc2c(ccc(F)c2Cl)OCCNC(=O)c2cnn3cnc1nc23] | 12-chloro-11-fluoro-14-methyl-6,7,13,14-tetrahydro-1,15-(azenometheno)pyrrolo[3,2-f][1,4,8,10]benzoxatriazacyclotridecin-4(5H)-one |

| Ex. | Structure | Chemical Name |
|---|---|---|
| 25 | 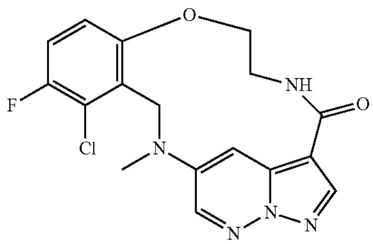 [SMILES: CN1Cc2c(ccc(F)c2Cl)OCCNC(=O)c2cnn3ncc1cc23] | 12-chloro-11-fluoro-14-methyl-6,7,13,14-tetrahydro-1,15-(azenometheno)pyrrolo[3,2-f][1,4,10]benzoxadiazacyclotridecin-4(5H)-one |
| 26 | 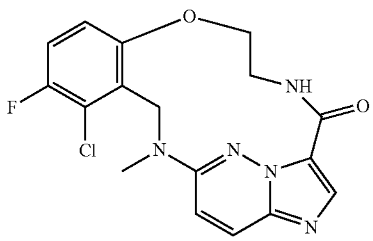 [SMILES: CN1Cc2c(ccc(F)c2Cl)OCCNC(=O)c2cnc3ccc1nn23] | 9-chloro-10-fluoro-7-methyl-7,8,15,16-tetrahydro-3,6-ethenoimidazo[5,1-f][1,4,7,8,10]benzoxatetraazacyclotridecin-17(14H)-one |
| 27 | 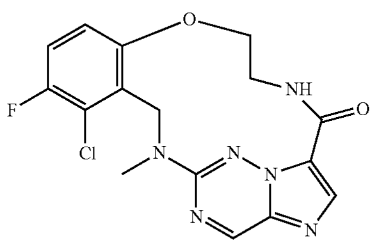 [SMILES: CN1Cc2c(ccc(F)c2Cl)OCCNC(=O)c2cnc3cnc1nn23] | 9-chloro-10-fluoro-7-methyl-7,8,15,16-tetrahydro-6,3-(azenometheno)imidazo[5,1-f][1,4,7,8,10]benzoxatetraazacyclotridecin-17(14H)-one |
| 28 | 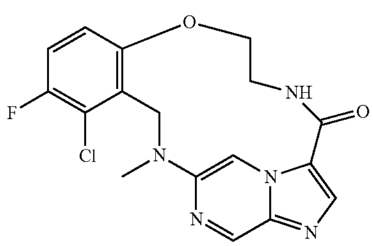 [SMILES: CN1Cc2c(ccc(F)c2Cl)OCCNC(=O)c2cnc3cnc1cn23] | 9-chloro-10-fluoro-7-methyl-7,8,15,16-tetrahydro-6,3-(azenometheno)imidazo[5,1-f][1,4,7,10]benzoxatriazacyclotridecin-17(14H)-one |
| 29 | 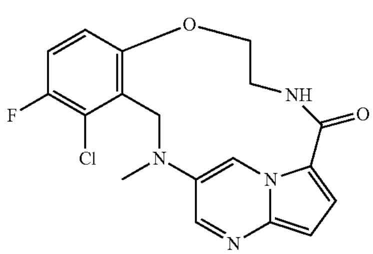 [SMILES: CN1Cc2c(ccc(F)c2Cl)OCCNC(=O)c2ccc3ncc1cn23] | 9-chloro-10-fluoro-7-methyl-7,8,15,16-tetrahydro-3,6-(azenometheno)pyrrolo[2,1-f][1,4,7,10]benzoxatriazacyclotridecin-17(14H)-one |
| 30 | 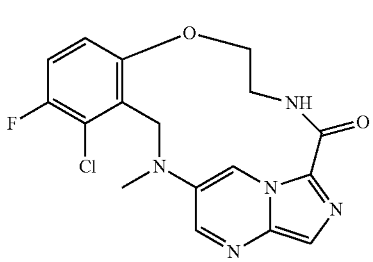 [SMILES: CN1Cc2c(ccc(F)c2Cl)OCCNC(=O)c2ncc3ncc1cn23] | 9-chloro-10-fluoro-7-methyl-7,8,15,16-tetrahydro-3,6-(azenometheno)imidazo[2,1-f][1,4,7,10]benzoxatriazacyclotridecin-17(14H)-one |

-continued

| Ex. | Structure | Chemical Name |
|---|---|---|
| 31 | 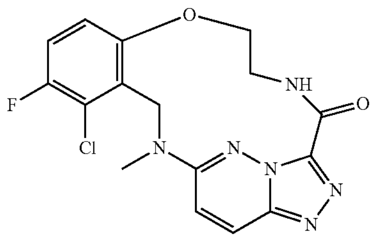 [SMILES: CN1Cc2c(ccc(F)c2Cl)OCCNC(=O)c2nnc3ccc1nn23] | 9-chloro-10-fluoro-7-methyl-7,8,15,16-tetrahydro-3,6-etheno[1,2,4]triazolo[3,4-f][1,4,7,8,10]benzoxatetraazacyclotridecin-17(14H)-one |
| 32 | 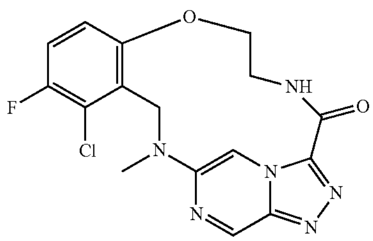 [SMILES: CN1Cc2c(ccc(F)c2Cl)OCCNC(=O)c2nnc3cnc1cn23] | 9-chloro-10-fluoro-7-methyl-7,8,15,16-tetrahydro-6,3-(azenometheno)[1,2,4]triazolo[3,4-f][1,4,7,10]benzoxatriazacyclotridecin-17(14H)-one |
| 33 | 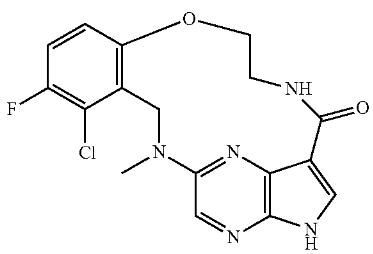 [SMILES: CN1Cc2c(ccc(F)c2Cl)OCCNC(=O)c2c[nH]c3ncc1nc23] | 8-chloro-9-fluoro-6-methyl-6,7,14,15-tetrahydro-2H-3,5-(azenometheno)pyrrolo[3,4-f][1,4,8,10]benzoxatriazacyclotridecin-16(13H)-one |
| 34 | 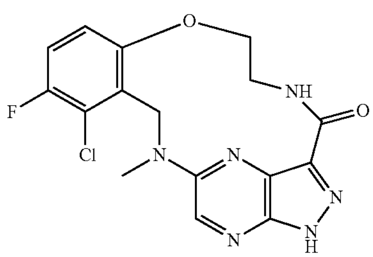 [SMILES: CN1Cc2c(ccc(F)c2Cl)OCCNC(=O)c2n[nH]c3ncc1nc23] | 8-chloro-9-fluoro-6-methyl-6,7,14,15-tetrahydro-2H-3,5-(azenometheno)pyrazolo[3,4-f][1,4,8,10]benzoxatriazacyclotridecin-16(13H)-one |
| 35 | 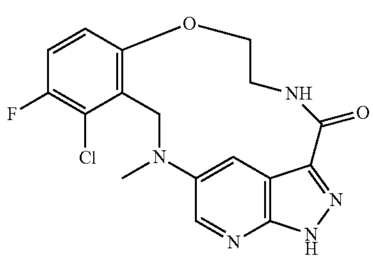 [SMILES: CN1Cc2c(ccc(F)c2Cl)OCCNC(=O)c2n[nH]c3ncc1cc23] | 8-chloro-9-fluoro-6-methyl-6,7,14,15-tetrahydro-2H-3,5-(azenometheno)pyrazolo[3,4-f][1,4,10]benzoxadiazacyclotridecin-16(13H)-one |
| 36 | 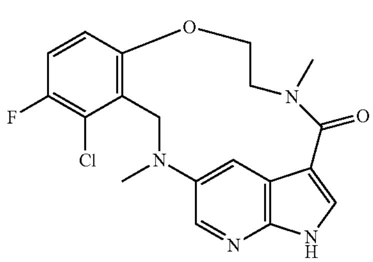 [SMILES: CN1CCOc2ccc(F)c(Cl)c2CN(C)c2cnc3[nH]cc(c3c2)C1=O] | 12-chloro-11-fluoro-5,14-dimethyl-6,7,13,14-tetrahydro-2H-1,15-(azenometheno)pyrrolo[3,4-f][1,4,10]benzoxadiazacyclotridecin-4(5H)-one |

| Ex. | Structure | Chemical Name |
|---|---|---|
| 37 | 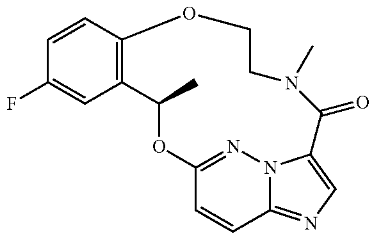 [SMILES: C[C@H]1Oc2ccc3ncc(n3n2)C(=O)N(C)CCOc2ccc(F)cc21] | (8R)-10-fluoro-8,16-dimethyl-15,16-dihydro-8H-3,6-ethenoimidazo[5,1-f][1,10,4,7,8]benzodioxatriazacyclotridecin-17(14H)-one |
| 37-1 | 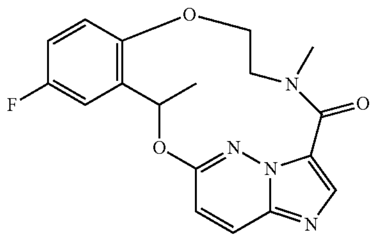 [SMILES: CC1Oc2ccc3ncc(n3n2)C(=O)N(C)CCOc2ccc(F)cc21] | 10-fluoro-8,16-dimethyl-15,16-dihydro-8H-3,6-ethenoimidazo[5,1-f][1,10,4,7,8]benzodioxatriazacyclotridecin-17(14H)-one |
| 38 | 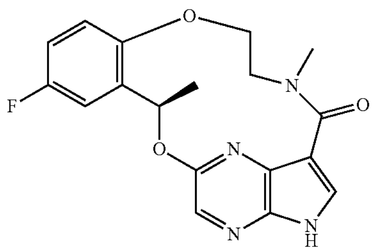 [SMILES: C[C@H]1Oc2cnc3[nH]cc(c3n2)C(=O)N(C)CCOc2ccc(F)cc21] | (7R)-9-fluoro-7,15-dimethyl-14,15-dihydro-2H,7H-3,5-(azenometheno)pyrrolo[3,4-f][1,10,4,8]benzodioxadiazacyclotridecin-16(13H)-one |
| 38-1 | | 9-fluoro-7,15-dimethyl-14,15-dihydro-2H,7H-3,5-(azenometheno)pyrrolo[3,4-f][1,10,4,8]benzodioxadiazacyclotridecin-16(13H)-one | and pharmaceutically acceptable salts thereof.

The following represent illustrative embodiments of compounds of Formula (I) or (I-A):

| Ex, | Structure | Chemical Name |
|---|---|---|
| 39 | 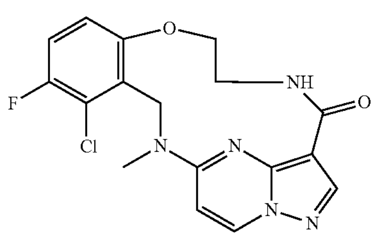 [SMILES: CN1Cc2c(ccc(F)c2Cl)OCCNC(=O)c2cnn3ccc1nc23] | 12-chloro-11-fluoro-14-methyl-6,7,13,14-tetrahydro-1,15-ethenopyrazolo[4,3-f][1,4,8,10]benzoxatriazacyclotridecin-4(5H)-one |

-continued

| Ex. | Structure | Chemical Name |
|---|---|---|
| 40 | 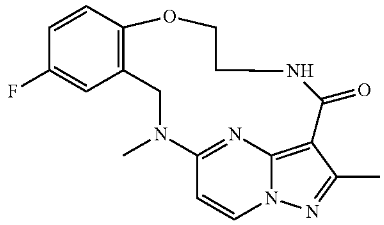 [SMILES: Cc1nn2ccc3nc2c1C(=O)NCCOc1ccc(F)cc1CN3C] | 11-fluoro-3,14-dimethyl-6,7,13,14-tetrahydro-1,15-ethenopyrazolo[4,3-f][1,4,8,10]benzoxatriazacyclotridecin-4(5H)-one |
| 41 | 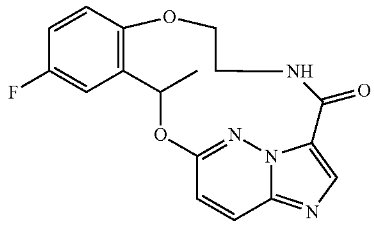 [SMILES: CC1Oc2ccc3ncc(n3n2)C(=O)NCCOc2ccc(F)cc21] | 10-fluoro-8-methyl-15,16-dihydro-8H-3,6-ethenoimidazo[5,1-f][1,10,4,7,8]benzodioxatriazacyclotridecin-17(14H)-one |
| 42 | 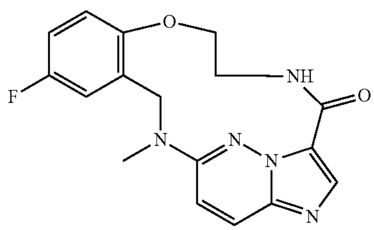 [SMILES: CN1Cc2cc(F)ccc2OCCNC(=O)c2cnc3ccc1nn23] | 10-fluoro-7-methyl-7,8,15,16-tetrahydro-3,6-ethenoimidazo[5,1-f][1,4,7,8,10]benzoxatetraazacyclotridecin-17(14H)-one |
| 43 | 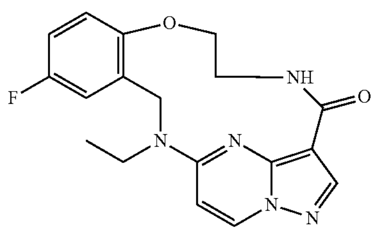 [SMILES: CCN1Cc2cc(F)ccc2OCCNC(=O)c2cnn3ccc1nc23] | 14-ethyl-11-fluoro-6,7,13,14-tetrahydro-1,15-ethenopyrazolo[4,3-f][1,4,8,10]benzoxatriazacyclotridecin-4(5H)-one |
| 44 | 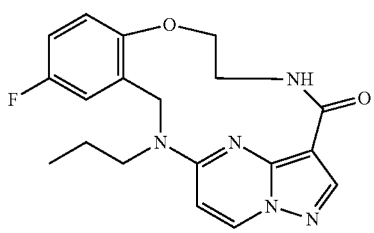 [SMILES: CCCN1Cc2cc(F)ccc2OCCNC(=O)c2cnn3ccc1nc23] | 11-fluoro-14-propyl-6,7,13,14-tetrahydro-1,15-ethenopyrazolo[4,3-f][1,4,8,10]benzoxatriazacyclotridecin-4(5H)-one |
| 45 | 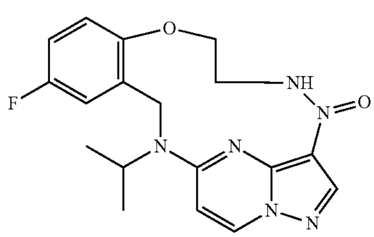 | 11-fluoro-14-(propan-2-yl)-6,7,13,14-tetrahydro-1,15-ethenopyrazolo[4,3-f][1,4,8,10]benzoxatriazacyclotridecin-4(5H)-one |

-continued

| Ex. | Structure | Chemical Name |
|---|---|---|
| 46 | 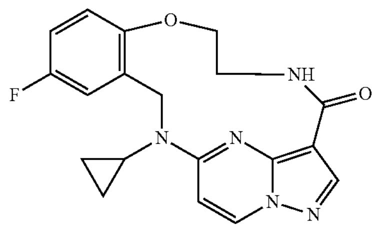 [SMILES: O=C1NCCOc2ccc(F)cc2CN(C2CC2)c2ccn3ncc1c3n2] | 14-cyclopropyl-11-fluoro-6,7,13,14-tetrahydro-1,15-ethenopyrazolo[4,3-f][1,4,8,10]benzoxatriazacyclotridecin-4(5H)-one |
| 47 | 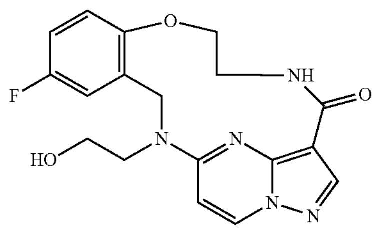 [SMILES: O=C1NCCOc2ccc(F)cc2CN(CCO)c2ccn3ncc1c3n2] | 11-fluoro-14-(2-hydroxyethyl)-6,7,13,14-tetrahydro-1,15-ethenopyrazolo[4,3-f][1,4,8,10]benzoxatriazacyclotridecin-4(5H)-one |
| 48 | 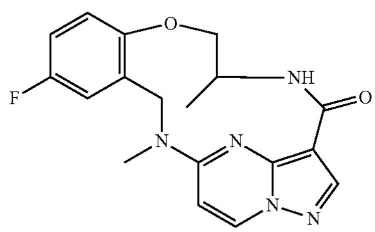 [SMILES: CC1COc2ccc(F)cc2CN(C)c2ccn3ncc(c3n2)C(=O)N1] | 11-fluoro-6,14-dimethyl-6,7,13,14-tetrahydro-1,15-ethenopyrazolo[4,3-f][1,4,8,10]benzoxatriazacyclotridecin-4(5H)-one |
| 49 | 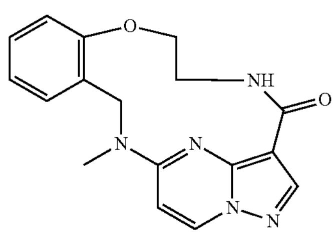 [SMILES: CN1Cc2ccccc2OCCNC(=O)c2cnn3ccc1nc23] | 14-methyl-6,7,13,14-tetrahydro-1,15-ethenopyrazolo[4,3-f][1,4,8,10]benzoxatriazacyclotridecin-4(5H)-one |
| 50 | 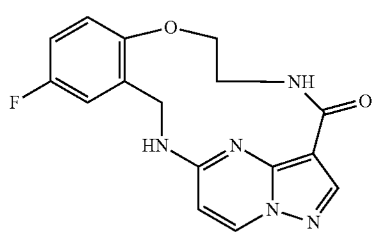 [SMILES: O=C1NCCOc2ccc(F)cc2CNc2ccn3ncc1c3n2] | 11-fluoro-6,7,13,14-tetrahydro-1,15-ethenopyrazolo[4,3-f][1,4,8,10]benzoxatriazacyclotridecin-4(5H)-one |
| 51 | 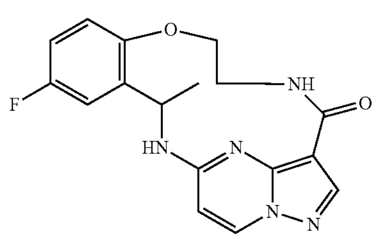 [SMILES: CC1Nc2ccn3ncc(c3n2)C(=O)NCCOc2ccc(F)cc21] | 11-fluoro-13-methyl-6,7,13,14-tetrahydro-1,15-ethenopyrazolo[4,3-f][1,4,8,10]benzoxatriazacyclotridecin-4(5H)-one |

| Ex. | Structure | Chemical Name |
|---|---|---|
| 51-1 | 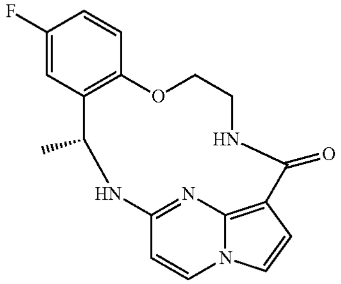 [SMILES: C[C@H]1Nc2ccn3ccc(c3n2)C(=O)NCCOc2ccc(F)cc21] | (13R)-11-fluoro-13-methyl-6,7,13,14-tetrahydro-1,15-ethenopyrazolo[4,3-f][1,4,8,10]benzoxatriazacyclotridecin-4(5H)-one |
| 52 | 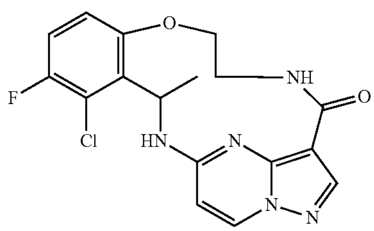 [SMILES: CC1Nc2ccn3ncc(c3n2)C(=O)NCCOc2ccc(F)c(Cl)c21] | 12-chloro-11-fluoro-13-methyl-6,7,13,14-tetrahydro-1,15-ethenopyrazolo[4,3-f][1,4,8,10]benzoxatriazacyclotridecht-4(5H)-one |
| 53 | 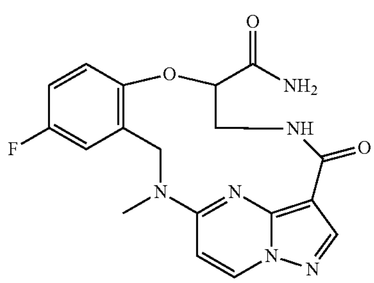 [SMILES: CN1Cc2cc(F)ccc2OC(C(N)=O)CNC(=O)c2cnn3ccc1nc23] | 1-fluoro-14-methyl-4-oxo-4,5,6,7,13,14-hexahydro-1,15-ethenopyrazolo[4,3-f][1,4,8,10]benzoxatriazacyclotridecine-7-carboxamide |
| 54 | 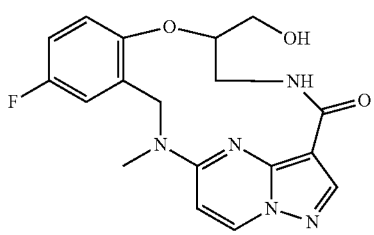 [SMILES: CN1Cc2cc(F)ccc2OC(CO)CNC(=O)c2cnn3ccc1nc23] | 11-fluoro-7-(hydroxymethyl)-14--methyl-6,7,13,14-tetrahydro-1,15-ethenopyrazolo[4,3-f][1,4,8,10]benzoxatriazacyclotridecin-4(5H)-one |
| 55 | 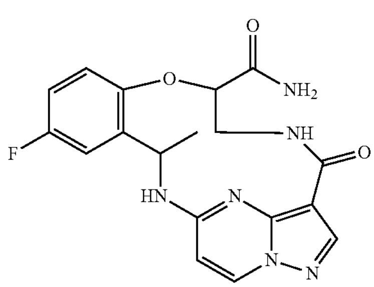 [SMILES: CC1Nc2ccn3ncc(c3n2)C(=O)NCC(C(N)=O)Oc2ccc(F)cc21] | 11-fluoro-13-methyl-4-oxo-4,5,6,7,13,14-hexahydro-1,15-ethenopyrazolo[4,3-f][1,4,8,10]benzoxatriazacyclotridecine-7-carboxamide |
| 56 | 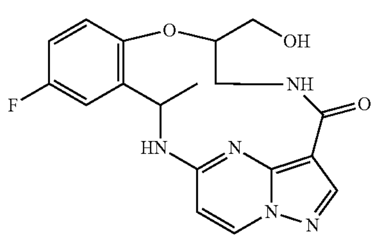 [SMILES: CC1Nc2ccn3ncc(c3n2)C(=O)NCC(CO)Oc2ccc(F)cc21] | 11-fluoro-7-(hydroxymethyl)-13-methyl-6,7,13,14-tetrahydro-1,15-ethenopyrazolo[4,3-f][1,4,8,10]benzoxatriazacyclotridecin-4(5H)-one |

-continued

| Ex. | Structure | Chemical Name |
|---|---|---|
| 57 | 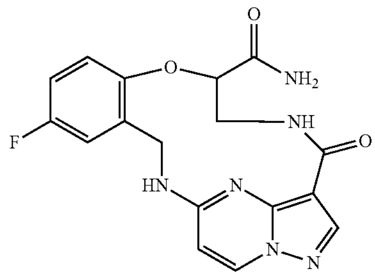 [SMILES: NC(=O)C1CNC(=O)c2cnn3ccc(nc23)NCc2cc(F)ccc2O1] | 11-fluoro-4-oxo-4,5,6,7,13,14-hexahydro-1,15-ethenopyrazolo[4,3-f][1,4,8,10]benzoxatriazacyclotridecine-7-carboxamide |
| 58 | 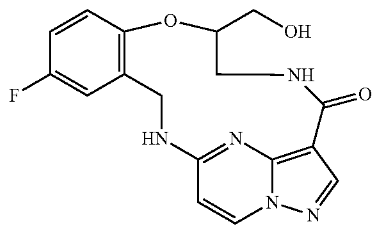 [SMILES: O=C1NCC(CO)Oc2ccc(F)cc2CNc2ccn3ncc1c3n2] | 11--fluoro-7-(hydroxymethyl)--6,7,13,14-tetrahydro-1,15-ethenopyrazolo[4,3-f][1,4,8,10]benzoxatriazacyclotridecin-4(5H)-one |
| 59 | 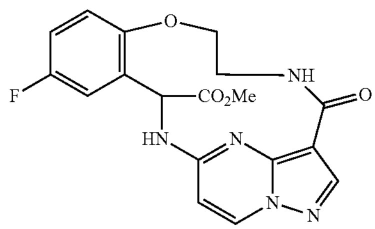 [SMILES: COC(=O)C1Nc2ccn3ncc(c3n2)C(=O)NCCOc2ccc(F)cc21] | methyl 11-fluoro-4-oxo-4,5,6,7,13,14-hexahydro-1,15-ethenopyrazolo[4,3-f][1,4,8,10]benzaxatriazacyclotridecine-13-carboxylate |
| 60 | 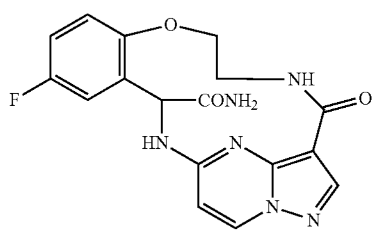 [SMILES: NC(=O)C1Nc2ccn3ncc(c3n2)C(=O)NCCOc2ccc(F)cc21] | 11-fluoro-4-oxo-4,5,6,7,13,14-hexahydro-1,15-ethenopyrazolo[4,3-f][1,4,8,10]benzexatriazacyclotridecine-13-carboxamide |
| 61 | 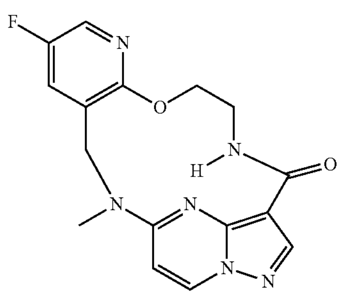 [SMILES: CN1Cc2cc(F)cnc2OCCNC(=O)c2cnn3ccc1nc23] | 11-fluoro-14-methyl-6,7,13,14-tetrahydro-1,15-ethenopyrazolo[4,3-f]pyrido[3,2-l][1,4,8,10]oxatriazacyclotridecin-4(5,H)-one |
| 62 | 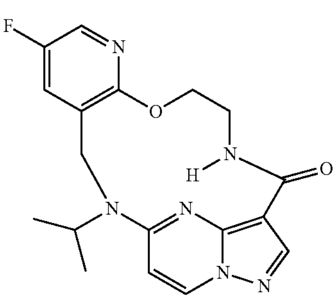 [SMILES: CC(C)N1Cc2cc(F)cnc2OCCNC(=O)c2cnn3ccc1nc23] | 11-fluoro-14-(propan-2-yl)-6,7,13,14-tetrahydro-1,15-ethenopyrazolo[4,3-f]pyrido[3,2-l][1,4,8,10]oxatriazacyclotridecin-4(5H)-one |

-continued

| Ex. | Structure | Chemical Name |
|---|---|---|
| 63 | 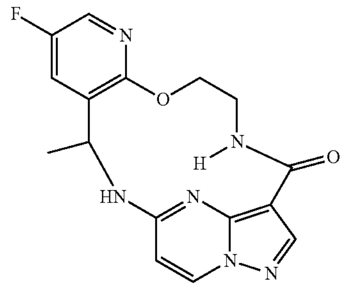 [SMILES: CC1Nc2ccn3ncc(c3n2)C(=O)NCCOc2ncc(F)cc21] | 11-fluoro-13-methyl-6,7,13,14-tetrahydro-1,15-ethenopyrazolo[4,3-f]pyrido[3,2-l][1,4,8,10]oxatriazacyclotridecin--4(5H)-one |
| 64 | 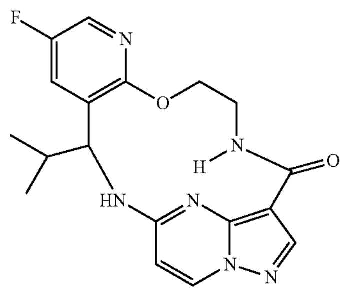 [SMILES: CC(C)C1Nc2ccn3ncc(c3n2)C(=O)NCCOc2ncc(F)cc21] | 11-fluoro-13-(propan-2-yl)-6,7,13,14-tetrahydro-1,15-ethenopyrazolo[4,3-f]pyrido[3,2-l][1,4,8,10]oxatriazacyclotridecin-4(5H)-one |
| 65 | 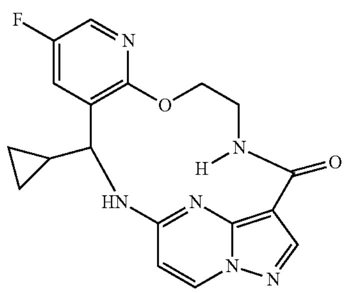 [SMILES: O=C1NCCOc2ncc(F)cc2C(C2CC2)Nc2ccn3ncc1c3n2] | 13-cyclopropyl-11-fluoro-6,7,13,14-tetrahydro-1,15-ethenopyrazolo[4,3-f]pyrido[3,2-l][1,4,8,10]oxatriazacyclotridecin-4(5H)-one |
| 66 | 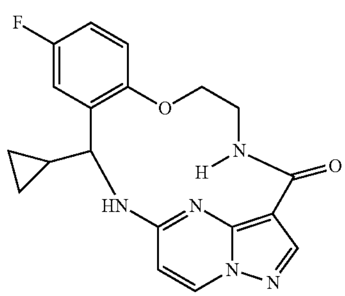 [SMILES: O=C1NCCOc2ccc(F)cc2C(C2CC2)Nc2ccn3ncc1c3n2] | 13-cyclopropyl-11-fluoro-6,7,13,14-tetrahydro-1,15-ethenopyrazolo[4,3-f][1,4,8,10]benzoxatriazacyclotridecin-4(5H)-one |
| 67 | 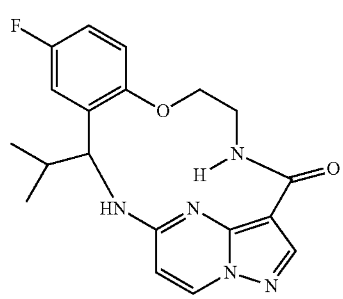 [SMILES: CC(C)C1Nc2ccn3ncc(c3n2)C(=O)NCCOc2ccc(F)cc21] | 11-fluoro-13-(propan-2-yl).6,7,13,14-tetrahydro-1,15-ethenopyrazolo[4,3-f][1,4,8,10]benzoxatriazacyclotridecin-4(5H)-one |

-continued

| Ex. | Structure | Chemical Name |
|---|---|---|
| 68 | 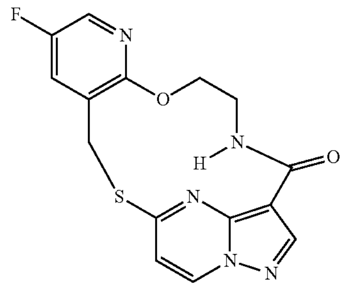 [SMILES: O=C1NCCOc2ncc(F)cc2CSc2ccn3ncc1c3n2] | 11-fluoro-6,7-dihydro-13H-1,15-ethenopyrazolo[4,3-f][1,10,4,8]benzoxathiadiazacyclotridecin-4(5H)-one |
| 69 | 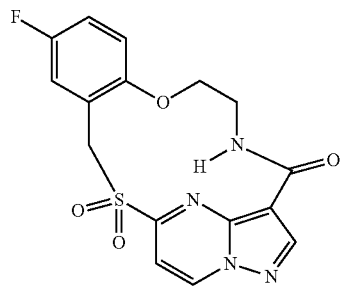 [SMILES: O=C1NCCOc2ccc(F)cc2CS(=O)(=O)c2ccn3ncc1c3n2] | 11-fluoro-6,7-dihydro-13H-1,15-ethenopyrazolo[4,3-f][1,10,4,8]benzoxathiadiazacyclotridecin-4(5H)-one 14,14-dioxide |
| 70 | 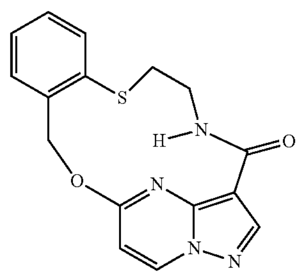 [SMILES: O=C1NCCSc2ccccc2COc2ccn3ncc1c3n2] | 6,7-dihydro-13H-1,15-ethenopyrazolo[4,3-f][10,1,4,8]benzoxathiadiazacyclotridecin-4(5H)-one |
| 71 | 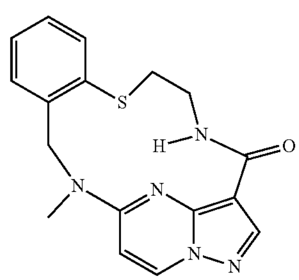 [SMILES: CN1Cc2ccccc2SCCNC(=O)c2cnn3ccc1nc23] | 14-methyl-6,7,13,14-tetrahydro-1,15-ethenopyrazolo[4,3-f][1,4,8,10]benzothiatriazacyclotridecin-4(5H)-one |
| 72 | 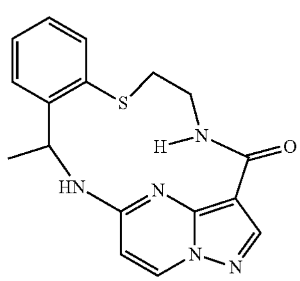 [SMILES: CC1Nc2ccn3ncc(c3n2)C(=O)NCCSc2ccccc21] | 13-methyl-6,7,13,14-tetrahydro-1,15-ethenopyrazolo[4,3-f][1,4,8,10]benzothiatriazacyclotridecin-4(5H)-one |

-continued

| Ex, | Structure | Chemical Name |
|---|---|---|
| 73 | 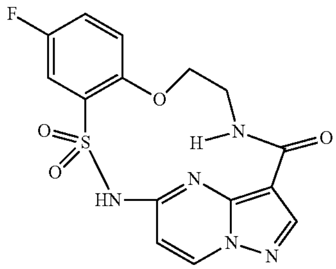 [SMILES: O=C1NCCOc2ccc(F)cc2S(=O)(=O)Nc2ccn3ncc1c3n2] | 11-fluoro-6,7-dihydro-5H-1,15-ethenopyrazolo[3,4-e][11,12,4,8]benzoxathiatriazacyclotridecin-4(14H)-one 13,13-dioxide |
| 74 | 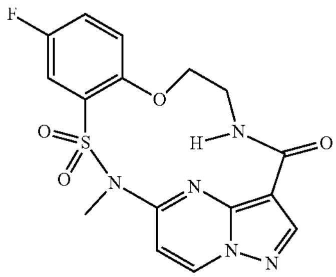 [SMILES: CN1c2ccn3ncc(c3n2)C(=O)NCCOc2ccc(F)cc2S1(=O)=O] | 11-fluoro-14-methyl-6,7-dihydro-5H-1,15-ethenopyrazolo[3,4-e][11,12,4,8]benzoxathiatriazacyclotridecin-4(14H)-one 13,13-dioxide |
| 75 | 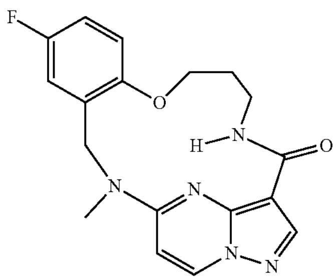 [SMILES: CN1Cc2cc(F)ccc2OCCCNC(=O)c2cnn3ccc1nc23] | 12-fluoro-15-methyl-5,6,7,8,14,15-hexahydro-4H-1,16-ethenopyrazolo[4,3-g][1,5,9,11]benzoxatriazacyclotetradecin-4-one |
| 76 | 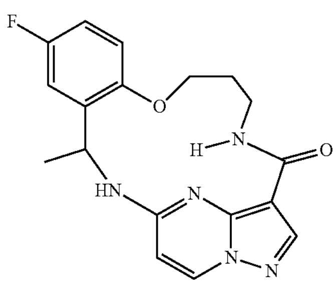 [SMILES: CC1Nc2ccn3ncc(c3n2)C(=O)NCCCOc2ccc(F)cc21] | 12-fluoro-14-methyl-5,6,7,8,14,15-hexahydro-4H-1,16-ethenopyrazolo[4,3-g][1,5,9,11]benzoxatriazacyclotetradecin-4-one |
| 76-1 | 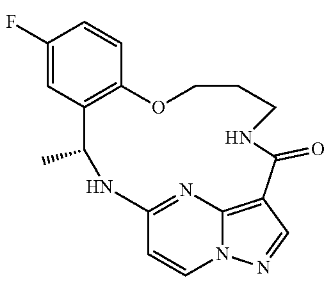 [SMILES: C[C@H]1Nc2ccn3ncc(c3n2)C(=O)NCCCOc2ccc(F)cc21] | (14R)-12-fluoro-14-methyl-5,6,7,8,14,15-hexahydro-4H-1,16-ethenopyrazolo[4,3-g][1,5,9,11]benzoxatriazacyclotetradecin-4-one |

-continued

| Ex. | Structure | Chemical Name |
|---|---|---|
| 77 | 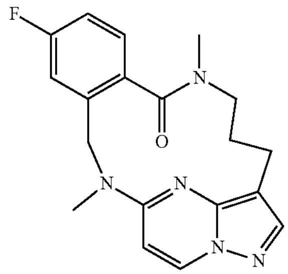 [SMILES: CN1CCCc2cnn3ccc(nc23)N(C)Cc2cc(F)ccc2C1=O] | 11-fluoro-7,14-dimethyl-4,5,6,7,13,14-hexahydro-8H-1,15-ethenopyrazolo[3,4-e][2,4,10]benzotriazacycloindecin-8-one |
| 78 | 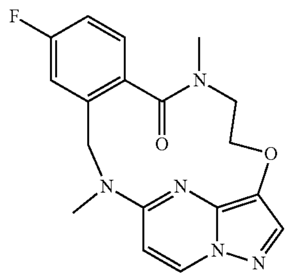 [SMILES: CN1CCOc2cnn3ccc(nc23)N(C)Cc2cc(F)ccc2C1=O] | 11-fluoro-7,14-dimethyl-6,7,13,14-tetrahydro-1,15-ethenopyrazolo[3,4-e][7,2,4,10]benzoxatriazacyclotridecin-8(5H)-one |
| 79 | 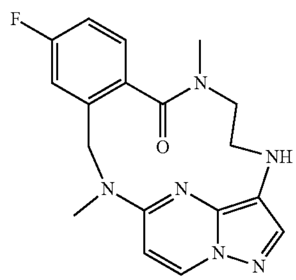 [SMILES: CN1CCNc2cnn3ccc(nc23)N(C)Cc2cc(F)ccc2C1=O] | 11-fluoro-7,14-dimethyl-4,5,6,7,13,14-hexahydro-8H-1,15-ethenopyrazolo[3,4-e][2,4,7,10]benzotetraazacyclotridecin-8-one |
| 80 | 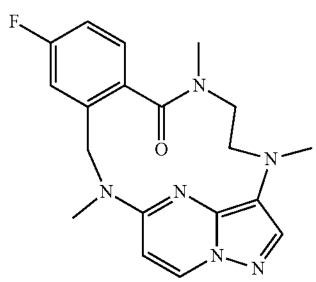 [SMILES: CN1CCN(C)c2cnn3ccc(nc23)N(C)Cc2cc(F)ccc2C1=O] | 11-fluoro-4,7,14-trimethyl-4,5,6,7,13,14-hexahydro-8H-1,15-ethenopyrazolo[3,4-e][2,4,7,10]benzotetraazacyclotridecin-8-one |
| 81 | 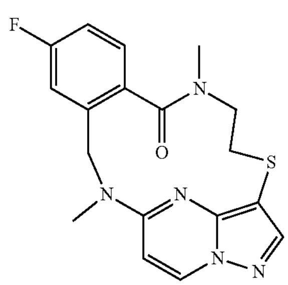 [SMILES: CN1CCSc2cnn3ccc(nc23)N(C)Cc2cc(F)ccc2C1=O] | 11-fluoro-7,14-dimethyl-6,7,13,14-tetrahydro-1,15-ethenopyrazolo[3,4-e][7,2,4,10]benzothiatriazacyclotridecin-8(5H)-one |

-continued

| Ex, | Structure | Chemical Name |
|---|---|---|
| 82 | 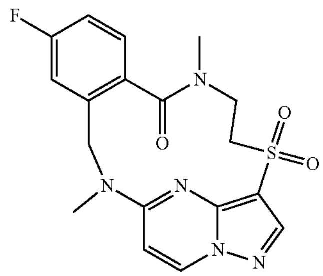 [SMILES: CN1CCS(=O)(=O)c2cnn3ccc(nc23)N(C)Cc2cc(F)ccc2C1=O] | 11-fluoro-7,14-dimethyl-6,7,13,14-tetrahydro-1,15-ethenopyrazolo[3,4-e][7,2,4,10]benzothiatriazacyclotridecin-8(5H)-one 4,4-dioxide |
| 83 | | 12-fluoro-8,15-dimethyl-5,6,7,8,14,15-hexahydro-9H-1,16-ethenopyrazol-[3,4-e][7,2,4,8,11]benzothiatetraazacyclotetradecin-9-one 4,4-dioxide | and pharmaceutically acceptable salts thereof.

The following represent illustrative embodiments of compounds of Formula (I) or (I-A):

| Ex. | Structure | Chemical Name |
|---|---|---|
| 84 | 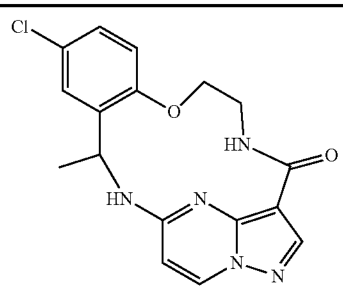 | 11-chloro-13-methyl-6,7,13,14-tetrahydro-1,15-ethenopyrazolo[4,3-f][1,4,8,10]benzoxatriazacyclotridecin-4(5H)-one |
| 85 | 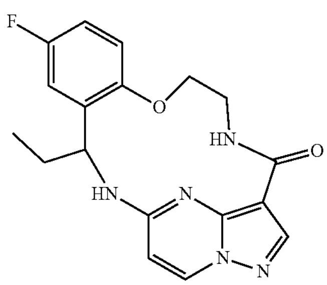 [SMILES: CCC1Nc2ccn3ncc(c3n2)C(=O)NCCOc2ccc(F)cc21] | 13-ethyl-11-fluoro-6,7,13,14-tetrahydro-1,15-ethenopyrazolo[4,3-f][1,4,8,10]benzoxatriazacyclotridecin-4(5H)-one |
| 86 | 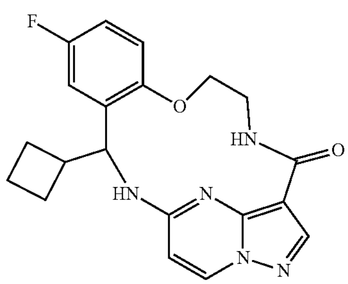 [SMILES: O=C1NCCOc2ccc(F)cc2C(C2CCC2)Nc2ccn3ncc1c3n2] | 13-cyclobutyl-11-fluoro-6,7,13,14-tetrahydro-1,15-ethenopyrazolo[4,3-f][1,4,8,10]benzoxatriazaryclotridecin-4(5H)-one |

-continued

| Ex. | Structure | Chemical Name |
|---|---|---|
| 87 | 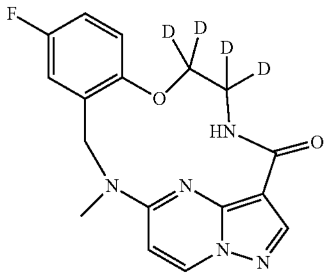 [SMILES: [2H]C1([2H])NC(=O)c2cnn3ccc(nc23)N(C)Cc2cc(F)ccc2OC1([2H])[2H]] | 11-fluoro-14-methyl(6,6,7,7-²H₄)-6,7,13,14-tetrahydro-1,15-ethenopyrazolo[4,3-f][1,4,8,10]benzoxatriazacyclotridecin-4(5H)-one |
| 88 | 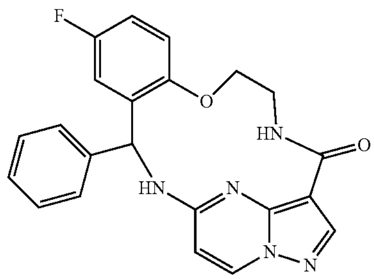 [SMILES: O=C1NCCOc2ccc(F)cc2C(c2ccccc2)Nc2ccn3ncc1c3n2] | 11-fluoro-13-phenyl-6,7,13,14-tetrahydro-1,15-ethenopyrazolo[4,3-f][1,4,8,10]benzoxatriazacyclotridecin-4(5H)-one |
| 89 | 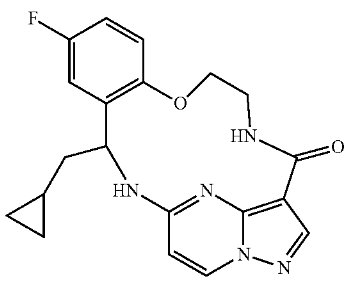 [SMILES: O=C1NCCOc2ccc(F)cc2C(CC2CC2)Nc2ccn3ncc1c3n2] | 13-(cyclopropylmethyl)-11-fluoro-6,7,13,14-tetrahydro-1,15-ethenopyrazolo[4,3-f][1,4,8,10]benzoxatriazacyclotridecin-4(5H)-one |
| 90 | 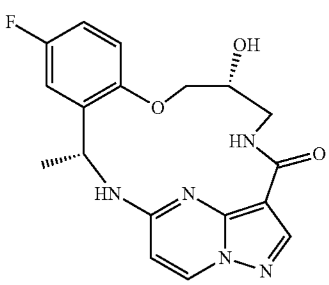 [SMILES: C[C@H]1Nc2ccn3ncc(c3n2)C(=O)NC[C@@H](O)COc2ccc(F)cc21] | (7R,14R)-12-fluoro-7-hydroxy-14-methyl-5,6,7,8,14,15-thexahydro-4H-1,16-ethenopyrazolo[4,3-g][1,5,9,11]benzoxatriazacyclotetradecin-4-one |
| 91 | 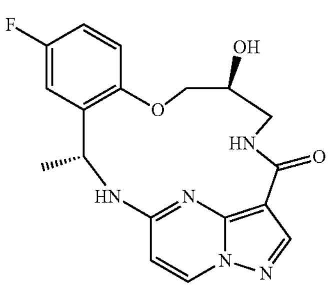 [SMILES: C[C@H]1Nc2ccn3ncc(c3n2)C(=O)NC[C@H](O)COc2ccc(F)cc21] | (7S,14R)-12-fluoro-7-hydroxy-14-methyl-5,6,7,8,14,15-hexahydro-4H-1,16-ethenopyrazolo[4,3-g][1,5,9,11]benzoxatriazacyclotetradecin-4-one |

-continued

| Ex. | Structure | Chemical Name |
| --- | --- | --- |
| 92 | 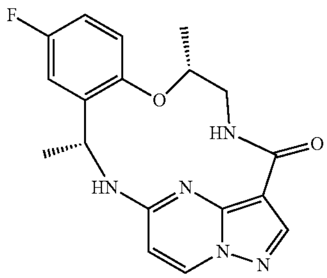 [SMILES: C[C@@H]1CNC(=O)c2cnn3ccc(nc23)N[C@H](C)c2cc(F)ccc2O1] | (7R,13R)-11-fluoro-7,13-dimethyl-6,7,13,14-tetrahydro-1,15-ethenopyrazolo[4,3-f][1,4,8,10]benzoxatriazacyclotridecin-4(5H)-one |
| 93 | 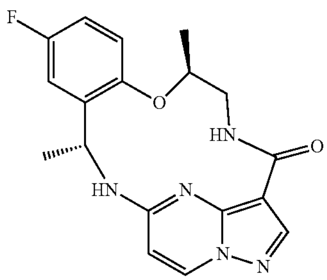 [SMILES: C[C@H]1CNC(=O)c2cnn3ccc(nc23)N[C@H](C)c2cc(F)ccc2O1] | (7S,13R)-11-fluoro-7,13-dimethyl-6,7,13,14-tetrahydro-1,15-ethenopyrazolo[4,3-f][1,4,8,10]benzoxatriazacyclotridecin-4(5H)-one |
| 94 | 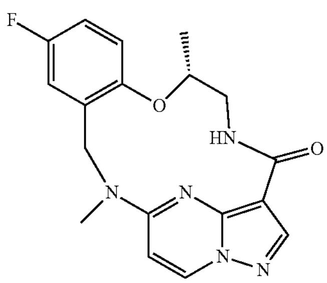 [SMILES: C[C@@H]1CNC(=O)c2cnn3ccc(nc23)N(C)Cc2cc(F)ccc2O1] | (7R)-11-fluoro-7,14-dimethyl-6,7,13,14-tetrahydro-1,15-ethenopyrazolo[4,3-f][1,4,8,10]benzoxatriazacyclotridecin-4(5H)-one |
| 95 | 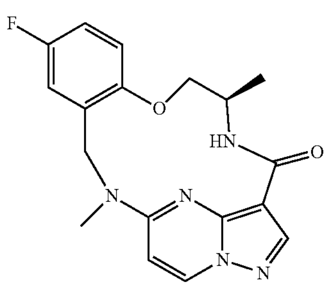 [SMILES: C[C@@H]1COc2ccc(F)cc2CN(C)c2ccn3ncc(c3n2)C(=O)N1] | (6R)-11-fluoro-6,14-dimethyl-6,7,13,14-tetrahydro-1,15-ethenopyrazolo[4,3-f][1,4,8,10]benzoxatriazacyclotridecin-4(5H)-one |
| 96 | 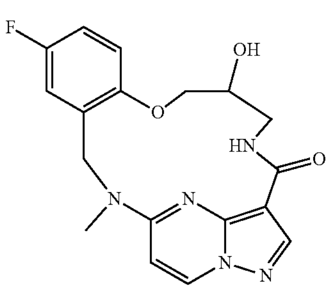 [SMILES: CN1Cc2cc(F)ccc2OCC(O)CNC(=O)c2cnn3ccc1nc23] | 12-fluoro-7-hydroxy-15-methyl-5,6,7,8,14,15-hexahydro-4H-1,16-ethenopyrazolo[4,3-g][1,5,9,11]benzoxatriazacyclotetradecin-4-one |

| Ex. | Structure | Chemical Name |
|---|---|---|
| 97 | 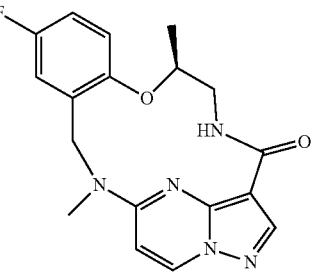 | (7S)-11-fluoro-7,14-dimethyl-6,7,13,14-tetrahydro-1,15-ethenopyrazolo[4,3-f][1,4,8,10]benzoxatriazacyclotridecin-4(5H)-one |
| 98 | 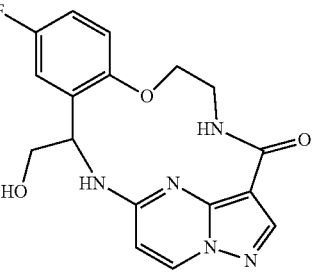 | 11-fluoro-13-(hydroxymethyl)-6,7,13,14-tetrahydro-1,15-ethenopyrazolo[4,3-f][1,4,8,10]benzoxatriazacyclotridecin-4(5H)-one |
| 99 | 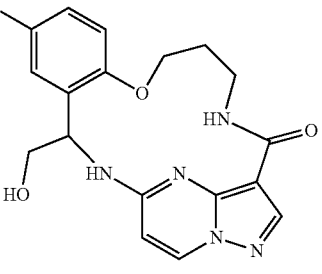 | 12-fluoro-14-(hydroxymethyl)-5,6,7,8,14,15-hexahydro-4H-1,16-ethenopyrazolo[4,3-g][1,5,9,11]benzoxatriazacyclotetradecin-4-one |
| 100 | 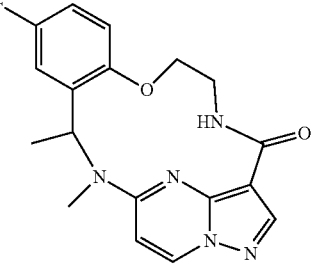 | 11-fluoro-13,14-dimethyl-6,7,13,14-tetrahydro-1,15-ethenopyrazolo[4,3-f][1,4,8,10]benzoxatriazacyclotridecin-4(5H)-one |
| 101 | 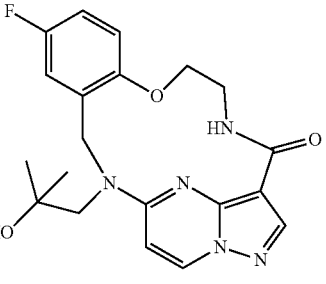 | 11-fluoro-14(2-hydroxy-2-methylpropyl)-6,7,13,14-tetrahydro-1,15-ethenopyrazolo[4,3-f][1,4,8,10]benzoxatriazacyclotridecin-4(5H)-one |

-continued

| Ex. | Structure | Chemical Name |
| --- | --- | --- |
| 102 | 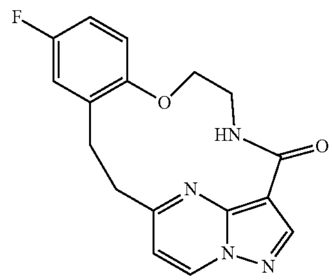 [SMILES: O=C1NCCOc2ccc(F)cc2CCc2ccn3ncc1c3n2] | 11-fluoro-6,7,13,14-tetrahydro-1,15-ethenopyrazolo[4,3-f][1,4,8]benzoxadiazacyclotridecin-4(5H)-one |
| 103 | 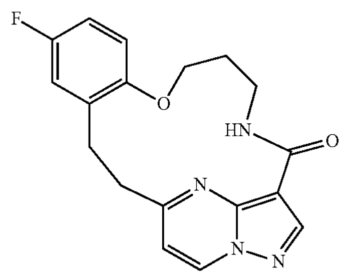 [SMILES: O=C1NCCCOc2ccc(F)cc2CCc2ccn3ncc1c3n2] | 12-fluoro-5,6,7,8,14,15-hexahydro-4H-1,16-ethenopyrazolo[4,3-g][1,5,9]benzoxadiazacyclotetradecin-4-one |
| 104 | 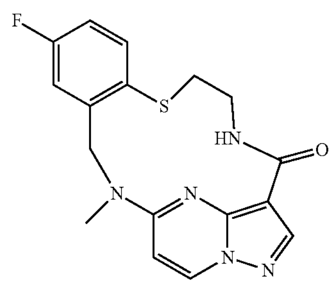 [SMILES: CN1Cc2cc(F)ccc2SCCNC(=O)c2cnn3ccc1nc23] | 11-fluoro-14-methyl-6,7,13,14-tetrahydro-1,15-ethenopyrazolo[4,3-f][1,4,8,10]benzothiatriazacyclotridecin-4(5H)-one |
| 105 | 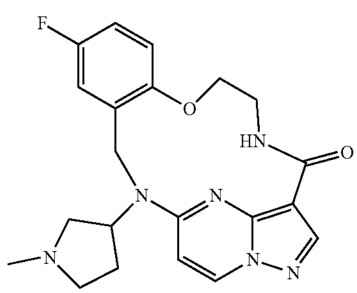 [SMILES: CN1CCC(N2Cc3cc(F)ccc3OCCNC(=O)c3cnn4ccc2nc34)C1] | 11-fluoro-14-(1-methylpyrrolidin-3-yl)-6,7,13,14-tetrahydro-1,15-ethenopyrazolo[4,3-f][1,4,8,10]benzoxatriazacyclotridecin-4(5H)-one |
| 106 | 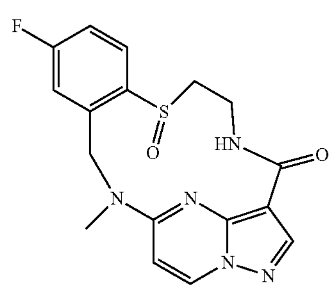 [SMILES: CN1Cc2cc(F)ccc2S(=O)CCNC(=O)c2cnn3ccc1nc23] | 11-fluoro-14-methyl-6,7,13,14-tetrahydro-1,15-ethenopyrazolo[4,3-f][1,4,8,10]benzothiatriazacyclotridecin-4(5H)-one 8-oxide |

| Ex. | Structure | Chemical Name |
|---|---|---|
| 107 | 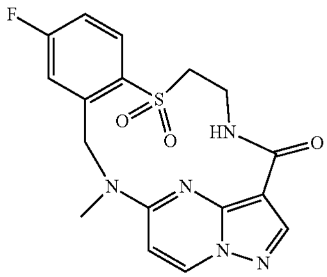 [SMILES: CN1Cc2cc(F)ccc2S(=O)(=O)CCNC(=O)c2cnn3ccc1nc23] | 11-fluoro-14-methyl-6,7,13,14-tetrahydro-1,15-ethenopyrazolo[4,3-f][1,4,8,10]benzothiatriazacyclotridecin-4(5H)-one 8,8-dioxide |
| 108 | 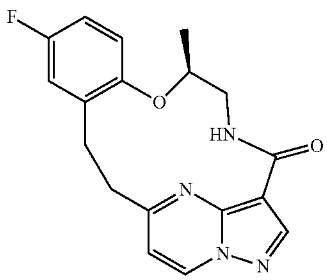 [SMILES: C[C@H]1CNC(=O)c2cnn3ccc(nc23)CCc2cc(F)ccc2O1] | (7S)-11-fluoro-7-methyl-6,7,13,14-tetrahydro-1,15-ethenopyrazolo[4,3-f][1,4,8]benzoxadiazacyclotridecin-4(5H)-one |
| 109 | 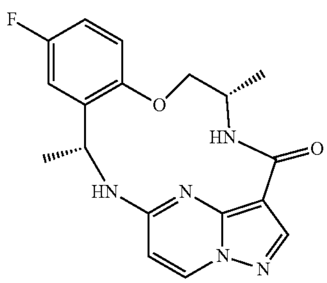 [SMILES: C[C@H]1COc2ccc(F)cc2[C@@H](C)Nc2ccn3ncc(c3n2)C(=O)N1] | (6S,13R)-11-fluoro-6,13-dimethyl-6,7,13,14-tetrahydro-1,15-ethenopyrazolo[4,3-f][1,4,8,10]benzoxatriazacyclotridecin-4(5H)-one |
| 110 | 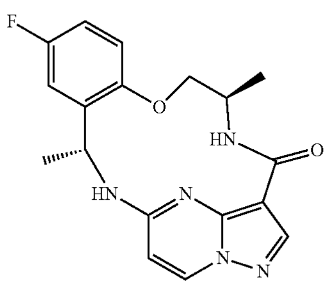 [SMILES: C[C@@H]1COc2ccc(F)cc2[C@@H](C)Nc2ccn3ncc(c3n2)C(=O)N1] | (6R,13R)-11-fluoro-6,13-dimethyl-6,7,13,14-tetrahydro-1,15-ethenopyrazolo[4,3-f][1,4,8,10]benzoxatriazacyclotridecin-4(5H)-one |
| 111 | 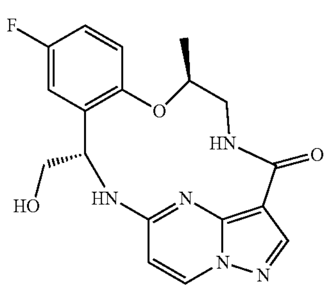 [SMILES: C[C@H]1CNC(=O)c2cnn3ccc(nc23)N[C@H](CO)c2cc(F)ccc2O1] | (7S,13S)-11-fluoro-13-(hydroxymethyl)-7-methyl-6,7,13,14-tetrahydro-1,15-ethenopyrazolo[4,3-f][1,4,8,10]benzoxatriazacyclotridecin-4(5H)-one |

| Ex. | Structure | Chemical Name |
|---|---|---|
| 112 | | 11-fluoro-6,7-dihydro-13H-1,15-ethenopyrazolo[4,3-f][1,10,4,8]benzoxathiadiazacyclotridecin-4(5H)-one | and pharmaceutically acceptable salts thereof.

Those skilled in the art will recognize that the species listed or illustrated herein are not exhaustive, and that additional species within the scope of these defined terms may also be selected.

Pharmaceutical Compositions

For treatment purposes, pharmaceutical compositions comprising the compounds described herein may further comprise one or more pharmaceutically-acceptable excipients. A pharmaceutically-acceptable excipient is a substance that is non-toxic and otherwise biologically suitable for administration to a subject. Such excipients facilitate administration of the compounds described herein and are compatible with the active ingredient. Examples of pharmaceutically-acceptable excipients include stabilizers, lubricants, surfactants, diluents, anti-oxidants, binders, coloring agents, bulking agents, emulsifiers, or taste-modifying agents. In preferred embodiments, pharmaceutical compositions according to the invention are sterile compositions. Pharmaceutical compositions may be prepared using compounding techniques known or that become available to those skilled in the art.

Sterile compositions are also contemplated by the invention, including compositions that are in accord with national and local regulations governing such compositions.

The pharmaceutical compositions and compounds described herein may be formulated as solutions, emulsions, suspensions, or dispersions in suitable pharmaceutical solvents or carriers, or as pills, tablets, lozenges, suppositories, sachets, dragees, granules, powders, powders for reconstitution, or capsules along with solid carriers according to conventional methods known in the art for preparation of various dosage forms. Pharmaceutical compositions of the invention may be administered by a suitable route of delivery, such as oral, parenteral, rectal, nasal, topical, or ocular routes, or by inhalation. Preferably, the compositions are formulated for intravenous or oral administration.

For oral administration, the compounds the invention may be provided in a solid form, such as a tablet or capsule, or as a solution, emulsion, or suspension. To prepare the oral compositions, the compounds of the invention may be formulated to yield a dosage of, e.g., from about 0.1 mg to 1 g daily, or about 1 mg to 50 mg daily, or about 50 to 250 mg daily, or about 250 mg to 1 g daily. Oral tablets may include the active ingredient(s) mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are exemplary disintegrating agents. Binding agents may include starch and gelatin. The lubricating agent, if present, may be magnesium stearate, stearic acid, or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, active ingredient(s) may be mixed with a solid, semi-solid, or liquid diluent. Soft gelatin capsules may be prepared by mixing the active ingredient with water, an oil, such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions, or syrups, or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

For parenteral use, including intravenous, intramuscular, intraperitoneal, intranasal, or subcutaneous routes, the agents of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms may be presented in unit-dose form such as ampoules or disposable injection devices, in multi-dose forms such as vials from which the appropriate dose may be withdrawn, or in a solid form or pre-concentrate that can be used to prepare an injectable formulation. Illustrative infusion doses range from about 1 to 1000 µg/kg/minute of agent admixed with a pharmaceutical carrier over a period ranging from several minutes to several days.

For nasal, inhaled, or oral administration, the inventive pharmaceutical compositions may be administered using, for example, a spray formulation also containing a suitable carrier. The inventive compositions may be formulated for rectal administration as a suppository.

For topical applications, the compounds of the present invention are preferably formulated as creams or ointments or a similar vehicle suitable for topical administration. For topical administration, the inventive compounds may be mixed with a pharmaceutical carrier at a concentration of about 0.1% to about 10% of drug to vehicle. Another mode of administering the agents of the invention may utilize a patch formulation to effect transdermal delivery.

As used herein, the terms "treat" or "treatment" encompass both "preventative" and "curative" treatment. "Preventative" treatment is meant to indicate a postponement of development of a disease, a symptom of a disease, or medical condition, suppressing symptoms that may appear, or reducing the risk of developing or recurrence of a disease or symptom. "Curative" treatment includes reducing the severity of or suppressing the worsening of an existing disease, symptom, or condition. Thus, treatment includes ameliorating or preventing the worsening of existing disease symptoms, preventing additional symptoms from occurring, ameliorating or preventing the underlying systemic causes of symptoms, inhibiting the disorder or disease, e.g., arresting the development of the disorder or disease, relieving the disorder or disease, causing regression of the disorder or disease, relieving a condition caused by the disease or disorder, or stopping the symptoms of the disease or disorder.

The term "subject" refers to a mammalian patient in need of such treatment, such as a human.

Exemplary diseases include cancer, pain, neurological diseases, autoimmune diseases, and inflammation. Cancer includes, for example, lung cancer, colon cancer, breast cancer, prostate cancer, hepatocellular carcinoma, renal cell carcinoma, gastric and esophago-gastric cancers, glioblastoma, head and neck cancers, inflammatory myofibroblastic tumors, and anaplastic large cell lymphoma. Pain includes, for example, pain from any source or etiology, including cancer pain, pain from chemotherapeutic treatment, nerve pain, pain from injury, or other sources. Autoimmune diseases include, for example, rheumatoid arthritis, Sjogren syndrome, Type I diabetes, and lupus. Exemplary neurological diseases include Alzheimer's Disease, Parkinson's Disease, Amyotrophic lateral sclerosis, and Huntington's disease. Exemplary inflammatory diseases include atherosclerosis, allergy, and inflammation from infection or injury.

In one aspect, the compounds and pharmaceutical compositions of the invention specifically target tyrosine receptor kinases, in particular MET, ALK, AXL, TRKs, and JAKs. Thus, these compounds and pharmaceutical compositions can be used to prevent, reverse, slow, or inhibit the activity of one or more of these kinases. In preferred embodiments, methods of treatment target cancer. In other embodiments, methods are for treating lung cancer or non-small cell lung cancer.

In the inhibitory methods of the invention, an "effective amount" means an amount sufficient to inhibit the target protein. Measuring such target modulation may be performed by routine analytical methods such as those described below. Such modulation is useful in a variety of settings, including in vitro assays. In such methods, the cell is preferably a cancer cell with abnormal signaling due to upregulation of MET, ALK. AXL, TRKs, and/or JAKs.

In treatment methods according to the invention, an "effective amount" means an amount or dose sufficient to generally bring about the desired therapeutic benefit in subjects needing such treatment. Effective amounts or doses of the compounds of the invention may be ascertained by routine methods, such as modeling, dose escalation, or clinical trials, taking into account routine factors, e.g., the mode or route of administration or drug delivery, the pharmacokinetics of the agent, the severity and course of the infection, the subject's health status, condition, and weight, and the judgment of the treating physician. An exemplary dose is in the range of about from about 0.1 mg to 1 g daily, or about 1 mg to 50 mg daily, or about 50 to 250 mg daily, or about 250 mg to 1 g daily. The total dosage may be given in single or divided dosage units (e.g., BID, TID, QID).

Once improvement of the patient's disease has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms. Patients may also require chronic treatment on a long-term basis.

Drug Combinations

The inventive compounds described herein may be used in pharmaceutical compositions or methods in combination with one or more additional active ingredients in the treatment of the diseases and disorders described herein. Further additional active ingredients include other therapeutics or agents that mitigate adverse effects of therapies for the intended disease targets. Such combinations may serve to increase efficacy, ameliorate other disease symptoms, decrease one or more side effects, or decrease the required dose of an inventive compound. The additional active ingredients may be administered in a separate pharmaceutical composition from a compound of the present invention or may be included with a compound of the present invention in a single pharmaceutical composition. The additional active ingredients may be administered simultaneously with, prior to, or after administration of a compound of the present invention.

Combination agents include additional active ingredients are those that are known or discovered to be effective in treating the diseases and disorders described herein, including those active against another target associated with the disease. For example, compositions and formulations of the invention, as well as methods of treatment, can further comprise other drugs or pharmaceuticals. e.g., other active agents useful for treating or palliative for the target diseases or related symptoms or conditions. For cancer indications, additional such agents include, but are not limited to, kinase inhibitors, such as EGFR inhibitors (e.g., erlotinib, gefitinib) . Raf inhibitors (e.g., vemurafenib), VEGFR inhibitors (e.g., sunitinib), standard chemotherapy agents such as alkylating agents, antimetabolites, anti-tumor antibiotics, topoisomerase inhibitors, platinum drugs, mitotic inhibitors, antibodies, hormone therapies, or corticosteroids. For pain indications, suitable combination agents include anti-inflammatories such as NSAIDs. The pharmaceutical compositions of the invention may additional comprise one or more of such active agents, and methods of treatment may additionally comprise administering an effective amount of one or more of such active agents.

Chemical Synthesis

Exemplary chemical entities useful in methods of the invention will now be described by reference to illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Furthermore, one of skill in the art will recognize that the transformations shown in the schemes below may be performed in any order that is compatible with the functionality of the particular pendant groups. Each of the reactions depicted in the general schemes is preferably run at a temperature from about 0° C. to the reflux temperature of the organic solvent used. Unless otherwise specified, the variables are as defined above in reference to Formula (I). Isotopically labeled compounds as described herein are prepared according to the methods described below, using suitably labeled starting materials. Such materials are generally available from commercial suppliers of radiolabeled chemical reagents.

General Method A:

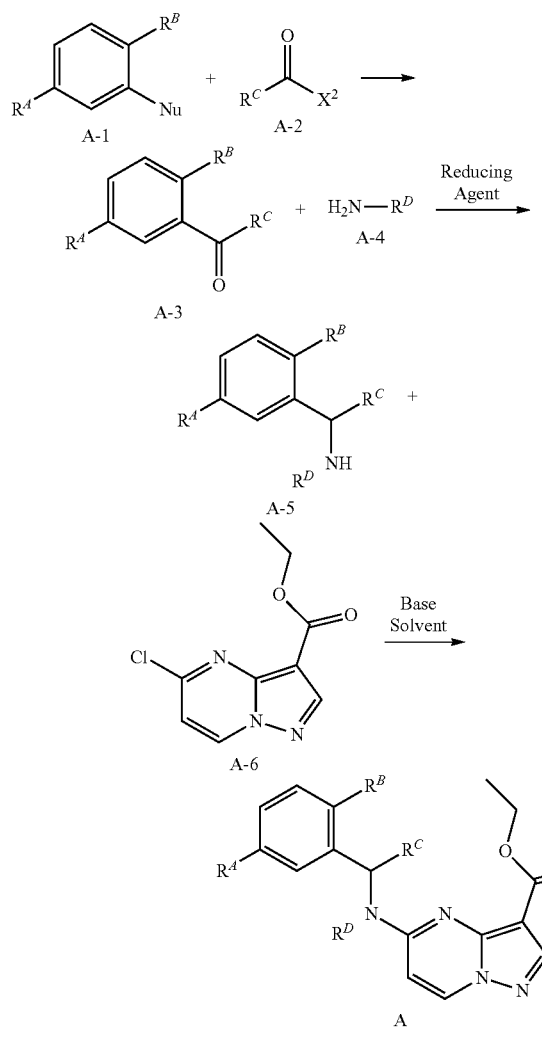

Tt will be appreciated that compounds of the formula A or A-1 can be made according to General Method A using appropriately functionalized starting materials and intermediates.

Step 1. To a solution of an appropriately functionalized compound A-1 (~1.00 eq.), where $R^A$ and $R^B$ are groups compatible with the reaction conditions described herein and Nu is a nucleophilic group such as an anion or a group capable of forming a nucleophile, such as a halide, in a reagent capable of promoting the compiling of A-1 and A-2, such as an acid (e.g. TfOH (0.6 M)) or an alkyl halide (e.g., n-BuLi) can be added A-2, where $R^C$ is a group compatible with the reaction conditions described herein and $X^2$ is, for example, a leaving group (~1.00 eq.) at an appropriate temperature (e.g. 0° C.). The mixture can be stirred at an appropriate temperature (e.g. 60° C.) until the reaction is completed. The reaction can then be returned to to ambient temperature, and the reaction mixture can be quenched, neutralized, washed, extracted, dried and/or concentrated under vacuum as needed to give A-3.

Step 2. A mixture of A-3, where $R^A$, $R^B$ and $R^C$ are groups compatible with the reaction conditions described herein (in some exemplary embodiments described herein, A-3 can be a commercially available aldehyde or ketone, or A-3 can be prepared from step 1, ~1.00 eq.) and commercially available amine A-4, where $R^C$ is a group compatible with the reaction conditions described herein, (~1.50 eq.) in an appropriate solvent (e.g. methanol (0.5 M)) can be stirred at an appropriate temperature (e.g. ambient temperature) for an appropriate amount of time or until the imine formation is complete by TLC or LC-MS. To the reaction solution can be added a reducing agent (e.g. NaBH₄ (~2.00 eq.)) portionwise. The mixture can be stirred at an appropriate temperature (e.g. ambient temperature) until TLC or LC-MS shows the reduction to be complete. The reaction can be quenched, washed, extracted, dried and or concentrated under vacuum as needed to provide A-5.

Step 3. A mixture of a prepared or commercial available A-5, where $R^A$, $R^B$ and $R^C$ are groups compatible with the reaction conditions described herein (~1 eq.), commercially available ethyl 5-chloropyrazolo[1,5-a]pyrimidine-3-carboxylate (A-6, ~1 eq.) and an appropriate base (e.g. diisopropylethylamine (~5 eq.)) in an appropriate solvent (e.g. butanol (0.4 M)) can be stirred at an appropriate temperature (e.g. 110° C.) for a set length of time or until the reaction is shown to be complete. The reaction can be returned to ambient temperature and diluted with water as needed. The mixture can be extracted, washed, dried, concentrated under reduced pressure and/or purified by chromatographic methods as needed to provide A.

In some exemplary embodiments, General Method A can be carried out as follows:

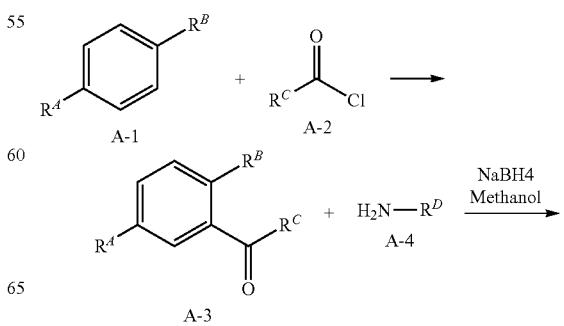

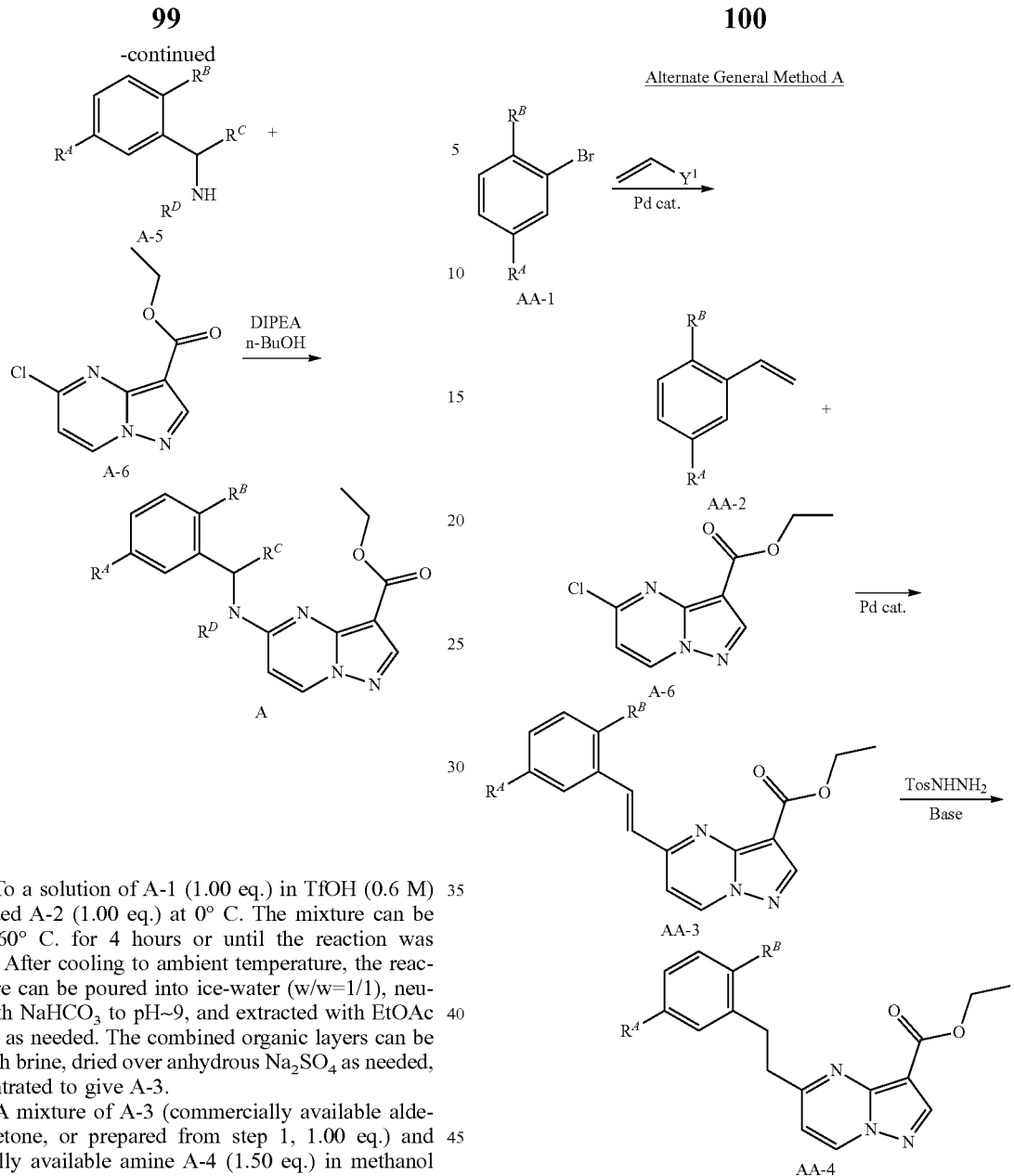

Step 1. To a solution of A-1 (1.00 eq.) in TfOH (0.6 M) can be added A-2 (1.00 eq.) at 0° C. The mixture can be stirred at 60° C. for 4 hours or until the reaction was completed. After cooling to ambient temperature, the reaction mixture can be poured into ice-water (w/w=1/1), neutralized with NaHCO$_3$ to pH~9, and extracted with EtOAc three times as needed. The combined organic layers can be washed with brine, dried over anhydrous Na$_2$SO$_4$ as needed, and concentrated to give A-3.

Step 2. A mixture of A-3 (commercially available aldehyde or ketone, or prepared from step 1, 1.00 eq.) and commercially available amine A-4 (1.50 eq.) in methanol (0.5 M) can be stirred at ambient temperature for 2 hour or until the imine formation is shown to be complete by TLC or LC-MS. To the reaction solution can be added NaBH$_4$ (2.00 eq.) portion-wise. The mixture can be stirred at ambient temperature until TLC or LC-MS shows the reduction to be complete. The reaction can be quenched with water and extracted three times with dichloromethane as needed. The combined organic phase can be washed with brine, dried with anhydrous Na$_2$SO$_4$, filtered and concentrated in vacuum to afford A-5.

Step 3. The prepared or commercial available A-5 (1 eq.), ethyl 5-chloropyrazolo[1,5-a]pyrimidine-3-carboxylate (A-6, 1 eq.) and diisopropylethylamine (5 eq.) in butanol (0.4 M) can be heated at 110° C. for 30 minutes or until the reaction is shown to be complete. The reaction can be cooled and diluted with water. The mixture can be extracted with dichloromethane four times (as needed) and the combined extracts can be dried over anhydrous sodium sulfate. After filtration, the mixture can be concentrated under reduced pressure and the residue can be purified via flash chromatography to provide A.

Coupling Step 1. The mixture of an appropriately functionalized AA-1 (~1.00 eq.), an appropriately functionalized vinyl coupling reagent (~1.00-1.50 eq.) and a palladium catalyst (~0.05 eq.) under appropriate reaction conditions can be heated to an appropriate temperature (e.g. ~90° C.) for an appropriate amount of time under inert atmosphere until TLC indicates that the starting material to be completely consumed. The reaction mixture can be poured into H$_2$O as needed. The mixture can be extracted and the organic phase washed, dried, concentrated, and purified via silica gel column chromatography as needed to afford AA-2.

Coupling Step 2. The mixture of a compound of the type AA-2 (~1.00 eq.), ethyl 5-chloropyrazolo[1,5-a]pyrimidine-3-carboxylate (A-6, ~1.00 eq.) and a palladium catalyst under appropriate reaction conditions can be heated to an appropriate temperature (e.g. 120° C.) for an appropriate length of time under inert atmosphere until TLC indicates the starting material to be completely consumed. The reaction mixture can be poured into H$_2$O as needed. The mixture can be extracted and the organic phase can be washed, dried, concentrated, and purified via silica gel column chromatography as needed to afford AA-3.

Step 3. To a mixture of AA-3 (~1.00 eq.) and 4-methylbenzenesulfonohydrazide (in molar excess) in a suitable solvent can be added an appropriate base (in molar excess) at an appropriate temperature under inert atmosphere. The mixture can be heated to an appropriate temperature (e.g. 65° C.) and stirred for an appropriate amount of time until TLC indicates the reaction to be complete. The mixture can be cooled and concentrated under reduced pressure as needed. The concentrated reaction mixture can be diluted with water as needed, and extracted. The combined organic phase can be washed, dried, filtered, concentrated in vacuum, and purified to afford AA-4.

General Method B

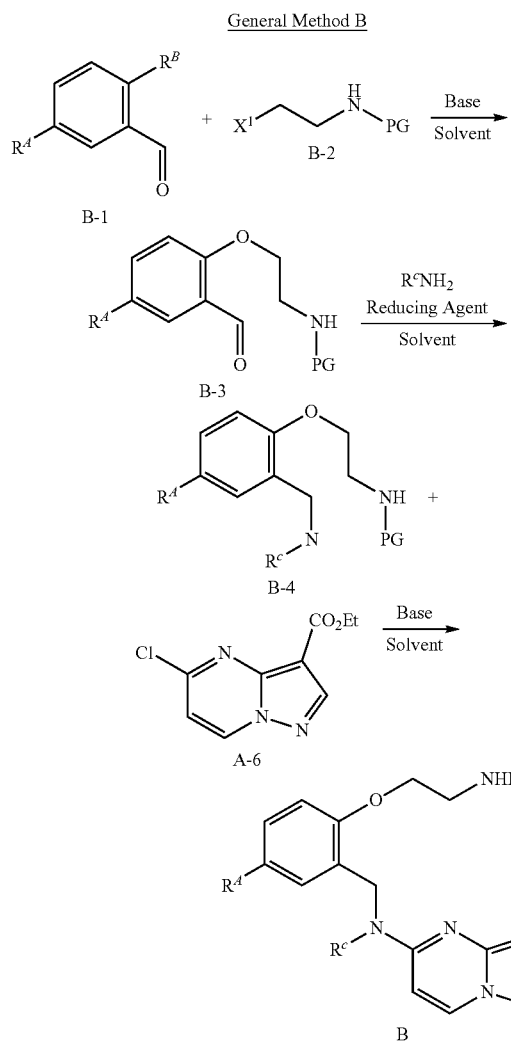

Step 1. A solution of aldehyde B-1 (~1.0 eq) where $R^A$ and $R^B$ are groups compatible with the reaction conditions described herein, B-2 (~1.0 eq) where $X^1$ is a leaving group and PG is a protecting group, an suitable base (in molar excess) and a catalyst in an suitable solvent can be heated and stirred for for an appropriate amount of time until the reaction is complete. Additional B-2 can be added and further heating applied as needed. The mixture can be cooled to ambient temperature and diluted with water as needed.

The mixture can be extracted, and the combined extracts can be washed, dried, and concentrated under reduced pressure as needed. The crude reaction product can be purified via flash chromatography to provide B-3.

Step 2. Aldehyde B-3 (~1.0 eq) and an appropriately functionalized amine (~2.0-4.0 eq) where $R^C$ is a group compatible with the reaction conditions described herein in an appropriate solvent can be heated and stirred for an appropriate amount of time. The mixture can be cooled to ambient temperature and a suitable reducing agent (~1.0 eq) can be added. The mixture can be stirred for an appropriate amount of time then quenched by addition of water as needed. The mixture can be extracted with an appropriate organic solvent, and the combined extracts can be washed, dried and concentrated under reduced pressure as needed. The crude reaction product can be purified via flash chromatography as needed to provide B-4.

Step 3. Compound B-4 (~1.0 eq), ethyl 5-chloropyrazolo[1,5-a]pyrimidine-3-carboxylate (A-6, ~1.0 eq) and a suitable base (in molar excess) in a suitable solvent can be heated for an appropriate amount of time. The reaction can be cooled and diluted with water as needed. The mixture can be extracted with a suitable organic solvent, and the combined extracts can be dried and concentrated under reduced pressure as needed. The crude reaction product can be purified via flash chromatography to provide B1.

In some exemplary embodiments, General Method B can be carried out as follows:

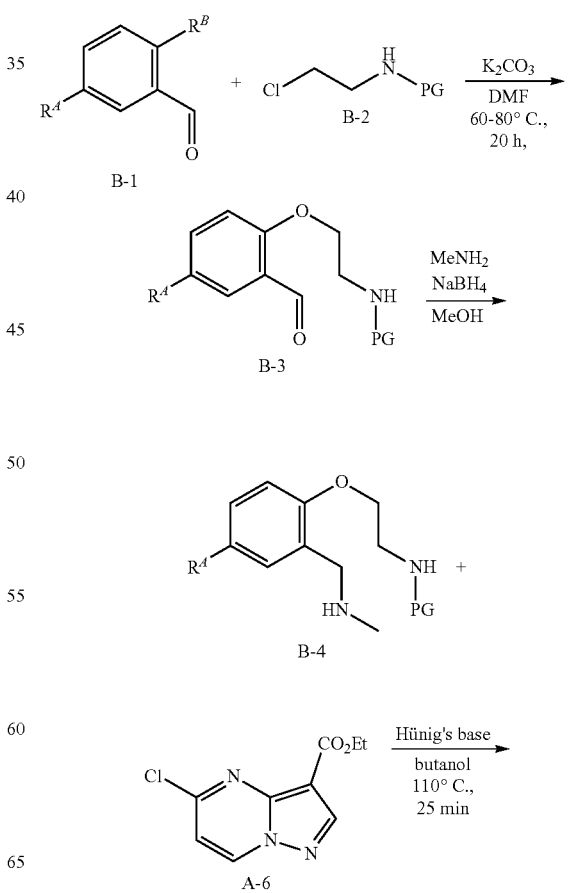

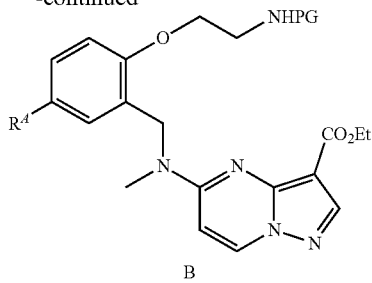

B

Step 1. A solution of aldehyde B-1 (~1.0 eq) where $R^A$ and $R^B$ are groups compatible with the reaction conditions described herein, B-2 (~1.0 eq) where $X^1$ is a leaving group and PG is a protecting group, potassium carbonate (in molar excess) and potassium iodide (catalytic amount) in DMF can be heated to 60° C. and stirred for ~15 hours. Additional chloride B-2 can be added and further heating at 80° C. can be applied as needed until the reaction is shown to be complete. The mixture can be cooled to ambient temperature and diluted by addition of water (250 mL) as needed. The mixture can be extracted with ethyl acetate (3×300 mL) and the combined extracts can be washed with water (200 mL) and brine (100 mL), can be dried with sodium sulfate, and concentrated under reduced pressure as needed. The crude reaction product can be purified via flash chromatography to provide B-3.

Step 2. Aldehyde B-3 (~1.0 eq) and methylamine (~2.5 eq) in methanol can be heated to 60° C. and stirred for ~1 hour. The mixture can be cooled to ambient temperature and sodium borohydride (~1.0 eq) can be added. The mixture can be stirred for ~30 minutes then quenched by addition of water (200 mL) as needed. The mixture can be extracted with dichloromethane and the combined extracts can be washed with brine (50 mL), can be dried with sodium sulfate and concentrated under reduced pressure as needed. The crude reaction product can be purified via flash chromatography to provide B-4.

Step 3. Amine B-4 (~1.0 eq), ethyl 5-chloropyrazolo[1,5-a]pyrimidine-3-carboxylate (A-6, ~1.0 eq) and hünig's base (in molar excess) in butanol can be heated at 110° C. for ~25 minutes. The reaction can be cooled and diluted with water (250 mL). The mixture can be extracted with dichloromethane and the combined extracts can be dried with sodium sulfate as needed. The mixture can be concentrated under reduced pressure as needed. The crude reaction product can be purified via flash chromatography to provide B.

General Method C

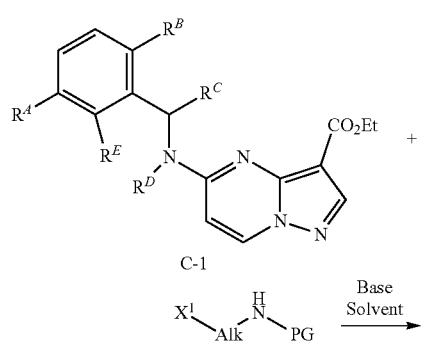

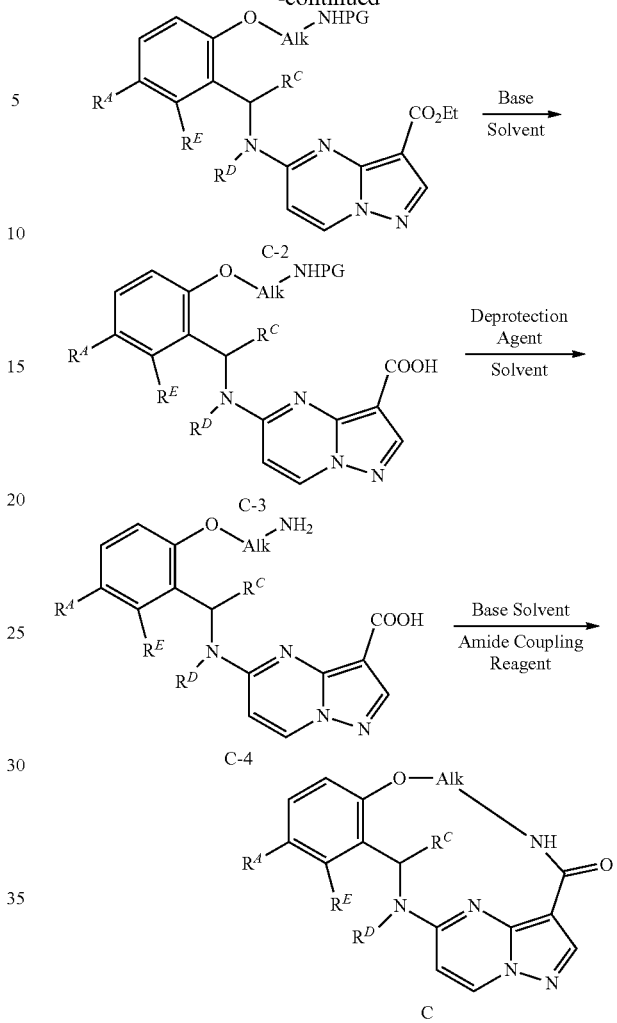

Step 1. To a solution of C-1 (~1.0 eq.) where $R^A$, $R^B$, $R^C$, $R^D$ and $R^E$ are groups compatible with the reaction conditions described herein, $X^1$AlkNHPG (~1.5-2.0 eq.) where $X^1$ is a leaving group, Alk is an appropriately functionalized alkyl group and PG is a protecting group in a suitable solvent can be added a suitable base (~3.0 eq.). The mixture can be heated to an appropriate temperature for an appropriate amount of time under inert atmosphere until complete conversion of the starting material to the product is shown by LC-MS. The mixture can be cooled to ambient temperature, diluted with water and extracted with an suitable organic solvent as needed. The combined organic extracts can be washed with water and brine, dried over $Na_2SO_4$, and concentrated as needed. The resulting residue can be purified via silica gel column chromatography as needed to afford C-2.

Step 2. To a solution of C-2 (1 eq.) where $R^A$, $R^C$, $R^D$ and $R^E$ are groups compatible with the reaction conditions described herein, Alk is an appropriately functionalized alkyl group and PG is a protecting group in a suitable solvent can be added a suitable base (in molar excess). The solution can be heated at to an appropriate temperature for an appropriate amount of time. The reaction can be neutralized with a suitable acid to pH<5, and the reaction mixture can be extracted with a suitable organic solvent. The combined organics can be washed and can be dried as needed. The crude reaction product mixture can be filtered, concentrated under reduced pressure, and dried under high vacuum as needed to provide C-3.

Step 3. To a solution of C-3 (~1.0 eq.) in a suitable organic solvent can be added a suitable acid (~4 eq.) at an appropriate temperature (e.g. 0° C.). The reaction mixture can be stirred at an appropriate temperature for an appropriate amount of time until the reaction is shown to be complete by LC-MS. The crude product can be filtered, washed, and can be dried under high vacuum to provide a C-4.

Step 4a. To a solution of C-4 (~1.0 eq.) in a suitable solvent can be added a suitable base (in molar excess). The solution can be cooled in an ice water bath and a suitable coupling agent (~1.5 eq.) can be added to produce an activated ester. The solution can be warmed to ambient temperature slowly and stirred until the starting material is shown to convert to the desired product by LC-MS. The mixture can be diluted with water and extracted with a suitable organic solvent as needed. The combined organic extracts can be washed, dried, and concentrated under reduced pressure as needed. The resulting residue can be purified by a silica gel column chromatography to afford C.

In some exemplary embodiments, General Method C can be carried out as follows:

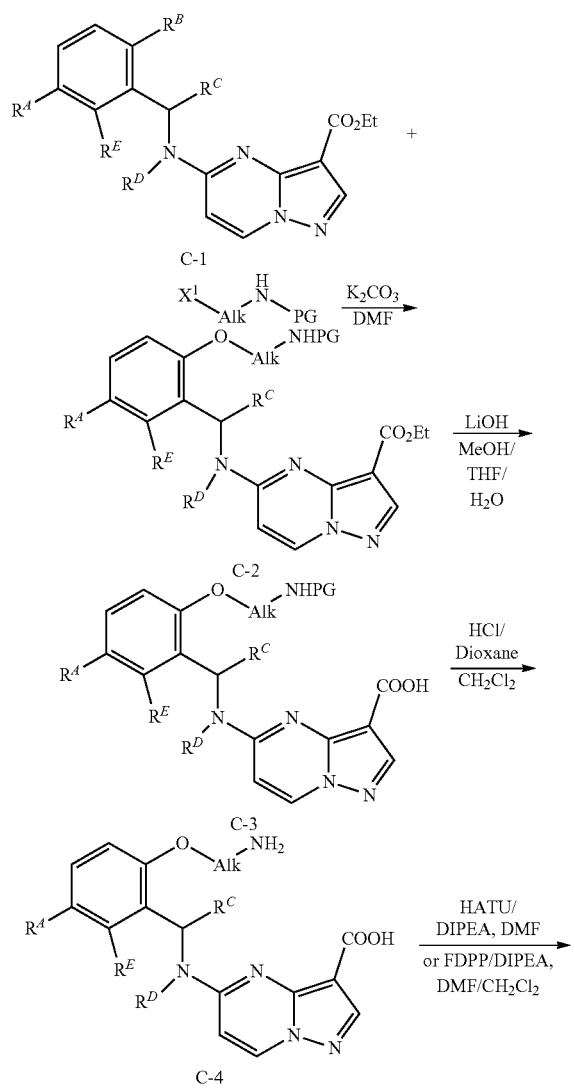

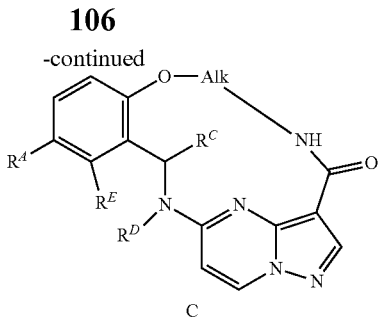

C

Step 1. To a solution of C-1 (~1.0 eq.), where $R^A$, $R^B$, $R^C$, $R^D$ and $R^E$ are groups compatible with the reaction conditions described herein, $X^1$AlkNHPG (~1.5-2.0 eq.) where $X^1$ is a leaving group, Alk is an appropriately functionalized alkyl group and PG is a protecting group in DMF (0.5 M) can be added $K_2CO_3$ (~3.0 eq.). The mixture can be heated at ~80° C. for ~2 hours or until complete conversion of the starting material to the product can be shown by LC-MS. The mixture can be cooled to ambient temperature, diluted with water as needed and extracted three times with EtOAc as needed. The combined organic layers can be then washed with water and brine, can be dried over $Na_2SO_4$, and concentrated as needed. The resulting residue can be purified via silica gel column chromatography eluting with EtOAc/Hexane (5-100%, 10CV) to afford C-2.

Step 2. To a solution of C-2 (~1 eq.) in methanol/THF/H2O (3:1:1, 0.2M) can be added LiOH·H2O (~5.0 eq.). The solution can be heated at ~70° C. for ~2 hours The reaction can be neutralized at ~0° C. with aq. HCl (2M) to pH<5, and extracted four times with $CH_2Cl_2$ as needed. The combined organic extracts can be washed with brine, and can be dried over $Na_2SO_4$ as needed. The crude product mixture can be filtered, concentrated under reduced pressure, and dried under high vacuum as needed to provide C-3.

Step 3. To a solution of C-3 (~1.0 eq.) in $CH_2Cl_2$ (0.25M) can be added HCl in dioxane (4 M, ~4 eq.) at ~0° C. The reaction can be stirred and allowed to warm from 0° C. to room temperature for about 27 hours or until the reaction can be shown to be complete by LC-MS. The resulting reaction mixture can be filtered, washed with $CH_2Cl_2$, and dried under high vacuum as needed to provide C-4.

Step 4a. Cyclization with HATU. To a solution of C-4 (~1.0 eq.) in ~10 mL of DMF (~0.005M) can be added DIPEA (~5.0 eq.). The solution can be cooled in an ice water bath and HATU (~1.5 eq.) can be added. The solution can be allowed to warm to ambient temperature and stirred until such time as complete conversion of the starting material to the desired product can be shown by LC-MS. The mixture can be diluted with water and extracted three times with EtOAc as needed. The combined organic extracts can be washed with water and brine, dried over $Na_2SO_4$, and concentrated under reduced pressure as needed. The resulting residue can be purified via silica gel column chromatography (0-5% MeOH/DCM) to afford C.

Step 4b. Cyclization with FDPP. To a solution of DIPEA (~5 eq.) in DMF/$CH_2Cl_2$ (3:1, ~0.005M) can be added C-4 (~1.00 eq.). After C-4 dissolves completely, pentafluorophenyl diphenylphosphinate (FDPP, ~1.05 eq.) can be added. The coupling can be allowed to stir for 30 minutes or until such time as the reaction is shown to be complete by LC-MS. The reaction solution can be diluted with $CH_2Cl_2$, washed three times with water, aqueous $Na_2CO_3$ (2 M) and brine, can be dried over $Na_2SO_4$ as needed. After filtration and concentration under reduced pressure, the residue can be purified via silica gel column chromatography eluting with MeOH/CH$_2$Cl$_2$ (0-5%) to provide C.

EXAMPLES

The following examples are offered to illustrate but not to limit the invention. One of skill in the art will recognize that the following synthetic reactions and schemes may be modified by choice of suitable starting materials and reagents in order to access other compounds of Formula (I) or (I-A). Bicyclic heteroaromatic groups with suitable functionality for use in the synthetic methods are commercially available.

Abbreviations

The examples described herein use materials, including but not limited to, those described by the following abbreviations known to those skilled in the art:

| Abbreviation | Name |
|---|---|
| TLC | thin layer chromatography |
| PLC | preparative Liquid chromatography |
| HPLC | high performance liquid chromatography |
| LCMS, LC-MS | liquid chromatography mass spectrometry |
| LRESIMS | low resolution electrospray ionization mass spectrometry |
| ELISA | enzyme-linked immuno assay |
| DCM | dichloromethane |
| DMSO | dimethylsufoxide |
| DIPEA, DIEA | di-isopropylethyl amine |
| CDI | 1,1'-Carbonyldiimidazole |
| THF | tetrahydrofuran |
| XantPhos | 4,5-bis(diphenylphosphino)-9,9-dimethylxanthene |
| TBSCl | tert-butyldimethylsilyl chloride |
| DMF | N,N-dimethylformamide |
| HATU | 1-[bis(dimethylamino)methylene]-1H-1,2,3-triazolo[4,5-b]pyridinium 3-oxid hexafluorophosphate |
| ACN | acetonitrile |
| EtOAc | ethyl acetate |
| DTAD | di-tert-butyl azodicarboxylate |
| FDFF | pentafluorophenyl diphenylphosphinate |
| FBS | fetal bovine serum |
| BSA | bovine serum albumin |
| PBS | phosphate buttered silane |
| DMEM | Dulbecco's modified eagle medium |
| EDTA | Ethylenediaminetetraacetic acid |
| RIPA | radioimmunoprecipitation assay |
| HEPES | 4-(2-hydroxyethyl)-1-piperazineethanesulfonic acid) |

Example A6

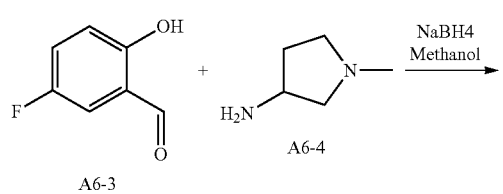

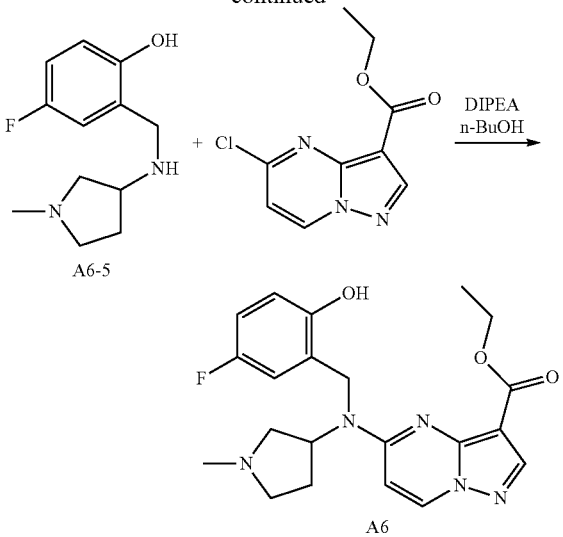

Step 1. To a solution of 5-fluoro-2-hydroxybenzaldehyde (500.00 mg, 3.57 mmol, 1.00 eq.) in MeOH (20.00 mL) was added 1-methylpyrrolidin-3-amine (357.43 mg, 3.57 mmol, 1.00 eq.) in one portion at 16° C. under N$_2$. The mixture was stirred at 16° C. for 10 hours under N$_2$. Then NaBH$_4$ (270.00 mg, 7.14 mmol, 2.00 eq.) was added and the mixture was stirred at 16° C. for 6 hours under N$_2$. TLC (DCM: MeOH=15:1) showed the reaction was completed. The reaction mixture was concentrated under reduced pressure to remove MeOH. The residue was diluted with water (50 mL) and extracted with DCM (20 mL×3). The combined organic layers were washed with brine (50 mL), dried over Na$_2$SO$_4$, filtered and concentrated under reduced pressure to give A6-5 (350.00 mg, 1.56 mmol, 43.71% yield) as yellow solid. $^1$HNMR (300 MHz, DMSO-d$_6$) δ 6.94 (dd, J=2.7, 9.3 Hz, 1H), 6.86 (dt, J=3.0, 8.6 Hz, 1H), 6.67 (dd, J=4.7, 8.7 Hz, 1H), 3.71 (s, 2H), 3.24-3.09 (m, 1H), 2.58 (dd, 1=7.1, 8.8 Hz, 1H), 2.48-2.32 (m, 2H), 2.30-2.17 (m, 4H), 2.05-1.82 (m, 1H), 1.60-1.43 (m, 1H).

Step 2. To a solution of A6-5 (300.00 mg, 1.34 mmol, 1.00 eq.) and ethyl 5-chloropyrazolo[1,5-a]pyrimidine-3-carboxylate (302.34 mg, 1.34 mmol, 1.00 eq.) in n-BuOH (40.00 mL) was added DIPEA (1.04 g, 8.04 mmol, 6.00 eq.) at 16° C. under N$_2$. The mixture was stirred at 120° C. for 2 hours. TLC (PE:EtOAc=1:1) showed the reaction was completed. The mixture was pour into water (50 mL) and extracted by DCM (50 mL×3). The mixture was purified by Pre-PLC to give A6 formic acid salt (290.00 mg, 701.43 umol, 52.35% yield) as a white solid.

Example A8

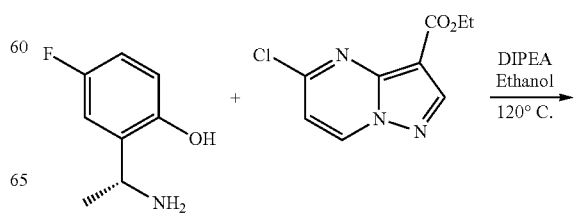

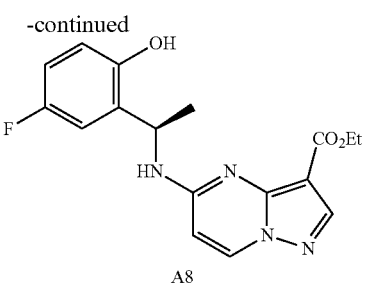

A8

To a solution of ethyl 5-chloropyrazolo[1,5-a]pyrimidine-3-carboxylate (1.25 g, 5.54 mmol) and (R)-2-(1-aminoethyl)-4-fluorophenol HCl salt (purchased from NetChem, Inc.) in EtOH (15.83 mL) was added Hunig's base (3.58 g, 27.70 mmol) and heated to 70° C. for 1.5 hour. The reaction was rotovaped to dryness, suspended in water, and extracted with DCM (5×50 mL). The combined extracts were dried with Na$_2$SO$_4$ and concentrated under reduced pressure. Flash chromatography (ISCO system, silica (40 g), 0-5% methanol in dichloromethane) provided A8 (1.89 g, 5.49 mmol, 99% yield).

Example A9

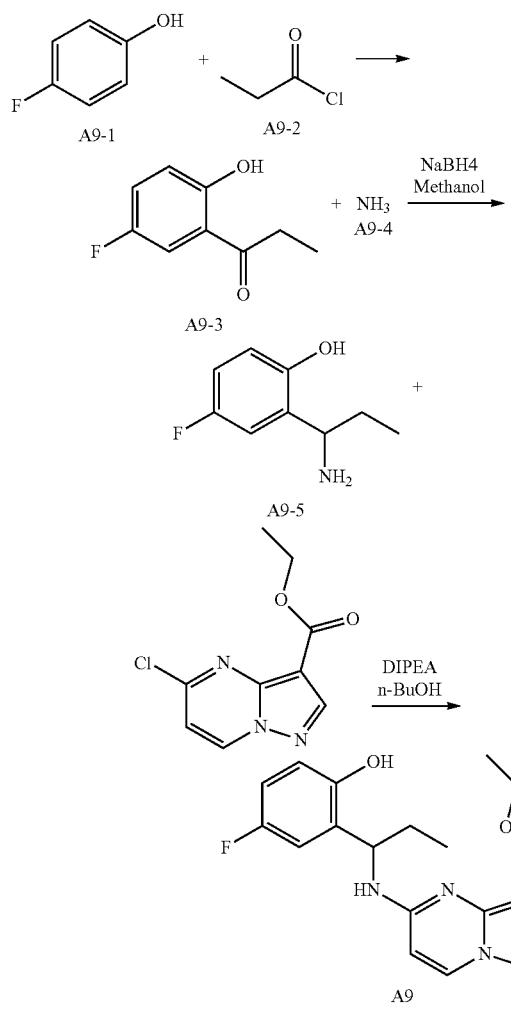

Step 1. To a solution of 4-fluorophenol (2.00 g, 17.84 mmol, 1.00 eq.) in TfOH (30.00 mL) was added propanoyl chloride (1.65 g, 17.84 mmol, 1.00 eq.) at 0° C. The mixture was stirred at 60° C. for 4 hours TLC showed the reaction was completed. The mixture was cooled to 25° C. poured into ice-water (w/w=1/1) (120 mL), neutrolized with NaHCO$_3$ to make pH ~9, and extracted with EtOAc (120 mL×3). The combined organic layers were washed by brine (50 mL), dried with anhydrous Na$_2$SO$_4$, and concentrated to give A9-3 (1.80 g, 10.70 mmol, 59.98% yield) as a colorless oil. $^1$HNMR (400 MHz, CDCl$_3$) δ 12.09 (s, 1H), 7.45 (dd, J=3.0, 9.0 Hz, 1H), 7.26-7.20 (m, 1H), 6.97 (dd, J=4.5, 9.0 Hz, 1H), 3.02 (q, J=7.3 Hz, 2H), 1.27 (t, J=7.2 Hz, 3H).

Step 2. Ammonia gas was bubbled into MeOH (20 mL) at −78° C. for 10 minutes. A9-3 (1.00 g, 5.95 mmol, 1.00 eq.) was added to the solution and stirred at 25° C. for 1 hr. To the reaction mixture was added Ti(i-PrO)$_4$ (1.63 g, 7.14 mmol, 1.20 eq.), and the mixture was stirred for another 1 hr. Then NaBH$_4$ (449.93 mg, 11.89 mmol, 2.00 eq.) was added. The mixture was stirred at 25° C. for 12 hours TLC showed the starting material was consumed completely. The residue was poured into water (50 mL) and stirred for 30 mins. The mixture was filtered and the filtrate was adjusted with HCl (1 M) to pH ~1 and extracted with EtOAc (50 mL×2). Sodium bicarbonate was added to the aqueous phase to adjust pH~9 and extracted with DCM (50 mL×2). The combined organic layers were washed with saturated brine (50 mL), dried with anhydrous Na$_2$SO$_4$, filtered and concentrated in vacuum to afford A9-5 (310.00 mg, 1.83 mmol, 30.79% yield) as a yellow solid. $^1$HNMR (400 MHz, CDCl$_3$) δ 6.86 (dt, J=3.0, 8.4 Hz, 1H), 6.79-6.74 (m, 1H), 6.67 (dd, J=2.9, 8.9 Hz, 1H), 3.98 (t, J=7.0 Hz, 1H), 1.92-1.81 (m, 1H), 1.80-1.68 (m, 1H), 0.95 (t, J=7.4 Hz, 3H).

Step 3. A9-5 was coupled with ethyl 5-chloropyrazolo[1,5-a]pyrimidine-3-carboxylate in the presence of DIPEA in n-BuOH to provide A9 as described in General Method A.

Example A 13-5: Preparation of 2-(O-amino-2-cyclopropylethyl)-4-fluorophenol

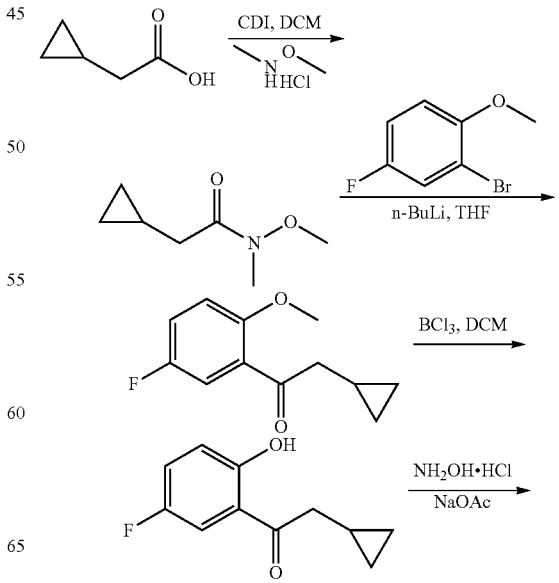

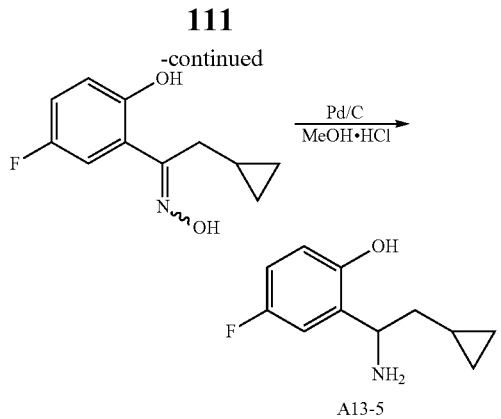

Step 1. To a mixture of 2-cyclopropylacetic acid (4.47 g, 44.60 mmol, 1.00 eq.) in DCM (150.00 mL) was added CDI (7.96 g, 49.10 mmol, 1.10 eq.) in one portion at 25° C. under N$_2$. The mixture was stirred at 25° C. for 1 hr. Then N-methoxymethanamine hydrochloride (4.79 g, 49.06 mmol, 1.10 eq.) was added. The mixture was stirred at 25° C. for another 12 hours. The reaction was quenched with 1N aqueous hydrochloric acid (50 mL), and separated into layers.

The aqueous layer was extracted with DCM (30 mL×2). The combined organic layer was washed with 50% saturated aqueous sodium carbonate (50 mL) and saturated brine (30 mL), dried with anhydrous Na$_2$SO$_4$, filtered and concentrated in vacuum to afford 2-cyclopropyl-N-methoxy-N-methylacetamide (6.00 g, 41.91 mmol, 93.96% yield) as an oil. $^1$H NMR (400 MHz, CDCl$_3$) δ 3.65 (s, 1H), 3.18 (s, 1H), 2.33 (d, J=6.8 Hz, 2H), 1.13-1.02 (m, 1H), 0.57-0.49 (m, 2H), 0.19-0.11 (m, 2H).

Step 2. To a mixture of 2-cyclopropyl-N-methoxy-N-methylacetamide (6.00 g, 29.27 mmol, 1.00 eq.) in THF (100.00 mL) was added n-BuLi (2.5 M, 12.88 mL, 1.10 eq.) dropwise at −78° C. under N$_2$. The mixture was stirred at −78° C. for 10 min. And then the mixture was treated with 2-bromo-4-fluoro-1-methoxybenzene (4.19 g, 29.27 mmol, 1.00 eq.) in THF (20 mL) over a period of 20 min. After stirring at −78° C. for 1 hr, the mixture was allowed to warm to 25° C. and stirred for one more hour. TLC showed the reaction was completed. The mixture was poured into 10% aqueous HCl solution (100 mL) and stirred for 10 min. The aqueous phase was extracted with ethyl acetate (300 mL×3). The combined organic phase was washed with brine (200 mL), dried over anhydrous Na$_2$SO$_4$, filtered and concentrated in vacuum. The residue was purified by silica gel chromatography (Petroleum ether/Ethyl acetate=50/1, 10/1) to afford 2-cyclopropyl-1-(5-fluoro-2-methoxyphenyl)ethan-1-one (2.4 g, 39.38% yield) as a colourless oil. $^1$H NMR (400 MHz, CDCl$_3$) δ 7.42 (dd, J=3.3, 8.8 Hz, 1H), 7.15 (ddd, J=3.3, 7.5, 9.0 Hz, 1H), 6.91 (dd, J=4.0, 9.0 Hz, 1H), 3.91-3.85 (m, 3H), 2.89 (d, J=6.8 Hz, 2H), 1.18-1.05 (m, 1H), 0.61-0.50 (m, 2H), 0.20-0.09 (m, 2H).

Step 3. To a solution of 2-cyclopropyl-1-(5-fluoro-2-methoxyphenyl)ethan-1-one (500.00 mg, 2.40 mmol, 1.00 eq.) in DCM (10.00 mL) was added BCl$_3$ (1 M, 3.00 ML, 1.25 eq.) in drop-wise at −78° C. under N$_2$. The mixture was stirred at −78° C. for 2 hr. TLC showed the reaction was completed. The mixture was warmed to 25° C. and poured into ice-water (w/w=1/1) (10 mL) and stirred for 10 min. The aqueous phase was extracted with ethyl acetate (30 mL×3). The combined organic phase was washed with saturated brine (30 mL), dried over anhydrous Na$_2$SO$_4$, filtered and concentrated in vacuum to afford 2-cyclopropyl-1-(5-fluoro-2-hydroxyphenyl)ethan-1-one (430.00 mg, 2.21 mmol, 92.3% yield) as an oil. $^1$H NMR (400 MHz, CDCl$_3$) δ 12.12 (s, 1H), 7.40 (dd, J=3.0, 8.8 Hz, 1H), 7.24 (ddd, J=3.0, 7.8, 9.0 Hz, 1H), 6.98 (dd, J=4.5, 9.3 Hz, 1H), 2.88 (d, J=6.8 Hz, 2H), 1.23-1.11 (m, 1H), 0.70-0.63 (m, 2H), 0.25 (q, J=5.0 Hz, 2H).

Step 4. To a solution of 2-cyclopropyl-1-(5-fluoro-2-hydroxyphenyl)ethan-1-one (400.00 mg, 1.92 mmol, 1.00 eq.) in MeOH (20.00 mL) was added NH$_2$OH·HCl (160.18 mg, 2.31 mmol, 1.20 eq.) and AcONa (189.09 mg, 2.31 mmol, 1.20 eq.) at 25° C. under N$_2$ for 12 hours. TLC (Petroleum ether/Ethyl acetate=3:1) showed the starting material was consumed completely. The reaction was quenched by water and then extracted with DCM (30 mL×3). The combined organic phase was washed with brine (30 ml), dried over anhydrous Na$_2$SO$_4$, filtered and concentrated in vacuo to give the pure product 2-cyclopropyl-1-(5-fluoro-2-hydroxyphenyl)ethan-1-one oxime (400.00 mg, 1.79 mmol, 93.32% yield) as a white solid. The solid was used for the next step without further purification.

Step 5. To a solution of 2-cyclopropyl-1-(5-fluoro-2-hydroxyphenyl)ethan-1-one oxime (260.00 mg, 1.16 mmol, 1.00 eq.) in MeOH/HCl (10.00 mL, 4N) was added Pd—C (10%, 100 mg) under N$_2$. The suspension was degassed under vacuum and purged with H$_2$ several times. The mixture was stirred under H$_2$ (50 psi) at 50° C. for 12 hours. LC-MS showed the starting material was consumed completely. The reaction mixture was filtered and the filtrate was concentrated to give 2-(1-amino-2-cyclopropylethyl)-4-fluorophenol (200.00 mg, 955.75 umol, 82.39% yield) as a white solid. $^1$H NMR (400 MHz, DMSO-d$_6$) δ 10.44-9.82 (m, 1H), 8.52 (br. s., 2H), 7.36 (dd, J=2.8, 9.5 Hz, 1H), 7.07-6.93 (m, 2H), 4.49 (d, J=5.5 Hz, 1H), 1.82-1.72 (m, 2H), 0.67-0.55 (m, 1H), 0.43-0.28 (m, 2H), 0.12-0.06 (m, 1H), (−0.03)-(−0.09) (m, 1H).

Example A14-5: Preparation of 2-(amino(phenyl)methyl)-4-fluorophenol

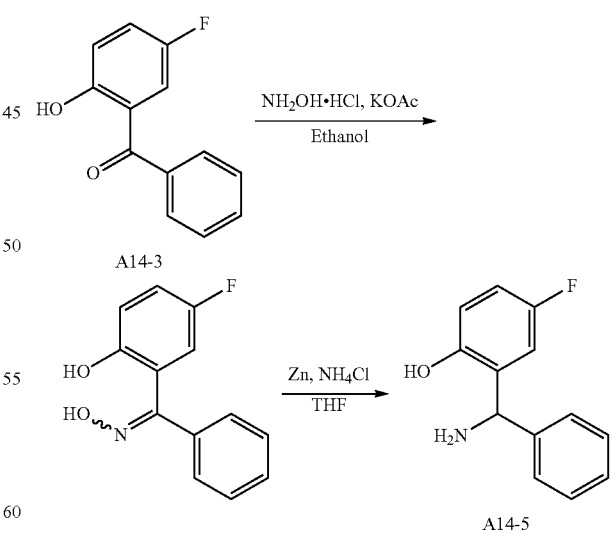

Step 1. To a solution of A 14-3 (2.00 g, 9.25 mmol, 1.00 eq.) and AcOK (1.10 g, 11.20 mmol, 1.20 eq.) in ethanol (30.00 mL) was added NH$_2$OH·HCl (642.80 mg, 9.25 mmol, 1.00 eq.) in one portion at 25° C. under N$_2$. The mixture was stirred at 25° C. for 30 mins, then heated to 90° C. and stirred for 5 hours The TLC showed the reaction was completed. The mixture was concentrated and water (50 mL) was added. The mixture was extracted with ethyl acetate (50 mL×3). The combined organic phase was washed by brine (50 mL), dried over anhydrous $Na_2SO_4$, filtered, and concentrated to give (5-fluoro-2-hydroxyphenyl)(phenyl) methanone oxime (1.50 g, 6.49 mmol, 70.13% yield) as a yellow solid. $^1$HNMR (400 MHz, CDCl$_3$) δ 7.50-7.37 (m, 5H), 7.19-7.07 (m, 2H), 6.71 (dd, J=2.9, 8.9 Hz, 1H).

Step 2. To a mixture of (5-fluoro-2-hydroxyphenyl)(phenyl)methanone oxime (900.00 mg, 4.18 mmol, 1.00 eq.) and Zn powder (1.09 g, 16.73 mmol, 4 eq.) in THF (10.00 mL) was added $NH_4Cl$ (2.24 g, 41.82 mmol, 10.00 eq.) in one portion at 25° C. under $N_2$. The mixture was stirred at 25° C. for 30 mins, then heated to 60° C. and stirred for 15 hours. The mixture was concentrated and water (100 mL) was added followed by extraction with ethyl acetate (50 mL×3). The combined organic layers were washed by brine, dried over anhydrous $Na_2SO_4$, filtered, and concentrated to give A14-5 (630.00 mg, 2.90 mmol, 69.38% yield) as a yellow solid. $^1$HNMR (400 MHz, CDCl$_1$) δ 7.42 (d, J=7.5 Hz, 2H), 7.33 (t, J=7.5 Hz, 2H), 7.27-7.20 (m, 1H), 6.93-6.80 (m, 2H), 6.70 (dd, J=4.9, 8.7 Hz, 1H), 5.28 (s, 1H).

Example A17

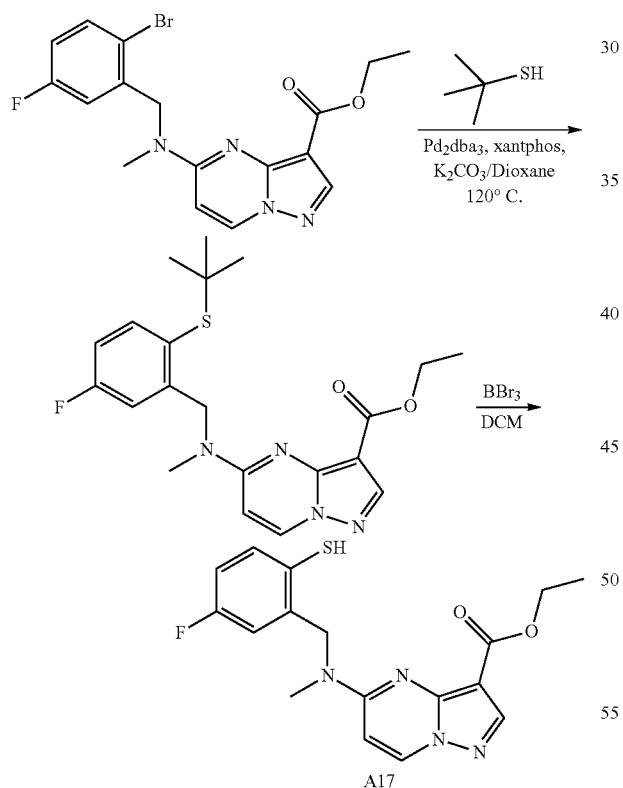

Step 1. To a solution of ethyl 5-((2-bromo-5-fluorobenzyl) (methyl)amino)pyrazolo[1,5-a]pyrimidine-3-carboxylate (prepared according to General Method A) (300.00 mg, 0.736 mmol, 1.00 eq.), 2-methylpropane-2-thiol (166.10 mg, 1.84 mmol, 2.50 eq.), Pd$_2$(dba)$_3$ (84.72 mg, 0.147 mmol, 0.20 eq.) in dioxane (8.00 mL) was added XantPhos (127.87 mg, 0.221 mmol, 0.30 eq.) and $K_2CO_3$ (101.81 mg, 0.736 mmol, 1.00 eq.). The mixture was de-gassed and heated to 120° C. for 24 hours under $N_2$. TLC (Petroleum ether/Ethyl acetate=1:1) showed the starting material was consumed completely. The reaction mixture was poured into $H_2O$ (20 mL) and extracted with ethyl acetate (50 mL×3). The organic phase was washed with brine (30 mL), dried over anhydrous $Na_2SO_4$, concentrated, and purified by a silica gel column chromatography (Petroleum ether/Ethyl acetate=2:1 to 1:1) to give ethyl 5-((2-(tert-butylthio)-5-fluorobenzyl)(methyl)amino)pyrazolo[1,5-a]pyrimidine-3-carboxylate (200.00 mg, 0.48 mmol, 65.18% yield,) as a yellow solid. $^1$H NMR (400 MHz, CDCl$_3$) δ 8.34 (s, 1H), 8.29 (br. s., 1H), 7.60 (dd, J=5.9, 8.4 Hz, 1H), 7.00 (t, J=7.7 Hz, 1H), 6.29 (br. s., 2H), 5.00 (br. s., 2H), 4.37 (d, J=6.8 Hz, 2H), 3.41 (br. s., 3H), 1.36-1.20 (m, 12H).

Step 2. To a solution of ethyl 5-((2-(tert-butylthio)-5-fluorobenzyl)(methyl)amino)pyrazolo[1,5-a]pyrimidine-3-carboxylate (300.00 mg, 0.720 mmol, 1.00 eq.) in DCM (8.00 mL) was added BBr$_3$ (902.21 mg, 3.60 mmol, 5.00 eq.) drop-wise at 0° C. under $N_2$. The mixture was stirred at 0° C. for 2.5 hours. TLC (Petroleum ether:Ethyl acetate=1:1) showed the reaction was completed. The mixture was poured into water (20 mL). The aqueous phase was extracted with dichloromethane (50 mL×3). The combined organic phase was washed with brine (30 mL), dried with anhydrous $Na_2SO_4$, filtered and concentrated in vacuum. The residue was purified by pre-HPLC (Column: Phenomenex Synergi C18 150*30 mm*4 um and Condition: 0.05% HCl-ACN) and lyophilized to afford A17 HCl salt (38.00 mg, 0.098 mmol, 13.61% yield) as a white solid.

Example A18

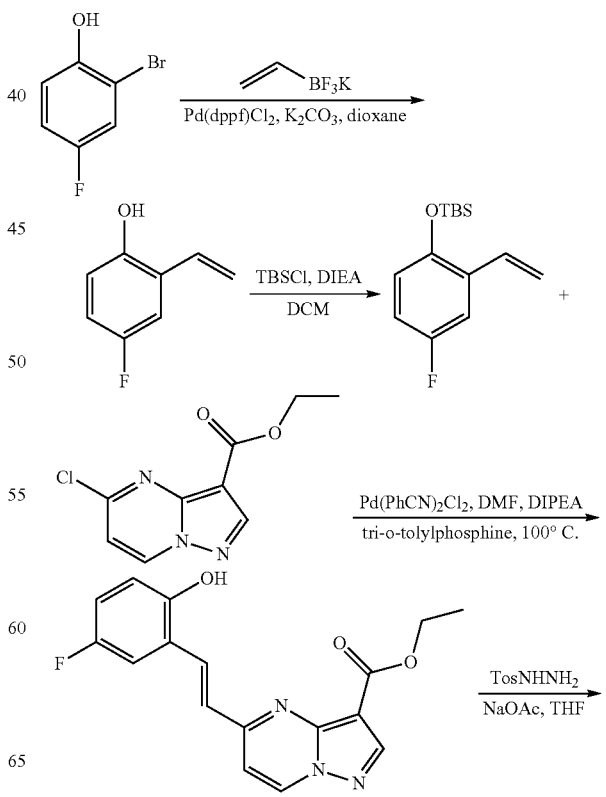

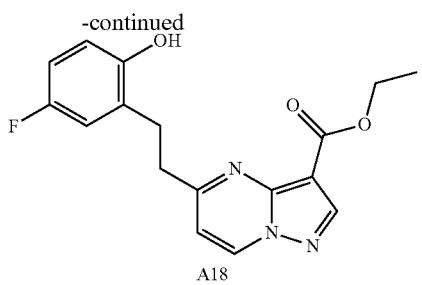

A18

Step 1. The mixture of 2-bromo-4-fluorophenol (10.00 g, 52.36 mmol, 1.00 eq.), trifluoro(vinyl)-borane potassium salt (9.84 g, 66.50 mmol, 1.27 eq.), Cs$_2$CO$_3$ (51.18 g, 157.08 mmol, 3.00 eq.) and Pd(PPh$_3$)$_2$Cl$_2$ (1.84 g, 2.62 mmol, 0.05 eq.) in THF (90.00 mL) and H$_2$O (10.00 mL) was de-gassed and then heated to 90° C. for 12 hours under N$_2$. TLC (Petroleum ether/Ethyl acetate=10/1) showed the starting material was consumed completely. The reaction mixture was poured into H$_2$O (100 mL). The mixture was extracted with ethyl acetate (300 mL×3). The organic phase was washed with saturated brine (200 mL), dried over anhydrous Na$_2$SO$_4$, concentrated, and purified with a silica gel column chromatography (eluted by EtOAc/Petroleum ether=1/30) to afford 4-fluoro-2-vinylphenol (3.50 g, 25.34 mmol, 48.39% yield) as a colorless oil. $^1$H NMR (400 MHz, CDCl$_3$) δ 7.12 (dd, J=3.0, 9.5 Hz, 1H), 6.89-6.81 (m, 1H), 6.79-6.73 (m, 1H), 5.75 (d, J=17.6 Hz, 1H), 5.64 (s, 1H), 5.39 (d, J=11.3 Hz, 1H).

Step 2. The mixture of 4-fluoro-2-vinylphenol (1.95 g, 14.12 mmol, 1.00 eq.), TBSCl (6.38 g, 42.35 mmol, 3.00 eq.) and 1H-imidazole (5.77 g, 84.70 mmol, 6.00 eq.) in DCM (20.00 mL) was stirred at 20° C. for 5 hours under N$_2$. TLC (Petroleum ether/Ethyl acetate=10:1) showed the starting material was consumed completely. The reaction mixture was poured into H$_2$O (30 mL). The mixture was extracted with dichloromethane (50 mL×3). The organic phase was washed with brine (50 mL), dried over anhydrous Na$_2$SO$_4$, concentrated, and purified by a silica gel column chromatography eluted with petroleum ether to afford tri-butyl(4-fluoro-2-vinylbenzyl)silane (2.30 g, 9.11 mmol, 64.54% yield) as a colorless oil.

Step 3. The mixture of tri-butyl(4-fluoro-2-vinylbenzyl)silane (2.30 g, 9.11 mmol, 1.00 eq.), ethyl 5-chloropyrazolo[1,5-a]pyrimidine-3-carboxylate (2.06 g, 9.11 mmol, 1.00 eq.), Pd(PhCN)$_2$Cl$_2$ (118.20 mg, 0.455.63 mmol, 0.05 eq.) and tris-o-tolylphosphane (277.36 mg, 0.911 mmol, 0.10 eq.), DIPEA (7.07 g, 54.68 mmol, 6.00 eq.) in DMF (25.00 mL) was de-gassed and then heated to 120° C. for 24 hours under N$_2$. TLC (Petroleum ether/Ethyl acetate=1:1) showed the starting material was consumed completely. The reaction mixture was poured into H$_2$O (30 mL). The mixture was extracted with ethyl acetate (100 mL×3). The organic phase was washed with saturated brine (30 mL), dried over anhydrous Na$_2$SO$_4$, concentrated, and purified by a silica gel column chromatography (EtOAc:petroleum ether=1:3) to afford ethyl (E)-5-(5-fluoro-2-hydroxystyryl)pyrazolo[1,5-a]pyrimidine-3-carboxylate (1.00 g, 2.26 mmol, 24.86% yield) as a white solid. $^1$H NMR (400 MHz, CDCl$_3$) δ 9.29 (br. s., 1H), 8.50 (d, J=7.0 Hz, 1H), 8.28 (br. s., 1H), 7.84 (d, J=16.6 Hz, 1H), 7.20-7.04 (m, 3H), 6.69 (d, J=5.8 Hz, 2H), 4.20 (q, J=6.9 Hz, 2H), 1.30-1.19 (m, 3H).

Step 4. To a mixture of ethyl (E)-5-(5-fluoro-2-hydroxystyryl)pyrazolo[1,5-a]pyrimidine-3-carboxylate (378.22 mg, 1.04 mmol, 1.00 eq.) and 4-methylbenzenesulfonohydrazide (3.29 g, 17.68 mmol, 17.00 eq.) in THF (4.00 mL) was added NaOAc (1.71 g, 20.80 mmol, 20.00 eq.) in one portion at 20° C. under N$_2$. The mixture was then heated to 65° C. and stirred for 12 hours. TLC showed the reaction was completed. The mixture was cooled to 20° C. and concentrated under reduced pressure at 45° C. Water (100 mL) was added to the residue. The aqueous phase was extracted with ethyl acetate (300 mL×2). The combined organic phase was washed with saturated brine (50 mL), dried with anhydrous Na$_2$SO$_4$, filtered, concentrated in vacuum, and purified by pre-HPLC (Column: Phenomenex Synergi Max-RP 250*50 mm*10 um, 0.225% FA-ACN) to afford A18 (120.00 mg, 0.347 mmol, 33.42% yield) as a white solid.

Example A20

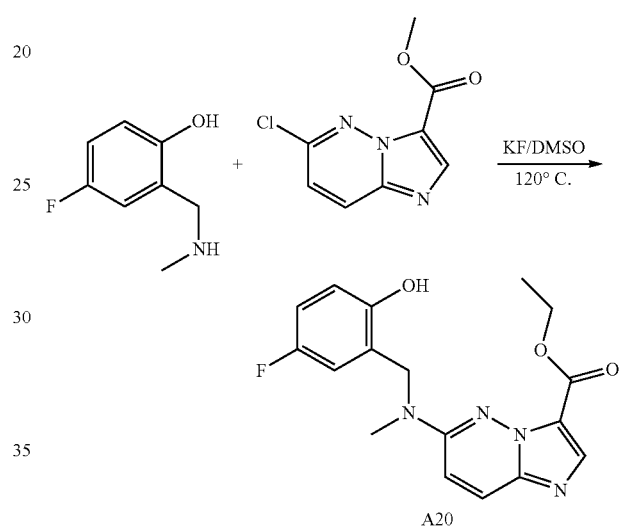

A20

To a mixture of 4-fluoro-2-methylaminomethyl-phenol (305.2 mg, 1.97 mmol) and 6-chloro-imidazo[1,2-b]pyridazine-3-carboxylic acid ethyl ester (230 mg, 1.02 mmol) in DMSO (5 mL) was added KF (180 mg, 3.01 mmol). The reaction mixture was stirred at 120° C. for 18 hours under nitrogen. The solution was then cooled to ambient temperature, diluted with water (20 mL) and extracted with EtOAc (3×50 mL). The combined organic layers were further washed with water (3×50 mL) and brine (50 mL), dried over Na$_2$SO$_4$ and concentrated. The residue was then purified by a silica gel column eluting with EtOAc/hexane (0-50%, 10 CV) to afford the desired product as a white solid (240 mg, 69%).

Example A22

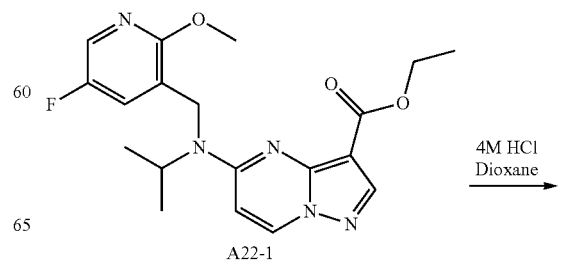

A22-1

4M HCl
Dioxane

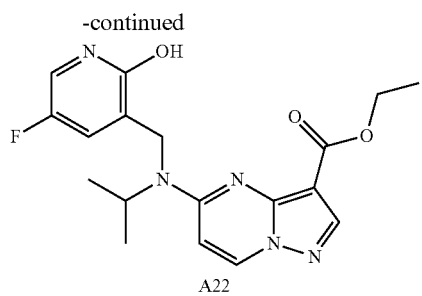

A22

A21-1 was prepared according to the General Method A. To a solution of A22-1 (150 mg, 0.387 mmol) in ethanol (2 mL) was added 4M HCl in dioxane (2 mL) and the reaction solution was heated at 75° C. for 2 hours The solvents were evaporated and the residue was neutralized with Et3N and purified on a silica gel cartridge eluting with methanol/ $CH_2Cl_2$ (0-12.5%) to provide A22 (144 mg, 100%).

Example A23

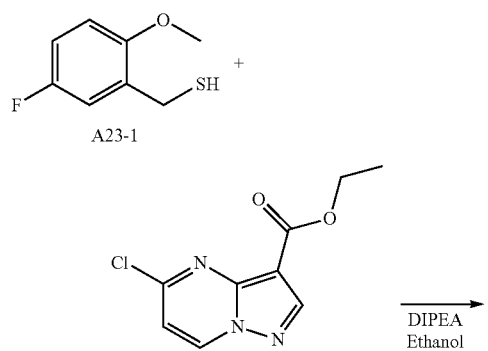

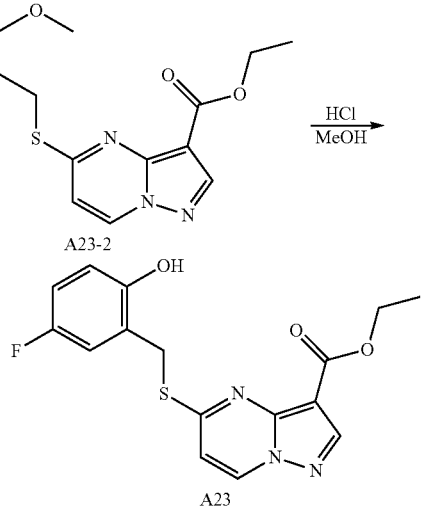

Step 1. To a mixture of (5-fluoro-2-methoxyphenyl)methanethiol (496.1 mg, 2.88 mmol) and 6-chloro-imidazo[1,2-b]pyridazine-3-carboxylic acid ethyl ester (650.0 mg, 2.88 mmol) in ethanol (14.4 mL) was added DIPEA (1.12 g, 8.64 mmol). The reaction mixture was stirred at 80° C. for 1 hour. The solution was cooled to ambient temperature, diluted with water (50 ml) and extracted with DCM (3×50 mL). The combined extracts were dried over $Na_2SO_4$ and concentrated under reduced pressure. The residue was purified with flash chromatography (ISCO system, silica (120 g) eluting with EtOAc/hexane (0-50%) to afford A23-2 (560 mg, 54% yield). A23-2 was crash out of column during purification.

Step 2. To a solution of A23-2 (498.7 mg, 1.38 mmol) in methanol (100 mL) was added 4M HCl in dioxane (10 mL) and the reaction solution was heated at 75° C. for 2 hours The solvents were evaporated and the residue was neutralized with Et3N and purified on a silica gel cartridge eluting with methanol/$CH_2Cl_2$ (0-12.5%) to provide A23 (470 mg, 98%).

A1-A24 were prepared according to the General Method A and the methods described herein.

| Example | Structure | Name | Analytical Data |
|---|---|---|---|
| A1 | 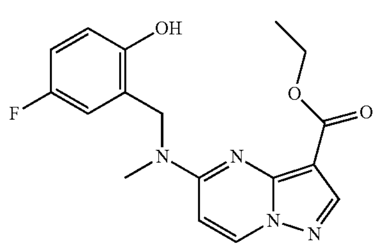 [SMILES: CCOC(=O)c1cnn2ccc(N(C)Cc3cc(F)ccc3O)nc12] | ethyl 5-((5-fluoro-2-hydroxybenzyl)(methyl)amino)pyrazolo[1,5-a]pyrimidine-3-carboxylate | MS: 345.2 (M + H)+; $^1$H NMR (500 MHz, Chloroform-d) δ 9.71 (bs, 1H), 8.32 (d, J = 7.9 Hz, 1H), 8.30 (s, 1H) , 6.98-6.87 (m, 3H), 6.37 (d, J = 7.9 Hz, 1H), 4.82 (s, 2H), 4.42 (q, J = 7.1 Hz, 2H), 3.21 (s, 3H), 1.39 (t, J = 7.1 Hz, 3H). |
| A2 | 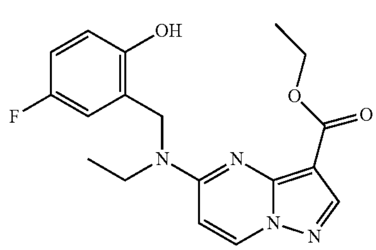 [SMILES: CCOC(=O)c1cnn2ccc(N(CC)Cc3cc(F)ccc3O)nc12] | ethyl 5-(ethyl(5-fluoro-2-hydroxybenzyl)amino)pyrazolo[1,5-a]pyrimidine-3-carboxylate | MS: 359.3 (M + H)+; $^1$H NMR (300 MHz, Chloroform-d) δ 9.75 (hs, 1H), 8.30-8.27 (m, 2H), 6.95-6.86 (m, 3H), 6.34 (d, J = 7.9 Hz, 1H), 4.79 (s, 2H), 4.40 (q, J = 7.2 Hz, 2H), 3.56 (q, J = 7.2 Hz, 2H), 1.38 (t, J = 7.2 Hz, 3H), 1.25 (t, J = 7.2 Hz, 3H), |

| Example | Structure | Name | Analytical Data |
|---|---|---|---|
| A3 | 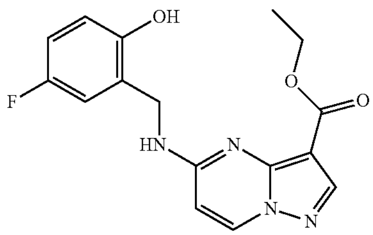 [SMILES: CCOC(=O)c1cnn2ccc(NCc3cc(F)ccc3O)nc12] | ethyl 5-((5-fluoro-2-hydroxybenzyl)amino)pyrazolo[1,5-a]pyrimidine-3-carboxylate | MS: 331.3 (M + H)+; 1H NMR (300 MHz, Chloroform-d) δ 9.61 (bs, 1H), 8.,52 (d, J = 7.5 Hz, 1H), 8.2S (bt, J = 5.1 Hz, 1H), 8.13 (s, 1H), 7.25-7.23 (m, 1H), 6.93-6.86 (m, 1H), 6.81-6.77 (m, 1H), 6.44 (d, J = 7.5 Hz, 1H), 4.51 (d, J = 5.1 Hz, 2H), 4.20 (q, J = 6.9 Hz, 2H), 1.39 (t, J = 6.9 Hz, 3H). |
| A4 | 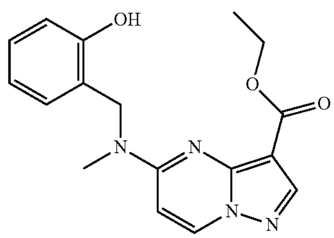 [SMILES: CCOC(=O)c1cnn2ccc(N(C)Cc3ccccc3O)nc12] | ethyl 5-((2-hydroxybenzyl)(methyl)amino)pyrazolo[1,5-a]pyrimidine-3-carboxylate | MS: 327.5 (M + H)+; 1H NMR (300 MHz, Chloroform-d) δ 9.79 (s, 1H), 8.30-8.27 (m, 2H), 7.26-7.21 (m, 2H), 6.96 (d, J = 7.8 Hz, 1H), 6.84 (t, J = 7.5 Hz, 1H), 6.34 (d, J = 8.1 Hz, 1H), 4.85 (s, 2H), 4.42 (q, J = 6.9 Hz, 2H), 3.18 (s, 3H), 1.40 (t, J = 6.9 Hz, 3H). |
| A5 | 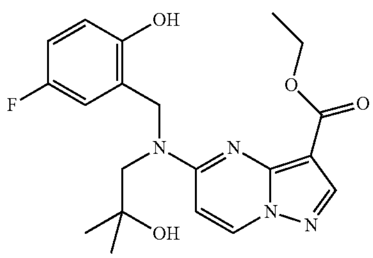 [SMILES: CCOC(=O)c1cnn2ccc(N(Cc3cc(F)ccc3O)CC(C)(C)O)nc12] | ethyl 5-((5-fluoro-2-hydroxybenzyl)(2-hydroxy-2-methylpropyl)amino)pyrazolo[1,5-a]pyrimidine-3-carboxylate | MS: 403.2 (M + H)+; 1H NMR (400 MHz, Chloroform-d) δ 8.32 (s, 1H), 8.26 (d, J = 8.0 Hz, 1H), 7.05-6.80 (m, 3H), 6.59 (br. s., 2H), 5.06 (br. s., 2H), 4.43 (q, J = 7.1 Hz, 2H), 3.62 (br. s., 2H), 1.60 (s, 1H), 1.46-1.36 (m, 9H). |
| A6 | 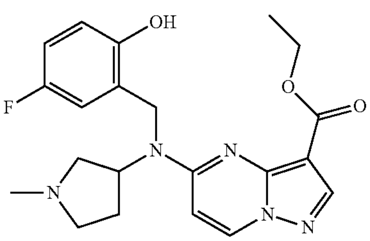 [SMILES: CCOC(=O)c1cnn2ccc(N(Cc3cc(F)ccc3O)C3CCN(C)C3)nc12] | ethyl 5-((5-fluoro-2-hydroxybenzyl)(1-methylpyrrolidin-3-yl)amino)pyrazolo[1,5-a]pyrimidine-3-carboxylate | MS: 414.2 (M + H)+; 1H NMR (400 MHz, Chloroform-d) δ 8.67 (br. s., 2H), 8.35 (d, J = 8.0 Hz, 1H), 8.24 (s, 1H), 7.14-7.07 (m., 1H), 6.83 (dt, J = 2.8, 8.4 Hz, 1H), 6.73 (hr. s., 1H), 6.60 (br. s., 1H), 5.13 (br. s., 1H), 4.75-4.62 (m, 2H), 4.34 (q, J = 6.9 Hz, 2H), 3.88 (br. s., 3H), 3.41 (br. s., 1H), 3.04 (br. s., 3H), 2.54 (br. s., 2H), 1.40 (t, J = 7.2 Hz, 3H). |
| A7 | 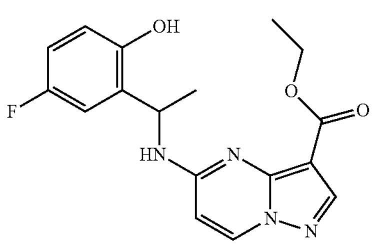 [SMILES: CCOC(=O)c1cnn2ccc(NC(C)c3cc(F)ccc3O)nc12] | ethyl 5-((1-(5-fluoro-2-hydroxyphenyl)ethyl)amino)pyrazolo[1,5-a]pyrimidine-3-carboxylate | MS: 345.3 (M + H)+; 1H NMR (300 MHz, Chloroform-d) δ 9.61 (bs, 1H), 8.24 (s, 1H), 8.17 (d, J = 7.2 Hz, 1H), 6.96-6.91 (m, 2H), 6.88-6.81 (m, 1H), 6.09 (d, J = 7.8 Hz, 1H), 5.72-5.63 (m, 1H), 5.45 (bd, J = 8.7 Hz, 1H), 4.43 (q, J = 7.2 Hz, 2H), 1.64 (d, J = 6.9 Hz, 3H), 1.41 (t, J = 7.2 Hz, 3H). |
| A8 | 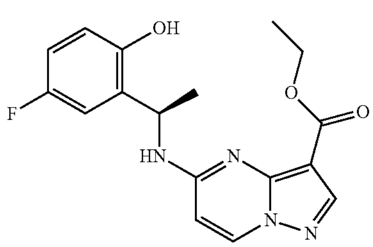 [SMILES: CCOC(=O)c1cnn2ccc(N[C@H](C)c3cc(F)ccc3O)nc12] | ethyl (R)-5-((1-(5-fluoro-2-hydroxyphenyl)ethyl)amino)pyrazolo[1,5-a]pyrimidine-3-carboxylate | MS: 345.2 (M + H)+. |

-continued

| Example | Structure | Name | Analytical Data |
|---|---|---|---|
| A9 | 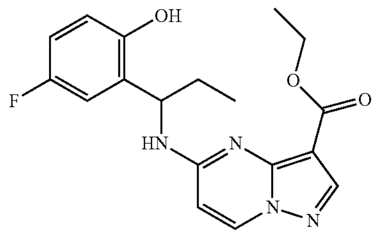 [SMILES: CCOC(=O)c1cnn2ccc(NC(CC)c3cc(F)ccc3O)nc12] | ethyl 5-((1-(5-fluoro-2-hydroxyphenyl)propyl)amino)pyrazolo[1,5-a]pyrimidine-3-carboxylate | MS: 359.2 (M + H)⁺; ¹H NMR (400 MHz, Chloroform-d) δ 8.99 (br. s., 1H), 8.27 (s, 1H),b 8.20 (d, J = 7.5 Hz, 1H), 6.98 (dd, J = 5.0, 8.8 Hz, 1H), 6.94-6.84 (m, 2H), 6.13 (d, J = 7.5 Hz, 1H), 5.41 (br. s., 2H), 4.57-4.40 (m, 2H), 2.11-1.95 (m, 2H), 1.44 (t, J = 7.2 Hz., 3H), 1.02 (t, J = 7.4 Hz, 3H), |
| A10 | 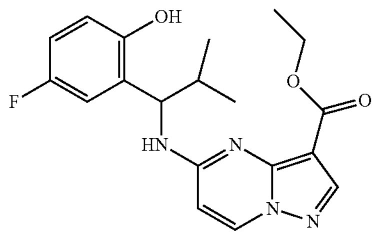 [SMILES: CCOC(=O)c1cnn2ccc(NC(c3cc(F)ccc3O)C(C)C)nc12] | ethyl 5-((1-(5-fluoro-2-hydroxyphenyl)-2-methylpropyl)amino)pyrazolo[1,5-a]pyrimidine-3-carboxylate | MS: 373.2 (M + H)⁺; ¹H NMR (400 MHz, Chloroform-d) δ 8.25 (s, 1H), 8.19 (d, J = 7.5 Hz, 1H), 6.99 (dd, J = 5.1, 8.7 Hz, 1H), 6.91-6.81 (m, 2H), 6.14 (d, J = 7.5 Hz, 1H), 5.11 (t, J = 9.7 Hz, 1H), 4.62-4.37 (m, 2H), 2.22 (qd, J = 6.5, 17.1 Hz, 1H), 1.43 (t, J = 7.2 Hz, 3H), 1.22 (d. J = 6.5 Hz, 3H), 0.89 (d, J = 6.5 Hz, 3H). |
| A11 | 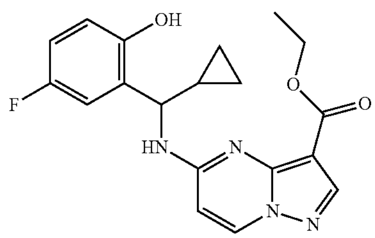 [SMILES: CCOC(=O)c1cnn2ccc(NC(c3cc(F)ccc3O)C3CC3)nc12] | ethyl 5-((cyclopropyl(5-fluoro-2-hydroxyphenyl)methyl)amino)pyrazolo[1,5-a]pyrimidine-3-carboxylate | MS: 371.2 (M + H)⁺; ¹H NMR (400 MHz, Chloroform-d) δ 8.25 (s, 1H), 8.21 (d, J = 7.5 Hz, 1H), 7.13 (dd, J = 3.0, 9.4 Hz, 1H), 7.00-6.94 (m, 1H), 6.91-6.84 (m, 1H), 6.14 (d, J = 7.7 Hz, 1H), 5.69 (d, J = 8.0 Hz, 1H), 4.70 (t, J = 8.3 Hz, 1H), 4.49-4.38 (m, 2H), 1.42 (t, J = 7.1 Hz, 4H), 0.83-0.74 (m, 1H), 0.72-0.63 (m, 1H), 0.57 (qd, J = 4.8, 9.6 Hz, 1H), 0.48-0.40 (m, 1H). |
| A12 | 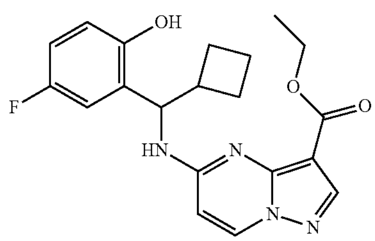 [SMILES: CCOC(=O)c1cnn2ccc(NC(c3cc(F)ccc3O)C3CCC3)nc12] | ethyl 5-((cyclobutyl(5-fluoro-2-hydroxyphenyl)methyl)amino)pyrazolo[1,5-a]pyrimidine-3-carboxylate | MS: 385.2 (M + H)⁺; ¹H NMR (400 MHz, Chloroform-d) δ 9.09 (br, s., 1H), 8.27 (s, 1H), 8.20 (d, J = 7.5 Hz, 1H), 6.98 (dd, J = 5.0, 8.8 Hz, 1H), 6.91-6.78 (m, 2H), 6.12 (d, J = 7.5 Hz, 1H), 5.45 (t, J = 9.4 Hz, 1H), 5.27 (d, J = 8.4 Hz, 1H), 4.51-4.45 (m, 2H), 2.98-2.89 (m, 1H), 2.29 (dd, J = 3.8, 7.5 Hz, 1H), 2.07-1.90 (m, 4H), 1.75-1.66 (m, 1H), 1.45 (t, J = 7.1 Hz, 3H). |
| A13 | 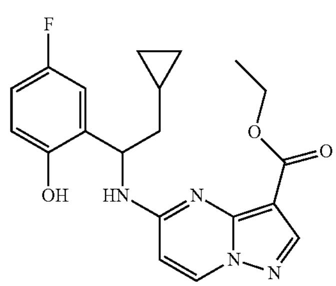 [SMILES: CCOC(=O)c1cnn2ccc(NC(CC3CC3)c3cc(F)ccc3O)nc12] | ethyl 5-((2-cyclopropyl-1-(5-fluoro-2-hydroxyphenyl)ethyl)amino)pyrazolo[1,5-a]pyrimidine-3-carboxylate | MS: 385.2 (M + H)⁺; ¹H NMR (400 MHz, Chloroform-d) δ 9.00 (br. s., 1H), 8.27 (s, 1H), 8.19 (d, J = 7.5 Hz, 1H), 7.00-6.82 (m, 3H), 6.15 (d, J = 7.5 Hz, 1H), 5.57 (br. s., 2H), 4.52-4.40 (m, 2H), 2.01-1.77 (m, 2H), 1.44 (t, J = 7.2 Hz, 3H), 0.72 (d, J = 6.5 Hz, 1H), 0.56-0.41 (m, 2H), 0.24-0.07 (m, 2H), |
| A14 | 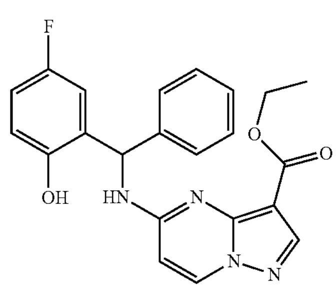 [SMILES: CCOC(=O)c1cnn2ccc(NC(c3ccccc3)c3cc(F)ccc3O)nc12] | ethyl 5-(((5--fluoro-2-hydroxyphenyl)(phenyl)methyl)amino)pyrazolo[1,5-a]pyrimidine-3-carboxylate | MS: 407.2 (M + H)⁺; ¹NMR (400 MHz, Chloroform-d) δ 9.66 (s, 1H), 8.64-8.55 (m, 2H), 8.16 (s, 1H), 7.33 (d, J = 4.4 Hz, 4H), 7.25 (qd, J = 4.3, 8.5 Hz, 1H), 7.11 (dd, J = 3.1, 9.7 Hz, 1H), 6.98-6.91 (m, 1H), 6.88-6.78 (m, 2H), 6.58 (d, J = 7.5 Hz, 1H), 4.18 (q, J = 7.0 Hz, 2H), 1.30 (t, J = 7.1 Hz, 4H). |

| Example | Structure | Name | Analytical Data |
|---|---|---|---|
| A15 | 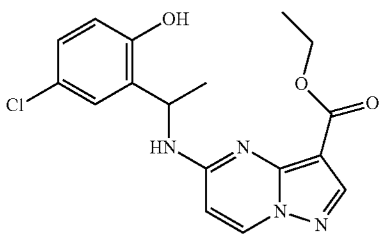 [SMILES: CCOC(=O)c1cnn2ccc(NC(C)c3cc(Cl)ccc3O)nc12] | ethyl 5-((1-(5-chloro-2-hydroxypheny)ethyl)amino)pyrazolo[1,5-a]pyrimidine-3-carboxylate | MS: 361.2 (M + H)+; 1H NMR (400 MHz, Chloroform-d) δ 9.42 (br. s., 1H), 8.27 (s, 1H), 8.20 (d, J = 7.5 Hz, 1H), 7.28 (s, 1H), 7.25 (d, J = 2.5 Hz, 1H), 7.13 (dd, J = 2.5, 8.8 Hz, 1H), 6.95 (d, J = 8.5 Hz, 1H), 6.11 (d, J = 7.5 Hz, 1H), 5.75-5.64 (m, 1H), 5.46 (d, J = 8.3 Hz, 1H), 4.52-4.40 (m, 2H), 1.68 (d, J = 6.8 Hz, 3H), 1.61 (s, 2H), 1.44 (t, J = 7.2 Hz, 3H). |
| A16 | 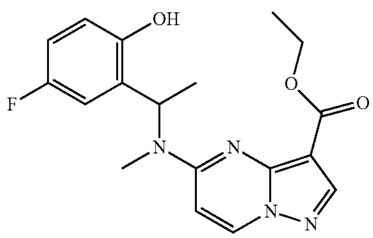 [SMILES: CCOC(=O)c1cnn2ccc(N(C)C(C)c3cc(F)ccc3O)nc12] | ethyl 5-((1-(5-fluoro-2-hydroxyphenyl)ethyl)(methyl)amino)pyrazolo[1,5-a]pyrimidine-3-carboxylate | MS: 359.2 (M + H)+; 1H NMR (400 MHz, Chloroform-d) δ 9.61 (s, 1H), 8.35-8.29 (m, 2H, 7.08-7.03 (m, 1H), 6.92 (dd, J = 1.3, 6.1 Hz, 2H), 6.45 (q, J = 6.9 Hz, 1H), 6,35 (d, J = 7.9 Hz, 1H), 4.51-4.36 (m, 2H), 3.00 (s, 3H), 1.65 (d, J = 7.0 Hz, 3H), 1.41 (t, J = 7.2 Hz, 3H). |
| A17 | 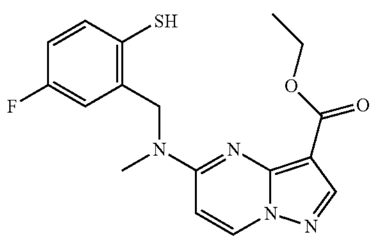 | ethyl 5-((5-fluoro-2-mercaptobenzyl)(methyl)amino)pyrazolo[1,5-a]pyrimidine-3-carboxylate | MS: 361.2 (M + H)+; 1H NMR (400 MHz, Chloroform-d) δ 9.19 (br. s,, 1H), 9.09 (d, J = 7.3 Hz, 1H), 8.51 (s, 1H), 7.91-7.81 (m, 2H), 7.48 (dt, J = 2.8, 8.5 Hz, 1H), 7.14 (d, J = 7.3 Hz, 1H), 4.29 (br. 2H), 4.18 (q, J = 7.0 Hz, 2H), 2.56 (br. s., 3H), 1.16 (t, J = 7.2 Hz, 3H). |
| A18 | 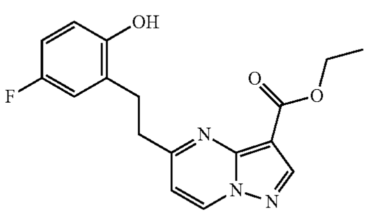 [SMILES: CCOC(=O)c1cnn2ccc(CCc3cc(F)ccc3O)nc12] | ethyl 5-(5-fluoro-2-hydroxyphenethyl)pyrazolo[1,5-a]pyrimidine-3-carboxylate | MS: 330.2 (M + H)+; 1NMR (400 MHz, Chloroform-d) δ 9.42 (s, 1H), 9.14 (d, J = 7.0 Hz, 1H), 8.55 (s, 1H), 7.18 (d, J = 7.0 Hz, 1H), 7.05 (dd. J = 3.0, 9.5 Hz, 1H), 6.86-6.80 (m, 1H), 6.79-6.74 (m, 1H), 4.30 (q, J = 7.2 Hz, 2H), 3.21-3.13 (m, 2H), 3.06-2.99 (m, 2H), 1.33 (t, J = 7.2 Hz, 3H). |
| A19 | 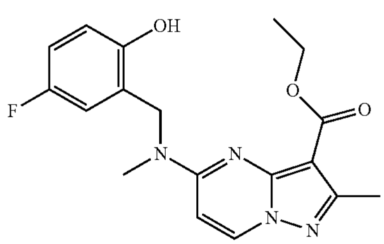 [SMILES: CCOC(=O)c1c(C)nn2ccc(N(C)Cc3cc(F)ccc3O)nc12] | ethyl 5-((5-fluoro-2-hydroxybenzyl)(methyl)amino)-2-methylpyrazolo[1,5-a]pyrimidine-3-carboxylate | MS: 359.2 (M + H)+. |
| A20 | 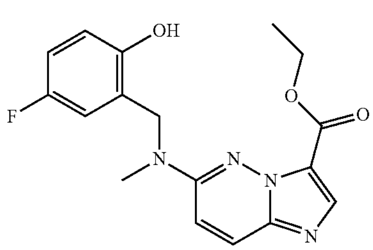 [SMILES: CCOC(=O)c1cnc2ccc(N(C)Cc3cc(F)ccc3O)nn12] | ethyl 6-((5-fluoro-2-hydroxybenzyl)(methyl)amino)imidazo[1,2-b]pyridazine-3-carboxylate | MS: 345.2 (M + H)+; 1 H NMR (500 MHz, Chloroform-d) δ 8.61 (s, 1H), 8.17 (s, 1H), 7.91 (d, J = 10.0 Hz, 1H), 7.00-6.86 (m, 4H), 4.78 (s, 2H), 4.47 (qd, J = 7.2, 0.5 Hz, 2H), 3.17 (s, 3H), 1.41 (td, J = 7.1, 0.5 Hz, 3H). |

| Example | Structure | Name | Analytical Data |
|---|---|---|---|
| A21 | 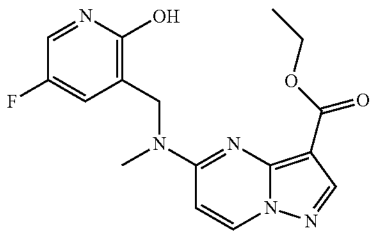 [SMILES: CCOC(=O)c1cnn2ccc(N(C)Cc3cc(F)cnc3O)nc12] | ethyl 5-(((5-fluoro-2-hydroxypyridin-3-yl)methyl)(methyl)amino)pyrazolo[1,5-a]pyrimidine-3-carboxylate | MS: 346.2 (M + H)+. |
| A22 | 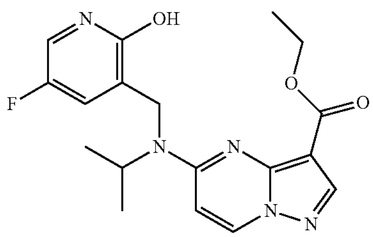 [SMILES: CCOC(=O)c1cnn2ccc(N(Cc3cc(F)cnc3O)C(C)C)nc12] | ethyl 5-(((5-fluoro-2-hydroxypyridin-3-yl)methyl)(isopropyl)amino)pyrazolo[1,5-a]pyrimidine-3-carboxylate | MS: 374.2 (M + H)+. |
| A23 | 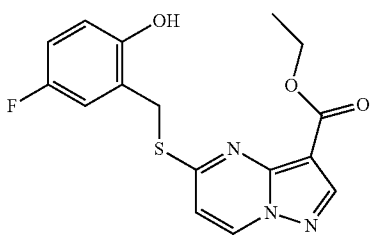 [SMILES: CCOC(=O)c1cnn2ccc(SCc3cc(F)ccc3O)nc12] | ethyl 5-((5-fluoro-2-hydroxybenzyl)thio)pyrazolo[1,5-a]pyrimidine-3-carboxylate | MS: 348.2 (M + H)+. |
| A24 | 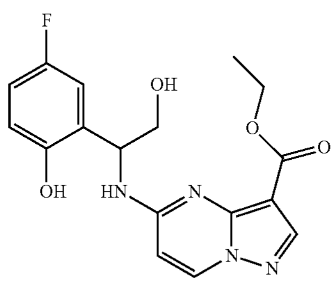 [SMILES: CCOC(=O)c1cnn2ccc(NC(CO)c3cc(F)ccc3O)nc12] | ethyl 5-((1-(5-fluoro-2-hydroxyphenyl)-2-hydroxyethyl)amino)pyrazolo[1,5-a]pyrimidine-3-carboxylate | MS: 361.2 (M + H)+. |

Example B7

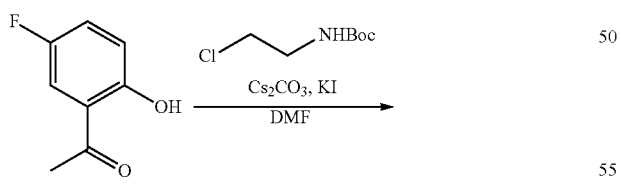

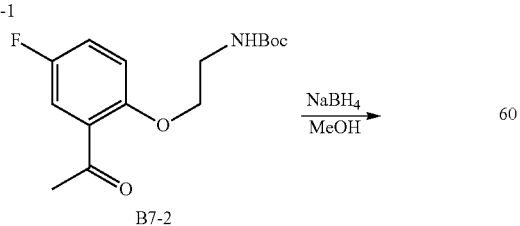

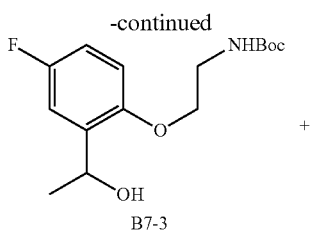

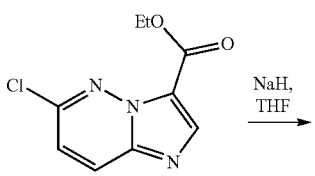

-continued

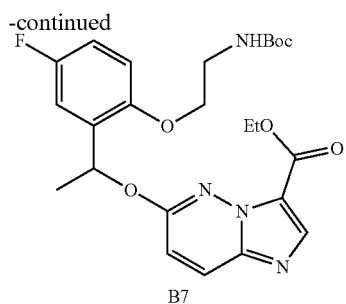

B7

Step 1. To a mixture of 1-(5-fluoro-2-hydroxy-phenyl)-ethanone (773 mg, 5.0 mmol) and (2-chloro-ethyl)-carbamic acid tert-butyl ester (1.80 g, 10.0 mmol) in DMF (20 mL) were added KI (2.0 mg, 0.012 mmol) and $Cs_2CO_3$ (3.26 g, 10.0 mmol). The mixture was stirred at 80° C. overnight. The mixture was then cooled to ambient temperature, diluted with EtOAc, and washed with 1N NaOH (5×10 mL) until LCMS showed no 1-(5-fluoro-2-hydroxy-phenyl)-ethanone peak. The organic layer was dried over $Na_2SO_4$ and concentrated. The residue was then purified by a silica gel column eluting with EtOAc/hexane (0-30%, 10 CV) to afford the desired product B7-2 as a yellowish solid (1.1 g, 73.8%): LC-MS (ESI) m/z 320.3 (M+Na)+.

Step 2. To a solution of B7-2 (1.0 g, 3.36 mmol) in MeOH (10 mL) was added $NaBH_4$ (640 mg, 16.8 mmol) in portion wise. The mixture was stirred at ambient temperature for 2 h until no starting material left by LCMS. The solution was then diluted with water (50 mL) and extracted with DCM (3×20 mL). The combined DCM layers were dried over $Na_2SO_4$ and concentrated. The residue was purified by a silica gel column eluting with EtOAc/hexane (0-50%, 10 CV) to afford the desired product B7-3 as a pale yellow solid (0.75 g, 75%). LC-MS (ESI) m/z 322.3 (M+Na)+; $^1$H NMR (500 MHz, Chloroform-d) δ 7.11 (dd, J=9.2, 3.4 Hz, 1H), 6.89 (ddd, J=9.0, 7.9, 3.2 Hz, 1H), 6.77 (dd, J=8.9, 4.4 Hz, 1H), 5.09 (q. J=6.6 Hz, 1H), 4.92 (d, J=4.4 Hz, 1H), 4.03 (t, J=5.2 Hz, 2H), 3.62-3.50 (m, 2H), 1.49 (d, J=6.4 Hz, 3H), 1.45 (s, 9H).

Step 3: To a solution of B7-3 (600 mg, 2.0 mmol) and {2-[4-fluoro-2-(1-hydroxy-ethyl)-phenoxy]-ethyl}-carbamic acid tert-butyl ester (450 mg, 2.0 mmol) in dry THF (40.0 mL) at −78° C. was added NaH (60%, 80 mg, 2.0 mmol) in portion. The suspension was stirred at −78° C. for 4 h and allowed to warm to 0° C. and stirred for additional 4 h. The mixture was then put in the freezer at −20° C. overnight. LC-MS showed a good conversion to the desired product. The mixture was then quenched with a mixture of ice and 1N HCl and extracted with EtOAc (3×20 mL). The organic layer was dried over $Na_2SO_4$, concentrated and purified twice to afford the desired product B7 as a yellow solid (240 mg, 25%):

B1-B7 were prepared according to the General Method B and methods described herein.

| Example | Structure | Name | Analytical Data |
|---|---|---|---|
| B1 | 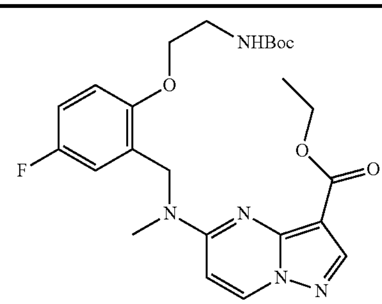 | ethyl 5-((2-(2-((tert-butoxycarbonyl)amino)ethoxy)-5-fluorobenzyl)(methyl)amino)pyrazolo[1,5-a]pyrimidine-3-carboxylate | MS: 488.3.1 (M + H)+; $^1$H NMR (500 MHz, Chloroform-d) δ 8.30 (s, 1H), 8.26 (s, 1H), 6.92 (td, J = 8.6, 3.3 Hz, 1H), 6.83-6.76 (m, 1H), 6.31 (s, 1H), 4.93 (s, 2H), 4.51-4.44 (m, 1H), 4.36 (q, J = 7.2 Hz, 2H), 4.03 (t, J = 4.9 Hz, 2H), 3.69-3.63 (m, 1H), 3.51 (s, 2H), 3.30 (s, 2H), 1.44 (s, 9H), 1.41-1.35 (t, J = 7.2 Hz, 3H). |
| B2 | 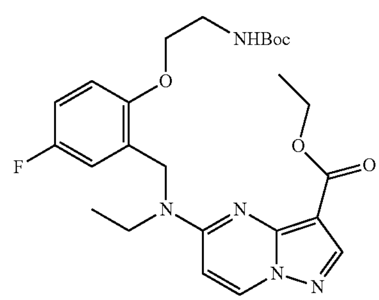 [SMILES: CCOC(=O)c1cnn2ccc(N(CC)Cc3cc(F)ccc3OCCNC(=O)OC(C)(C)C)nc12] | ethyl 5-((2-(2-((tert-butoxycarbonyl)amino)ethoxy)-5-fluorobenzyl)(ethyl)amino)pyrazolo[1,5-a]pyrimidine-3-carboxylate | MS: 502.2 (M + H)+. |
| B3 | 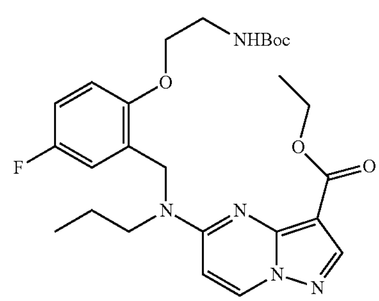 [SMILES: CCCN(Cc1cc(F)ccc1OCCNC(=O)OC(C)(C)C)c1ccn2ncc(C(=O)OCC)c2n1] | ethyl 5-((2--(2-((tert-butoxycarbonyl)amino)ethoxy)-5-fluorobenzyl)(propyl)amino)pyrazolo[1,5-a]pyrimidine-3-carboxylate | MS: 516.3 (M + H)+. |

-continued

| Example | Structure | Name | Analytical Data |
|---|---|---|---|
| B4 | 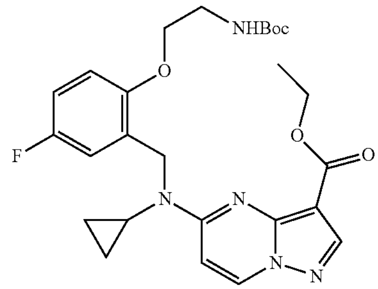 [SMILES: CCOC(=O)c1cnn2ccc(N(Cc3cc(F)ccc3OCCNC(=O)OC(C)(C)C)C3CC3)nc12] | ethyl 5-((2-(2-((tert-butoxycarbonyl)amino)ethoxy)-5-fluorobenzyl)(cyclopropyl)amino)pyrazolo[1,5-a]primidine-3-carboxylate | MS: 514.2 (M + H)+. |
| B5 | 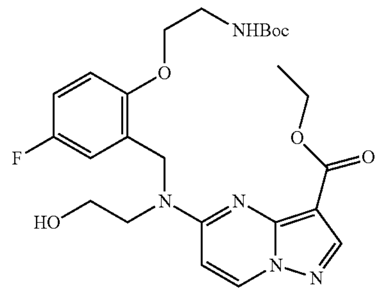 [SMILES: CCOC(=O)c1cnn2ccc(N(CCO)Cc3cc(F)ccc3OCCNC(=O)OC(C)(C)C)nc12] | ethyl 5-((2-(2-((tert-butoxycarbonyl)amino)ethoxy)-5-fluorobenzyl)(2-hydroxyethyl)amino)pyrazolo[1,5-a]pyrimidine-3-carboxylate | MS: 518.3 (M + H)+. |
| B6 | 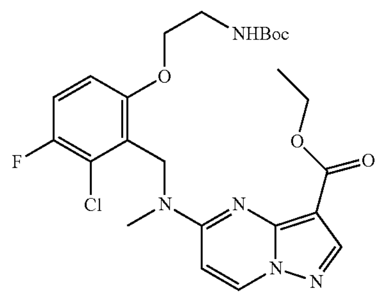 [SMILES: CCOC(=O)c1cnn2ccc(N(C)Cc3c(OCCNC(=O)OC(C)(C)C)ccc(F)c3Cl)nc12] | ethyl 5-((6-(2-((tert-butoxycarbonyl)amino)ethoxy)-2-chloro-3-fluorobenzyl)(methyl)amino)pyrazolo[1,5-a]pyrimidine-3-carboxylate | MS: 522.5 (M + H)+. |
| B7 | 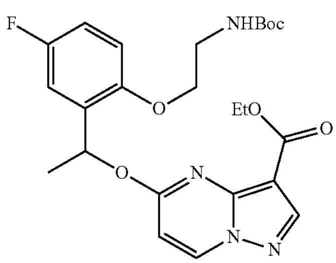 [SMILES: CCOC(=O)c1cnn2ccc(OC(C)c3cc(F)ccc3OCCNC(=O)OC(C)(C)C)nc12] | ethyl 6-(1-(2-(2-((tert-butoxycarbonyl)amino)ethoxy)-5-fluorophenyl)ethoxy)imidazo[1,2-b]pyridazine-3-carboxylate | LC-MS (ESI) m/z 511.6 (M + Na)+; $^1$H NMR (500 MHz, Chloroform-d) δ 8.16 (s, 1H), 7.90 (d, J = 9.7 Hz, 1H), 7.16 (dd, J = 9.0, 3.2 Hz, 1H), 0.95 (d, J = 9.5 Hz, 1H), 6.90-6.88 (m, 1H), 6.81-6.78 (m, 1H), 6.68 (q, J = 6.2 Hz. 1H), 5.84-5.68 (m, 1H), 4.38 (q, J = 7.2 Hz, 2H), 4.15-4.09 (m, 2H), 3.60-3.52 (m, 2H), 1.65 (d, J = 6.4 Hz, 3H), 1.38 (d, J = 7.2 Hz, 3H), 1.35 (s, 9H). |

Examples 2 and 2-1

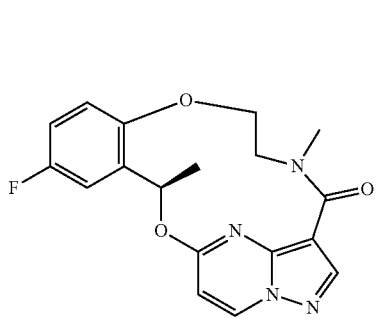

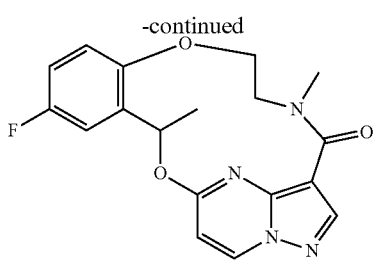

Synthesis A:

Example 2 may be prepared as shown in the following scheme, starting with racemic or enantiomerically enriched starting materials:

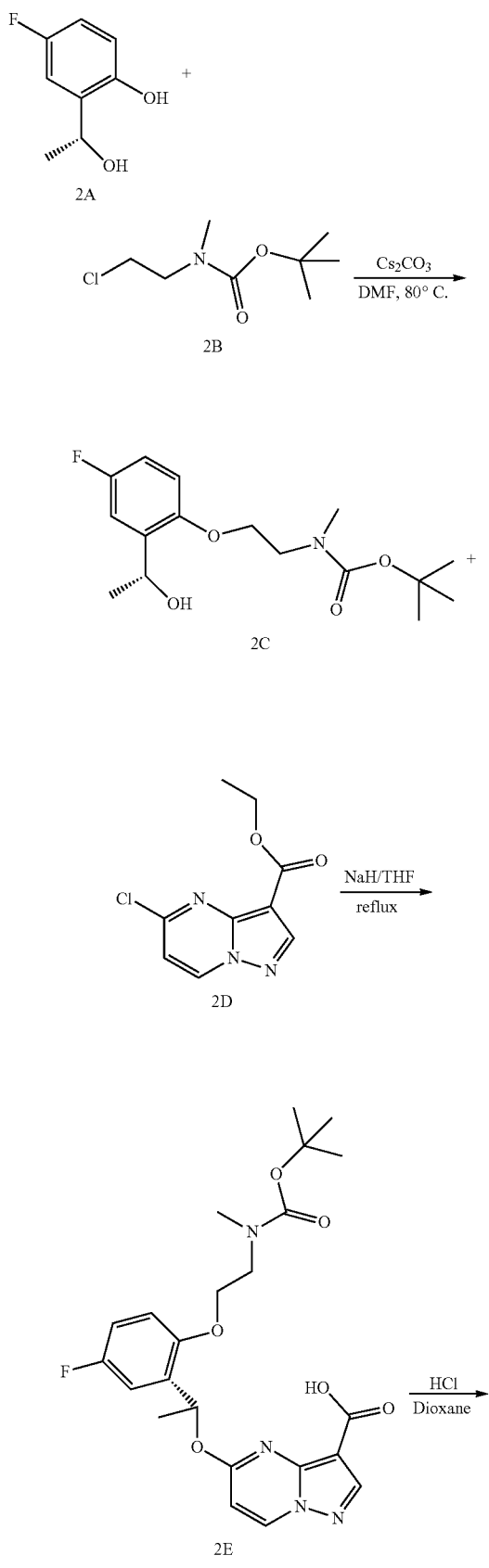

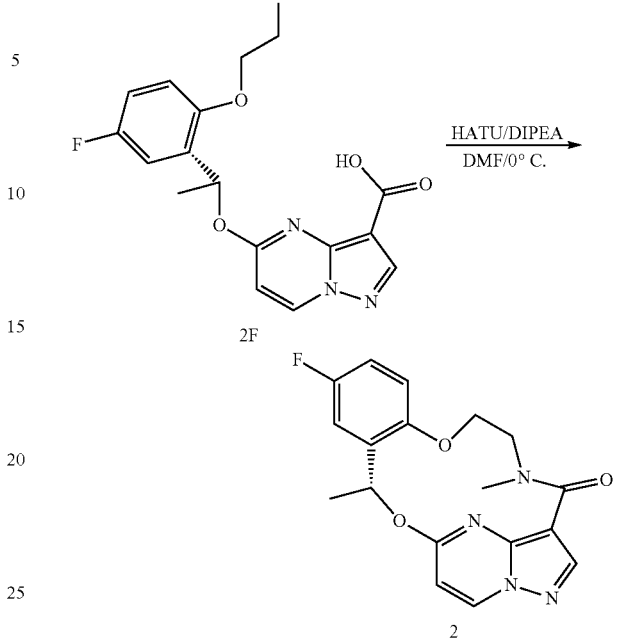

Step 1. To a mixture of compounds 2A (1 equiv.) and 2B (1.2 equiv.) in anhydrous DMF (0.2 M) is added $Cs_2CO_3$ (1.5 equiv.) and the reaction is heated in an oil bath at 80° C. under nitrogen overnight. The mixture is cooled, poured into water, and extracted with EtOAc three times. The combined organic layers are washed with water five times, washed with brine, and dried over $Na_2SO_4$. After condensation, the residue is purified on a flash column eluting with EtOAc/Hexanes to provide compound 2C.

Step 2. To a solution of compound 2C (1 equiv.) in anhydrous THF (0.2 M) is added NaH (1.2 equiv.). The reaction mixture is stirred at ambient temperature for 0.5 hours. To the mixture is added compound 2D and the reaction is heated at reflux under nitrogen overnight. The reaction is cooled to ambient temperature and diluted with a portion of water (⅓ of THF volume) and NaOH (3 equiv.). The mixture is stirred and heated at 70° C. for 2 hours or until the ester is completely hydrolyzed to the corresponding acid. After cooling, the organic layer is separated and the water layer is neutralized to pH~5. The resulting precipitate is filtered, washed with water three times, and dried under vacuum to provide compound 2E, which is used without further purification.

Step 3. To a solution of compound 2E (1 equiv.) in $CH_2Cl_2$ (0.2 M) is added 4 M HCl/dioxane (10 equiv.) and the mixture is stirred until compound 2E is completely converted to compound 2F. The mixture is concentrated, and the residue is purified by reverse phase preparative HPLC to provide compound 2F.

Step 4. A solution of compound 2F (1 equiv.) and DIPEA (10 equiv.) in DMF (0.2 M) is added drop-wise to a solution of HATU (1.4 equivalent) in DMF (0.1 M) at 0° C. After addition is complete, the mixture is stirred at 0° C. for a further 30 min. Water is added and the mixture is extracted with EtOAc three times. The combined organic layers are washed with saturated $NaHCO_3$ twice, then with brine, dried over $Na_2SO_4$, and concentrated. The residue is purified on a silica gel column eluting with EtOAc/Hexanes to provide Example 2.

Synthesis B:

Examples 2 and 2-1 may also be prepared according to the following scheme, using racemic or enantiomerically enriched starting materials:

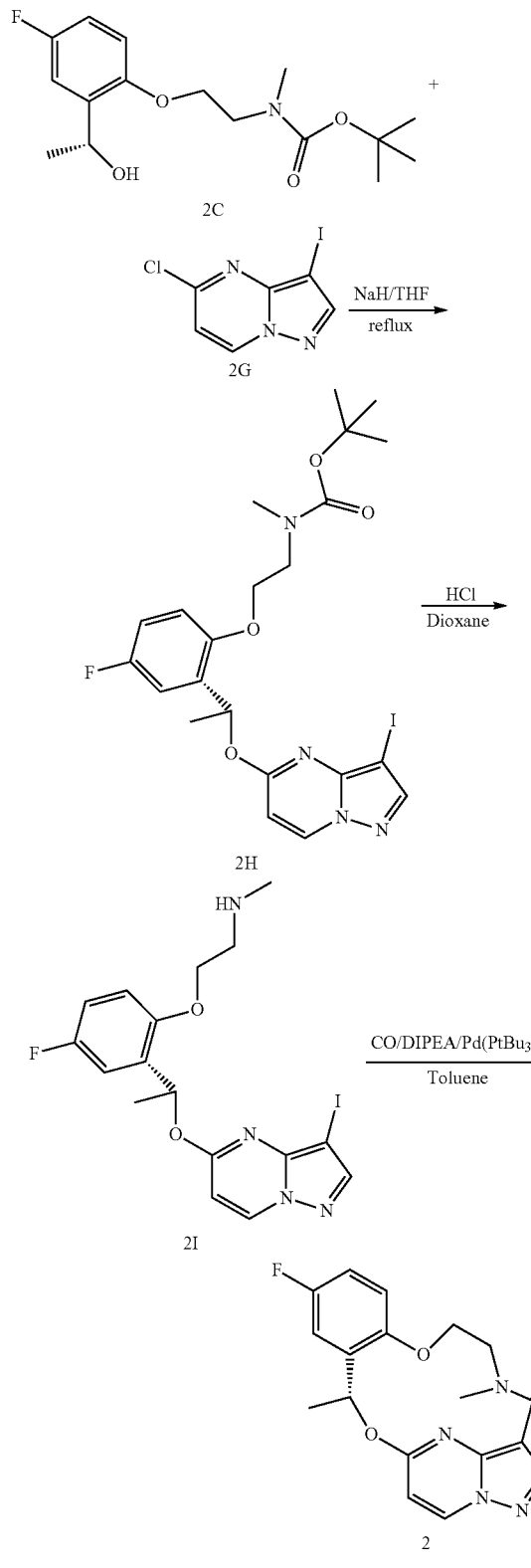

Step 1. Compound 2C is reacted with compound 2G under the conditions described in Synthesis A, Step 2, to provide compound 2H.

Step 2. Compound 2H is converted to compound 2I under the conditions described in Synthesis A, Step 3.

Step 3. To a solution of compound 2I (1 equiv.) and DIPEA (2 equiv.) in toluene (0.01 M) is added Pd(P-tBu$_3$)$_2$ (1 equiv.). The reaction mixture is heated at 100° C. under 4 bar CO overnight, and then concentrated. The residue is purified on a silica gel column eluting with EtOAc/hexanes to provide Example 2.

Examples 10 and 10-1

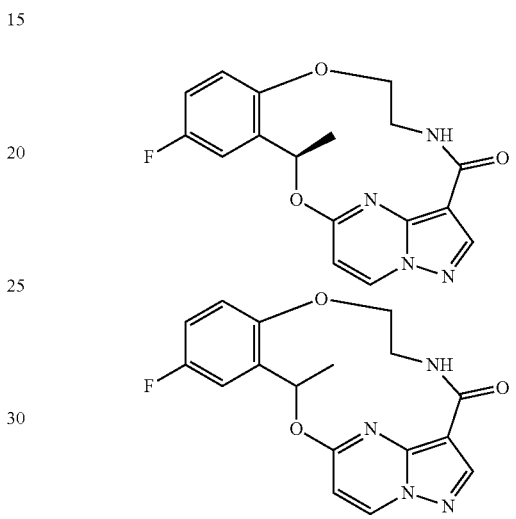

Examples 10 and 10-1 may be prepared as shown in the following scheme using racemic or enantiomerically enriched starting materials:

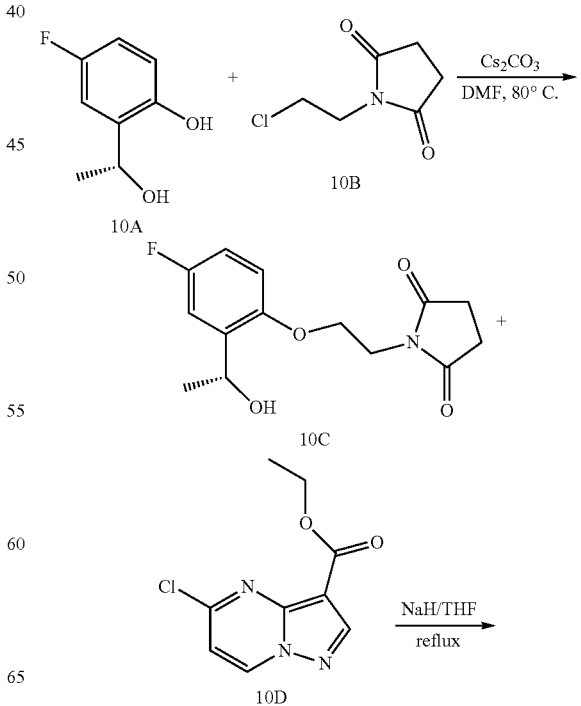

Example 11-1

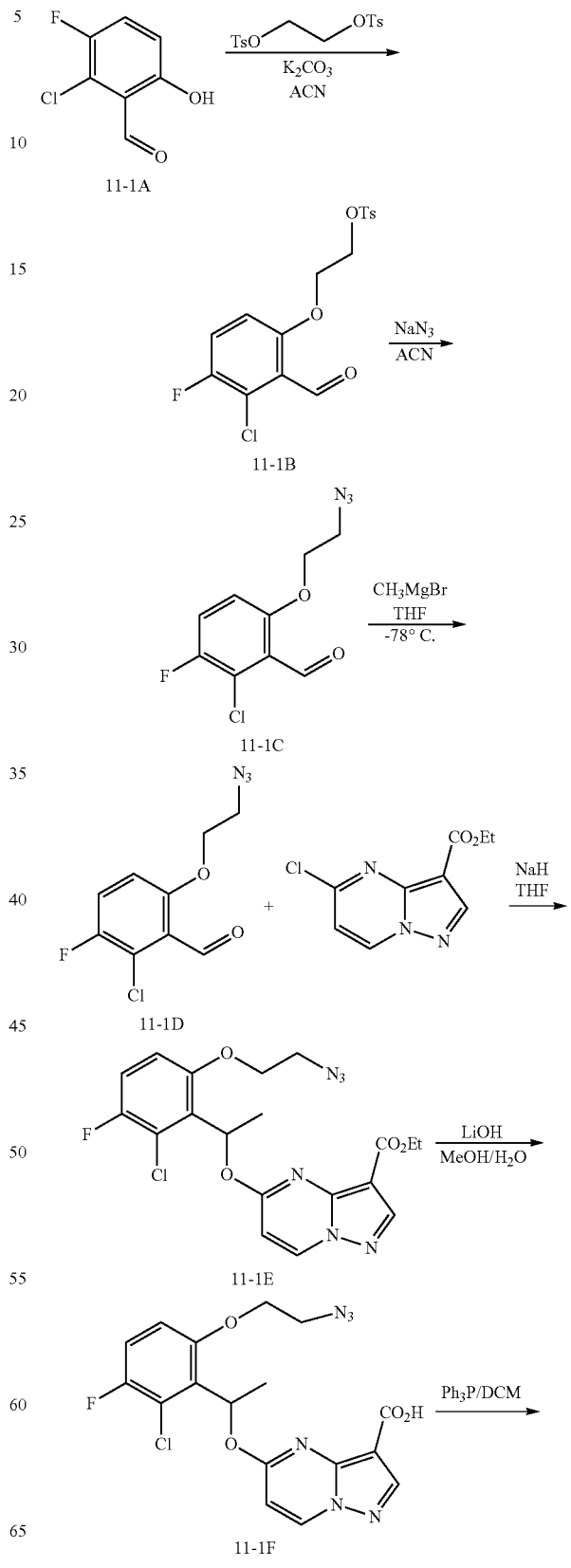

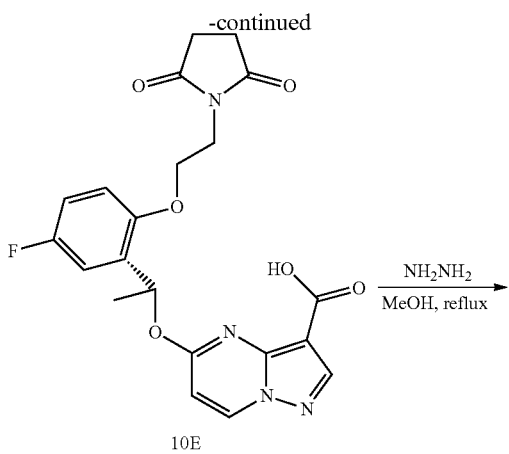

Step 1. Compound 10C is prepared from compounds 10A and 10B using the method described in Example 2, Synthesis A, Step 1.

Step 2. Compound 10E is prepared from compounds 10C and 10D using the method described in Example 2, Synthesis A, Step 2.

Step 3. A mixture of compound 10E (1 equiv.) and $NH_2-NH_2$ (10 equiv.) in methanol (0.2 M) is heated at reflux until compound 10E is completely converted to compound 10F. The mixture is concentrated and the residue is purified in a reverse phase preparative HPLC to provide compound 10F.

Step 4. Compound 10F is converted into Example 10 according to the method described for Example 2, Synthesis A, Step 4.

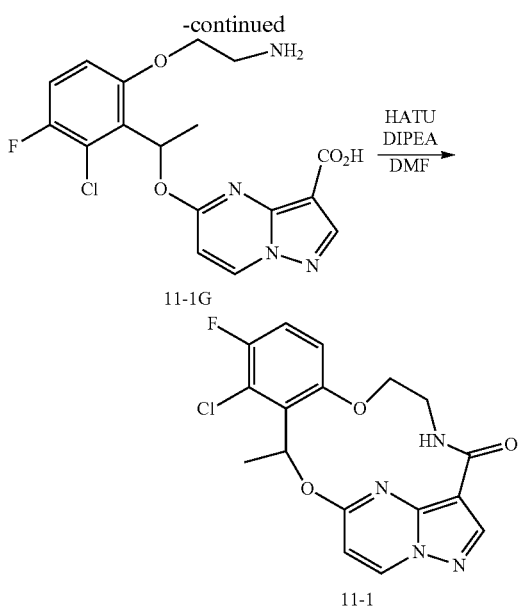

Step 1: To a solution of 2-chloro-3-fluoro-6-hydroxybenzaldehyde (175 mg, 1.0 mmol), bis-tos ethylene glycol (740 mg, 2.0 mmol) in ACN (5 mL), $K_2CO_3$ (276 mg, 2.0 mmol) and KI (2 mg) was added. The reaction mixture was stirred at 120° C. for 24 hours The solid was filtered off and the filtrate was concentrated and purified by column chromatography to afford the desired product 11-1B as a white solid. The material was used directly in the next step.

Step 2: To a solution of 11-1B (373 mg, 1 mmol) in ACN (5 mL), $NaN_3$ (650 mg, 10 mmol) was added and the mixture was stirred at 120° C. for 24 hours The solid was filtered off and the residue was concentrated and purified by column chromatography to afford 11-1C as a white solid (200 mg, 82%). $^1$H NMR (500 MHz, Chloroform-d) δ 10.49 (d, J=1.1 Hz, 1H), 7.31 (dd, J=9.2, 8.2 Hz, 1H), 6.88 (dd, J=9.2, 3.7 Hz, 1H), 4.21 (dd, J=5.4, 4.5 Hz, 2H), 3.67 (dd, J=5.4, 4.5 Hz, 2H).

Step 3: To a solution of 11-1C (100 mg, 0.41 mmol) in anhydrous THF (5 mL) at −78° C., methyl magnesium bromide (1N in $Et_2O$, 0.82 mL, 0.82 mmol) was added. The mixture was allowed to warm to room temperature and stirred for 2 hours until TLC shows no starting material present. The solution was then cooled to 0° C. and quenched with sat. aq $NH_4OAc$ and extracted with EtOAc (20 mL×3). The combined organic was dried over $Na_2SO_4$ and concentrated. The residue 11-1D was used directly in the next step. $^1$H NMR (500 MHz, Chloroform-d) δ 6.97 (dd, J=9.2, 8.3 Hz, 1H), 6.77 (dd, J=9.1, 4.1 Hz, 1H), 5.27 (q, J=6.7 Hz, 1H), 4.34-4.29 (m, 1H), 4.22-4.16 (m, 1H), 4.04-3.98 (m, 1H), 3.95-3.88 (m, 2H), 1.51 (d, J=6.7 Hz, 3H).

Step 4: To a solution of 5-Chloro-pyrazolo[1,5-a]pyrimidine-3-carboxylic acid ethyl ester (100 mg, 0.44 mmol) and 11-1D (110 mg, 0.41 mmol) in anhydrous THF (5.0 mL) at −78° C., NaH (60%, 17 mg, 0.44 mmol) was added. The mixture was allowed to warm to rt and stirred for 8 hours until a good amount of desired product was formed. The mixture was then diluted with water/ice and extracted with DCM (3×20 mL). The organic layer was dried over $Na_2SO_4$, concentrated and purified by silica gel column chromatography to afford 11-1E as a yellow liquid (20 mg, 0.045 mmol, 6%), which is used directly in the next step.

Step 5: To a solution of 11-1E (20 mg, 0.045 mmol) in MeOH (1 mL), LiOH (16 mg, 0.38 mmol) was added, followed by 1 mL of $H_2O$. The mixture was allowed to stir at 60° C. for 4 hours until LCMS and TLC shows the reaction was complete. The solution was cooled to rt, partially concentrated and acidified by 1N HCl until pH 2-3. The aqueous mixture was extracted with DCM (3×10 mL). The organic layer was dried over $Na_2SO_4$ and concentrated. The residue 11-1F was used directly in the next step.

Step 6: To a solution of 11-1F (20 mg, 0.045 mmol) in DCM (5 mL), $PPh_3$ (24 mg, 0.09 mmol) was added. The solution was stirred for 1 hr until TLC shows a complete conversion of the starting material to the desired product. The mixture was then used directly in the next step without further characterization. 11-1G MS ESI$^+$ m/z 417.7 (M+Na)$^+$.

Step 7: To a solution of 11-1G obtained from previous step in DMF (10 mL), DIPEA (0.20 mL, 1.15 mmol) was added. The solution was chilled with dry ice/acetone bath and HATU (40.0 mg, 0.11 mmol) was added. The solution was allowed to warm to rt slowly and LCMS shows a clean transformation of the starting material to the desired product. The mixture was then diluted with water (50 mL) and extracted with EtOAc (3×50 mL). The combined organic layer was washed with water (3×50 mL) and brine (50 mL) and dried over $Na_2SO_4$. The solvent was removed and the resulting residue was purified by silica column chromatography (0-5% MeOH/DCM) afford the desired product as a white solid (2.6 mg, 20% yield).

Examples 14 and 14-1

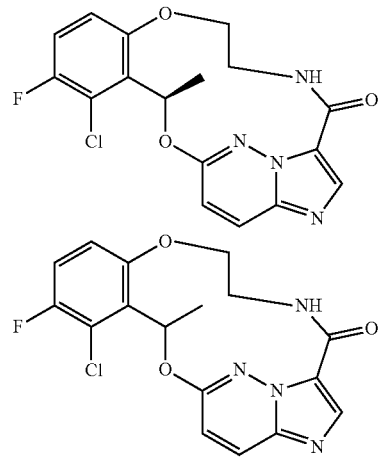

Examples 14 and 14-1 may be prepared according to the following scheme using racemic or enantiomerically enriched starting materials:

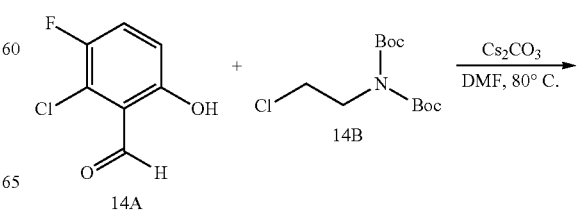

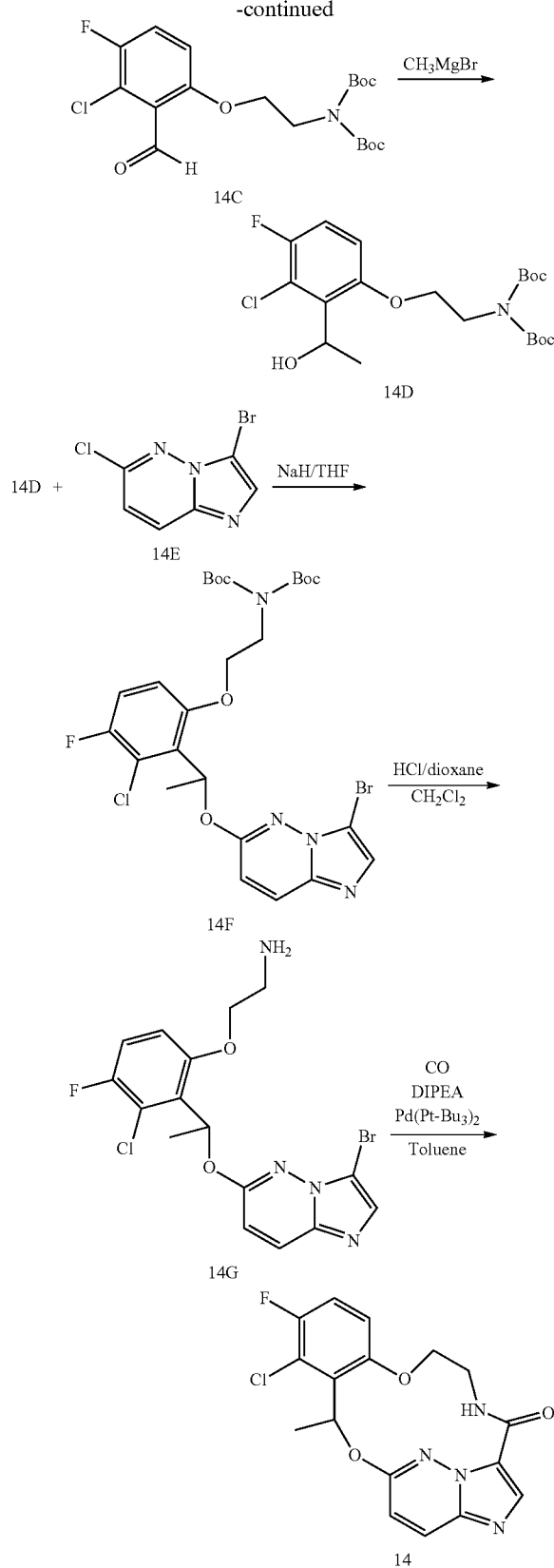

at 80° C. under nitrogen overnight. The mixture is cooled, poured into water, and extracted with EtOAc three times. The combined organic layers are washed with water five times, washed with brine, and dried over $Na_2SO_4$. After condensation, the residue is purified on a flash silica gel column eluting with EtOAc/Hexanes to provide 14C.

Step 2. To a cooled (−78° C.) solution of 14C (1 equiv.) in anhydrous THF (0.2 M) is added MeMgBr (3 equiv, 3 M in diethyl ether). The reaction is stirred for 2 h from −78° C. to 0° C., and quenched with saturated aqueous $NH_4Cl$, and then extracted with EtOAc (2×). The organics are dried over $MgSO_4$, filtered and concentrated. This residue is purified by a silica gel column chromatography eluting with EtOAc/Hexanes to afford 14D.

Step 3. To a solution of compound 14D (1 equiv.) in anhydrous THF (0.2 M) is added NaH (1.2 equiv.). The reaction mixture is stirred at ambient temperature for 0.5 hours. To the mixture is added 14E and the reaction is heated to reflux under nitrogen overnight. The reaction is cooled to ambient temperature, and then poured into water. The product is extracted with EtOAc three times. The combined organics are washed with brine, dried over Na2SO4, and concentrated. The residue is purified with a silica gel column eluting with EtOAc/Hexanes to provide the product 14F.

Step 4. To a solution of compound 14F (1 equiv.) in $CH_2Cl_2$ (0.2 M) is added 4 M HCl/dioxane (10 equiv.) and the mixture is stirred until all of 14F is converted to 14G. After concentration, the residue is purified in a reverse phase preparative HPLC to provide 14G.

Step 5. To a solution of 14G (1 equiv.) and DIPEA (2 equiv.) in toluene (0.01 M) is added Pd(P-t-Bu$_3$)$_2$ (1 equiv.). The reaction mixture is heated at 100° C. under 4 bar CO overnight, and then concentrated. The residue is purified on a silica gel column eluting with EtOAc/hexanes to provide 14.

Examples 15 and 15-1

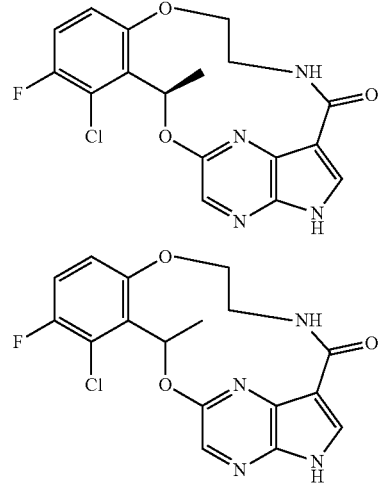

Step 1. To a mixture of compounds 14A (1 equiv.) and 14B (1.2 equiv.) in anhydrous DMF (0.2 M) is added $Cs_2CO_3$ (1.5 equiv.) and the reaction is heated in an oil bath Examples 15 and 15-1 may be prepared according to the following scheme using racemic or enantiomerically enriched starting materials:

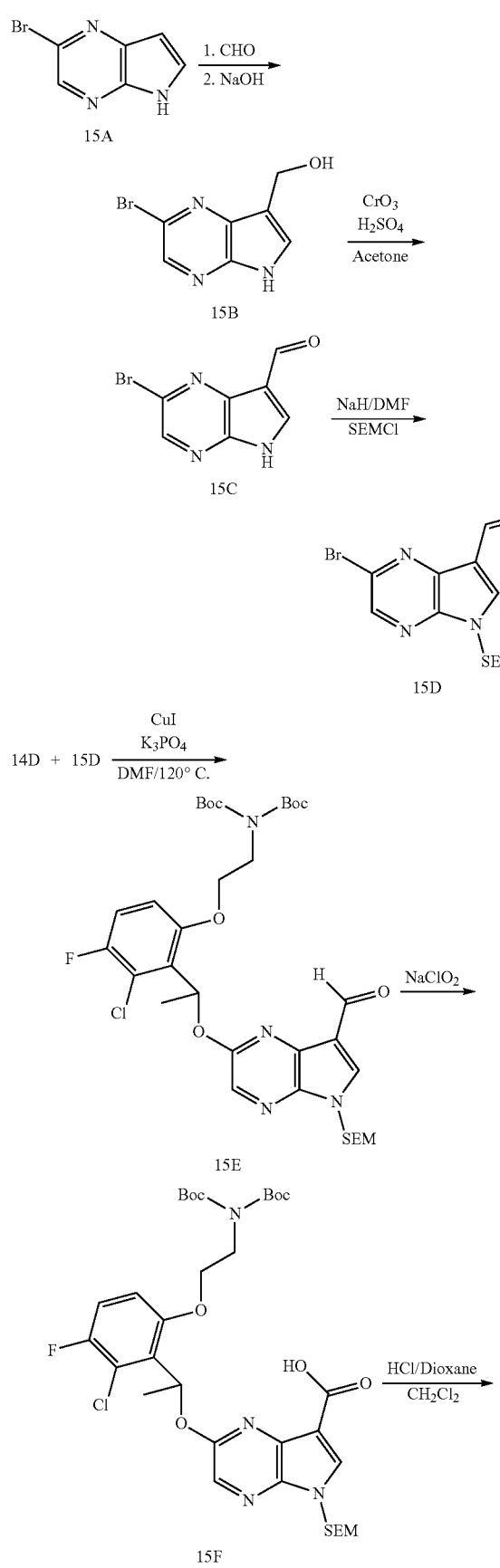
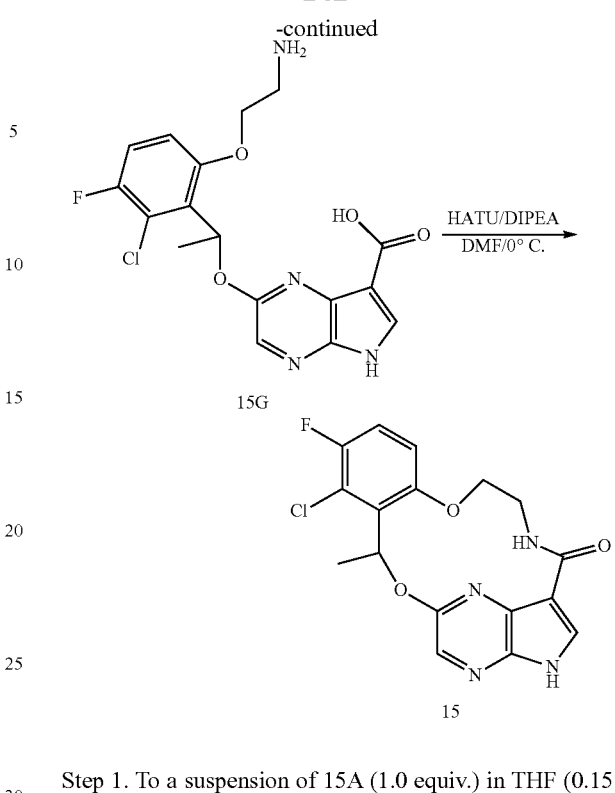

Step 1. To a suspension of 15A (1.0 equiv.) in THF (0.15 M) is added a solution of 2.0 M aqueous NaOH (3 equiv.). The homogeneous reaction mixture is stirred overnight, and then the organics are removed under reduced pressure. The aqueous residue is brought to pH~4 with 1.0 M aqueous HCl. The resulting precipitate is collected by filtration and rinsed with H₂O to afford a solid of 15B. The filtrate is extracted with EtOAc (2×), and the organics are concentrated under reduced pressure to provide an additional portion of 15B.

Step 2. A stock solution of Jones reagent (2.67 M) is prepared by carefully adding concentrated H₂SO₄ (2.3 mL) to CrO₃ (2.67 g) and then diluting to 10 mL with H₂O. To a suspension of 15B (1.0 equiv.) in acetone (0.067 M) is slowly added Jones reagent (1.2 equiv.). The reaction mixture is stirred for 15 min and then quenched with i-PrOH and filtered through a pad of diatomaceous earth, rinsing with acetone. The filtrate is concentrated to provide 15C which is used without further purification.

Step 4. To a solution of 15C (1.0 equiv.) in DMF (0.40 M) at 0° C. is added NaH (60% in mineral oil, 1.5 equiv.). The reaction mixture is stirred at room temperature for 30 min and then cooled back to 0° C., and 2-(trimethylsilyl) ethoxymethyl chloride (4.3 mL, 1.2 equiv.) is slowly added. The reaction mixture is warmed to room temperature, stirred for 1 h, and then quenched with H₂O and extracted with EtOAc (3×). The combined organics are washed with H₂O (3×) and brine, and then dried over MgSO₄ and concentrated. The residue is purified by a flash silica-gel chromatography eluting with 20-30% EtOAc/hexanes to give 15D.

Step 5. To a reaction mixture of 14D (1.0 equiv.), copper (T) iodide (0.05 equiv.), 8-hydroxyquinoline (0.1 equiv.), and potassium phosphate tribasic (2.0 equiv.) in DMF (0.2 M) under nitrogen atmosphere is added 15D (1.2 equiv.) and the reaction mixture is heated at 120° C. for 24 h. The reaction mixture is cooled to room temperature and then diluted with EtOAc. The mixture is filtered through a pad of diatomaceous earth and the filtrated is evaporated under vacuum. The crude residue is purified on a silica gel column eluting with EtOAC/Hexanes to give 15E.

Step 6. A 0° C. suspension of 15E (1.0 equiv.) in 1,4-dioxane (0.062 M) and water (1/3 of THF) is treated with sulfamic acid (6.0 equiv.). A solution of sodium chlorite (1.3 equiv.) and potassium dihydrogen phosphate (12 equiv.) in water (1.2 M) is added via dropping funnel over 20 min. After the addition is complete, the ice bath is removed and the reaction mixture is stirred at room temperature for 3 h. THF is added, and the reaction mixture is stirred at room temperature for an additional 3 h. The reaction mixture is diluted with water and extracted with EtOAc (2×). The combined organic layers are washed with water and brine and then dried over $Na_2SO_4$, filtered, and concentrated. The residue is triturated with ethyl acetate/hexanes to afford 15F.

Step 7. To a solution of compound 15F (1 equiv.) in $CH_2Cl_2$ (0.2 M) is added 4 M HCl/dioxane (10 equiv.) and the mixture is stirred until all of 15F is converted to 15G. After concentration, the residue is purified in a reverse phase preparative HPLC to provide 15G.

Step 8. A solution of compound 15G (1 equiv.) and DIPEA (10 equiv.) in DMF (0.2 M) is added drop-wise to a solution of HATU (1.4 equiv.) in DMF (0.1 M) at 0° C. After complete addition, the mixture is stirred at 0° C. for a further 30 min. Water is added and the mixture is extracted with EtOAc three times. The combined organics are washed with saturated $NaHCO_3$ twice, brine, dried over $Na_2SO_4$, and evaporated. The residue is purified with a silica gel column eluted with EtOAc/Hexanes to provide 15.

Examples 18 and 18-1

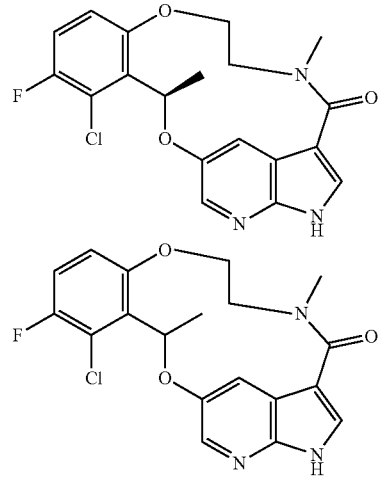

Examples 18 and 18-1 may be prepared according to the following scheme using racemic or enantiomerically enriched starting materials:

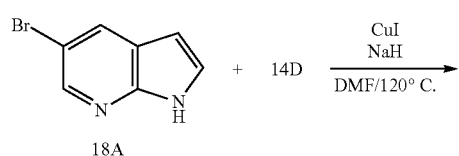

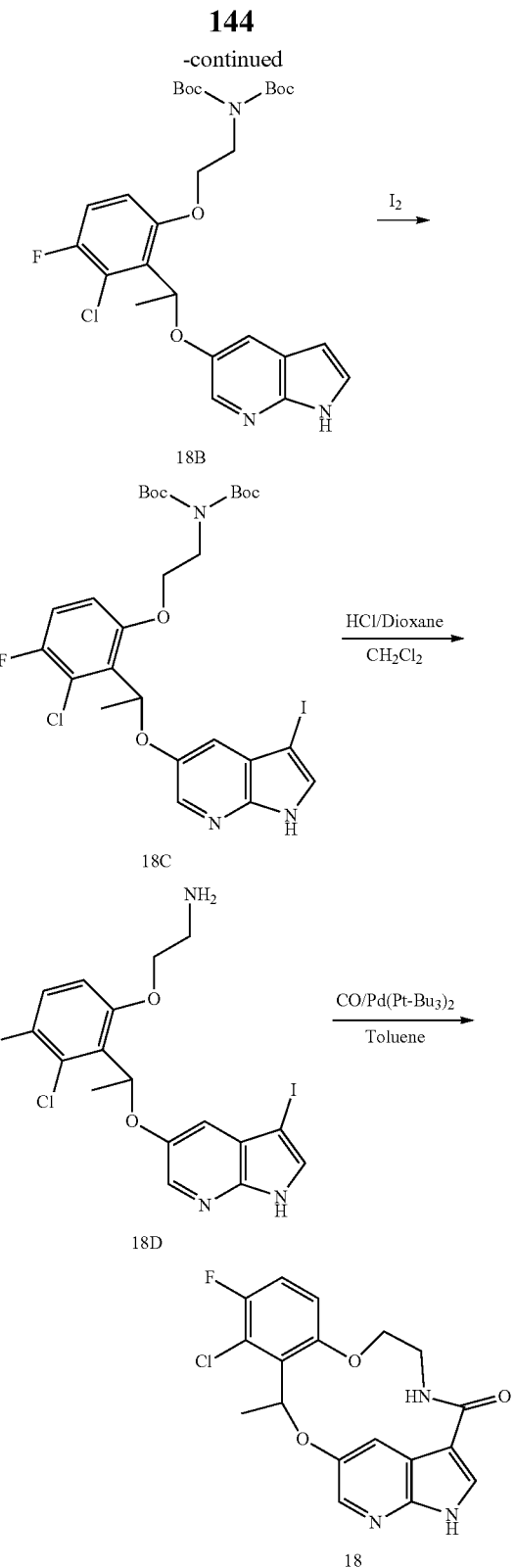

Step 1. To a reaction mixture of 14D (1.0 equiv.), 18A (1.2 equiv.), and copper(I) iodide (0.05 equiv.) in DMF (0.2 M) under nitrogen atmosphere is added NaH (3.0 equiv.). The reaction mixture is heated at 120° C. for 24 h, and then is cooled to room temperature and diluted with EtOAc. The mixture is filtered through a pad of diatomaceous earth and the filtrated is evaporated under vacuum. The crude residue is purified on a silica gel column eluting with EtOAc/Hexanes to give 18B.

Step 2. To a reaction mixture of 18B (1.0 equiv.) in DMF (0.2 M) are added KOH (2 equiv.) and $I_2$ (1.1 equiv.). The reaction mixture is stirred at room temperature for 1 h, and then quenched with $NaHSO_3$ and extracted with EtOAc. The combined organics are washed with saturated $NaHCO_3$ twice, brine, dried over $Na_2SO_4$, and evaporated. The residue is purified with a silica gel column eluted with EtOAc/Hexanes to provide 18C.

Step 3. To a solution of compound 18C (1 equiv.) in $CH_2Cl_2$ (0.2 M) is added 4 M HCl/dioxane (10 equiv.) and the mixture is stirred until all of 18C is converted to 18D. After concentration, the residue is purified in a reverse phase preparative HPLC to provide 18D.

Step 4. To a solution of 18D (1 equiv.) and DIPEA (2 equiv.) in toluene (0.01 M) is added $Pd(P\text{-}t\text{-}Bu_3)_2$ (1 equiv.). The reaction mixture is heated at 100° C. under 4 bar CO overnight, and then concentrated. The residue is purified on a silica gel column eluting with EtOAc/hexanes to provide 18.

Example 20

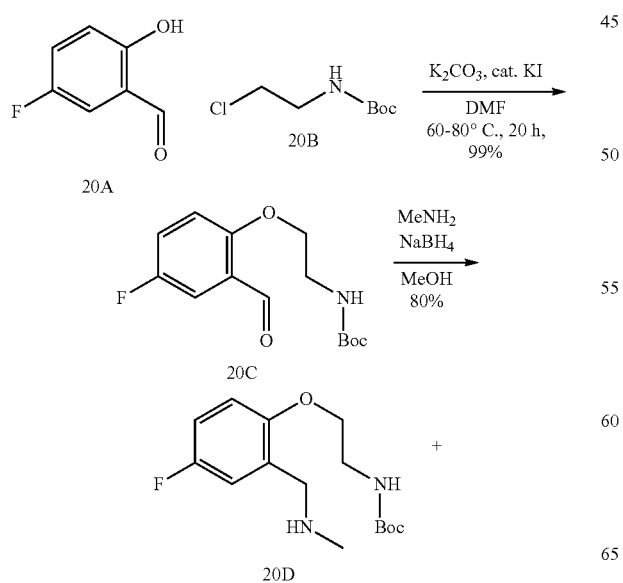

Example 20 was prepared according to the following scheme:

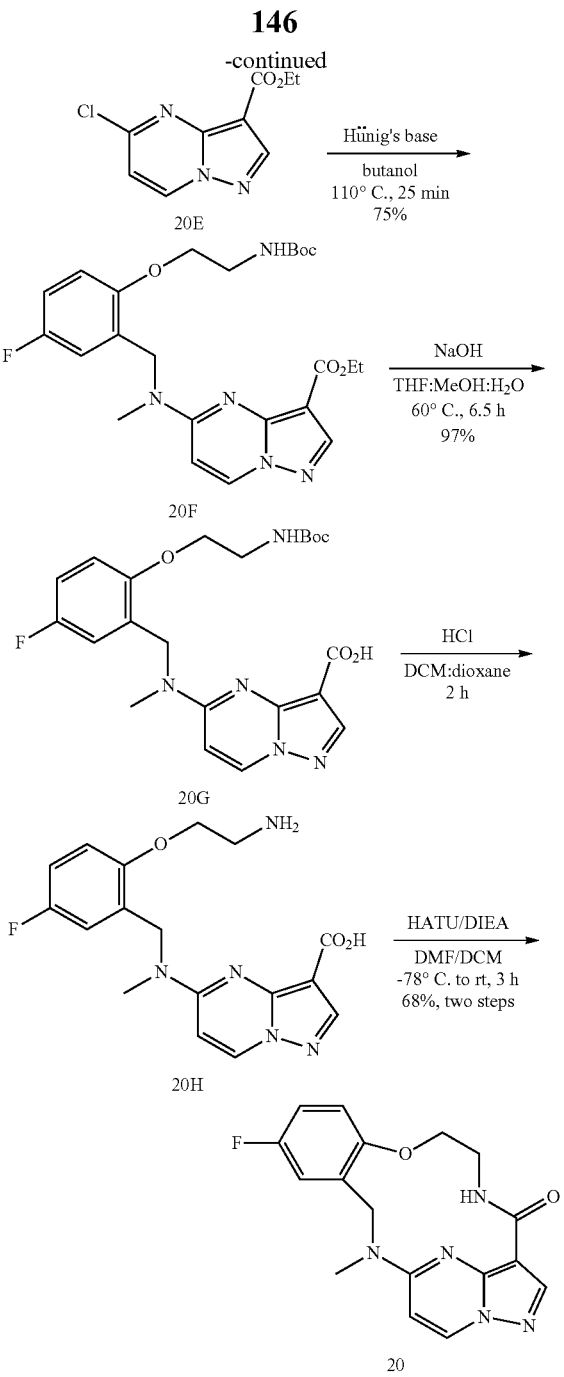

Step 1. tert-Butyl (2-(4-fluoro-2-formylphenoxy)ethyl) carbamate (20C). A solution of aldehyde 20A (1.5 g, 11 mmol), chloride 20B (2.1 g, 12 mmol), potassium carbonate (7.4 g, 54 mmol) and potassium iodide (36 mg, 0.2 mmol) in DMF (11 mL) were heated to 60° C. and stirred for 15 hours. Additional chloride 20B (1.0 g, 6 mmol) and further heating at 80° C. for 5 hours completed the reaction. The mixture was cooled to room temperature and diluted by addition of water (250 mL). The mixture was extracted with ethyl acetate (3×300 mL) and the combined extracts were washed with water (200 mL) and brine (100 mL), dried with sodium sulfate, and concentrated under reduced pressure. Flash chromatography (ISCO system, silica, 0-20% ethyl acetate in hexane) provided 20C (3.0 g, 99%) as a viscous oil. LRESIMS m/z 306.1 [M+Na]$^+$, calcd. for $C_{14}H_{18}F_1N_1Na_1O_4$ 306.1.

Step 2. tert-Butyl (2-(4-fluoro-2-((methylamino)methyl)phenoxy)ethyl)carbamate (20D). Aldehyde 20C (2.5 g, 8.8 mmol) and methylamine (0.69 g, 22 mmol) in methanol (88 mL) were heated to 60° C. and stirred for 1 hour. The mixture was cooled to room temperature and sodium borohydride (0.33 g, 8.8 mmol) was added. The mixture was stirred for 30 minutes then quenched by addition of water (200 mL). The mixture was extracted with dichloromethane (4×100 mL) and the combined extracts dried with brine (50 mL), sodium sulfate and concentrated under reduced pressure. Flash chromatography (ISCO system, silica, 0-100% of (10% methanol in ethyl acetate) in hexane) provided the title compound (2.1 g, 80%) as a gel. LRESIMS m/z 299.2 [M+H]$^+$, calcd. for $C_{15}H_{24}F_1N_2O_3$ 299.2.

Step 3. Ethyl 5-((2-(2-((tert-butoxycarbonyl)amino)ethoxy)-5-fluorobenzyl)(methyl)amino)pyrazolo[1,5-a]pyrimidine-3-carboxylate (20F). Amine 20D (2.1 g, 7.0 mmol), ester 20E (1.59 g, 7.0 mmol) and Hunig's base (7.0 mL, 5.2 g, 40 mmol) in butanol (17 mL) were heated at 110° C. for 25 minutes. The reaction was cooled and diluted with water (250 mL). The mixture was extracted with dichloromethane (4×100 mL) and the combined extracts dried with sodium sulfate. The mixture was concentrated under reduced pressure. F lash chromatography (ISCO system, silica, 20-100% ethyl acetate in hexane) provided the title compound (2.1 g, 75%) as a solid. LRESIMS m/z 488.3 [M+H]$^+$, calcd. for $C_{24}H_{31}F_1N_5O_5$ 488.2.

Step 4. 5-((2-(2-((tert-Butoxycarbonyl)amino)ethoxy)-5-fluorobenzyl)(methyl)amino)pyrazolo[1,5-a]pyrimidine-3-carboxylic acid (20G). Sodium hydroxide (40 mL, 2 M in water) was added to a stirred solution of ester 20F (2.1 g, 4.3 mmol) in tetrahydrofuran:methanol (3:2, 100 mL) at room temperature. The reaction was heated to 60° C. and stirred for 6.5 hours. The mixture was cooled to 0° C. and acidified with hydrochloric acid (45 mL, 2 M in water) then diluted with water (100 mL). The mixture was extracted with ethyl acetate (4×150 mL) and the combined extracts dried with brine (50 mL) and sodium sulfate. The mixture was concentrated under reduced pressure to provide the title compound (1.92 g, 97%) as a solid. LRESIMS m/z 460.2 [M+H]$^+$, calcd. for $C_2H_{27}F_1N_5O_5$ 460.2.

Step 5. 5-((2-(2-Aminoethoxy)-5-fluorobenzyl)(methyl)amino)pyrazolo[1,5-a]pyrimidine-3-carboxylic acid (20H). Hydrochloric acid (5 mL, 4M in dioxane) was added to a stirred solution of carboxylic acid 20G (1.92 g, 4.2 mmol) in dichloromethane (25 mL) at room temperature. The reaction was stirred for 2 hours then concentrated under reduced pressure to provided the title compound as a solid. LRESIMS m/z 360.2 [M+H]$^+$, calcd. for $C_{17}H_{10}F_1N_5O_3$ 360.2.

Step 6. Under an atmosphere of argon HATU (1.67 g, 4.4 mmol) was added to a stirred solution of carboxylic acid 20H (1.50 g, 4.2 mmol) and Hünig's base (7.28 mL, 5.40 g, 41.8 mmol) in DMF:dichloromethane (5:1, 60 mL) at −78° C. The reaction was slowly warmed to room temperature and stirred for 3 hours then quenched water (300 mL). The mixture was extracted with ethyl acetate (3×100 mL) then dichloromethane (2×100 mL) and the combined extracts dried with brine (50 mL) and sodium sulfate. The mixture was concentrated under reduced pressure. Flash chromatography (ISCO system, silica, 1-4% methanol in dichloromethane) followed by recrystallization from ethyl acetate/methanol provided Example 20 (0.98 g, 68%, 2 steps) as a solid. LRESIMS m/z 342.2 [M+H]$^+$, calcd. for $C_{17}H_{17}F_1N_5O_2$ 342.1; $^1$H NMR (500 MHz, DMSO-d$_6$) δ 9.43 (dd, J=6.9, 2.7 Hz, 1H), 8.76 (d, J=7.9 Hz, 1H), 8.10 (s, 1H), 7.19-7.25 (m, 1H), 7.03-7.07 (m, 2H), 6.72 (d, J=7.9 Hz, 1H), 5.64 (dd, J=14.9, 1.5 Hz, 1H), 4.48 (dt, J=10.2, 4.3 Hz, 1H), 4.04-4.10 (m, 2H), 3.81-3.87 (m, 1H), 3.58 (s, 3H), 3.38-3.46 (m, 1H).

Alternative Synthesis of Example 20:

Example 20 was also prepared by the following alternative route:

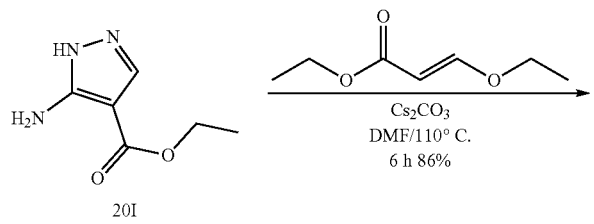

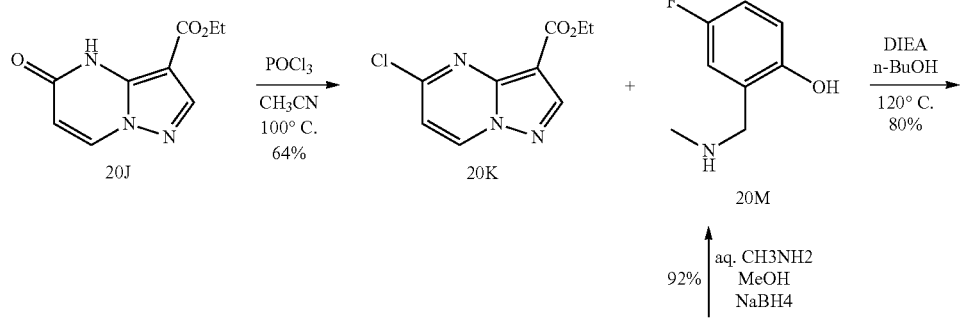

-continued

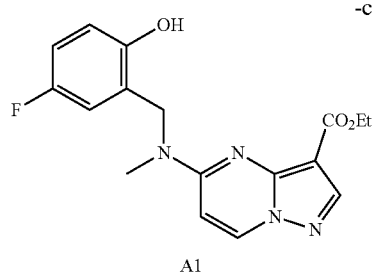

A1

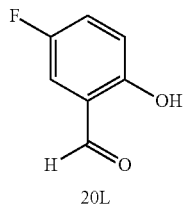

20L

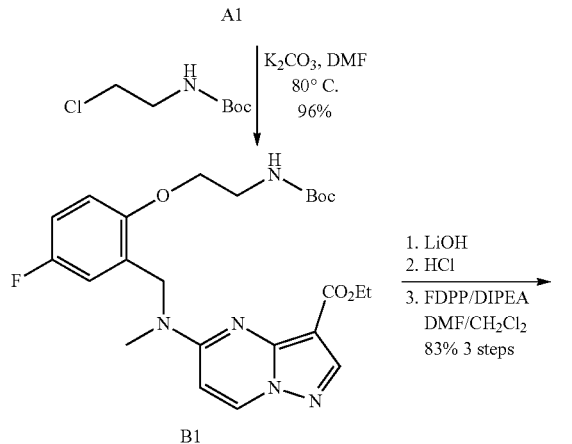

B1

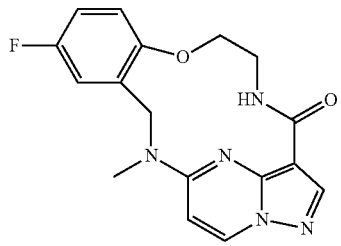

20

Step 1. Ethyl 5-oxo-4H-pyrazolo[1,5-a]pyrimidine-3-carboxylate (20J). To a mixture of 20I (150.00 g, 1.08 mmol) and ethyl (E)-3-ethoxyprop-2-enoate (292.16 g, 2.03 mol) in DMF (3.2 L) was added $Cs_2CO_3$ (656.77 g, 2.02 mol) in one portion at 20° C. under $N_2$. The mixture was stirred at 110° C. for 6 hours. The mixture was cooled to 20° C. and filtered through a pad of diatomaceous earth. The filter cake was washed with ethyl acetate (3×30 mL). The filtrate was added to $H_2O$ (2 L) and acidified with HOAc to pH=4. The resultant precipitate was filtered to afford 20J (173.00 g, 834.98 mmol, 86.36% yield) as a white solid. $^1$H NMR (400 MHz, DMSO-$d_6$) δ 8.54 (d, J=7.91 Hz, 1H), 8.12 (s, 1H), 6.13 (d, J=7.91 Hz, 1H), 4.27 (q, J=7.11 Hz, 2H), 1.28 (t, J=7.09 Hz, 3H).

Step 2. 5-Chloropyrazolo[1,5-a]pyrimidine-3-carboxylate (20K). To a mixture of 20J (158.00 g, 762.59 mmol) in MeCN (1.6 L) was added $POCl_3$ (584.64 g, 3.81 mol) at 20° C. under $N_2$. The mixture was stirred at 100° C. for 2 hours. The mixture was cooled to 20° C. and poured into ice-water (5000 mL) in portions at 0° C. and stirred for 20 min. The precipitate was filtered and dried to afford 20K (110.00 g, 487.52 mmol, 63.93% yield) as a white solid. $^1$H NMR (400 MHz, DMSO-$d_6$) δ 9.33 (d, J=7.28 Hz, 1H), 8.66 (s, 1H), 7.41 (d, J=7.15 Hz, 1H), 4.31 (q, J=7.15 Hz, 2H), 1.32 (t, J=7.09 Hz, 3H).

Step 3. 4-Fluoro-2-methylaminomethyl-phenol (20M). To a solution of 20 L (5.00 g, 35.69 mmol, 1.00 eq.) in MeOH (50.00 mL) was added aqueous methanamine (8.8 mL, 71.38 mmol, 25%, 2.00 eq) in one portion at 25° C. under $N_2$. The mixture was stirred at 25° C. for 3 hours, then $NaBH_4$ (2.70 g, 71.38 mmol, 2.00 eq) was added portion-wise. And the mixture was stirred at 25° C. for another 9 hours. TLC showed the reaction was completed. The mixture was concentrated in reduced pressure at 45° C. The residue was poured into water (50 mL). The aqueous phase was extracted with dichloromethane (3×200 mL) and the combined organic phase was washed with brine (200 mL), dried over anhydrous $Na_2SO_4$, filtered and concentrated in vacuum to afford 20M (5.10 g, 32.87 mmol, 92.09% yield) as a colourless solid. $^1$H NMR (400 MHz, $CDCl_3$) δ 6.86 (dt, J=3.0, 8.7 Hz, 1H), 6.78-6.69 (m, 2H), 3.93 (s, 2H), 2.48 (s, 3H).

Step 4. 5-[(5-Fluoro-2-hydroxy-benzyl)-methyl-amino]-pyrazolo[1,5-a]pyrimidine-3-carboxylic acid ethyl ester (A1). To a suspension of 20M (33.70 g, 217.17 mmol, 1.00 eq.) and 20K (49.00 g, 217.17 mmol, 1.00 eq.) in n-BuOH (740.00 mL), DIPEA (159.98 g, 1.24 mol, 5.70 eq.) was added. The reaction mixture was stirred at 120° C. for 2 hours under nitrogen. TLC showed reaction completion. The solution was cooled to 25° C., and then removed the solvent. The residue was diluted with water (500 mL) and extracted with dichloromethane (3×500 mL). The combined organic extracts was washed with brine (300 mL), dried over anhydrous $Na_2SO_4$ and concentrated under vacuum. The residue was triturated by EtOAc (100 mL) to give A1 (60.00 g, 174.25 mmol, 80.24% yield) as a white solid. $^1$H NMR (500 MHz, Chloroform-t) δ 9.71 (s, 1H), 8.32 (d, J=7.9 Hz, 1H), 8.30 (s, 1H), 6.98-6.87 (m, 3H), 6.37 (d, J=7.9 Hz, 1H), 4.82 (s, 2H1), 4.42 (q, J=7.1 Hz, 2H), 3.21 (s, 3H), 1.39 (t, J=7.1 Hz, 3H).

Step 5. 5-{[2-(2-tert-Butoxycarbonylamino-ethoxy)-5-fluoro-benzyl]-methyl-amino}-pyrazolo[1,5-a]pyrimidine-3-carboxylic acid ethyl ester (B1). To a solution of A1 (102.85 g, 298.6 mmol, 1 eq.), (2-chloro-ethyl)-carbamic acid tert-butyl ester (56.33 g, 313.5 mmol, 1.05 eq.) in DMF (854 mL) were added $K_2CO_3$ (206.41 g, 1493 mmol, 5.0 eq.). The mixture was heated at 80° C. for 20 hours with ~85% conversion of the starting material to the product by LC-MS. Additional portions of (2-chloro-ethyl)-carbamic acid tert-butyl ester (5.633 g, 31.35 mmol, 0.1 eq.) and $K_2CO_3$ (41.282 g, 298.6 mmol, 1 eq.) were added to the reaction flask. The reaction was continued at 80° C. for an additional 21 hours. The mixture was then cooled to room temperature, quenched with water (1000 ml) and extracted with EtOAc (3×900 mL). The combined organic extracts were then washed with water (3×700 mL) and brine (500 mL), dried over Na₂SO₄, and concentrated. The resulting residue was purified by a silica gel column eluting with EtOAc/Hexane (0-70% to afford B1 as a white solid (128.74 g, 96.7% yield). LC-MS (ESI) m/z 510.1 (M+Na)⁺; ¹H NMR (500 MHz, Chloroform-d) δ 8.30 (s, 1H), 8.26 (s, 1H), 6.92 (td, J=8.6, 3.3 Hz, 1H), 6.83-6.76 (m, 1H), 6.31 (s, 1H), 4.93 (s, 2H), 4.51-4.44 (m, 1H), 4.36 (q, J=7.2 Hz, 2H), 4.03 (t, J=4.9 Hz, 2H), 3.69-3.63 (m, 1H), 3.51 (s, 2H), 3.30 (s, 2H), 1.44 (s, 9H), 1.41-1.35 (t, J=7.2 Hz, 3H).

Step 6. 11-Fluoro-14-methyl-6,7,13,14-tetrahydro-1,15-ethenopyrazolo[4,3-f][1,4,8,10]benzoxatriazacyclotridecin-4(5H)-one (20). To a solution of B1 (128.74 g, 264.07 mmol, 1 eq.) in methanol (750 mL) and THF (250 mL) was added LiOH·H₂O (55.40 g, 1320 mmol, 5.0 eq.) in H₂O (250 mL). The clear solution was heated at 70° C. for 2 hours. The reaction was neutralized at 0° C. with aq. HCl (2M, 250 mL) to pH<5, and then extracted with CH₂Cl₂ (1×1000 mL, 3×500 mL). The combined organics were washed with brine (300 mL), and dried over Na₂SO₄. After filtration, evaporation, and high vacuum dry, a white solid was obtained (126.47 g, 275.25 mmol, 104% yield). To a solution of the acid (121.30 g, 264 mmol) in CH₂Cl₂ (996 mL) was added HCl in dioxane (4 M, 204 mL) at 0° C. Keep stirring from 0° C. to room temperature for 27 hours until the de-Boc was complete by LC-MS. The white solid was filtered, washed with DCM (400 mL), and high vacuum dried to provide a white solid of the amine 3HCl salt (123.55 gram) which was used directly without further purification. To a solution of DIPEA (169.4 g, 228 mL, 1310 mmole) in DMF (3.7 L) and CH₂Cl₂ (1.0 L) was added the acid amine HCl salt (22.92 g, 49.0 mmol, 1.00 eq.). After the solid salt was dissolved completely, pentafluorophenyl diphenylphosphinate (FDPP) in CH₂Cl₂ (1.1 M, 19.76 g, 51.44 mmol, 1.05 eq.) was added. The coupling was complete in 30 minutes by LC-MS, and then the second portions of the salt and FDPP was added following the same procedure as the first portion. The addition of the salt followed by FDPP was repeated every 30 minutes and monitored by LC-MS for every cycle of the addition. A total of the salt (123.55 g, 264 mmol, 1.00 eq) and FDPP (106.44 g, 277 mmol, 1.05 eq.) were added to the reaction flask in portion. The reaction solution was concentrated to a volume of ~500 mL and a lot of precipitate was formed. The solid product 20 was filtered and washed with DMF (50 mL×3). The filtrate was poured into water (2 L) and additional product was precipitated out. The solid product was filtered and washed with water (100 mL×3). The combined solid product was dried, and re-dissolved in 10% methanol in dichloromethane (1.5 L) and then ethyl acetate was added (1 L). The solution was condensed to ~500 mL and a lot of white solid was formed. After filtration and high vacuum dry, a white solid compound 20 was obtained (74.58 g, 83% yield).

Powder X-ray Diffraction (PXRD) of Example 20.

A sample of Example 20, crystalline polymorph form 1, was transferred to a zero background plate for PXRD analysis. The PXRD data was obtained using a Bruker D8 X-ray diffractometer according to manufacturer recommended procedures. Parameters for scan: 2-theta range: 4.5 to 39.1 degrees; step size: 0.02 degrees; step time: 1 second; analysis time: 180 seconds.

Diffraction peaks are typically measured with an error of ±0.1 degrees (2θ).

Results are shown in FIG. 1. The data is summarized in Table 1.

TABLE 1

| 2-θ (degrees) | d-value | Peak Intensity (Counts) | Peak Intensity (%) |
| --- | --- | --- | --- |
| 10.68 | 9.611 | 31.15 | 5.2 |
| 11.96 | 8.586 | 19.11 | 2.9 |
| 15.26 | 6.737 | 20.92 | 4.4 |
| 19.64 | 5.244 | 27.57 | 6.4 |
| 21.94 | 4.701 | 452.41 | 100 |
| 23.96 | 4.309 | 91.85 | 18.2 |
| 26.82 | 3.857 | 10.92 | 2.2 |

Differential Scanning Calorimetry (DSC) of Example 20.

Figure 2:
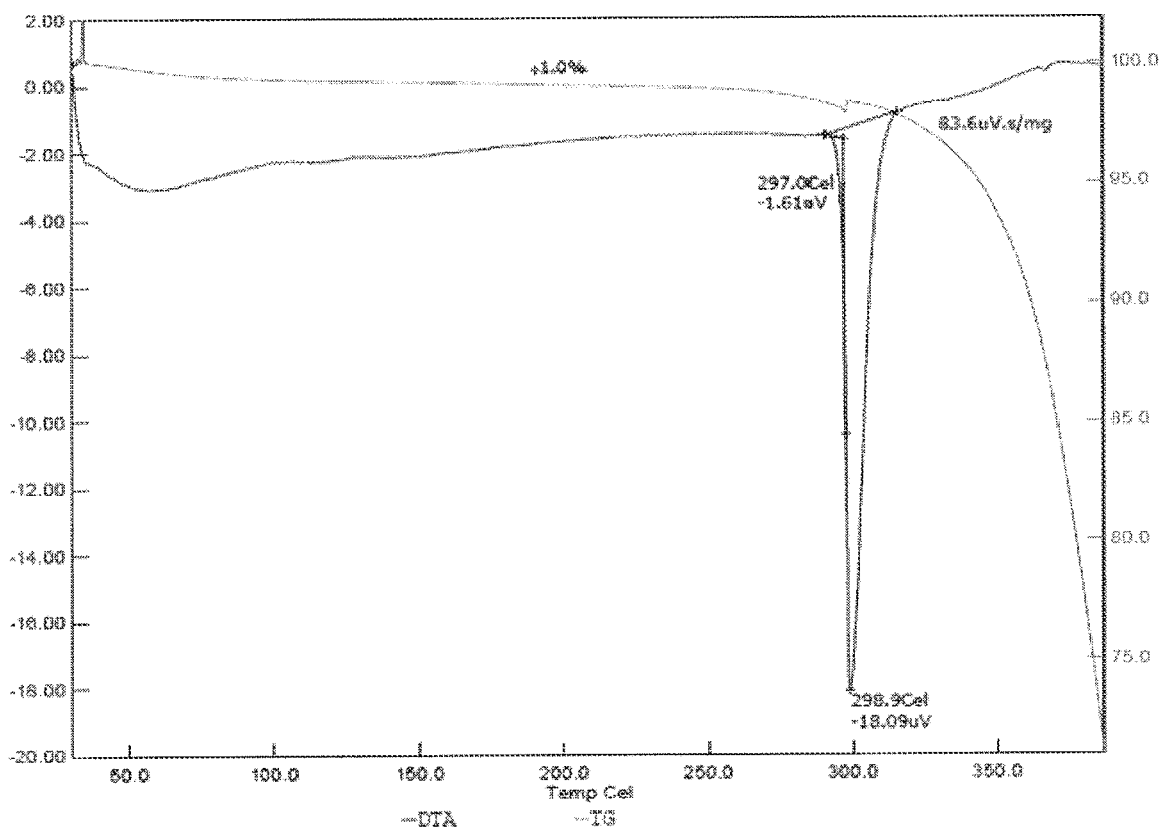
FIG. 2 shows a differential scanning calorimetry thermogram of the the crystalline polymorph form 1 of the free base of 11-fluoro-14-methyl-6,7,13,14-tetrahydro-1,15-ethenopyrazolo[4,3-f][1,4,8,10]benzoxatriazacyclo-tridecin-4(5H)-one (Example 20).

DSC measurements, shown in FIG. 2, were carried out using a Seiko Model SSC/5200 Differential Scanning Calorimeter. A 7.92 mg sample of Example 20, crystalline polymorph form 1, was equilibrated at 36° C., and then ramped to 380° C. at a rate of 10° C./min. The sample of Example 20, crystalline polymorph form 1, showed a melting point of 298.9° C.

Example 26

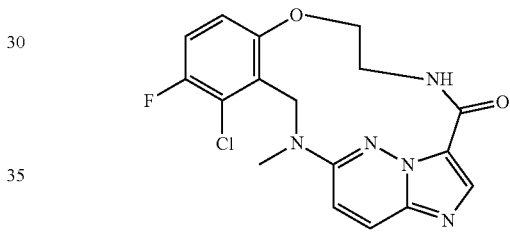

Example 26 may be prepared according to the following scheme:

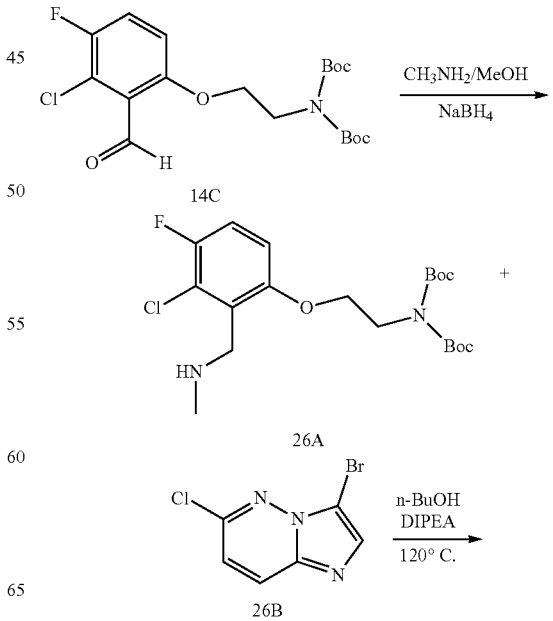

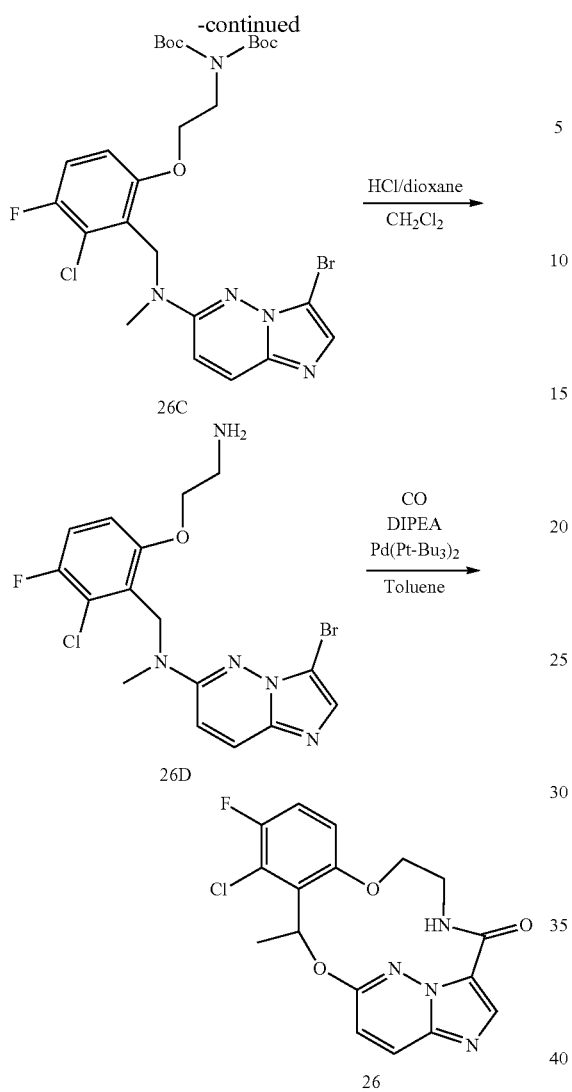

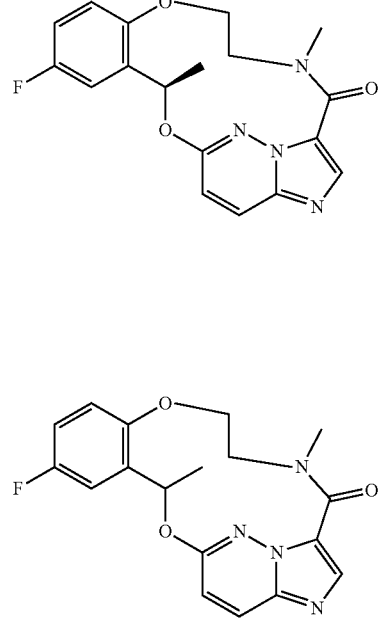

The reaction mixture is heated at 100° C. under 4 bar CO overnight, and then concentrated. The residue is purified on a silica gel column eluting with EtOAc/hexanes to provide 26.

Examples 37 and 37-1

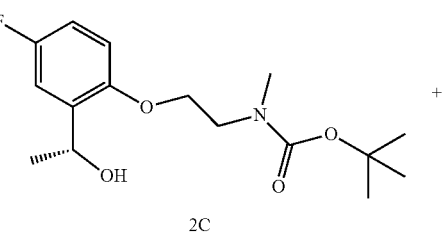

Examples 37 and 37-1 may be prepared according to the following scheme from racemic or enantiomerically enriched starting materials:

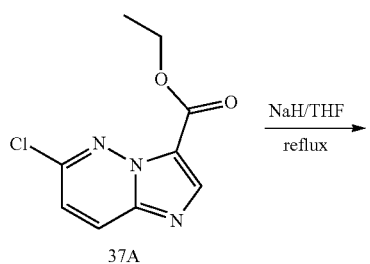

Step 1. Titanium(IV) isopropoxide (1.3 equiv.) is added to a commercially available solution of methylamine in methanol (2 M, 3 equiv.) followed by the addition of the starting aldehyde 14C (1.0 equiv.). The reaction mixture is stirred at ambient temperature for 5 h, after which sodium borohydride (1.0 equiv.) is added and the resulting mixture is further stirred for another period of 2 h. The reaction is then quenched by the addition of water, the resulting inorganic precipitate is filtered and washed with EtOAc. The organic layer is separated and the aqueous part is further extracted with EtOAc (×2). The combined extracts are dried ($K_2CO_3$) and concentrated in vacuo to give 26A.

Step 2. A mixture of compound 26A (1 equiv.) and DIPEA (2 equiv.) in n-BuOH (0.2 M) is heated at 120° C. overnight, cooled to ambient temperature, and then concentrated. The residue is purified with a silica gel column eluting with EtOAc/Hexanes to provide the product 26B.

Step 3. To a solution of compound 26B (1 equiv.) in $CH_2Cl_2$ (0.2 M) is added 4 M HCl/dioxane (10 equiv.) and the mixture is stirred until all of 26B is converted to 26C. After concentration, the residue is purified in a reverse phase preparative HPLC to provide 26C.

Step 4. To a solution of 26C (1 equiv.) and DIPEA (2 equiv.) in toluene (0.01 M) is added Pd(P-t-Bu$_3$)$_2$ (1 equiv.).

-continued

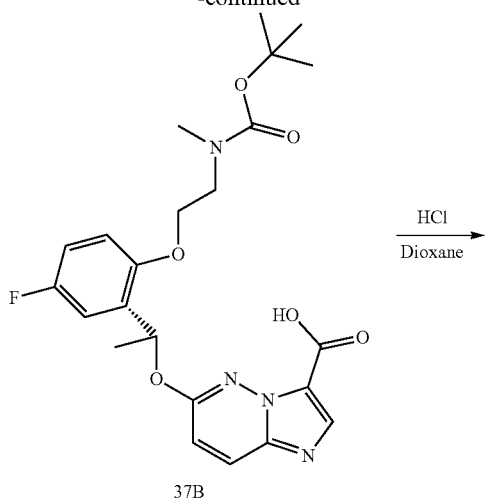

37B

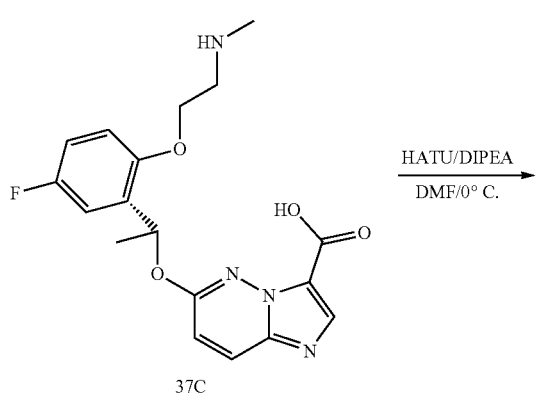

37C

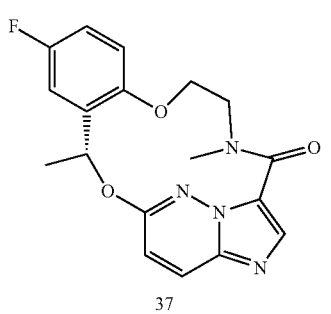

37

Step 1. Compound 37B is prepared from compound 2C and compound 37A using the method described for Example 2, Synthesis A. Step 2.

Step 2. Compound 37C is prepared from compound 37B using the method described in Example 2, Synthesis A, Step 3.

Step 3. Example 37 is prepared from compound 37C using the method described in Example 2. Synthesis A. Step 4.

Examples 38 and 38-1

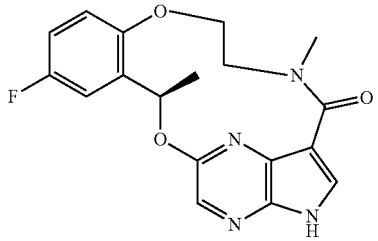

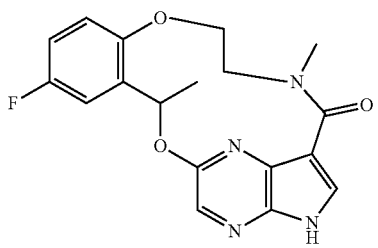

Examples 38 and 38-1 may be prepared according to the following scheme from racemic or enantiomerically enriched starting materials:

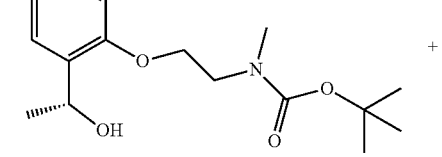

2C

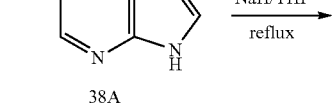

38A

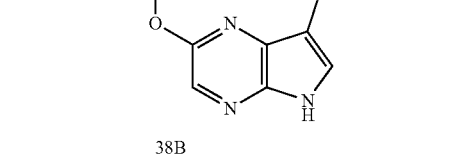

38B

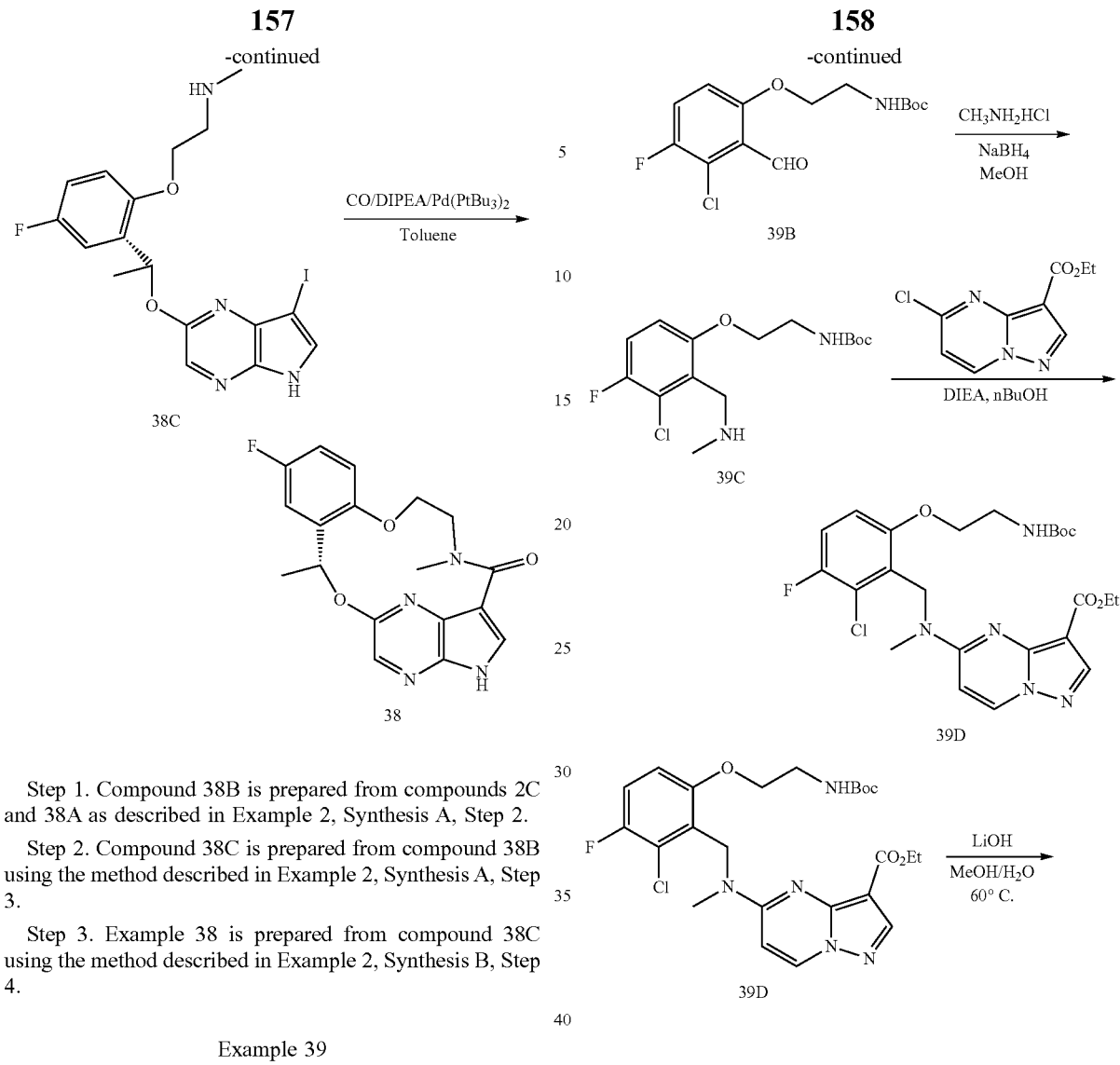
Step 1. Compound 38B is prepared from compounds 2C and 38A as described in Example 2, Synthesis A, Step 2.
Step 2. Compound 38C is prepared from compound 38B using the method described in Example 2, Synthesis A, Step 3.
Step 3. Example 38 is prepared from compound 38C using the method described in Example 2, Synthesis B, Step 4.
Example 39
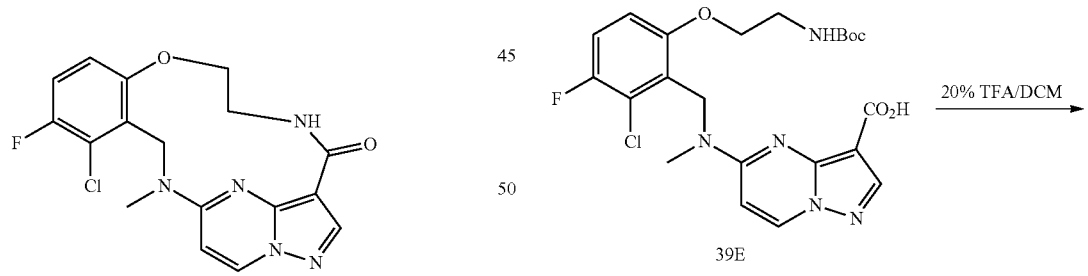
Example 39 was prepared according to the following schemes:
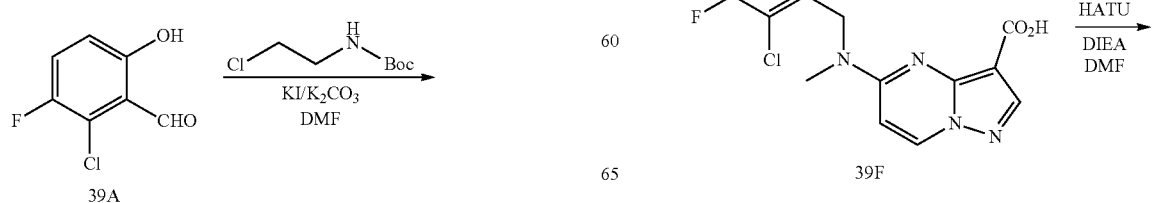

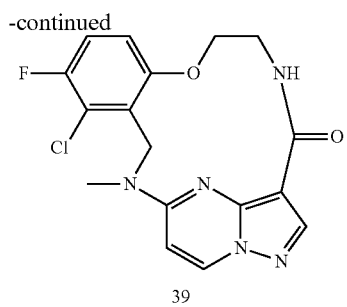

39

Step 1. 2-(3-Chloro-4-fluoro-2-formyl-phenoxy)-ethyl]-carbamic acid tert-butyl ester (39B). To a solution of 2-chloro-3-fluoro-6-hydroxy-benzaldehyde (39A, 53 mg, 0.3 mmol) and (2-chloro-ethyl)-carbamic acid tert-butyl ester (135 mg, 0.75 mmol) in DMF (5 mL) were added KI (2.0 mg, 0.012 mmol) and K$_2$CO$_3$ (105 mg, 0.75 mmol). The mixture was microwaved at 100° C. for 2 h. The mixture was then diluted with water (20 mL) and extracted with EtOAc (3×20 mL). The combined organic layers were washed with water (3×20 mL) and brine (20 mL), dried over Na$_2$SO$_4$ and concentrated to afford 39B. The crude residue was used directly in the next step. LC-MS: (ESI) m/z 340.3 (M+Na)$^+$.

Step 2. {[2-(3-Chloro-4-fluoro-2-methylaminomethyl-phenoxy}-ethyl]-carbamic acid tert-butyl ester (39C). To a solution of 39B (95.4 mg, 0.3 mmol) in MeOH (3 mL) was added methylamine hydrochloride (50.7 mg, 0.75 mmol). The mixture was stirred at 60° C. for 30 min. The solution was then cooled to ambient temperature and NaBH$_4$ (11.1 mg, 0.3 mmol) was added. The mixture was stirred at ambient temperature for 2 h. The solution was then diluted with water (50 mL) and extracted with DCM (3×20 mL). The combined organic layers were dried over Na$_2$SO$_4$ and concentrated to afford 39C. The crude residue was used directly in the next step. LC-MS: (ESI) r/z 333.3 (M+H)$^+$.

Step 3. 5-{[6-(2-tert-Butoxycarbonylamino-ethoxy)-2-chloro-3-fluoro-benzyl]-methyl-amino}-pyrazolo[1,5-a]pyrimidine-3-carboxylic acid ethyl ester (39D). To a solution of 20K (67.5 mg, 0.3 mmol) and 39C (99.9 mg, 0.3 mmol) in n-BuOH (2.0 mL) was added DIEA (1.0 mL). The mixture was heated under microwave at 150° C. for 2 hours The mixture was then diluted with water and extracted with DCM (3×20 mL). The organic layer was dried over Na$_2$SO$_4$, concentrated and purified by silica gel column chromatography to afford 17 as a yellow liquid. LC-MS: (EST) m/z 522.5 (M+H)$^+$.

Step 4. 5-{[6-(2-tert-Butoxycarbonylamino-ethoxy)-2-chloro-3-fluoro-benzyl]-methyl-amino}-pyrazolo[1,5-a]pyrimidine-3-carboxylic acid (39E). To a solution of 39D (40 mg, 0.0776 mmol) in MeOH (1 mL) was added LiOH (16 mg, 0.38 mmol) and H$_2$O (1 mL). The mixture was stirred at 60° C. for 4 h. The solution was cooled to ambient temperature, partially concentrated and acidified by aqueous HCl (1 N) until pH 2-3. The aqueous mixture was extracted with DCM (3×10 mL). The organic layer was dried over Na$_2$SO$_4$ and concentrated to afford 39E. The crude residue was used directly in the next step. LC-MS: (ESI) m/z 494.3 (M+H)$^+$.

Step 5. 5-{[6-(2-Amino-ethoxy)-2-chloro-3-fluoro-benzyl]-methyl-amino}-pyrazolo[1,5-a]pyrimidine-3-carboxylic acid (39F). To a solution of 39E (40 mg, 0.0776 mmol) in DCM (2 mL), TFA (0.4 mL) was added. The solution was stirred for 1 hr. The solvent was removed under rotavap. The residue was re-dissolved with DCM and re-concentrated (3×) to afford 39F as a foam-like solid. LC-MS: (EST) m/z 393.5 (M+H)$^+$.

Step 6. To a solution of 39F (36 mg, 0.078 mmol) in 10 mL of DCM was added DIEA (0.20 mL, 1.15 mmol). The solution was chilled with dry ice/acetone bath and HATU (40.0 mg, 0.11 mmol) was added. The solution was allowed to warm to ambient temperature slowly. The mixture was diluted with water (50 mL) and extracted with EtOAc (3×50 mL). The combined organic layer was washed with water (3×50 mL) and brine (50 mL), dried over Na$_2$SO$_4$, and concentrated. The resulting residue was purified by a silica column (0-5% MeOH/DCM) afford Example 39 as a white solid (6.2 mg, 23.4%). LC-MS: (ESI) m/z 376.5 (M+H)$^+$. $^1$H NMR (500 MHz, chloroform-d) δ 9.51 (s, 1H), 8.40-8.33 (m, 2H), 7.03 (ddd, J=8.9, 8.0, 0.7 Hz, 1H), 6.78 (dd, J=9.3, 4.2 Hz, 1H), 6.40 (d, J=7.9 Hz, 1H), 5.97 (dd, J=15.0, 2.1 Hz, 1H), 4.49-4.43 (m, 1H), 4.31 (ddd, J=10.9, 6.4, 4.5 Hz, 1H), 4.12-4.03 (m, 11H), 3.91 (d, J=14.9 Hz, 1H), 3.72-3.63 (m, 1H), 3.56 (s, 3H).

Example 40

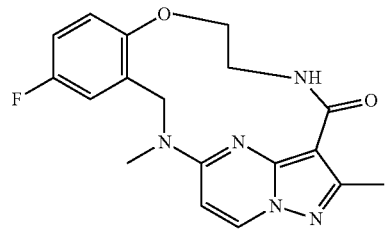 [SMILES: Cc1nn2ccc3nc2c1C(=O)NCCOc1ccc(F)cc1CN3C]

Example 40 was prepared as shown in the following scheme:

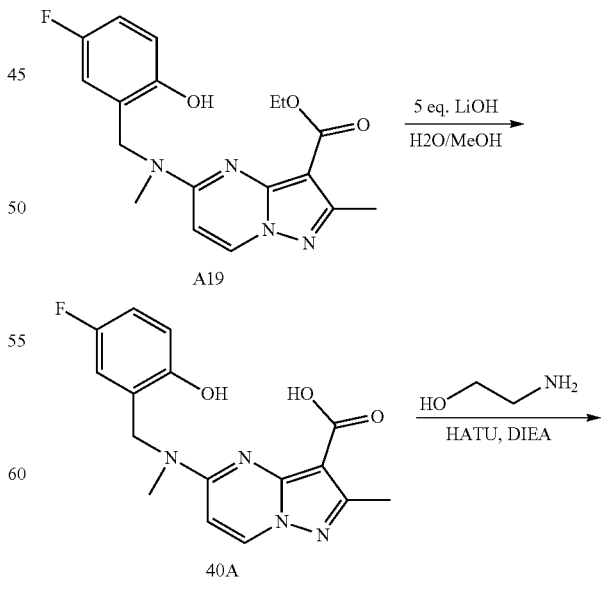

161

-continued

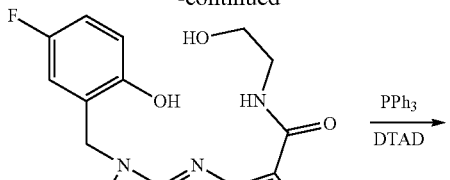

40B

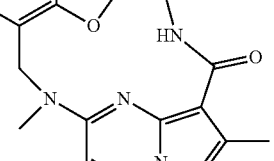

40

Step 1. 5-[(5-Fluoro-2-hydroxy-benzyl)-methyl-amino]-2-methyl-pyrazolo[1,5-a]pyrimidine-3-carboxylic acid (40B). To a solution of 19A (75 mg, 0.14 mmol) in MeOH (2 mL) was added LiOH (60 mg, 1.4 mmol) and $H_2O$ (2 mL). The mixture was stirred at 60° C. for 4 h. The solution was cooled to ambient temperature, partially concentrated and acidified by aqueous HCl (1 N) until pH 2-3. The resulting suspension was extracted with EtOAc (3×20 mL). The organic layer was dried over $Na_2SO_4$ and concentrated to afford 40A. LC-MS (ESI) m/z 331.6 (M+H)$^+$.

Step 2. 5-[(5-Fluoro-2-hydroxy-benzyl)-methyl-amino]-2-methyl-pyrazolo[1,5-a]pyrimidine-3-carboxylic acid (2-hydroxy-ethyl)-amide (40B). To a solution of 40A (140 mg, 0.42 mmol) and 2-amino-ethanol (244 mg, 4 mmol) in DCM (5 mL) at 0° C. were added DIEA (0.20 mL, 1.15 mmol) and HATU (380.0 mg, 1.0 mmol). The solution was allowed to warm to ambient temperature slowly. The mixture was then diluted with water (25 mL) and extracted with EtOAc (3×25 mL). The combined organic layers were washed with HCl (1N, 3×20 mL) and brine (50 mL), dried over $Na_2SO_4$ and concentrated. The resulting residue was purified by a silica gel column eluting with 0-5% MeOH/DCM (10 CV) afford 40B as a white solid (74 mg, 47%). LC-MS (ESI) m/z 374.3 (M+H)$^+$.

Step 3. To a solution of 40B (74 mg, 0.2 mmol) in THF (3 ml) and DCM (3 mL) at 0° C. were added $PPh_3$ (131 mg, 0.5 mmol) and di-tert-butyl azodicarboxylate (DTAD) (115 mg, 0.5 mmol). The mixture was allowed to warm to ambient temperature and stirred for additional 4 h. The solvent was removed and the residue was purified by a silica gel column eluting with 0-10%, MeOH/DCM (10 CV), followed by preparative TLC to afford Example 40 as a white solid (15 mg). LC-MS (ESI) n/z 356.5 (M+H)$^+$; $^1$H NMR (500 MHz, chloroform-d) δ 8.12 (d, J=7.7 Hz, 1H), 6.93 (ddd, J=9.0, 3.1, 0.9 Hz, 1H), 6.78 (ddd, J=9.0, 7.3, 3.0 Hz, 1H), 6.71 (dd, J=9.1, 4.5 Hz, 1H), 6.28 (d, J=7.7 Hz, 1H), 5.77 (dd, J=15.2, 1.7 Hz, 1H), 4.38-4.33 (m, 1H), 3.98 (s, 1H), 3.91 (d, J=1.4 Hz, 1H), 3.78 (dd, J=15.1, 0.9 Hz, 1H), 3.45 (s, 3H), 3.43-3.36 (m, 1H), 2.45 (s, 3H).

162

Example 41

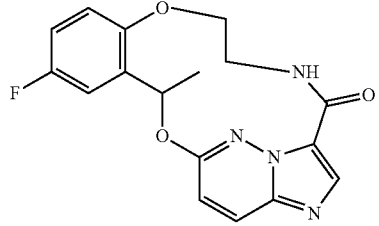 [SMILES: CC1Oc2ccc3ncc(n3n2)C(=O)NCCOc2ccc(F)cc21]

Example 41 was prepared using the method shown in the following scheme:

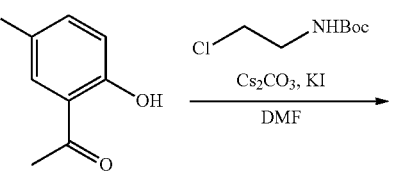

41A

41B

+

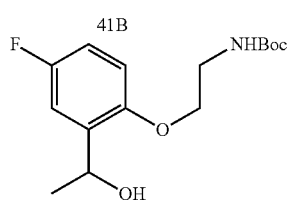

20K

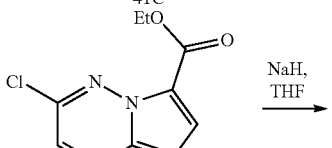

41D

Step 1. [2-(2-Acetyl-4-fluoro-phenoxy)-ethyl]-carbamic acid tert-butyl ester (41B). To a mixture of 1-(5-fluoro-2-hydroxy-phenyl)-ethanone (41A, 773 mg, 5.0 mmol) and (2-chloro-ethyl)-carbamic acid tert-butyl ester (1.80 g, 10.0 mmol) in DMF (20 mL) were added KI (2.0 mg, 0.012 mmol) and $Cs_2CO_3$ (3.26 g, 10.0 mmol). The mixture was stirred at 80° C. overnight. The mixture was then cooled to ambient temperature, diluted with EtOAc, and washed with 1 N NaOH (5×10 mL) until LCMS showed no 1-(5-fluoro-2-hydroxy-phenyl)-ethanone peak. The organic layer was dried over Na$_2$SO$_4$ and concentrated. The residue was then purified by a silica gel column eluting with EtOAc/hexane (0-30%, 10 CV) to afford the desired product 41B as a yellow solid (1.1 g, 73.8%). LC-MS (ESI) n/z 320.3 (M+Na)$^+$.

Step 2. tert-Butyl (2-(4-fluoro-2-(1-hydroxyethyl)phenoxy)ethyl)carbamate (41C). To a solution of 41B (1.0 g, 3.36 mmol) in MeOH (10 mL) was added NaBH$_4$ (640 mg, 16.8 mmol) in portions. The mixture was stirred at ambient temperature for 2 h. The solution was then diluted with water (50 mL) and extracted with DCM (3×20 mL). The combined DCM layers were dried over Na$_2$SO$_4$ and concentrated. The residue was purified by a silica gel column eluting with EtOAc/hexane (0-50%, 10 CV) to afford the desired product as a pale yellow solid (0.75 g, 75%). LC-MS (EST) m/z 322.3 (M+Na)$^+$; $^1$H NMR (500 MHz, chloroform-d) δ 7.11 (dd, J=9.2, 3.4 Hz, 1H), 6.89 (ddd, J=9.0, 7.9, 3.2 Hz, 1H), 6.77 (dd, J=8.9, 4.4 Hz, 1H), 5.09 (q, J=6.6 Hz, 1H), 4.92 (d, J=4.4 Hz, 1H), 4.03 (t, J=5.2 Hz, 2H), 3.62-3.50 (m, 2H), 1.49 (d, J=6.4 Hz, 3H), 1.45 (s, 9H).

Step 3. 6-{1-[2-(2-tert-Butoxycarbonylamino-ethoxy)-5-fluoro-phenyl]-ethoxy}-imidazo[1,2-b]pyridazine-3-carboxylic acid ethyl ester (41D). To a solution of 41C (600 mg, 2.0 mmol) and {2-[4-fluoro-2-(1-hydroxy-ethyl)-phenoxy]-ethyl}-carbamic acid tert-butyl ester (450 mg, 2.0 mmol) in dry THF (40.0 mL) at −78° C. was added NaH (60%, 80 mg, 2.0 mmol) in portions. The suspension was stirred at −78° C. for 4 h and allowed to warm to 0° C. and stirred for additional 4 h. The mixture was then put in the freezer at −20° C. overnight. The mixture was then quenched with a mixture of ice and 1 N HCl and extracted with EtOAc (3×20 mL). The organic layer was dried over Na$_2$SO$_4$, concentrated and purified twice to afford the desired product as a yellow solid (240 mg, 25%). LC-MS (ESI) m/z 511.6 (M+Na)$^+$; $^1$H NMR (500 MHz, chloroform-d) δ 8.16 (s, 1H), 7.90 (d, J=9.7 Hz, 1H), 7.16 (dd, J=9.0, 3.2 Hz, 1H), 0.95 (d, J=9.5 Hz, 1H), 6.90-6.88 (m, 1H), 6.81-6.78 (m, 1H), 6.68 (q. J=6.2 Hz, 1H), 5.84-5.68 (m, 1H), 4.38 (q, J=7.2 Hz, 2H), 4.15-4.09 (m, 2H), 3.60-3.52 (m, 2H), 1.65 (d, J=6.4 Hz, 3H), 1.38 (d, J=7.2 Hz, 3H), 1.35 (s, 9H).

Step 4. Compound 41D was converted to Example 41 using methods analogous to those described herein. MS: 343.2 (M+H)$^+$; $^1$H NMR (500 MHz, Chloroform-d) δ 9.82 (d, J=7.0 Hz, 1H), 8.27 (s, 1H), 8.09 (d, J=9.5 Hz, 1H), 7.18 (dd, J=8.9, 3.2 Hz, 1H), 7.01-6.94 (m, 2H), 6.83 (dd, J=9.0, 4.3 Hz, 1H), 6.60-6.53 (m, 1H), 4.63-4.52 (m, 1H), 4.27-4.16 (m, 1H), 4.16-4.04 (m, 1H), 3.70-3.56 (m, 1H), 1.70 (d, J=6.4 Hz, 3H)

Example 42

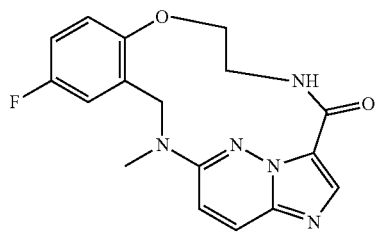 [SMILES: CN1Cc2cc(F)ccc2OCCNC(=O)c2cnc3ccc1nn23]

Example 42 was prepared using the methods shown in the following scheme:

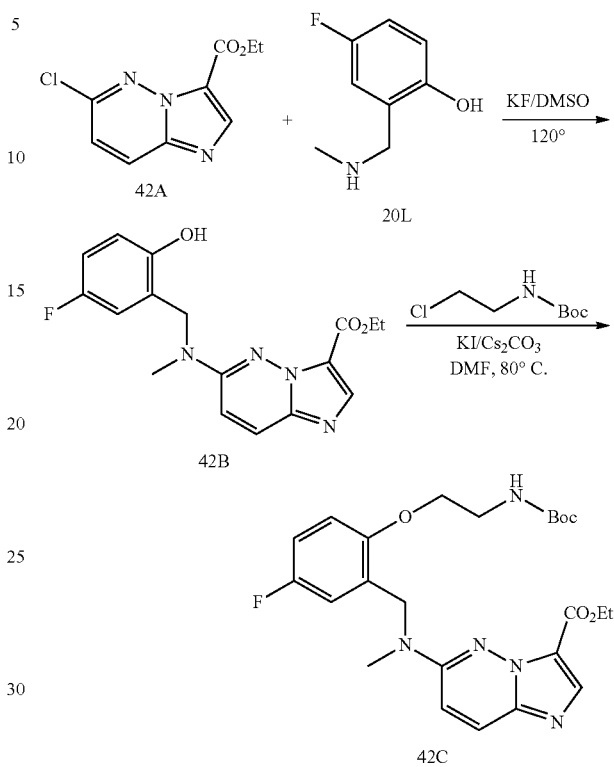

Step 1. 6-[(5-Fluoro-2-hydroxy-benzyl)-methyl-amino]-imidazo[1,2-b]pyridazine-3-carboxylic acid ethyl ester (42B). To a mixture of 4-fluoro-2-methylaminomethyl-phenol (20 L, 305.2 mg, 1.97 mmol) and 6-chloro-imidazo[1,2-b]pyridazine-3-carboxylic acid ethyl ester (42A, 230 mg, 1.02 mmol) in DMSO (5 mL) was added KF (180 mg, 3.01 mmol). The reaction mixture was stirred at 120° C. for 18 hours under nitrogen. The solution was then cooled to ambient temperature, diluted with water (20 mL) and extracted with EtOAc (3×50 mL). The combined organic layers were further washed with water (3×50 mL) and brine (50 mL), dried over Na$_2$SO$_4$ and concentrated. The residue was then purified by a silica gel column eluting with EtOAc/hexane (0-50%, 10 CV) to afford the desired product as a white solid (240 mg, 69%). LC-MS (ESI) m/z 345.2 (M+H)$^+$; $^1$H NMR (500 MHz, chloroform-d) δ 8.61 (s, 1H), 8.17 (s, 1H), 7.91 (d, J=10.0 Hz, 1H), 7.00-6.86 (m, 4H), 4.78 (s, 2H), 4.47 (qd, J=7.2, 0.5 Hz, 2H), 3.17 (s, 3H), 1.41 (td, J=7.1, 0.5 Hz, 3H).

Step 2. 6-{[2-(2-tert-Butoxycarbonylamino-ethoxy)-5-fluoro-benzyl]-methyl-amino}-imidazo[1,2-b]pyridazine-3-carboxylic acid ethyl ester (42C). To a solution of 6-[(5-fluoro-2-hydroxy-benzyl)-methyl-amino]-imidazo[1,2-b]pyridazine-3-carboxylic acid ethyl ester (2B, 200 mg, 0.58 mmol) and (2-chloro-ethyl)-carbamic acid tert-butyl ester (209 mg, 1.16 mmol) in DMF (5 mL) were added K$_2$CO$_3$ (200 mg, 1.45 mmol) and K1 (2.0 mg, 0.012 mmol). The mixture was heated at 90° C. for 4 h under nitrogen. The mixture was then diluted with water (20 mL) and extracted with EtOAc (3×10 mL). The combined organic layers were then washed with water (3×5 mL) and brine (2×5 mL). The organic layer was dried over Na$_2$SO$_4$ and concentrated. The resulting residue was purified by a silica gel column eluting with EtOAc/hexane (0-100%, 10 CV) to afford 42C as a white solid (203 mg, 76%). LC-MS (ESI) m/z 510.1 (M+Na)+; 1H NMR (500 MHz, Chloroform-d) δ (ppm) 8.16 (s, 1H), 7.85 (d, J=9.9 Hz, 1H), 7.00 (dd, J=8.9, 3.2 Hz, 1H), 6.95-6.87 (m, 2H), 6.80 (dd, J=8.9, 4.3 Hz, 1H), 4.95 (s, 1H), 4.74 (s, 2H), 4.41 (q, J=7.2 Hz, 2H), 4.04 (t, J=5.2 Hz, 2H), 3.56-3.50 (m, 2H), 3.26 (s, 3H), 1.43 (s, 9H), 1.40 (t, J=7.2 Hz, 3H).

Step 3. Compound 42C was converted to Example 42 using methods analogous to those described herein. MS: 342.5 (M+H)+; 1H NMR (500 MHz, chloroform-d) δ 10.01 (d, J=6.9 Hz, 1H), 8.17 (s, 1H), 8.04 (d, J=10.0 Hz, 1H), 7.07-7.04 (m, 1H), 7.00 (d, J=10.0 Hz, 1H), 6.96-6.92 (m, 1H), 6.84 (dd, J=9.1, 4.5 Hz, 1H), 5.69 (dd, J=15.8, 1.6 Hz, 1H), 4.55 (dt, J=9.9, 3.7 Hz, 1H), 4.20-4.09 (m, 2H), 3.98 (dd, J=15.9, 1.0 Hz, 1H), 3.66-3.62 (m, 1H), 3.61 (s, 3H).

Example 51-1

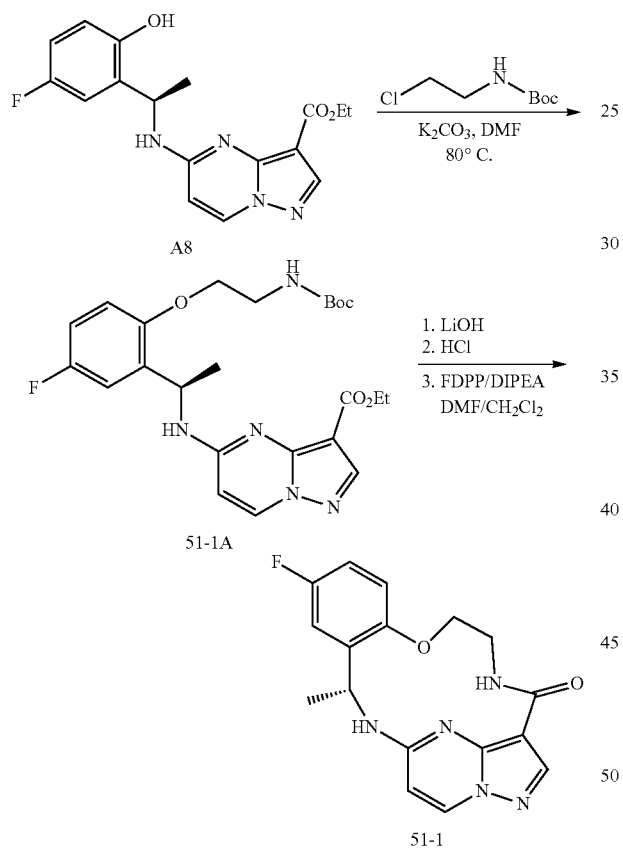

Step 1 To a solution of A8 (399.4 mg, 1.16 mmol) and tert-butyl (2-chloroethyl)carbamate (260.5 mg, 1.45 mmol) in DMF (5.8 mL) was added K2CO3 (801.6 mg, 5.80 mmol) and heated at 80° C. with stirring for 6 hours. The reaction was cooled to ambient temperature and diluted with DCM (3 mL), filtered through a syringe filter, and concentrated under reduced pressure. Flash chromatography (ISCO system, silica (12 g), 0-70% ethyl acetate in hexane) provided 51-1A (407.4 mg, 0.836 mmol, 72% yield).

Step 2. To a solution of 51-1A (407.4 mg, 0.836 mmol) in MeOH (6 mL) and THF (4 mL) was added LiOH aqueous solution (2M, 4.0 mL) at ambient temperature. The reaction solution was heated at 70° C. for 2 hours The reaction flask was cooled to ambient temperature, diluted with water and methanol, and then quenched with HCl aqueous solution (2 M, 4 mL) to pH<5. The mixture was extracted with DCM (3×5 mL), dried with Na2SO4, concentrated under reduced, and dried on high vacuum overnight. To a solution of the acid product in DCM (6 mL) was added 4 M HCl in 1,4-dioxane (2.97 mL). The mixture was stirred at room temperature for 3 hours, and then concentrated under reduced pressure and dried on high vacuum. To a solution of the de-Boc product and FDPP (352.9 mg, 0.918 mmol) in DMF (21 mL) was added Hunig's base (539.5 mg, 0.327 mmol) at room temperature. The mixture was stirred for 2.5 hours, and then quenched the reaction with 2 M Na2CO3 solution (21 mL). The mixture was stirred for 15 min and then extracted with DCM (4×10 mL). The combined extracts were dried with Na2SO4 and concentrated under reduced pressure. The residue was purified with flash chromatography (ISCO system, silica (12 g), 0-11.25% methanol in dichloromethane) to provide 51-1 (164.0 mg, 0.480 mmol, 57.55% yield for three steps).

Example 53

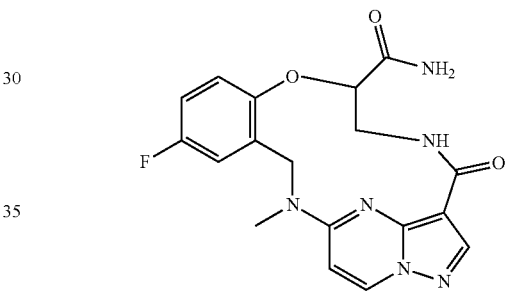

Example 53 was prepared using the methods shown in the following scheme:

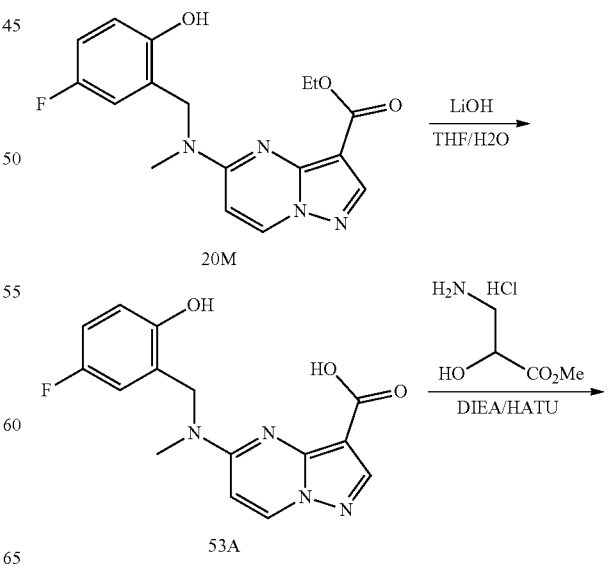

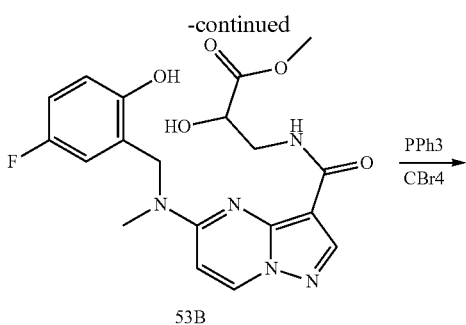

53B

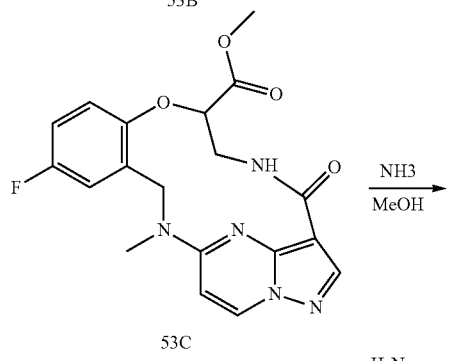

53C

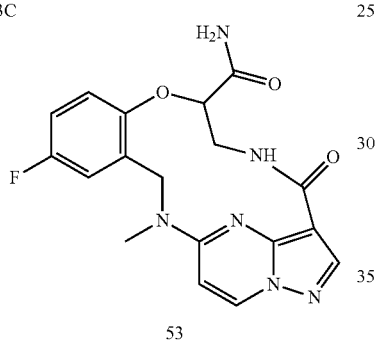

53

Step 1. 5-[1-(5-Fluoro-2-hydroxy-phenyl)-ethylamino]-pyrazolo[1,5-a]pyrimidine-3-carboxylic acid (53A). To a solution 5-[(5-fluoro-2-hydroxy-benzyl)-methyl-amino]-pyrazolo[1,5-a]pyrimidine-3-carboxylic acid ethyl ester (20M, 300 mg, 0.87 mmol) in MeOH (5 mL), LiOH (420 mg, 10 mmol) was added, followed by 5 mL of H$_2$O. The mixture was allowed to stir at 60° C. for 4 h. The solution was cooled to ambient temperature, partially concentrated and acidified with 1 N HCl until pH 2-3. The resulting suspension was extracted with EtOAc (3×20 mL). The combined organic layers were dried over Na$_2$SO$_4$ and concentrated. The residue was used directly in the next step. LCMS (ESI$^+$) m/z 317.4 (M+H)$^+$.

Step 2. 3-({5-[(5-Fluoro-2-hydroxy-benzyl)-methyl-amino]-pyrazolo[1,5-a]pyrimidine-3-carbonyl}-amino)-2-hydroxy-propionic acid methyl ester (53B). To a solution of 53A (80 mg, 0.25 mmol) and 3-amino-2-hydroxy-propionic acid methyl ester hydrochloride (70 mg, 0.5 mmol) in DCM (5 mL) at 0° C. was added DIPEA (1.0 mL, 5.7 mmol), followed by HATU (140.0 mg, 0.5 mmol). The solution was allowed to warm to ambient temperature slowly. The mixture was diluted with water (25 mL) and extracted with EtOAc (3×25 mL). The combined organic layers were washed with 1 N HCl (3×20 mL) and brine (50 mL), and dried over Na$_2$SO$_4$. The solvent was removed and the resulting white solid was used directly in the next step. LC-MS (ESI$^+$) m/z 418.4 (M+H)$^+$.

Step 3. Methyl 11-fluoro-14-methyl-4-oxo-4,5,6,7,13,14-hexahydro-1,15-ethenopyrazolo[4,3-f][1,4,8,10]benzoxatriazacyclotridecine-7-carboxylate (53C). To a solution of 53B (83 mg, 0.2 mmol) in DCM (5 mL) was added PPh$_3$ (263 mg, 1.0 mmol), followed by CBr$_4$ (332 mg, 1.0 mmol). The mixture was stirred at ambient temperature overnight. The solvent was removed and the residue was re-dissolved in DMF (5 mL), followed by the addition of K$_2$CO$_3$ (116.8 mg, 0.84 mmol). The mixture was then stirred at 80° C. until a complete formation of the desired product. The mixture was then diluted with EtOAc and washed with water. The organic layer was dried over Na$_2$SO$_4$ and concentrated. The residue was purified by silica column (0-10%, MeOH/DCM) to afford 53C as a white solid (40 mg). LC-MS (ESI$^+$) m/z 400.2 (M+H)$^+$.

Step 4. To 53C (20 mg, 0.05 mmol) was added NH$_3$ in MeOH solution (7 N, 2 mL). The mixture was stirred at 60° C. overnight. The solvent was removed and the residue was purified by silica column (0-10%, MeOH/DCM) to afford Example 53 as an off-white solid (8 mg). LC-MS (ESI$^+$) m/z 385.5 (M+H)$^+$; $^1$H NMR (300 MHz, Chloroform-d) δ 8.41 (s, 1H), 8.34 (d, J=7.9 Hz, 1H), 8.17 (s, 1H), 6.99-6.92 (m, 2H), 6.77 (dd, J=6.2, 3.5 Hz, 1H), 6.38 (d, J=7.9 Hz, 1H), 5.63-5.44 (m, 2H), 5.09 (dd, J=11.0, 8.4 Hz, 1H), 4.38 (dd, J=14.7, 11.0 Hz, 1H), 4.28-4.17 (m, 1H), 4.17-4.07 (m, 2H), 3.22 (s, 3H).

Example 54

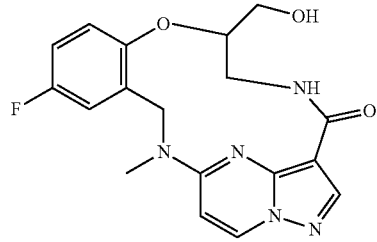 [SMILES: CN1Cc2cc(F)ccc2OC(CO)CNC(=O)c2cnn3ccc1nc23]

Example 54 was prepared using the method shown in the following scheme:

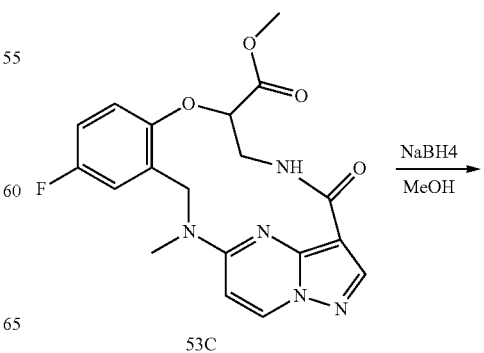

53C

-continued

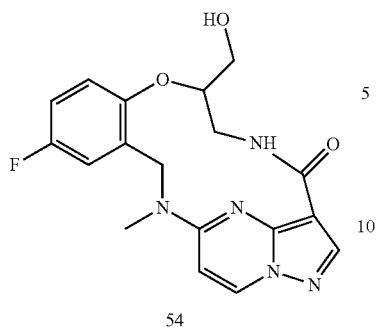

54

To a solution of Compound 53C (20 mg, 0.05 mmol) in MeOH (2 mL) was added NaBH₄ (19 mg, 0.5 mmol) portion wise. The mixture was stirred for 4 h. The solvent was removed and the residue was purified by silica column (0-10%, MeOH/DCM) to afford the desired product as a white solid (8 mg). LC-MS (ESI⁺) m/z 372.5 (M+H)⁺; ¹H NMR (300 MHz, Chloroform-d) δ 8.39 (s, 1H), 8.32 (d, J=7.9 Hz, 1H), 7.01-6.85 (m, 3H), 6.35 (d, J=8.0 Hz, 1H), 5.55-5.43 (m, 1H), 4.92-4.82 (m, 1H), 4.09-3.98 (m, 2H), 3.80-3.70 (m, 3H), 3.23 (s, 3H).

Example 93

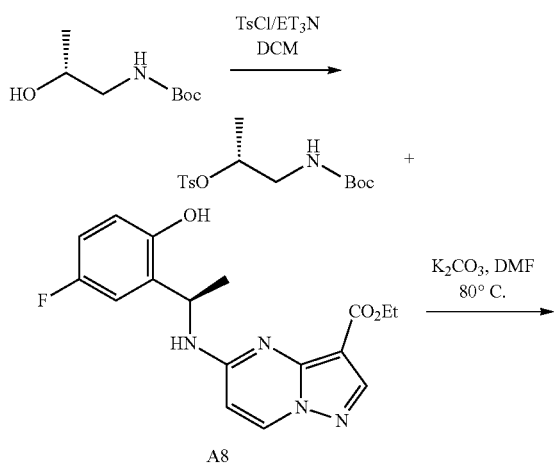

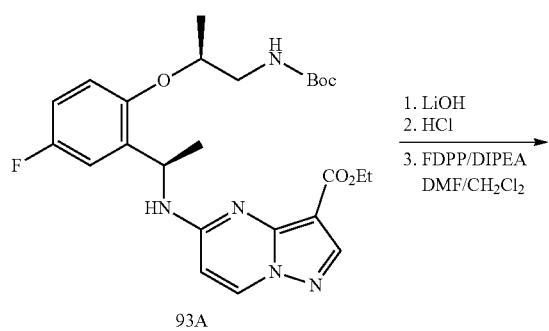

93A

-continued

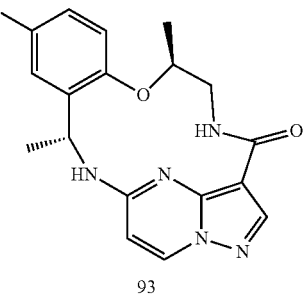

93

Step 1. To a solution of tert-butyl (R)-(2-hydroxypropyl) carbamate (1.00 g, 5.71 mmol) and tosyl chloride (1.14 g, 6.00 mmol) in DCM (29 mL) was added triethylamine (1.44 g, 14.28 mmol and the mixture was stirred at room temp for 48 hour. The reaction solution was concentrated under reduced pressure and the residue was purified with flash chromatography (ISCO system, silica (40 g), 0-20% ethyl acetate in hexane) to provide (R)-1-((tert-butoxycarbonyl) amino)propan-2-yl 4-methylbenzenesulfonate (1.12 g, 3.40 mmol, 59.54% yield).

Step 2. To a solution of A8 (100.00 mg, 0.290 mmol) and (R)-1-((tert-butoxycarbonyl)amino)propan-2-yl 4-methyl-benzenesulfonate (143.50 mg, 0.436 mmol) in DMF (1.45 mL) was added K₂CO₃ (200.7 mg, 1.45 mmol) and heated at 80° C. with stirring for 16 hour. The reaction was cooled to ambient temperature and diluted with DCM (3 mL), filtered through a syringe filter, and concentrated under reduced pressure. Flash chromatography (ISCO system, silica (12 g), 0-60% ethyl acetate in hexane) provided 93A (32.90 mg, 0.0656 mmol, 22.59% yield).

Step 3. To a solution of 93A (32.90 mg, 0.0656 mmol) in MeOH (3 mL) and THF (2 mL) was added LiOH aqueous solution (2M, 2 mL) at ambient temperature. The reaction solution was heated at 70° C. for 2 hours The reaction flask was cooled to ambient temperature, diluted with water and methanol, and then quenched with HCl aqueous solution (2 M, 2 mL) to pH<5. The mixture was extracted with DCM (3×5 mL), dried with Na₂SO₄, concentrated under reduced and dried on high vacuum overnight. To a solution of the acid product in DCM (4 mL) was added 4 M HCl in 1,4-dioxane (2.0 mL). The mixture was stirred at room temperature for 3 hours, and then concentrated under reduced pressure and dried on high vacuum. To a solution of the de-Boc product and FDPP (27.62 mg, 0.0719 mmol) in DMF (1.6 mL) was added Hunig's base (42.23 mg, 0.327 mmol) at room temperature. The mixture was stirred for 2.5 hours, and then quenched the reaction with 2 M Na₂CO₃ solution (2 mL). The mixture was stirred for 15 min then extracted with DCM (4×10 mL). The combined extracts were dried with Na₂SO₄ and concentrated under reduced pressure. The residue was purified with flash chromatography (ISCO system, silica (12 g), 0-10% methanol in dichloromethane) to provide 93 (10.1 mg, 0.0284 mmol, 43.49% yield for three steps).

Examples 104, 106 and 107

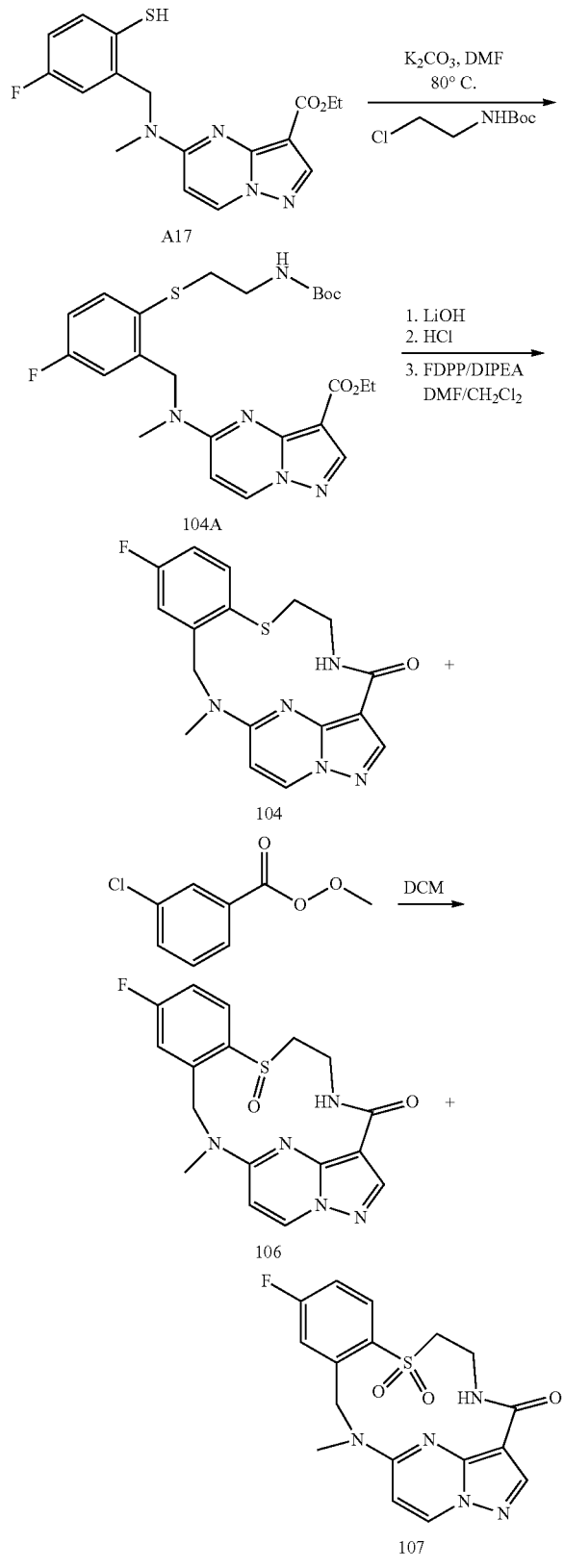

Step 1. To a solution of A17·HCl (38 mg, 0.096 mmol) and tert-butyl (2-chloroethyl)carbamat (12.9 mg, 0.072 mmol) in DMF (0.5 mL) was added $K_2CO_3$ (33.1 mg, 0.24 mmol) and heated at 80° C. with stirring for 1.5 hour. The reaction was cooled to ambient temperature and diluted with DCM (3 mL), filtered through a syringe filter, and concentrated under reduced pressure. Flash chromatography (ISCO system, silica (12 g), 0-60% ethyl acetate in hexane) provided 104A (20.8 mg, 0.0413 mmol 86.3% yield).

Step 2. 104 was prepared according to General Method C from 104A as a white solid.

Step 3. To a solution of 104 (4.6 mg, 0.0129 mmol) in DCM (0.3 mL) was added methyl 3-chlorobenzoperoxoate (2.2 mg, 0.0129 mmol) and the reaction was stirred for 20 minutes followed by addition of saturated $NaHCO_3$ solution (3 mL) and extraction with DCM (4×4 mL). The combined extracts were dried with $Na_2SO_4$ and concentrated under reduced pressure. Flash chromatography (ISCO system, silica (12 g), 0-12.5% methanol in dichloromethane) provided 106 (0.5 mg, 10.4% yield) and 107 (1.7 mg, 33.9% yield).

The following examples were prepared using methods analogous to those described herein especially General Methods A, B and C as described herein.

| Ex. | Analytical Data |
|---|---|
| 11-1 | MS: 377.7 $(M + H)^+$; $^1H$ NMR (500 MHz, chloroform-d) δ 8.49 (d, J = 7.9 Hz, 1H), 8.29 (s, 1H), 7.13 (dd, J = 9.2, 7.8 Hz, 1H), 7.02 (d, J = 7.3 Hz, 1H), 6.92 (dd, J = 9.4, 3.9 Hz, 1H), 6.82 (d, J = 7.7 Hz, 1H), 4.63-4.55 (m, 1H), 4.45 (dd, J = 10.8, 5.4 Hz, 1H), 4.31-4.23 (m, 1H), 4.00 (dd, J = 16.2, 8.7 Hz, 1H), 1.70 (d, J = 6.9 Hz, 3H). |
| 20 | MS: 342.2 $[M + H]^+$. $^1H$ NMR (500 MHz, DMSO-$d_6$) 9.43 (dd, J = 6.9, 2.7 Hz, 1 H), 8.76 (d, J = 7.9 Hz, 1 H). 8.10 (s, 1 H), 7.19-7.25 (m, 1 H), 7.03-7.07 (m, 2 H), 6.72 (d, J = 7.9 Hz, 1 H), 5.64 (dd, J = 14.9, 1.5 Hz, 1 H), 4.48 (dt, J = 10.2, 4.3 Hz, 1 H), 4.04-4.10 (m, 2 H), 3.81-3.87 (m, 1 H), 3.58 (s, 3 H), 3.38-3.46 (m, 1 H). |
| 39 | LC-MS (ESI) m/z 376.5 $(M + H)^+$. $^1H$ NMR (500 MHz, chloroform-d) δ 9.51 (s, 1H), 8.40-8.33 (m, 2H), 7.03 (ddd, J = 8.9, 8.0, 0.7 Hz, 1H), 6.78 (dd, J = 9.3, 4.2 Hz, 1H), 6.40 (d, J = 7.9 Hz, 1H), 5.97 (dd, J = 15.0, 2.1 Hz, 1H), 4.49-4.43(m, 1H), 4.31 (ddd, J = 10.9, 6.4, 4.5 Hz, 1H), 4.12-4.03 (m, 1H), 3.91 (d, J = 14.9 Hz, 1H), 3.72-3.63 (m, 1H), 3.56 (s, 3H). |
| 40 | MS: 356.5 $(M + H)^+$; $^1H$ NMR (500 MHz, chloroform-d) δ 8.12 (d, J = 7.7 Hz, 1H), 6.93 (ddd, J = 9.0, 3.1, 0.9 Hz, 1H), 6.78 (ddd, J = 9.0, 7.3, 3.0 Hz, 1H), 6.71 (dd, J = 9.1, 4.5 Hz, 1H), 6.28 (d, J = 7.7 Hz, 1H), 5.77 (dd, J = 15.2, 1.7 Hz, 1H), 4.38-4.33 (m, 1H), 3.98 (s, 1H), 3.91 (d, J = 1.4 Hz, 1H), 3.78 (dd, J = 15.1, 0.9 Hz, 1H), 3.45 (s, 3H), 3.43-3.36 (m, 1H), 2.45 (s, 3H). |
| 41 | MS: 343.2 $(M + H)^+$; $^1H$ NMR (500 MHz, Chloroform-d) δ 9.82 (d, J = 7.0 Hz, 1H), 8.27 (s, 1H), 8.09 (d, J = 9.5 Hz, 1H), 7.18 (dd, J = 8.9, 3.2 Hz, 1H), 7.01-6.94 (m, 2H), 6.83 (dd, J = 9.0, 4.3 Hz, 1H), 6.60-6.53 (m, 1H), 4.63-4.52 (m, 1H), 4.27-4.16 (m, 1H), 4.16-4.04 (m, 1H), 3.70-3.56 (m, 1H), 1.70 (d, J = 6.4 Hz, 3H). |
| 42 | MS: 342.5 $(M + H)^+$; $^1H$ NMR (500 MHz, chloroform-d) δ 10.01 (d, J = 6.9 Hz, 1H), 8.17 (s, 1H), 8.04 (d, J = 10.0 Hz, 1H), 7.07-7.04 (m, 1H), 7.00 (d, J = 10.0 Hz, 1H), 6.96-6.92 (m, 1H), 6.84 (dd, J = 9.1, 4.5 Hz, 1H), 5.69 (dd, J = 15.8, 1.6 Hz, 1H), 4.55 (dt, J = 9.9, 3.7 Hz, 1H), 4.20-4.09 (m, 2H), 3.98 (dd, J = 15.9, 1.0 Hz, 1H), 3.66-3.62 (m., 1H), 3.61 (s, 3H). |

| Ex. | Analytical Data |
|---|---|
| 43 | MS: 356.6 (M + H)⁺; ¹H NMR (500 MHz, Chloroform-d) δ 8.27 (d, J = 7.9 Hz, 1H), 8.17 (s, 1H), 6.96 (ddd, J =9.0, 3.1, 0.9 Hz, 1H), 6.88-6.81 (m, 1H), 6.77 (dd, J = 9.0, 4.7 Hz, 1H), 6.41 (d, J = 7.9 Hz, 1H), 5.71-5.63 (m, 1H), 4.43 (dt, J = 10.0, 4.4 Hz, 1H), 4.09 (ddd, J = 10.3, 8.4, 4.0 Hz, 1H), 3.96-3.92 (m, 1H), 3.87 (dd, J = 15.0, 0.8 Hz., 1H), 3.77 (dd, J = 15.0, 7.2 Hz, 1H), 3.55-3.51 (m, 2H), 1.33 (t, J = 7.2 Hz, 3H). |
| 44 | MS: 370.1 (M + H)⁺; ¹H NMR (500 MHz, DMSO-d₆) 9.28 (dd, J = 5.8, 4.0 Hz, 1H), 8.71 (d, J = 7.9 Hz, 1 H), 8.08 (s, 1 H), 7.16 (dd, J = 9.5, 3.0 Hz, 1H), 6.98-7.09 (m, 2H), 6.82 (d, J = 8.0 Hz, 1 H), 5.48 (d, J = 15.0 Hz, 1 H), 4.42-4.51 (m, 1 H), 4.16-4.23 (m, 1 H), 4.04-4.14 (m, 2 H), 3.74-3.82 (m, 2 H), 3.39-3.46 (m, 1 H), 1.58-1.81 (m, 2 H), 0.97 (t, J = 7.3 HZ, 3 H). |
| 45 | MS: 370.1 (M + H)⁺; ¹H NMR (500 MHz, DMSO-d₆) 8.87-8.98 (m, 1 H), 8.69-8.79 (m, 1 H), 8.04-8.12 (m, 1 H), 7.10-7.18 (m, 1 H), 6.92-7.04 (m, 3 H), 5.09-5.18 (m, 1 H), 4.61-4.69 (m, 1 H), 4.50-4.56 (m, 1 H), 4.41-4.49 (m, 1 H), 4.16 (d, J = 15.30 Hz, 1 H), 3.57-3.68 (m, 2 H), 1.23-1.27 (m, 6 H). |
| 46 | MS: 368.1 (M + H)⁺; ¹H NMR (500 MHz, DMSO-d₆) 9.35 (dd, J = 7.0, 2.7 Hz, 1 H), 8.81 (d, J = 7.8 Hz, 1 H). 8.07-8.15 (m, 1 H), 7.19 (dd, J = 9.2, 2.3 Hz, 1 H), 7.01-7.08 (m, 2 H), 6.98 (d, J = 7.8 Hz, 1 H), 5.53 (dd, J = 15.1, 1.5 Hz, 1 H), 4.47 (dt, J = 10.22, 4.25 Hz, 1 H), 4.34 (t, J = 5.08 Hz, 1 H), 4.14 (d, J = 15.30 Hz, 1 H), 4.02-4.10 (m, 2 H), 3.79-3.92 (m, 1 H), 1.12-1.16 (m, 1 H), 1.03-1.08 (m, 2 H), 0.81-0.86 (m, 1 H). |
| 47 | MS: 372.1 (M + H)⁺; ¹H NMR (500 MHz, DMSO-d₆) 9.25 (t, J = 4.9 Hz, 1 H), 8.71 (d, J = 7.9 Hz. 1 H), 8.07 (s, 1 H), 7.22 (dd, J = 9.5, 3.0 Hz, 1 H), 7.05-7.11 (m, 1 H), 6.96-7.04 (m, 1 H). 6.83 (d, J = 8.0 Hz, 1 H), 5.51 (d, J = 14.6 Hz, 1 H), 4.96 (t, J = 5.4 Hz, 1 H), 4.42-4.51 (m, 1 H), 4.24 (ddd, J = 10.9, 6.8, 4.2 Hz, 1 H), 4.09-4.20 (m, 2 H), 3.91 (dt, J = 15.2, 5.5 Hz, 1 H), 3.67-3.82 (m, 3 H), 3.39-3.51 (m, 1 H). |
| 48 | MS: 356.1 (M + H)⁺; ¹H NMR (500 MHz, DMSO-d₆) 9.70 (d, J = 8.6 Hz, 1 H), 8.76 (d, J = 8.0 Hz, 1 H), 8.09 (s, 1 H), 7.25 (dd, J = 9.5, 3.0 Hz, 1 H), 7.01-7.11 (m, 1 H), 6.94-7.00 (m, 1 H), 6.71 (d, J = 8.0 Hz, 1 H), 5.64-5.73 (m, 1 H), 4.34 (d, J = 9.6 Hz, 1 H), 4.28 (t, J = 8.9 Hz, 1 H), 4.10 (d, J = 15.0 Hz, 1 H), 3.94 (dd, J = 9.6, 3.6 Hz, 1 H), 3.58 (s, 3 H), 1.36 (d, J = 6.8 Hz, 3 H). |
| 49 | MS: 324.1 (M + H)⁺; ¹H NMR (500 MHz, DMSO-d₆) 9.52 (d, J = 4.5 Hz, 1 H), 8.74 (d, J = 7.9 Hz, 1 H), 8.09 (s, 1 H), 7.44 (d, J = 7.6 Hz, 1 H), 7.18-7.25 (m, 1 H), 7.02 (d, J = 7.9 Hz, 1 H), 6.93 (t, J = 7.4 Hz, 1 H), 6.71 (d, J = 7.9 Hz, 1 H), 5.69 (d, J = 14.8 Hz, 1 H), 4.47 (dt, J = 10.1, 4.1 Hz, 1 H), 4.01-4.13 (m, 2 H), 3.83-3.90 (m, 1 H), 3.54-3.61 (m, 3 H), 3.38-3.46 (m, 1 H). |
| 50 | MS: 328.1 (M + H)⁺; ¹H NMR (500 MHz, DMSO-d₆) 9.80 (d, J = 7.82 Hz, 1 H), 8.89 (t, J = 6.00 Hz, 1 H), 8.58 (d, J = 7.62 Hz, 1 H), 8.03-8.08 (m, 1 H), 7.12-7.18 (m, 1 H), 6.99-7.05 (m, 2 H), 6.39 (d, J = 7.62 Hz, 1 H), 5.13-5.21 (m, 1 H), 4.46-4.53 (m, 1 H), 3.87-4.00 (m, 4 H). |
| 51 | MS: 342.3 (M + H)⁺; ¹H NMR (500 MHz, chloroform-d with CD₃OD) δ 8.14 (s, 1H), 7.81-7.72 (m, 1H), 7.10 (dd, J = 9.0, 3.0 Hz, 1H), 6.88 (ddd, J = 9.0, 7.6, 3.0 Hz, 1H), 6.80 (dd, J = 9.2, 4.4 Hz, 1H), 6.20 (d, J = 7.4 Hz, 1H), 5.75 (td, J = 7.2, 1.9 Hz, 1H), 4.52-4.46 (m, 1H), 4.09 (tdd, J = 9.6, 6.4, 3.9 Hz, 2H), 3.60-3.52 (m, 1H), 1.52 (d, J = 7.3 Hz, 3H). |
| 51-1 | MS: 342.2 (M + H)⁺. ¹H NMR (500 MHz, DMSO-d₆) δ ppm 9.71 (br d, J = 5.21 Hz, 1 H), 8.77 (br d, J = 6.86 Hz, 1 H), 8.57 (d, J = 7.41 Hz, 1 H), 8.04 (s, 1 H), 7.11-7.22 (m, 1 H), 6.96-7.04 (m, 2 H), 6.36 (d, J = 7.68 Hz, 1 H), 5.63 (br dd, J = 6.86, 5.49 Hz, 1 H), 4.50 (dt, J = 10.15, 3.98 Hz, 1 H), 4.01 (td, J = 9.61, 3.84 Hz, 1H), 3.87 (dt, J = 10.09, 3.74 Hz, 1 H), 3.35-3.46 (m, 1 H), 1.45 (d, J = 7.14 Hz, 3 H). |
| 52 | MS: 376.5 (M + H)⁺; ¹H NMR (500 MHz, Chloroform-d) δ 9.92 (s, 1H), 8.29-8.18 (m, 2H), 7.01 (dd, J = 9.2, 8.2 Hz, 1H), 6.77 (dd, J = 9.2, 4.2 Hz, 1H), 6.37-6.26 (m, 1H), 6.19 (d, J = 7.6 Hz, 1H), 6.12 (s, 1H), 4.53-4.45 (m, 1H), 4.14 (d, J = 6.3 Hz, 1H), 4.04-3.98 (m, 1H), 3.57 (d, J = 7.3 Hz, 3H), 1.74 (d, J = 7.3 Hz, 3H). |
| 55 | MS: 385.6 (M + H)⁺; ¹H NMR (300 MHz, Methanol-d₄) 8.35 (d, J = 7.6 Hz, 1 H), 8.24 (s, 1H), 7.24-6.96 (m, 3H), 6.82 (m, 2H), 6.41 (dd, J = 7.7, 4.8 Hz, 1H), 5.59 (m, 1H), 5.31 5.05 (m, 1 H), 4.39-4.21 (m, 1 H), 3.17-3.02 (m, 1 H), 1.58 (d, J = 6.9 Hz, 3H). |
| 56 | MS: 372.3 (M + H)⁺; ¹H NMR (300 MHz, Methanol-d₄) 8.35 (d, J = 7.6 Hz, 1 H), 8.18 (s, 1 H), 7.05 (d, J = 9.4 Hz, 1 H), 6.82 (dd, J = 6.5, 1.8 Hz, 1 H), 6.39 (d, J = 7.6 Hz, 1 H), 5.60 (m, 1 H), 4.92 (m, 2H), 4.08 (dd, J = 13.1, 9.9 Hz, 1 H), 3.91-3.81 (m, 2 H), 3.73 (dd, J = 12.6, 5.1 Hz, 1 H), 1.58 (d, J = 6.9 Hz, 3H). |
| 57 | MS: 371.4 (M + H)⁺. ¹H NMR (300 MHz, Methanol-d₄) δ 8.46 (d, J = 7.6 Hz, 1H), 8.41 (s, 1H), 7.00 (dd, J = 9.1, 2.9 Hz, 1H), 6.88-6.78 (m, 2H), 6.58 (d, J = 7.7 Hz, 1H), 5.20 (s, 1H), 4.65 (s, 2H), 3.49 (q, J = 7.3 Hz, 2H). |
| 58 | MS: 358.5 (M + H)⁺.)⁺. ¹H NMR (300 MHz, Chloroform-d) δ 8.37 (s, 1H), 8.21 (d, J = 7.6 Hz, 1H), 6.90 (d, J = 7.5 Hz, 3H), 6.10 (d, J = 7.6 Hz, 1H), 5.88 (s, 1H), 5.11-4.85 (m, 3H), 4.20 (dd, J = 15.1, 5.7 Hz, 1H), 4.05 (dd, J = 14.0, 9.9 Hz, 1H), 3.83-3.68 (m, 3H), 3.44 (d, J = 7.3 Hz, 1H). |
| 59 | MS: 386.1 (M + H)⁺; ¹H NMR (500 MHz, DMSO-d₆) 9.97 (s, 1 H), 8.57 (d, J = 7.6 Hz. 1 H), 8.40 (d, J = 5.9 Hz, 1 H), 8.10 (s, 1 H), 6.85 (dd, J = 8.9, 4.8 Hz, 1 H), 6.60 (d, J = 7.6 Hz, 1 H), 7.23 (dd, J = 9.3, 3.2 Hz, 1 H), 7.00 (td, J = 8.6, 3.2 Hz, 1 H), 5.90 (d, J = 6.4 Hz, 1 H), 4.27-4.34 (m, 2 H), 3.90 (t, J = 9.33 Hz, 2 H), 3.66 (s, 3 H). |
| 60 | MS: 371.1 (M + H)⁺; ¹H NMR (500 MHz, DMSO-d₆) 9.98 (bs, 1H), 8.54 (d, J = 7.6 Hz, 1 H), 8.33 (d, J = 6.24 Hz, 1 H), 8.07 (s, 1 H), 7.44 (bs, 1 H), 7.28 (bs, 1 H), 7.18 (dd, J = 9.6, 3.2 Hz, 1H), 6.94 (td, J = 8.5, 3.2 Hz, 1 H), 6.83 (dd, J = 8.9, 4.9 Hz, 1 H), 6.66 (d, J = 7.5 Hz, 1 H), 5.86 (d, J = 6.4 Hz, 1 H), 4.22-4.36 (m, 2 H), 3.84-3.97 (m, 2 H). |
| 61 | MS: 343.2 (M + H)⁺. ¹H NMR (500 MHz, DMSO-d₆) δ ppm 9.22 (dd, J = 6.87, 2.86 Hz. 1 H), 8.78 (d, J = 7.45 Hz, 1 H), 8.10 (s, 1 H), 8.06 (d, J = 3.44 Hz, 1 H), 7.80 (d, J = 8.59, 2.86 Hz, 1 H), 6.74 (d, J = 8.02 Hz, 1 H), 5.44 (d, J = 14.89, 1.72 Hz, 1 H), 4.69 (ddd, J = 10.88, 8.59, 4.58 Hz, 1 H), 4.32-4.39 (m, 1H). 4.21 (d, J = 15.47 , 1 H), 3.80-3.88 (m, 1 H), 3.58 (s, 3 H), 3.41-3.49 (m, 1 H). |
| 62 | MS: 371.2 (M + H)⁺. ¹H NMR (500 MHz, DMSO-d₆) δ ppm 8.72-8.80 (m, 2 H), 8.08 (s, 1 H), 8.01 (d, J = 2.74 Hz, 1 H), 7.49 (dd, J = 8.78. 2.74 Hz, 1 H), 7.00 (d, J = 8.23 Hz, 1 H), 4.94-5.00 (m, 2 H), 4.57-4.68 (m, 1 H), 4.26-4.39 (m, 2 H), 3.66-3.77 (m, 1 H), 3.49-3.55 (m, 1 H), 1.56 (d, J = 6.59 Hz, 3 H), 1.22 (d, J = 6.60 Hz, 3 H). |
| 66 | MS: 368.2 (M + H)⁺. ¹H NMR (500 MHz, DMSO-d₆) δ ppm 9.56 (dd, J = 6.87, 2.86 Hz, 1 H), 9.02 (d, J = 6.87 Hz, 1 H), 8.58 (d, J = 8.02 Hz, 1 H), 8.03 (s, 1 H), 7.18 (dd, J = 9.74, 2.86 Hz, 1 H), 6.97-7.08 (m, 2 H), 6.41 (d, J = 7.45 Hz, 1 H), 4.68-4.80 (m, 1 H), 4.48 (dt, J = 10.60, 4.15 Hz, 1 H), 4.05 (ddd, J = 10.45, 8.45, 4.01 Hz, 1 H), 3.75-3.84 (m, 1 H), 3.36-3.43 (m, 1 H), 1.26-1.38 (m, 1 H). 0.63 (tt, J = 8.74, 4.44 Hz, 1 H), 0.37-0.49 (m, 2 H), 0.28 (dq, J = 9.31, 4.53 Hz, 1 H). |
| 67 | MS: 370.2 (M + H)⁺. ¹H NMR (500 MHz, DMSO-d₆) δ ppm 9.75 (br d, J = 6.30 Hz, 1 H), 8.78 (d, J = 7.45 Hz, 1 H), 8.57 (d, J = 8.02 Hz, 1 H) 8.04 (s, 1 H), 7.06 (dt, J = 9.16, 1.43 Hz, 1 H), 6.98-7.02 (m, 2 , 6.39 (d, J = 7.45 Hz, 1 H), 5.13 (ddd, J = 10.02, 7.73, 1.72 Hz, 1 H), 4.51 (dt, J = 9.88, 3.65 Hz, 1 H) 3.94 (td, J = 9.88, 3.72 Hz, 1 H), 3.82-3.90 (m, 1 H), 3.39-3.43 (m, 1 H), 1.96-2.09 (m, 1 H), 1.12 (d, J =0 6.30 Hz, 3 H), 0.68 (d, J = 6.30 Hz, 3 H). |
| 75 | MS: 356.2 (M + H)⁺. ¹H NMR (500 MHz, DMSO-d₆) δ ppm 8.73 (d, J = 8.02 Hz, 1 H), 8.25 (t, J = 4.30 Hz, 1 H). 8.10 (s, 1 H), 7.14-7.21 (m, 1 H), 7.00-7.04 (m, 2 H), 6.68 (d, J = 8.02 Hz, 1 H), 5.75 (br d, J = 14.32 Hz, 1 H), 4.33-4.43 (m, 1 H), 4.22 (br d, J = 6.87 Hz, 1 H), 4.05 (br d, J = 14.89 Hz, 1 H), 3.59-3.68 (m, 1 H), 3.59-3.68 (m, 1 H), 3.37-3.45 (m, 1 H), 1.98-2.17 (m, 2 H). |
| 76-1 | MS: 356.2 (M + H)⁺. ¹H NMR (500 MHz, DMSO-d₆) δ ppm 8.68 (d, J = 7.45 Hz, 1 H), 8.53 (d, J = 7.45 Hz, 1 H), 8.40 (s, 1 H), 8.03 (s, 1 H), 7.11-7.18 (m, 1 H), 6.96-7.00 (m, 2 H), 6.32 (d, J = 7.45 Hz, 1 H), 5.65-5.74 (m, 1 H), 4.29-4.36 (m, 1 H), 4.20-4.26 (m, 1 H), 3.54-3.62 (m 1 H), 3.39-3.47 (m, 1 H), 1.98-2.17 (m, 2 H), 1.41 (d, J = 7.45 Hz, 3 H). |
| 84 | MS: 358.2 (M + H)⁺. ¹H NMR (500 MHz, DMSO-d₆) δ ppm 8.78 (d, J = 26.79 Hz, 1 H), 8.58 (d, J = 7.62 Hz, 1 H), 8.05 (s, 1 H), 7.36 (d, J = 2.61 Hz, 1 H), 7.21 (dd, J = 8.85, 2.68 Hz, 1 H), 7.03 (d, J = 8.85 Hz, 1 H), 6.36 (d, J = 7.68 Hz, 1 H), 5.62 (quin, J = 6.90 Hz, 1 H), 4.52 (dt, J = 10.15, 3.98 |

| Ex. | Analytical Data |
|---|---|
| 85 | Hz, 1 H), 3.98-4.11 (m, 1 H), 3.80-3.92 (m, 1 H), 3.35-3.47 (m, 1 H) 1.45 (d, J = 7.07 Hz, 3 H).
MS: 356.2 (M + H)+. 1H NMR (500 MHz, DMSO-d6) δ ppm 9.73 (br d, J = 5.49 Hz, 1 H), 8.74 (d, J = 7.14 Hz, 1 H), 8.57 (d, J = 7.68 Hz, 1 H), 8.04 (s, 1 H), 7.06-7.14 (m, 1 H), 6.97-7.03 (m, 2 H), 6.37 (d, J = 7.68 Hz, 1 H), 5.33-5.45 (m, 1 H), 4.51 (dt, J = 10.15, 3.43 Hz, 1 H), 3.98 (d, J = 9.88, 3.84 Hz, 1 H), 3.82-3.93 (m, 1 H), 3.39 (td, J = 9.61, 2.74 Hz, 1 H), 1.85-1.99 (m, 1 H), 1.62-1.76 (m, 1 H), 0.87 (t, J = 7.14 Hz, 3 H). |
| 86 | MS: 382.2 (M + H)+. 1H NMR (500 MHz, DMSO-d6) δ ppm 9.74 (dd, J = 7.16, 2.00 Hz, 1 H), 8.64 (d, J = 6.87 Hz, 1 H), 8.57 (d, J = 7.45 Hz, 1 H) 8.05 (s, 1 H), 6.95-7.06 (m, 3 H), 6.38 (d, J = 8.02 Hz, 1 H), 5.47 (ddd, J = 10.60, 7.16, 1.15 Hz, 1 H), 4.54 (dt, J = 10.17, 3.79 Hz, 1 H), 4.01 (td, J = 9.59, 3.72 Hz, 1 H), 3.80-3.90 (m, 1 H), 3.39-3.48 (m, 1 H), 2.66-2.77 (m, 1 H), 2.12-2.23 (m, 1 H), 1.83 (br d, J = 2.29 Hz, 3 H), 1.55-1.73 (m, 2 H). |
| 87 | MS: 346.2 (M + H)+. 1H NMR (500 MHz, DMSO-d6) δ ppm 9.40 (s, 1 H), 8.77 (d, J = 8.23 Hz, 1 H), 8.10 (s, 1 H), 7.19-7.26 (m, 1 H), 7.01-7.08 (m, 2 H), 6.72 (d, J = 8.23 Hz, 1 H), 5.64 (dd, J = 15.09, 1.37 Hz, 1 H), 4.08 (d, J = 14.82 Hz, 1 H), 3.58 (s, 3 H). |
| 88 | MS: 404.2 (M + H)+. 1H NMR (500 MHz, DMSO-d6) δ ppm 9.70 (dd, J = 6.87, 2.86 Hz, 1 H), 9.26 (d, J = 7.45 Hz, 1 H), 8.66 (d, J = 7.45 Hz, 1 H), 8.09 (s, 1 H), 7.35-7.45 (m, 4 H), 7.28-7.34 (m, 1 H), 7.15 (dd, J = 9.16, 3.44 Hz, 1 H), 7.09-7.13 (m, 1 H), 7.04-7.09 (m, 1 H), 6.92 (d, J = 6.87 Hz, 1 H), 6.52 (d, J = 7.45 Hz, 1 H), 4.56 (dt, J = 10.31, 4.01 Hz, 1 H), 4.08-4.14 (m, 1 H), 3.87 (ddt, J = 13.75, 7.59, 3.94, 3.94 Hz, 1 H), 3.44-3.49 (m, 1 H). |
| 89 | MS: 382.2 (M + H)+. 1H NMR (500 MHz, DMSO-d6) δ ppm 9.76 (dd, J = 7.45, 2.29 Hz, 1 H), 8.77 (d, J = 7.45 Hz, 1 H), 8.58 (d, J = 8.02 Hz, 1 H), 8.05 (s, 1 H), 7.09 (dt, J = 9.74, 1.72 Hz, 1 H), 7.00 (dd, J = 6.30, 1.72 Hz, 2 H), 6.38 (d, J = 7.45 Hz, 1 H), 5.56-5.63 (m, 1 H), 4.31 (dt, J = 10.17, 3.79 Hz, 1 H), 3.99 (td, J = 9.59, 3.72 Hz, 1 H), 3.86 (ddt, J = 13.75, 7.45, 3.72, 3.72 Hz, 1 H), 3.38-3.43 (m, 1 H), 1.94 (ddd, J = 13.89, 7.88, 6.30 Hz, 1 H) 1.44 (dt, J = 14.03, 7.30 Hz, 1 H), 0.63-0.73 (m, 1 H), 0.37-0.45 (m, 1 H), 0.27-0.34 (m, 1 H), 0.18 (dq, J = 9.24, 4.75 Hz, 1 H), −0.12--0.04 (m, 1 H). |
| 90 | MS: 372.2 (M + H)+. 1H NMR (500 MHz, DMSO-d6) δ ppm 8.68 (d, J = 8.02 Hz, 1 H), 8.52 (d, J = 7.45 Hz, 1 H), 8.36 (t, J = 4.01 Hz, 1 H), 8.04 (s, 1 H), 7.16 (dd, J = 9.45, 3.15 Hz, 1 H), 7.06 (dd, J = 9.17, 4.58 Hz, 1 H), 6.95-7.02 (m, 1 H), 6.30 (d, J = 8.02 Hz, 1 H), 5.66-5.75 (m, 1 H), 5.45 (d, J = 4.58 Hz, 1 H), 4.12-4.25 (m, 2 H), 4.05 (d, J = 9.16 Hz, 1 H), 3.60-3.67 (m, 1 H), 3.28-3.31 (m, 1 H), 1.42 (d, J = 6.87 Hz, 3 H). |
| 91 | MS: 372.2 (M + H)+. 1H NMR (500 MHz, DMSO-d6) δ ppm 8.70 (d, J = 6.87 Hz, 1 H), 8.53 (d, J = 7.45 Hz, 1 H), 8.47 (dd, J = 8.31, 2.00 Hz, 1 H), 8.03 (s, 1 H), 7.07-7.13 (m, 1 H), 6.97-7.03 (m, 2 H), 6.34 (d, J = 7.45 Hz, 1 H), 5.60 (quind, J = 7.02, 7.02, 7.02, 7.02, 1.72 Hz, 1 H), 5.36 (d, J = 4.01 Hz, 1 H), 4.42 (br d, J = 10.88 Hz, 1 H), 4.01-4.14 (m, 2 H), 3.88-3.97 (m, 1 H), 3.10-3.17 (m, 1 H), 1.41 (d, J = 7.45 Hz, 3 H). |
| 92 | MS: 356.2 (M + H)+. 1H NMR (500 MHz, DMSO-d6) δ ppm 9.41 (dd, J = 6.01, 3.72 Hz, 1 H), 8.71 (d, J = 7.45 Hz, 1 H), 8.58 (d, J = 7.45 Hz, 1 H), 8.06 (s, 1 H), 7.14 (dd, J = 9.74, 3.44 Hz, 1 H), 7.07 (dd, J = 9.17, 4.58 Hz, 1 H), 6.96 (ddd, J = 9.17, 8.02, 3.44 Hz, 1 H), 6.35 (d, J = 7.45 Hz, 1 H), 5.63-5.74 (m, 1 H), 4.77-4.89 (m, 1 H) 3.73-3.85 (m, 1 H), 3.52-3.58 (m, 1 H), 1.43 (d, J = 6.87 Hz, 3 H), 1.19 (br d, J = 6.30 Hz, 3 H). |
| 93 | MS: 356.2 (M + H)+. 1H NMR (500 MHz, DMSO-d6) δ ppm 9.82 (dd, J = 8.02, 2.29 Hz, 1 H), 8.81 (d, J = 6.87 Hz, 1 H), 8.58 (d, J = 7.45 Hz, 1 H), 8.04 (s, 1 H), 7.12 (dd, J = 9.45, 3.15 Hz, 1 H), 6.99-7.05 (m, 1 H), 6.94-6.99 (m, 1 H), 6.36 (d, J = 7.45 Hz, 1 H), 5.53 (quind, J = 6.87, 6.87, 6.87, 6.87, 1.15 Hz, 1 H), 4.45-4.52 (m, 1 H), 3.90 (ddd, J = 13.46, 8.31, 4.01 Hz, 1 H), 3.10-3.17 (m, 1 H), 1.46 (d, J = 6.30 Hz, 3 H), 1.44 (d, J = 7.45 Hz, 3 H). |
| 94 | MS: 356.2 (M + H)+. 1H NMR (500 MHz, DMSO-d6) δ ppm 9.49 (dd, J = 7.45, 2.86 Hz, 1 H), 8.77 (d, J = 7.45 Hz, 1 H), 8.09 (s, 1 H), 7.15 (dd, J = 9.45, 3.15 Hz, 1 H), 7.04-7.09 (m, 1 H), 6.97-7.03 (m, 1 H), 6.73 (d, J = 8.02 Hz, 1 H), 5.54 (dd, J = 14.89, 1.72 Hz, 1 H), 4.55 (ddd, J = 7.59, 5.87, 4.30 Hz, 1 H), 4.08 (d, J = 14.89 Hz, 1 H), 3.85-3.92 (m, 1 H), 3.59 (s, 3 H), 3.16 (ddd, J = 13.60, 7.88, 3.15 Hz, 1 H), 1.45 (d, J = 6.30 Hz, 3 H). |
| 95 | MS: 356.2 (M + H)+. 1H NMR (500 MHz, DMSO-d6) δ ppm 9.71 (d, J = 8.59 Hz, 1 H) 8.76 (d, J = 8.02 Hz, 1 H) 8.09 (s, 1 H) 7.25 (dd, J = 9.45, 3.15 Hz, 1 H) 7.02-7.09 (m, 1 H), 6.95-7.00 (m, 1 H) 6.71 (d, J = 8.02 Hz, 1 H) 5.68 (dd, J = 14.89, 1.15 Hz, 1 H) 4.34 (dd, J = 9.45, 1.43 Hz, 1 H) 4.24-4.30 (m, 1 H) 4.10 (d, J = 14.89 Hz, 1 H) 3.94 (dd, J = 9.74, 4.01 Hz, 1 H) 3.58 (s, 3 H) 1.36 (d, J = 6.87 Hz, 3 H). |
| 96 | MS: 372.2 (M + H)+. 1H NMR (500 MHz, DMSO-d6) δ ppm 8.64 (d, J = 8.23 Hz, 1 H) 8.27 (br s, 1 H) 8.08 (s, 1 H) 7.15 (br d, J = 6.59 Hz, 1 H) 7.04-7.10 (m, 1 H) 6.96-7.02 (m, 1 H) 6.66 (d, J = 8.23 Hz, 1 H) 5.11 (br s, 1 H) 4.28 (br s, 2 H) 4.15 (br s, 1 H) 4.06 (br s, 1 H) 3.90 (br s, 2 H) 3.57 (s, 3 H) 3.29 (br s, 1 H). |
| 97 | MS: 356.2 (M + H)+. 1H NMR (500 MHz, DMSO-d6) δ ppm 9.49 (dd, J = 7.45, 2.86 Hz, 1 H), 8.77 (d, J = 8.02 Hz, 1 H), 8.09 (s, 1H), 7.15 (dd, J = 9.74, 2.86 Hz, 1 H), 7.04-7.10 (m, 1 H), 6.97-7.03 (m, 1 H), 6.73 (d, J = 8.02 Hz, 1 H), 5.54 (dd, J = 14.89, 1.72 Hz, 1 H), 4.50-4.60 (m, 1 H), 4.08 (d, J = 15.47 Hz, 1 H), 3.84-3.92 (m, 1 H), 3.59 (s, 3 H), 3.16 (ddd, J = 13.46, 7.73, 2.86 Hz, 1 H), 1.45 (d, J = 6.30 Hz, 3 H). |
| 98 | MS: 358.2 (M + H)+. 1H NMR (500 MHz, DMSO-d6) δ ppm 9.76 (dd, J = 7.45, 2.29 Hz, 1 H), 8.82 (d, J = 6.87 Hz, 1 H), 8.58 (d, J = 7.45 Hz, 1 H), 8.05 (s, 1 H), 7.06-7.15 (m, 1 H), 6.99-7.04 (m, 2 H), 6.45 (d, J = 8.02 Hz, 1 H), 5.57-5.66 (m, 1 H), 5.16-5.25 (m, 1 H), 4.52 (dt, J = 10.17, 3.79 Hz, 1 H), 3.99 (td, J = 9.74, 4.01 Hz, 1 H), 3.87 (ddt, J = 13.82, 7.52, 3.94, 3.94 Hz, 1 H), 3.71 (ddd, J = 11.17, 8.31, 6.30 Hz, 1 H), 3.59 (dt, J = 11.17, 5.01 Hz, 1 H), 3.36-3.45 (m, 1 H). |
| 99 | MS: 372.2 (M + H)+. 1H NMR (500 MHz, DMSO-d6) δ ppm 8.72 (d, J = 8.02 Hz, 1 H), 8.53 (d, J = 7.45 Hz, 1 H). 8.40 (t, J = 4.01 Hz, 1 H). 8.04 (s, 1 H), 7.09 (dd, J = 9.16, 2.86 Hz, 1 H), 6.95-7.05 (m, 2 H), 6.42 (d, J = 7.45 Hz, 1 H), 5.63-5.72 (m, 1 H), 5.16 (t, J = 5.44 Hz, 1 H), 4.29-4.37 (m, 1 H), 4.19-4.27 (m, 1 H), 3.65 (ddd, J = 11.17, 8.31, 6.30 Hz, 1 H), 3.53-3.61 (m, 2 H), 3.41-3.48 (m, 1 H), 2.00-2.18 (m, 2 H). |
| 100 | MS: 356.2 (M + H)+. 1H NMR (500 MHz, DMSO-d6) δ ppm 9.46 (d, J = 7.16, 2.58 Hz, 1 H), 8.77 (d, J = 8.02 Hz, 1 H), 8.11 (s, 1 H), 7.22 (dd, J = 9.74, 2.29 Hz, 1 H), 7.01-7.06 (m, 2 H), 6.74 (d, J = 8.02 Hz, 1 H), 6.20-6.30 (m, 1 H), 4.50 (dt, J = 10.31, 4.01 Hz, 1 H), 4.05 (ddd, J = 10.31, 9.16, 4.01 Hz, 1 H), 3.85 (ddt, J = 13.68, 7.52, 3.72, 3.72 Hz, 1 H), 3.38-3.49 (m, 4 H), 1.53 (d, J = 7.45 Hz, 3 H). |
| 101 | MS: 400.2 (M + H)+. 1H NMR (500 MHz, DMSO-d6) δ ppm 9.58 (dd, J = 7.45, 2.86 Hz, 1 H), 8.50 (s, 1 H), 8.01 (s, 1 H), 7.36 (d, J = 9.16, 2.86 Hz, 1 H), 7.00-7.14 (m, 2 H), 5.61 (dd, J = 14.61, 1.43 Hz, 1 H), 4.44-4.52 (m, 1 H), 4.14 (d, J = 12.60 Hz, 1 H), 4.00-4.09 (m, 2 H), 3.81-3.92 (m, 2 H), 3.39-3.47 (m, 1 H), 1.40 (s, 3 H), 1.38 (s, 3 H). |
| 102 | MS: 327.2 (M + H)+. 1H NMR (500 MHz, DMSO-d6) δ ppm 9.58-9.70 (m, 1 H), 9.09 (d, J = 6.87 Hz, 1 H), 8.42 (s, 1 H), 7.22 (dd, J = 9.74, 2.86 Hz, 1 H), 7.11 (d, J = 7.45 Hz, 1 H), 6.84-6.97 (m, 2 H), 4.37-4.50 (m, 1 H), 3.90-4.06 (m, 3 H), 3.42-3.64 (m, 3 H), 2.54-2.62 (m, 1 H). |
| 103 | MS: 341.2 (M + H)+. 1H NMR (500 MHz, DMSO-d6) δ ppm 9.04 (d, J = 6.87 Hz, 1 H), 8.56 (t, J = 4.01 Hz, 1 H), 8.40 (s, 1 H). 7.19 (d, J = 9.74, 2.86 Hz, 1 H), 7.06 (d, J = 6.87 Hz, 1 H), 6.81-6.96 (m, 2 H), 4.19-4.29 (m, 1 H), 3.53-3.63 (m, 4 H), 3.24-3.31 (m, 2 H), 2.09-2.21 (m, 2 H). |
| 104 | MS: 358.2 (M + H)+. 1H NMR (500 MHz, DMSO-d6) δ ppm 8.79 (d, J = 8.02 Hz, 1 H), 8.70 (dd, J = 7.45, 2.86 Hz, 1 H), 8.07 (s, 1 H), 7.59 (d, J = 8.59, 5.73 Hz, 1 H) 7.10 (td, J = 8.59, 2.86 Hz, 1 H), 7.04 (dd, J = 10.02, 2.58 Hz, 1 H), 6.78 (d, J = 8.02 Hz, 1 H), 5.79 (dd, J = 15.75, 1.43 Hz, 1 H), 4.17 (d, J = 16.04 Hz, 1 H), 3.73-3.82 (m, 1 H), 3.59 (s, 3 H), 3.52-3.58 (m, 1 H), 3.26-3.30 (m, 1 H), 3.18-3.23 (m, 1 H). |
| 105 | MS: 411.2 (M + H)+. |
| 106 | MS: 374.2 (M + H)+. 1H NMR (500 MHz, DMSO-d6) δ ppm 8.84 (d, J = 8.02 Hz, 1 H), 8.09-8.19 (m, 2 H), 8.07 (s, 1 H), 7.35 (td, J = 8.45, 2.58 Hz, 1 H), 7.22 (dd, J = 10.31, 2.29 Hz, 1 H), 6.86 (d, J = 8.02 Hz, 1 H), 5.75 (d, J = 16.61 Hz, 1 H), 4.57 (d, J = 16.61 Hz, 1 H), 4.11-4.15 (m, 1 H), 3.79-3.87 (m, 2 H), 3.59 (s, 3 H), 3.48-3.57 (m, 1 H). |

-continued

| Ex. | Analytical Data |
|---|---|
| 107 | MS: 390.2 (M + H)⁺. $^1$H NMR (500 MHz, DMSO-$d_6$) δ ppm 8.83 (d, J = 8.02 Hz, 1 H), 8.12 (dd, J = 9.16, 5.73 Hz, 1 H), 8.07 (s, 1 H), 7.82 (br t, J = 5.16 Hz, 1 H), 7.39 (td, J = 8.59, 2.86 Hz, 1 H), 7.14-7.21 (m, 1 H), 6.84 (d, J = 7.45 Hz, 1 H), 5.37-5.54 (m, 1 H), 4.61-4.76 (m, 1 H), 3.83-3.93 (m, 1 H), 3.57-3.63 (m, 5H), 3.46-3.54 (m, 1 H). |
| 108 | MS: 371.2 (M + H)⁺. $^1$H NMR (500 MHz, DMSO-$d_6$) δ ppm 9.73 (br d, J = 6.87 Hz, 1 H) 9.09 (d, J = 8.00 Hz, 1 H) 8.41 (s, 1 H) 7.20 (dd, J = 9.74, 2.86 Hz, 1 H) 7.11 (d, J = 6.87 Hz, 1 H) 6.94 (dd, J = 9.16, 4.58 Hz, 1 H) 6.78-6.88 (m, 1 H) 4.44 (ddd, J = 8.88, 5.44, 4.01 Hz, 1 H) 3.99-4.06 (m, 1 H) 3.88-3.97 (m, 1H) 3.67-3.73 (m, 1 H) 3.47-3.53 (m, 1 H) 3.12-3.21 (m, 1 H) 2.54-2.62 (m, 1 H) 1.43 (d, J = 6.30 Hz, 3 H). |
| 109 | MS: 371.2 (M + H)⁺. $^1$H NMR (500 MHz, DMSO-$d_6$) δ ppm 9.43 (d, J = 2.29 Hz, 1 H) 8.73 (d, J = 6.87 Hz, 1 H) 8.57 (d, J = 7.50 Hz, 1 H) 8.01 (s, 1 H) 7.16 (dd, J = 9.17, 2.86 Hz, 1 H) 7.00-7.11 (m, 2 H) 6.34 (d, J = 7.45 Hz, 1 H) 5.61-5.73 (m, 1 H) 4.37 (dd, J = 10.31, 4.01 Hz, 1 H) 4.00 (ddt, J = 8.45, 4.30, 2.22, 2.22 Hz, 1 H) 3.88-3.96 (m, 1 H) 1.48 (d, J = 6.87 Hz, 3 H) 1.42 (d, J = 7.45 Hz, 3 H). |
| 110 | MS: 371.2 (M + H)⁺. $^1$H NMR (500 MHz, DMSO-$d_6$) δ ppm 9.95 (d, J = 8.59 Hz, 1 H) 8.79 (d, J = 6.87 Hz, 1 H) 8.58 (d, J = 7.15 Hz, 1 H) 8.04 (s, 1 H) 7.16 (dd, J = 9.45, 3.15 Hz, 1 H) 6.98-7.05 (m, 1 H) 6.92-6.97 (m, 1 H) 6.34 (d, J = 8.02 Hz, 1 H) 5.67 (quind, J = 7.02, 7.02, 7,02, 7.02, 1.72 Hz, 1 H) 4.35 (dd, J = 9.45, 1.43 Hz, 1 H) 4.20-4.30 (m, 1 H) 3.93 (dd, J = 9.74, 4.01 Hz, 1 H) 1.47 (d, J = 7.45 Hz, 3 H) 1.37 (d, J = 6.87 Hz, 3 H) |
| 111 | MS: 371.2 (M + H)⁺. |
| 112 | MS: 345.2 (M + H)⁺. |

Additional examples are prepared using methods analogous to those described above.

Biological Example 1: Biochemical Kinase Assays

MET/ALK/AXL/TRKs enzyme inhibition may be measured by Omnia (Invitrogen Inc.) continuous fluorometric assay. Reactions are conducted in 50 μL volumes in 96-well plates at 30° C. Mixtures contain 1 nM human recombinant target kinase domain, 2 μM phosphoacceptor peptide, test compound (11-dose, 3-fold serial dilutions, 2% DMSO final) or DMSO only, 0.2 mM DTT, and 10 mM $MgCl_2$ in 20 mM Hepes, pH 7.5, and the reactions are initiated by addition of ATP (100 μM final concentration) following a 20 min pre-incubation. The initial rates of phosphopeptide formation are measured over 20 min using a Tecan Safire microplate reader with wavelength settings of 360 nm for excitation and 485 min for emission. The $K_i$ values are calculated by fitting the data to the equation for competitive inhibition using nonlinear regression method (GraphPad Prism, GraphPad Software. San Diego, CA).

Biological Example 2: Cellular Kinase Phosphorylation ELISA Assays

The experiments are performed based on the procedures described in the publication (Christensen. J. et al., "Cytoreductive antitumor activity of PF-2341066, a novel inhibitor of anaplastic lymphoma kinase and c-Met, in experimental models of anaplastic large-cell lymphoma", Mol. Cancer Ther. 2007, 6 (12): 3314-3322.) All experiments are done under standard conditions (37° C. and 5% $CO_2$). $IC_{50}$ values are calculated by concentration/response curve fitting using a Microsoft Excel based four-parameter method. Cells are seeded in 96-well plates in medium supplemented with 10% fetal bovine serum (FBS) and transferred to serum-free medium [with 0.04% bovine serum albumin (BSA)] after 24 h. In experiments investigating ligand-dependent RTK phosphorylation, corresponding growth factors are added for up to 20 min. After incubation of cells with an inhibitor for 1 h and/or appropriate ligands for the designated times, cells are washed once with HBSS supplemented with 1 mmol/L $Na_3VO_4$, and protein lysates are generated from cells. Subsequently, phosphorylation of selected protein kinases is assessed by a sandwich ELISA method using specific capture antibodies to coat 96-well plates and a detection antibody specific for phosphorylated tyrosine residues. Antibody-coated plates are (a) incubated in the presence of protein lysates at 4° C. overnight, (b) washed seven times in 1% Tween 20 in PBS, (c) incubated in a horseradish peroxidase conjugated anti-total-phosphotyrosine (PY-20) antibody (1:500) for 30 min, (d) washed seven times again, (e) incubated in 3,3,5,5-tetramethylbenzidine peroxidase substrate (Bio-Rad) to initiate a colorimetric reaction that is stopped by adding 0.09 N $H_2SO_4$, and (f) measured for absorbance in 450 nm using a spectrophotometer. Cell lines that are used for individual kinases include A549 for MET, Karpas 299 for ALK, 293-AXL for AXL, PAET RKA for TRKA, and PAE-TRKB for TRKB.

Biological Example 3: Kinase Binding Assays

Kinase binding assays were performed at DiscoveRx using the general KINOMEscan $K_d$ Protocol (Fabian, M. A. et al., "A small molecule-kinase interaction map for clinical kinase inhibitors," Nat. Biotechnol. 2005, 23(3):329-36). For most assays, kinase-tagged T7 phage strains were prepared in an E. coli host derived from the BL21 strain. E. coli were grown to log-phase and infected with T7 phage and incubated with shaking at 32° C. until lysis. The lysates were centrifuged and filtered to remove cell debris. The remaining kinases were produced in HEK-293 cells and subsequently tagged with DNA for qPCR detection. Streptavidin-coated magnetic beads were treated with biotinylated small molecule ligands for 30 minutes at room temperature to generate affinity resins for kinase assays. The liganded beads were blocked with excess biotin and washed with blocking buffer (SeaBlock (Pierce), 1% BSA, 0.05% Tween 20, 1 mM DTT) to remove unbound ligand and to reduce nonspecific binding. Binding reactions were assembled by combining kinases, liganded affinity beads, and test compounds in 1× binding buffer (20% SeaBlock, 0.17×PBS, 0.05% Tween 20, 6 mM DTT). All reactions were performed in polystyrene 96-well plates in a final volume of 0.135 mL. The assay plates were incubated at room temperature with shaking for 1 hour and the affinity beads were washed with wash buffer (1×PBS, 0.05% Tween 20). The beads were then re-suspended in elution buffer (1×PBS, 0.05% Tween 20, 0.5 μM non-biotinylated affinity ligand) and incubated at room temperature with shaking for 30 minutes. The kinase concentration in the eluates was measured by qPCR. Results for compounds tested in this assay are presented in Table 2. With this method, Example 20 also had a binding affinity with PLK4 kinase ($K_d$ 2.9 nM).

TABLE 2

| Ex. | TRKA $K_d$ (nM) | TRKB $K_d$ (nM) | TRKC $K_d$ (nM) | JAK1 $K_d$ (nM) | JAK2 $K_d$ (nM) | JAK3 $K_d$ (nM) | ALK $K_d$ (nM) | ROS1 $K_d$ (nM) |
|---|---|---|---|---|---|---|---|---|
| 11-1 | 1900 | | | | | | >30000 | 1900 |
| 20 | 0.031 | 0.18 | 0.30 | >1000 | 4.8 | 120 | 80 | 21 |
| 39 | 0.23 | | | | 27 | | 180 | 4.7 |
| 40 | | | | | | | 600 | 410 |
| 41 | 6.00 | | | 280 | 2.6 | 33 | 200 | |
| 42 | 0.088 | | | | | | | |
| 43 | 0.086 | | | | 3.7 | | | |
| 45 | 0.082 | | | | 7.8 | | | |
| 49 | 0.14 | | | | 24 | | | |
| 50 | 0.20 | | | | 0.57 | | | |
| 51 | 0.065 | | | 65 | 0.15 | 4.3 | | |
| 51-1 | 0.051 | | | 37 | 0.048 | 1.8 | 6.8 | 0.73 |
| 52 | 6.5 | | | | | | 270 | 62 |
| 75 | 0.015 | | | | | | | |
| 92 | | | | | 6.5 | | | |
| 93 | | | | | 0.12 | | 8.2 | |
| 98 | | | | | 0.082 | | 5.7 | |
| 103 | | | | | 0.74 | | 14 | |
|  | | | | | 1.9 | | 28 | |

Biological Example 4: Ba/F3 Cell Proliferation Assay

TRKA Ba/F3 cell proliferation assays were performed by ACD (Advanced Cellular Dynamics). Ba/F3 cell lines were maintained in RPMI-1640 culture media containing 10% fetal bovine serum and antibiotics. Cells in logarithmic-phase growth were harvested and 5,000 cells were distributed into each well of a 384-well plate in 50 µL of growth media. Fifty nanoliters diluted compound were added to appropriate wells, in duplicate, and the cells were cultured for 48 hours at 37° C. in a humidified 5% $CO_2$ incubator. Viability was determined by adding 15 µL CellTiter-Glo and measuring luminescence, which is reported as relative light units (RLU) measured in counts per second. The data (RLU) for each compound were normalized to the average maximal response obtained in the presence of vehicle (DMSO) alone. These data were used to derive the percent inhibition (100–% maximal response) and the average of two data points/concentration was used to calculate the $IC_{50}$ values (concentration causing a half-maximal inhibition of cell survival) via non-linear regression analysis using GraphPad Prism software (GraphPad, Inc., San Diego, CA). With this method, Example 20 inhibited cell proliferation of TRKA Ba/F3 cells with an $IC_{50}$ of 3.0 nM. Data for compounds tested in this assay are presented in Table 3.

Biological Example 5: EML4-ALK Ba/F3 Stable Cell Line Creation and Cell Proliferation Assay The EML4-ALK wild-type gene (variant 1) was synthesized at GenScript and cloned into pCDH-CMV-MCS-EF1-Puro plasmid (System Biosciences, Inc). Ba/F3-EML4-ALK wild type cell line was generated by infecting Ba/F3 cells with lentivirus containing EML4-ALK wide-type. Stable cell lines were selected by puromycin treatment, followed by IL-3 withdrawal. 5000 cells were seeded in 384 well white plate overnight before compound treatment. Cell proliferation was measured using CellTiter-Glo luciferase-based ATP detection assay (Promega) following the manufactures's protocol after 48 hours of various concentration of compound incubation. $IC_{50}$ determinations were performed using GraphPad Prism software (GraphPad, Inc., San Diego, CA.). Data for compounds tested in this assay are presented in Table 3

Biological Example 6: Cell Proliferation Assays

Colorectal cell lines KM 12 (harboring endogenous TPM3-TRKA fusion gene) cells were cultured in DMEM medium, supplemented with 10% fetal bovine serum and 100 U/mL of penicillin/streptomycin. 5000 cells were seeded in 384 well white plate for 24 hours before compounds treatment. Cell proliferation was measured using CellTiter-Glo luciferase-based ATP detection assay (Promega) following the manufactures's protocol after 72 hours incubation. $IC_{50}$ determinations were performed using GraphPad Prism software (GraphPad, Inc., San Diego, CA).

Alternatively: Colorectal cell line KM12 (harboring endogenous TPM3-TRKA fusion gene) cells were cultured in DMEM medium, supplemented with 10% fetal bovine serum and 100 U/mL of penicillin/streptomycin. Essential thrombocythemia cell line SET-2 cells (harboring endogenous JAK2 V618F point mutation) or T cell lymphoma Karpas-299 cell line (harboring endogenous NPM-ALK fusion gene) were cultured in RPMI medium, supplemented with 10% fetal bovine serum and 100 U/mL of penicillin/streptomycin. 5000 cells were seeded in 384 well white plate for 24 hours before compounds treatment. Cell proliferation was measured using CellTiter-Glo luciferase-based ATP detection assay (Promega) following the manufactures's protocol after 72 hours incubation. $IC_{50}$ determinations were performed using GraphPad Prism software (GraphPad, Inc., San Diego, CA).

Data for compounds tested in these assays are presented in Table 3.

TABLE 3

| Ex. | KM 12 cell prolif. $IC_{50}$ (nM) | SET2 cell proli. $IC_{50}$ (nM) | Karpas 299 cell proli. $IC_{50}$ (nM) | EML4-ALK Ba/F3 cell proli. $IC_{50}$ (nM) |
|---|---|---|---|---|
| 11-1 | >10000 | >10000 | >10000 | |
| 20 | 0.86 | 2000 | 1000 | |
| 39 | 3.8 | 8800 | 3800 | |
| 40 | 204 | >10000 | >10000 | |
| 41 | 118 | 1500 | 3900 | |
| 42 | 4.0 | 2000 | 3400 | |
| 43 | 2,6 | 1700 | 2800 | |
| 44 | 9.9 | 2030 | 4100 | |
| 45 | 0.35 | 8000 | >10000 | |
| 46 | 1.5 | 7000 | 7100 | |
| 47 | 31 | >10000 | >10000 | |

TABLE 3-continued

| Ex. | KM 12 cell prolif. IC$_{50}$ (nM) | SET2 cell proli. IC$_{50}$ (nM) | Karpas 299 cell proli. IC$_{50}$ (nM) | EML4-ALK Ba/F3 cell proli. IC$_{50}$ (nM) |
|---|---|---|---|---|
| 48 | 62 | 6000 | 6000 | |
| 49 | 6.7 | 7000 | 3900 | |
| 50 | 74 | 6000 | 4100 | |
| 51 | 3.2 | 425 | 832 | |
| 51-1 | 1.3 | 234 | 289 | 248 |
| 52 | 52 | 3600 | 7800 | |
| 59 | >1000 | | | |
| 60 | >1000 | | | |
| 61 | 0.6 | 3747 | 3900 | |
| 62 | 0.9 | 4000 | | |
| 66 | 17.5 | 1543 | 1900 | |
| 67 | 2.8 | 1231 | 1200 | |
| 75 | 0.6 | 4436 | 3900 | |
| 76-1 | 5.8 | 1003 | 3800 | |
| 84 | 0.8 | 3146 | 4200 | |
| 85 | 0.9 | 928 | 1080 | |
| 86 | | 1998 | 1000 | |
| 87 | 0.3 | 7734 | 1591 | |
| 88 | 50.4 | 1900 | 3129 | |
| 89 | 0.2 | 859 | 1398 | |
| 90 | 1.8 | 5911 | 1653 | |
| 91 | 1.8 | 1536 | 961 | |
| 92 | 0.3 | 142. | 88.7 | 78.6 |
| 93 | 0.5 | 242 | 23.7 | 21.1 |
| 94 | 0.2 | >10000 | >10000 | |
| 95 | 0.4 | 2673 | 4107 | |
| 96 | 0.6 | 6000 | 5000 | |
| 97 | 0.3 | 6500 | 1419 | |
| 98 | 7.4 | 808 | 281 | |
| 99 | 6.3 | 6848 | 506 | |
| 100 | 0.6 | 5834 | 5364 | |
| 101 | >1000 | 6000 | >10000 | |
| 102 | 1.2 | 2450 | 2304 | |
| 103 | 15 | >10000 | 1956 | |
| 104 | 0.3 | 2353 | 5747 | |
| 105 | 500 | >10000 | >5000 | |
| 106 | 176 | >10000 | >10000 | |
| 107 | 75.6 | 3000 | >10000 | |
| 108 | 3.6 | 870 | 619 | |
| 109 | 0.86 | 398 | 725 | |
| 110 | 0.7 | 219 | 163 | |
| 111 | 76 | 1996 | 329 | |

Biological Example 7: Cellular Mechanism of Action Studies-TRKA and Downstream Signal Targets Phosphorylation Assays Colorectal cell lines KM 12 (harboring endogenous TPM3-TRKA fusion gene) cells were cultured in DMEM medium, supplemented with 10% fetal bovine serum and 100 U/mL of penicillin/streptomycin. One million cells were seeded in 6-well plate for 24 hours before compounds treatment. Cells were washed with 1xPBS and collected after 5 hours treatment and lysed in RIPA buffer (50 mM Tris, pH 7.4, 150 mM NaCl, 1% NP-40, 0.5% Deoxycholate, 0.1% SDS) supplemented with 10 mM EDTA. Halt protease and phosphatase inhibitors (Thermo Scientific). Protein lysates (20 μg) were resolved on 4-12% Bolt Bis-Tris precasted gels with MES running buffer (Life Technologies), transferred to nitrocellulose membranes using Trans-Blot Turbo Transfer System (Bio-Rad) and detected with antibodies targeting phosphorylated TRK A (Cell Signaling Technology, Y496, Y680, Y681, clone C50F3; 1:1000 dilution), total TRK A (Santa Cruz Biotechnology, sc-11; clone C-14, 1:2000 dilution), phosphorylated AKT (Cell signaling, S473, D9E, #9271; 1:5000 dilution), total AKT (Cell Signaling Technology, 40D4; 1:2000 dilution), phosphorylated ERK (Cell Signaling Technology, Thr 202/204, D13.14.4E, #4370; 1:2000 dilution), total ERK (Cell Signaling Technology; 1:1000 dilution) and Tubulin (Sigma. T4026, 1:5000 dilution). Antibodies were typically incubated overnight at 4° C. with gentle shaking, followed by washes and incubation with the appropriate HRP-conjugated secondary antibodies. Membranes were exposed to chemiluminescent substrate for 5 min at room temperature (SuperSignal West Femto, Thermo Scientific). Images were obtained with a C-Digit Imaging System (LI-COR Biosciences). The relative density of the hands was obtained directly via Image Studio Digits from LICOR. The half inhibitory concentration (IC$_{50}$) values were calculated using non-linear regression analysis through GraphPad Prism software (GraphPad, Inc., San Diego, CA). With this method, Example 20 inhibited autophosphorylation of TPM3-TRKA with an IC$_{50}$ of 1.07 nM and the phosphorylation of its downstream signaling targets AKT and ERK with IC$_{50}$'s of 2.80 nM and 2.00 nM, respectively, in KM12 cells.

Biological Example 8: Caspase Activity Assays

KM12 cells were maintained in DMEM medium supplemented with 10% fetal bovine serum and antibiotics. 500,000 cells were seeded in 12-well plate and various concentration of compounds were introduced for 72 hours For staurosporine treatment, 500 nM of STS were added at time of 60 hours and incubation of 12 hours as a positive control. All the cells were collected and washed with 1xPBS twice and then lysed in a lysis buffer (20 mM HEPES, 150 mM NaCl, 10 mM KCl, 5 mM EDTA, 1% NP40) supplemented with Halt protease and phosphatase inhibitors (Thermo Scientific). For caspase assays, around 20 μL (20 μg) of cell lysate were incubated with 20 μL of caspase3 glo reagent (Promega), measuring enzyme activity by the release of luminescence after 20 min incubation at 37° C. For western blotting, cell lysates were boiled and analyzed by SDS-PAGE/immunoblotting using PARP, or actin antibodies. With this method, Example 20 induced apoptosis of KM 12 cells.

What is claimed is:

1. A compound having structure:

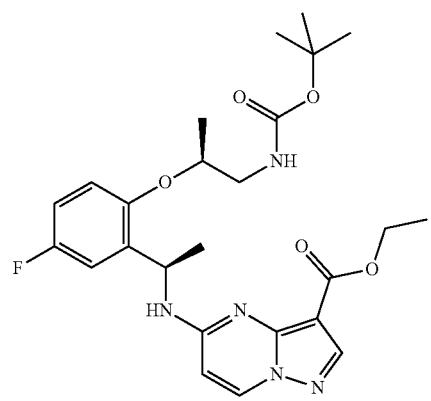 [SMILES: CCOC(=O)c1cnn2ccc(N[C@H](C)c3cc(F)ccc3O[C@@H](C)CNC(=O)OC(C)(C)C)nc12]

2. A compound having structure:
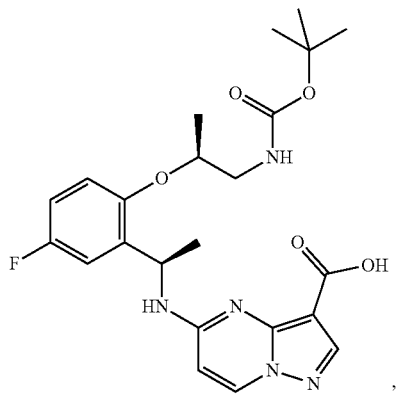 [SMILES: C[C@@H](CNC(=O)OC(C)(C)C)Oc1ccc(F)cc1[C@@H](C)Nc1ccn2ncc(C(=O)O)c2n1]
or a salt thereof.
3. The compound of claim 2 that is
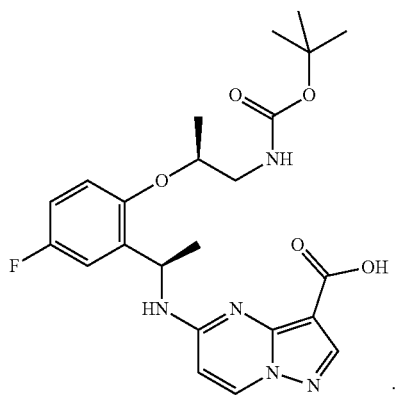 [SMILES: C[C@@H](CNC(=O)OC(C)(C)C)Oc1ccc(F)cc1[C@@H](C)Nc1ccn2ncc(C(=O)O)c2n1]
4. A compound having structure:
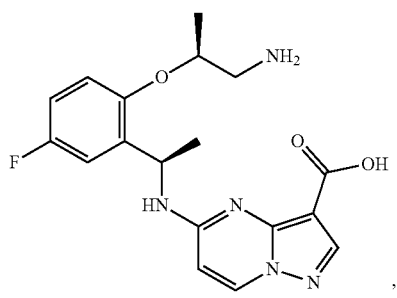 [SMILES: C[C@@H](CN)Oc1ccc(F)cc1[C@@H](C)Nc1ccn2ncc(C(=O)O)c2n1]
or a salt thereof.
5. The compound of claim 4 that is
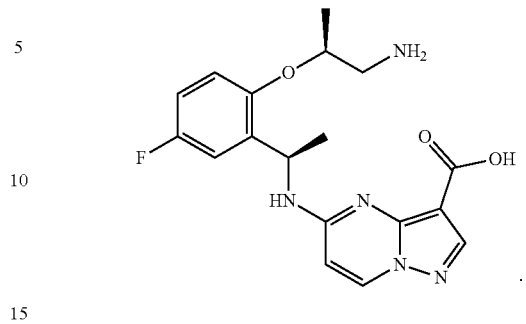
6. A compound having structure:
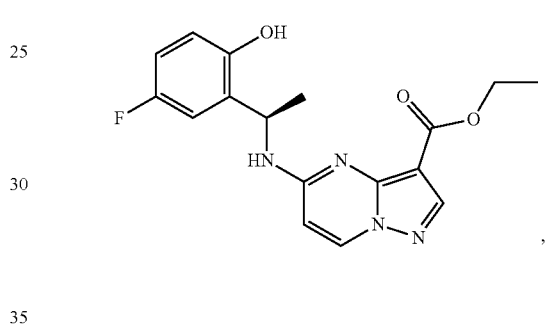
or a salt thereof.
7. The compound of claim 6 that is
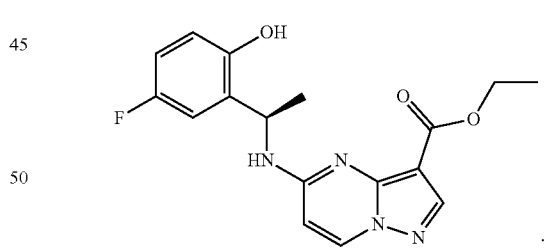
* * * * *